(12) United States Patent
Satoh et al.

(10) Patent No.: US 7,745,459 B2
(45) Date of Patent: Jun. 29, 2010

(54) QUINOLIZINONE COMPOUND AND USE THEREOF AS HIV INTEGRASE INHIBITOR

(75) Inventors: Motohide Satoh, Osaka (JP); Hisateru Aramaki, Osaka (JP); Hiroshi Nakamura, Osaka (JP); Masafumi Inoue, Osaka (JP); Hiroshi Kawakami, Osaka (JP); Hisashi Shinkai, Osaka (JP); Yuji Matsuzaki, Osaka (JP); Kazunobu Yamataka, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 999 days.

(21) Appl. No.: 11/230,330

(22) Filed: Sep. 20, 2005

(65) Prior Publication Data

US 2006/0084665 A1  Apr. 20, 2006

Related U.S. Application Data

(60) Provisional application No. 60/615,504, filed on Oct. 1, 2004, provisional application No. 60/711,446, filed on Aug. 25, 2005.

(30) Foreign Application Priority Data

Sep. 21, 2004 (JP) ............................. 2004-272820
Aug. 12, 2005 (JP) ............................. 2005-234884

(51) Int. Cl.
*A01N 43/90* (2006.01)
*A61K 31/44* (2006.01)
*C07D 455/02* (2006.01)

(52) U.S. Cl. ...................................... 514/306; 546/138
(58) Field of Classification Search ................. 514/306; 546/138
See application file for complete search history.

(56) References Cited

U.S. PATENT DOCUMENTS

| | | | |
|---|---|---|---|
| 4,650,804 A | 3/1987 | Kitaura et al. | |
| 6,624,159 B2 | 9/2003 | Anderson et al. | |
| 2002/0025960 A1 | 2/2002 | Bundy et al. | |
| 2004/0229903 A1 | 11/2004 | Fukumoto et al. | |
| 2005/0054645 A1 | 3/2005 | Miyazaki et al. | |
| 2005/0239819 A1 | 10/2005 | Satoh et al. | |
| 2006/0052361 A1 | 3/2006 | Miyazaki et al. | |

FOREIGN PATENT DOCUMENTS

| | | |
|---|---|---|
| EP | 0 157 346 | 1/1990 |
| EP | 1 437 354 A1 | 7/2004 |
| EP | 1 564 210 A1 | 8/2005 |
| JP | B-6-49701 | 3/1985 |
| JP | 5-503709 A | 5/1991 |
| JP | A-2004-502770 | 6/2001 |
| JP | A-2004-502771 | 6/2001 |
| WO | WO 91/16894 A1 | 11/1991 |
| WO | WO 00/17197 | 9/1999 |
| WO | WO 99/62513 | 12/1999 |
| WO | WO 01/00578 A1 | 1/2001 |
| WO | WO 02/04444 A2 | 1/2002 |
| WO | WO 02/04445 A1 | 1/2002 |
| WO | WO 03/029253 A1 | 4/2003 |
| WO | WO 2004/019933 A1 | 3/2004 |
| WO | WO 2004/024078 A2 | 3/2004 |
| WO | WO 2004/035576 A2 | 4/2004 |
| WO | WO 2004/035577 A2 | 4/2004 |
| WO | WO 2004/039803 A2 | 5/2004 |
| WO | WO 2004/046115 A1 | 6/2004 |

OTHER PUBLICATIONS

Carey FA and Sundberg RJ, "Advanced Organic Chemistry, 3rd Ed., Part A: Structure and Mechanisms," Plenum Press, New York, 1990.*
Kawasuji T, Yoshinaga T, Sato A, Yodo M, Fujiwara T, and Kiyama R, "A platform for designing HIV integrase inhibitors. Part 1: 2-Hydroxy-3-heteroaryl acrylic acid derivatives as novel HIV integrase inhibitor and modeling of hydrophilic and hydrophobic pharmacophores," Bioorganic & Medicinal Chemistry, Dec. 2006, 14(24), 8430-8445.*

(Continued)

*Primary Examiner*—San-ming Hui
*Assistant Examiner*—Paul Zarek
(74) *Attorney, Agent, or Firm*—Finnegan, Henderson, Farabow, Garrett & Dunner, LLP

(57) ABSTRACT

A pharmaceutical agent having an anti-HIV action, particularly, a pharmaceutical agent having an integrase inhibitory action, is provided.

The present invention relates to a quinolizinone compound represented by the following formula [I]

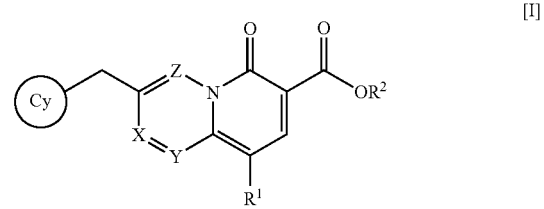

wherein each symbol is as defined in the specification, a pharmaceutically acceptable salt thereof, and an anti-HIV agent containing same as an active ingredient.

The compound of the present invention has an HIV integrase inhibitory action and is useful as an anti-HIV agent for the prophylaxis or therapy of AIDS. Moreover, by a combined use with other anti-HIV agents such as protease inhibitors, reverse transcriptase inhibitors and the like, the compounds can become a more effective anti-HIV agent. Since the compound has a high inhibitory activity specific for integrases, the compound can provide a safe pharmaceutical agent for human with a fewer side effects.

33 Claims, No Drawings

OTHER PUBLICATIONS

Maurin C, Bailly F, and Cotelle P, "Structure-activity relationships of HIV-1 integrase inhibitors—enzyme-ligand interactions," Current Medicinal Chemistry, Sep. 2003, 10(18), 1795-1810.*

Zouhiri F, Mouscadet JF, Mekouar K, Desmaële D, Savouré D, Leh H, Subra F, Le Bret M, Auclair C, and d'Angelo J, "Structure-activity relationships and binding mode of styrylquinolines as potent inhibitors of HIV-1 integrase and replication of HIV-1 in cell culture," Journal of Medicinal Chemistry, Apr. 2000, 43(8), 1533-1540.*

Guidelines for the Use of Antiretroviral Agents in HIV-Infected Adults and Adolescent, pp. i-iii and 1-111, (Aug. 13, 2001).

Göschke, Richard et al., the Nonchiral Bislactin Diethoxy Ether as a Highly Stereo-Inducing Synthon for Sterically Hindered, γ-Branched α-Amino Acids: A Practical, Large-Scale Route to an Intermediate of the Novel Renin Inhibitor Aliskiren, Helvetica Chemica Acta, vol. 86, pp. 2848-2870 (2003).

Vincent, K.A., et al. Characterization of Human Immunodeficiency Virus Type I Integrase Expressed in *Eschericia coli* and Analysis of Variants and Amino-Terminal Mutations, J. Virol. 67:425-437 (1993).

Evans, David A., Total Synthesis of the Polyether Antibiotic Ionomycin, Journal of the American Chemical Society, 1990, 112, 5290-5313.

Evans, D.A., et al., Asymmetric Alkylation Reactions of Chiral Imide Emolates. A Practical Approach to the Enantioselective Synthesis of α-Substituted Carboxylic Acid Derivatives, Journal of the American Chemical Society, 1982, 104, 1737-1739.

PCT International Search Report (PCT/JP2005/017556) dated Oct. 25, 2005.

* cited by examiner

QUINOLIZINONE COMPOUND AND USE THEREOF AS HIV INTEGRASE INHIBITOR

CROSS REFERENCE TO RELATED APPLICATIONS

This application claims the benefit of priority of Japanese Patent Application Nos. 2004-272820, filed Sep. 21, 2004, and 2005-234884, filed Aug. 12, 2005; and U.S. Provisional Application Nos. 60/615,504, filed Oct. 1, 2004, and 60/711,446 filed Aug. 25, 2005.

TECHNICAL FIELD

The present invention relates to a novel quinolizinone compound useful as an anti-HIV agent and a pharmaceutically acceptable salt thereof. The present invention also relates to a novel use of a certain quinolizinone compound and a pharmaceutically acceptable salt thereof as an anti-HIV agent. More particularly, the present invention relates to an anti-HIV agent containing a quinolizinone compound that particularly shows an anti-HIV action based on an integrase inhibitory activity thereof, or a pharmaceutically acceptable salt thereof.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell, and destroys these immunocompetent cells to cause immunodeficiency.

Accordingly, a pharmaceutical agent that eradicates HIV in the body or suppresses its growth is effective for the treatment or prophylaxis of AIDS.

HIV possesses a bimolecular RNA gene in a shell, and which is covered with an envelope protein. The RNA codes for several enzymes (protease, reverse transcriptase, integrase) characteristic of the virus, and the like. Translated reverse transcriptase and integrase are present in the shell, and protease is present inside and outside the shell.

HIV attaches to and invades a host cell, causes uncoating, and releases a complex of RNA and integrase and the like into the cytoplasm. From the RNA, DNA is transcribed by reverse transcriptase, and a full length double stranded DNA is produced. The DNA is imported into the nucleus of the host cell and integrated by integrase into the DNA of the host cell. The integrated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, zidovudine, didanosine, lamivudine and the like have been already on the market as reverse transcriptase inhibitors, and indinavir, nelfinavir and the like as protease inhibitors.

In addition, a multiple drug combination therapy concurrently using these pharmaceutical agents has been employed. For example, a combined use of two reverse transcriptase inhibitors (zidovudine and didanosine), and a combined use of three agents of reverse transcriptase inhibitors (zidovudine and lamivudine) and a protease inhibitor (nelfinavir) and the like have been clinically applied. Such multiple drug combination therapy is becoming a mainstream of AIDS therapy (see e.g., Guidelines for the Use of Antiretroviral Agents in HIV-Infected Adults and Adlescent. Aug. 13, 2001).

However, some of these pharmaceutical agents are known to cause side effects such as liver function failure, central nervous disorders (e.g., vertigo), and the like. In addition, acquisition of resistance to a pharmaceutical agent causes a problem. Even worse, emergence of an HIV that shows multiple drug resistance in a multiple drug combination therapy has been known.

Under the circumstances, a further development of a novel pharmaceutical agent, particularly a development of an anti-HIV agent based on a new mechanism, has been desired, wherein a development of an anti-HIV agent having an integrase inhibitory activity is expected, because an integrase characteristic of retrovirus is an essential enzyme for the growth of HIV.

Nevertheless, an effective integrase inhibitor has not been found as yet.

Known antiviral agents comparatively similar to the anti-HIV agent of the present invention are described in the following.

WO2004/046115 describes compound A below and the like as anti-HIV agents having an integrase inhibitory activity (see WO2004/046115 (page 134, Example 1-99)).

Compound [A]

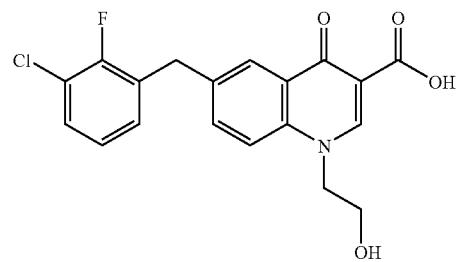

However, this publication does not include the quinolizinone compound disclosed in the present specification, or any description suggestive thereof.

In addition, JP-A-2004-502771 (patent family: WO2002/004445) describes compound B below and the like as antiviral agents, particularly as agents against herpes viruses, and compound C below as intermediates thereof (see JP-A-2004-502771 (page 85, Example 7)).

Compound [B]

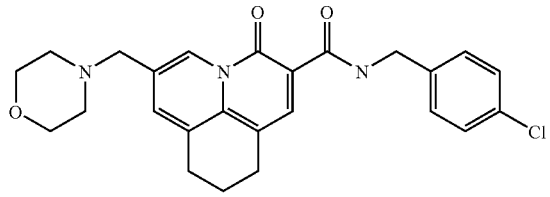

Compound [C]

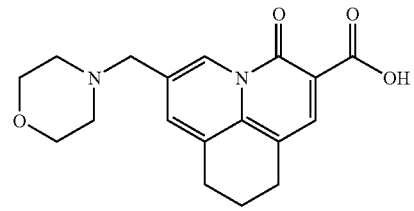

Moreover, JP-A-2004-502770 (patent family: WO2002/004444) describes compound D below and the like as antiviral agents, particularly as agents against herpes viruses (see JP-A-2004-502770 (page 57, formula AI.8)). In addition, WO2004/019933 describes compound D below and the like as therapeutic agents for atherosclerosis and restenosis (see WO2004/019933 (page 64, compound (52))).

Compound [D]

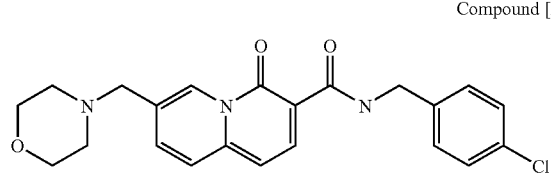

However, these publications do not include the quinolizinone compound disclosed in the present specification, or any description suggestive thereof.

Now, known compounds comparatively similar to the compound of the present invention are described in the following.

WO2003/029253 (patent family: EP1437354) describes compound E below and the like as compounds having an antibacterial activity (see WO2003/029253 (page 54, Example 119)).

Compound [E]

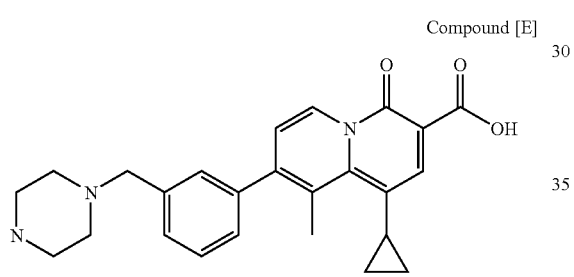

However, this publication does not describe the quinolizinone compound disclosed in the present specification, nor the antiviral activity of the quinolizinone compound, or anything suggestive thereof.

Besides these, there are many antibacterial agents having a cyclic substituent (e.g., pyrrolidin-1-yl group) at the 8-position of quinolizinone skeleton. However, those antibacterial agents are different from the quinolizinone compound disclosed in the present specification in both the chemical structure and use thereof.

In addition, JP-B-6-49701 (patent family: EP157346) describes the following compound F, compound G and the like as compounds having an inhibitory activity against allergies and ulcers (see JP-B-6-49701 (pages 15-16, Example 3, (1) and (4))).

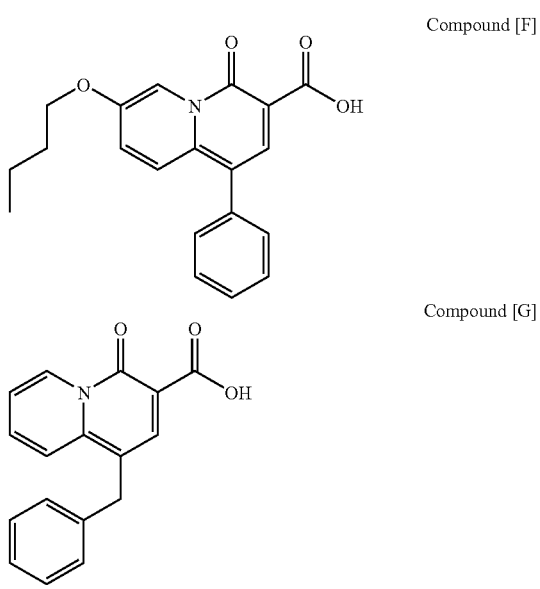

Compound [F]

Compound [G]

Moreover, WO2000/17197 describes the following compound H, compound i and the like as anticancer agents having an integrin inhibitory action, or vascular vessel regeneration inhibitors having an integrin inhibitory action (see WO2000/17197 (compound XIII at pages 71-74 and compound XLI at page 102)).

Compound [H]

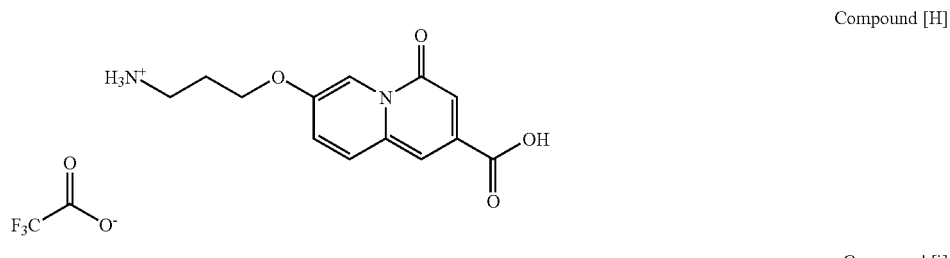

Compound [i]

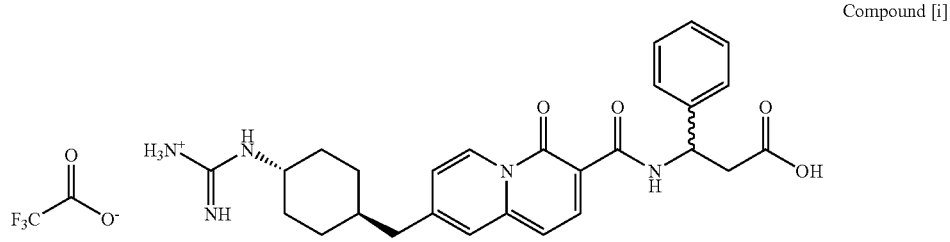

However, these publications do not describe the quinolizinone compound disclosed in the present specification, nor the antiviral activity of the quinolizinone compound, nor anything suggestive thereof.

DISCLOSURE OF THE INVENTION

From the findings based on the pharmacological researches and clinical results obtained so far, an anti-HIV agent is effective for the prophylaxis of the onset of AIDS and the treatment thereof, and particularly a compound having an integrase inhibitory action can provide an effective anti-HIV agent.

It is therefore an object of the present invention to provide a pharmaceutical agent having an anti-HIV action, particularly a pharmaceutical agent having an integrase inhibitory action.

The present inventors have conducted intensive studies in an attempt to find a compound having an anti-HIV action, particularly a compound having an integrase inhibitory action, and completed the present invention.

Accordingly, the present invention is shown in the following.

(1) An anti-HIV agent comprising a quinolizinone compound represented by the following formula [I] or a pharmaceutically acceptable salt thereof as an active ingredient:

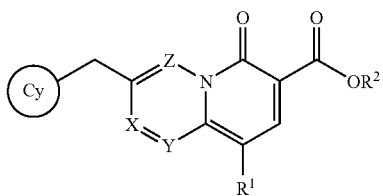

wherein
ring Cy is a $C_{3-10}$ carbon ring group optionally substituted by 1 to 5 substituents selected from the following group A or a heterocyclic group optionally substituted by 1 to 5 substituents selected from the following group A,
wherein the heterocyclic group is a saturated or unsaturated ring group containing, besides carbon atom(s), at least one hetero atom selected from a nitrogen atom, an oxygen atom and a sulfur atom,
wherein the group A is a group consisting of a cyano group, a phenyl group, a nitro group, a halogen atom, a $C_{1-4}$ alkyl group, a halo $C_{1-4}$ alkyl group, a halo $C_{1-4}$ alkyloxy group,
—$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$,
wherein $R^{a1}$ and $R^{a2}$ are the same or different and each is a hydrogen atom, a $C_{1-4}$ alkyl group or a benzyl group, and $R^{a3}$ is a $C_{1-4}$ alkyl group;
$R^1$ is a hydrogen atom,
a group selected from the following group B or a $C_{1-10}$ alkyl group optionally substituted by 1 to 3 substituents selected from a halogen atom and the following group B,
wherein the group B is a group consisting of a $C_{3-10}$ carbon ring group optionally substituted by 1 to 5 substituents selected from the above-mentioned group A, a heterocyclic group (the heterocyclic group is as defined above) optionally substituted by 1 to 5 substituents selected from the above-mentioned group A,
a cyano group, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$, —$NR^{a5}COOR^{a6}$, —$NR^{a4}CO$—$NR^{a5}R^{a12}$, —$NR^{a4}CO$—$COOR^{a5}$, —O—W—$OR^{a5}$, —$NR^{a4}$—W—$OR^{a5}$, —$NR^{a4}$—W—$SO_2NR^{a5}R^{a12}$, —$NR^{a4}CO$—W—$R^{a5}$, —$NR^{a4}CO$—W—$OR^{a5}$, —$NR^{a4}CO$—W—$COOR^{a5}$ and —$NR^{a4}CO$—W—$NR^{a5}COR^{a6}$,
wherein $R^{a4}$, $R^{a5}$ and $R^{a12}$ are the same or different and each is a hydrogen atom, a $C_{1-4}$ alkyl group, a $C_{3-10}$ carbon ring group optionally substituted by 1 to 5 substituents selected from the above-mentioned group A or a heterocyclic group (the heterocyclic group is as defined above) optionally substituted by 1 to 5 substituents selected from the above-mentioned group A, $R^{a6}$ is a $C_{1-4}$ alkyl group, a $C_{3-10}$ carbon ring group optionally substituted by 1 to 5 substituents selected from the above-mentioned group A or a heterocyclic group (the heterocyclic group is as defined above) optionally substituted by 1 to 5 substituents selected from the above-mentioned group A, and W is a $C_{1-10}$ alkylene group;
$R^2$ is a hydrogen atom or a $C_{1-4}$ alkyl group;
Z is C—$R^{31}$ or a nitrogen atom,
wherein $R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group or a halo $C_{1-4}$ alkyloxy group;
X is C—$R^{32}$ or a nitrogen atom; and
Y is C—$R^{33}$ or a nitrogen atom,
wherein $R^{32}$ and $R^{33}$ are the same or different and each is a hydrogen atom, a cyano group, a nitro group, a halogen atom,
a $C_{3-10}$ carbon ring group optionally substituted by 1 to 5 substituents selected from the above-mentioned group A,
a heterocyclic group (the heterocyclic group is as defined above) optionally substituted by 1 to 5 substituents selected from the above-mentioned group A,
a $C_{1-10}$ alkyl group optionally substituted by 1 to 3 substituents selected from a halogen atom and the above-mentioned group B,
—$OR^{a7}$, —$SR^{a7}$, —$NR^{a7}R^{a8}$, —$NR^{a7}COR^{a9}$, —$COOR^{a10}$ or —N=CH—$NR^{a10}R^{a11}$,
wherein $R^{a7}$ and $R^{a8}$ are the same or different and each is a hydrogen atom, a group selected from the above-mentioned group B or a $C_{1-10}$ alkyl group optionally substituted by 1 to 3 substituents selected from a halogen atom and the above-mentioned group B, $R^{a9}$ is a $C_{1-4}$ alkyl group, and $R^{a10}$ and $R^{a11}$ are the same or different and each is a hydrogen atom or a $C_{1-4}$ alkyl group.

(2) The anti-HIV agent of the above-mentioned (1), wherein X is C—$R^{32}$ and Z is C—$R^{31}$.

(3) The anti-HIV agent of the above-mentioned (1), wherein ring Cy is a group represented by the formula:

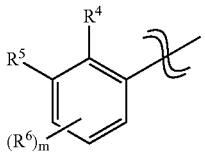

wherein
R$^6$ is a group selected from the group A (the group A is as defined in the above-mentioned (1));
R$^4$ and R$^5$ are the same or different and each is a group selected from a hydrogen atom and the group A (the group A is as defined in the above-mentioned (1)), or
R$^4$ and R$^5$ may form a fused ring together with a benzene ring they substitute; and
m is 0 or an integer of 1 to 3, and when m is 2 or 3, then R$^6$ of each may be the same or different.

(4) A quinolizinone compound represented by the following formula [II] or a pharmaceutically acceptable salt thereof:

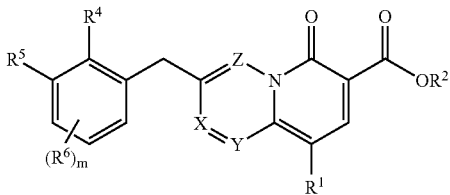

wherein
R$^6$ is a group selected from the following group A,
    wherein the group A is a group consisting of a cyano group, a phenyl group, a nitro group, a halogen atom, a C$_{1-4}$ alkyl group, a halo C$_{1-4}$ alkyl group, a halo C$_{1-4}$ alkyloxy group,
    —OR$^{a1}$, —SR$^{a1}$, —NR$^{a1}$R$^{a2}$, —CONR$^{a1}$R$^{a2}$, —SO$_2$NR$^{a1}$R$^{a2}$, —COR$^{a3}$, —NR$^{a1}$COR$^{a3}$, —SO$_2$R$^{a3}$, —NR$^{a1}$SO$_2$R$^{a3}$, —COOR$^{a1}$ and —NR$^{a2}$COOR$^{a3}$,
    wherein R$^{a1}$ and R$^{a2}$ are the same or different and each is a hydrogen atom, a C$_{1-4}$ alkyl group or a benzyl group, and R$^{a3}$ is a C$_{1-4}$ alkyl group;
R$^4$ and R$^5$ are the same or different and each is a group selected from a hydrogen atom and the above-mentioned group A, or
R$^4$ and R$^5$ may form a fused ring together with a benzene ring they substitute;
m is 0 or an integer of 1 to 3, and when m is 2 or 3, then R$^6$ of each may be the same or different;
R$^1$ is a hydrogen atom,
    a group selected from the following group B or a C$_{1-10}$ alkyl group optionally substituted by 1 to 3 substituents selected from a halogen atom and the following group B,
        wherein the group B is a group consisting of a C$_{3-10}$ carbon ring group optionally substituted by 1 to 5 substituents selected from the above-mentioned group A,
        a heterocyclic group optionally substituted by 1 to 5 substituents selected from the above-mentioned group A, wherein the heterocyclic group is a saturated or unsaturated ring group containing, besides carbon atom (s), at least one hetero atom selected from a nitrogen atom, an oxygen atom and a sulfur atom,
    a cyano group, —OR$^{a4}$, —SR$^{a4}$, —NR$^{a4}$R$^{a5}$, —CONR$^{a4}$R$^{a5}$, —SO$_2$NR$^{a4}$R$^{a5}$, —COR$^{a6}$, —NR$^{a4}$COR$^{a6}$, —SO$_2$R$^{a6}$, —NR$^{a4}$SO$_2$R$^{a6}$, —COOR$^{a4}$, —NR$^{a5}$COOR$^{a6}$, —NR$^{a4}$CO—NR$^{a5}$R$^{a12}$, —NR$^{a4}$CO—COOR$^{a5}$, —O—W—OR$^{a5}$, —NR$^{a4}$—W—OR$^{a5}$, —NR$^{a4}$—W—SO$_2$NR$^{a5}$R$^{a12}$, —NR$^{a4}$CO—W—R$^{a5}$, —NR$^{a4}$CO—W—OR$^{a5}$, —NR$^{a4}$CO—W—COOR$^{a5}$ and —NR$^{a4}$CO—W—NR$^{a5}$COR$^{a6}$,
    wherein R$^{a4}$, R$^{a5}$ and R$^{a12}$ are the same or different and each is a hydrogen atom, a C$_{1-4}$ alkyl group, a C$_{3-10}$ carbon ring group optionally substituted by 1 to 5 substituents selected from the above-mentioned group A or a heterocyclic group (the heterocyclic group is as defined above) optionally substituted by 1 to 5 substituents selected from the above-mentioned group A, R$^{a6}$ is a C$_{1-4}$ alkyl group, a C$_{3-10}$ carbon ring group optionally substituted by 1 to 5 substituents selected from the above-mentioned group A or a heterocyclic group (the heterocyclic group is as defined above) optionally substituted by 1 to 5 substituents selected from the above-mentioned group A, and W is a C$_{1-10}$ alkylene group;
R$^2$ is a hydrogen atom or a C$_{1-4}$ alkyl group;
Z is C—R$^{31}$ or a nitrogen atom,
    wherein R$^{31}$ is a hydrogen atom, a cyano group, a hydroxy group, an amino group, a nitro group, a halogen atom, a C$_{1-4}$ alkyl group, a C$_{1-4}$ alkoxy group, a C$_{1-4}$ alkylsulfanyl group, a halo C$_{1-4}$ alkyl group or a halo C$_{1-4}$ alkyloxy group;
X is C—R$^{32}$ or a nitrogen atom; and
Y is C—R$^{33}$ or a nitrogen atom,
    wherein R$^{32}$ and R$^{33}$ are the same or different and each is a hydrogen atom, a cyano group, a nitro group, a halogen atom,
    a C$_{3-10}$ carbon ring group optionally substituted by 1 to 5 substituents selected from the above-mentioned group A,
    a heterocyclic group (the heterocyclic group is as defined above) optionally substituted by 1 to 5 substituents selected from the above-mentioned group A,
    a C$_{1-10}$ alkyl group optionally substituted by 1 to 3 substituents selected from a halogen atom and the above-mentioned group B,
    —OR$^{a7}$, —SR$^{a7}$, —NR$^{a7}$R$^{a8}$, —NR$^{a7}$COR$^{a9}$, —COOR$^{a10}$ or —N=CH—NR$^{a10}$R$^{a11}$,
        wherein R$^{a7}$ and R$^{a8}$ are the same or different and each is a hydrogen atom, a group selected from the above-mentioned group B or a C$_{1-10}$ alkyl group optionally substituted by 1 to 3 substituents selected from a halogen atom and the above-mentioned group B, R$^{a9}$ is a C$_{1-4}$ alkyl group, and R$^{a10}$ and R$^{a11}$ are the same or different and each is a hydrogen atom or a C$_{1-4}$ alkyl group.

(5) The quinolizinone compound of the above-mentioned (4), wherein X is C—R$^{32}$ and Z is C—R$^{31}$, or a pharmaceutically acceptable salt thereof.

(6) The quinolizinone compound of the above-mentioned (4) or (5), wherein R$^{31}$ is a hydrogen atom, a cyano group, a hydroxy group or a C$_{1-4}$ alkoxy group, or a pharmaceutically acceptable salt thereof.

(7) The quinolizinone compound of the above-mentioned (4) or (5), wherein $R^{31}$ is a hydrogen atom, or a pharmaceutically acceptable salt thereof.

(8) The quinolizinone compound of the above-mentioned (4) or (5), wherein
$R^{32}$ is a hydrogen atom, a cyano group, a halogen atom, a heterocyclic group (the heterocyclic group is as defined in the above-mentioned (4)) optionally substituted by 1 to 5 substituents selected from the group A (the group A is as defined in the above-mentioned (4)),
a $C_{1-10}$ alkyl group optionally substituted by 1 to 3 substituents selected from a halogen atom and the group B (the group B is as defined in the above-mentioned (4)), —$OR^{a7}$, —$SR^{a7}$, —$NR^{a7}R^{a8}$, —$NR^{a7}COR^{a9}$, —$COOR^{a10}$ or —$N=CH—NR^{a10}R^{a11}$,
wherein $R^{a7}$, $R^{a8}$, $R^{a9}$, $R^{a10}$ and $R^{a11}$ are as defined in the above-mentioned (4), or a pharmaceutically acceptable salt thereof.

(9) The quinolizinone compound of the above-mentioned (4) or (5), wherein
$R^{32}$ is a hydrogen atom, a cyano group, a halogen atom, a $C_{1-10}$ alkyl group optionally substituted by 1 to 3 substituents selected from a halogen atom and the group B (the group B is as defined in the above-mentioned (4)), —$OR^{a7}$, —$SR^{a7}$, —$NR^{a7}R^{a8}$, —$NR^{a7}COR^{a9}$ or —$COOR^{a10}$,
wherein $R^{a7}$, $R^{a8}$, $R^{a9}$ and $R^{a10}$ are as defined in the above-mentioned (4), or a pharmaceutically acceptable salt thereof.

(10) The quinolizinone compound of the above-mentioned (4) or (5), wherein
$R^{32}$ is a hydrogen atom, —$OR^{a7}$, —$SR^{a7}$ or —$NR^{a7}R^{a8}$,
wherein $R^{a7}$ and $R^{a8}$ are as defined in the above-mentioned (4), or a pharmaceutically acceptable salt thereof.

(11) The quinolizinone compound of the above-mentioned (4), wherein Y is C—$R^{33}$, or a pharmaceutically acceptable salt thereof.

(12) The quinolizinone compound of the above-mentioned (4) or (11), wherein
$R^{33}$ is a hydrogen atom, a cyano group, a halogen atom, a heterocyclic group (the heterocyclic group is as defined in the above-mentioned (4)) optionally substituted by 1 to 5 substituents selected from the group A (the group A is as defined in the above-mentioned (4)),
a $C_{1-10}$ alkyl group optionally substituted by 1 to 3 substituents selected from a halogen atom and the group B (the group B is as defined in the above-mentioned (4)), —$OR^{a7}$, —$SR^{a7}$, —$NR^{a7}R^{a8}$, —$NR^{a7}COR^{a9}$, —$COOR^{a10}$ or —$N=CH—NR^{a10}R^{11}$,
wherein $R^{a7}$, $R^{a8}$, $R^{a9}$, $R^{a10}$ and $R^{a11}$ are as defined in the above-mentioned (4), or a pharmaceutically acceptable salt thereof.

(13) The quinolizinone compound of the above-mentioned (4) or (11), wherein
$R^{33}$ is a hydrogen atom,
a $C_{1-10}$ alkyl group optionally substituted by 1 to 3 substituents selected from a halogen atom and the group B (the group B is as defined in the above-mentioned (4)), —$OR^{a7}$ or —$NR^{a7}R^{a8}$,
wherein $R^{a7}$ and $R^{a8}$ are as defined in the above-mentioned (4), or a pharmaceutically acceptable salt thereof.

(14) The quinolizinone compound of the above-mentioned (4) or (11), wherein
$R^{33}$ is a hydrogen atom, —$OR^{a7}$ or —$NR^{a7}R^{a8}$,
wherein $R^{a7}$ and $R^{a8}$ are as defined in the above-mentioned (4), or a pharmaceutically acceptable salt thereof.

(15) The quinolizinone compound of any of the above-mentioned (8) to (14), wherein $R^{a7}$ and $R^{a8}$ are the same or different and each is a $C_{1-10}$ alkyl group optionally substituted by 1 to 3 substituents selected from a halogen atom and the group B (the group B is as defined in the above-mentioned (4)), or a pharmaceutically acceptable salt thereof.

(16) The quinolizinone compound of the above-mentioned (4), wherein
$R^4$ and $R^5$ are the same or different and each is a hydrogen atom, a cyano group, a phenyl group, a nitro group, a halogen atom, a $C_{1-4}$ alkyl group, a halo $C_{1-4}$ alkyl group, a halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$NR^{a1}COR^{a3}$, —$SO_2R^{a3}$, —$NR^{a1}SO_2R^{a3}$, —$COOR^{a1}$ or —$NR^{a2}COOR^{a3}$,
wherein $R^{a1}$, $R^{a2}$ and $R^{a3}$ are as defined in the above-mentioned (4), or a pharmaceutically acceptable salt thereof.

(17) The quinolizinone compound of the above-mentioned (4), wherein
$R^4$ is a hydrogen atom, a phenyl group, a halogen atom, a $C_{1-4}$ alkyl group, a halo $C_{1-4}$ alkyloxy group,
—$OR^{a1}$, —$NR^{a1}R^{a2}$, —$CONR^{a1}R^{a2}$, —$SO_2NR^{a1}R^{a2}$, —$NR^{a1}COR^{a3}$, —$SO_2R^{a3}$, —$NR^{a1}SO_2R^{a3}$ or —$COOR^{a1}$,
wherein $R^{a1}$, $R^{a2}$ and $R^{a3}$ are as defined in the above-mentioned (4), or a pharmaceutically acceptable salt thereof.

(18) The quinolizinone compound of the above-mentioned (4), wherein $R^4$ is a hydrogen atom or a halogen atom, or a pharmaceutically acceptable salt thereof.

(19) The quinolizinone compound of the above-mentioned (4), wherein
$R^5$ is a hydrogen atom, a cyano group, a phenyl group, a nitro group, a halogen atom, a $C_{1-4}$ alkyl group, a halo $C_{1-4}$ alkyl group, —$OR^{a1}$, —$SR^{a1}$, —$NR^{a1}R^{a2}$, —$CONR^{a1}R^{a2}$, —$SO_2NR^{a1}R^{a2}$ or —$NR^{a1}COR^{a3}$,
wherein $R^{a1}$, $R^{a2}$ and $R^{a3}$ are as defined in the above-mentioned (4), or a pharmaceutically acceptable salt thereof.

(20) The quinolizinone compound of the above-mentioned (4), wherein $R^6$ is a halogen atom, or a pharmaceutically acceptable salt thereof.

(21) The quinolizinone compound of the above-mentioned (4), wherein m is 0 or 1, or a pharmaceutically acceptable salt thereof.

(22) The quinolizinone compound of the above-mentioned (4), wherein
$R^1$ is a hydrogen atom,
a $C_{3-10}$ carbon ring group optionally substituted by 1 to 5 substituents selected from the group A (the group A is as defined in the above-mentioned (4)), a cyano group, —NR$^{a4}$R$^{a5}$, —NR$^{a4}$COR$^{a6}$, —NR$^{a4}$SO$_2$R$^{a6}$, —COOR$^{a4}$, —NR$^{a5}$COOR$^{a6}$, —O—W—OR$^{a5}$, —NR$^{a4}$—W—OR$^{a5}$, —NR$^{a4}$—W—SO$_2$NR$^{a5}$R$^{a12}$,
  wherein R$^{a4}$, R$^{a5}$, R$^{a6}$ and R$^{a12}$ are as defined in the above-mentioned (4), or
a C$_{1-10}$ alkyl group optionally substituted by 1 to 3 substituents selected from a halogen atom and the group B (the group B is as defined in the above-mentioned (4)),
or a pharmaceutically acceptable salt thereof.

(23) The quinolizinone compound of the above-mentioned (4), wherein
R$^1$ is a hydrogen atom, a cyano group, —NR$^{a4}$COR$^{a6}$, —NR$^{a4}$SO$_2$R$^{a6}$, —COOR$^{a4}$, —NR$^{a5}$COOR$^{a6}$, —O—W—OR$^{a5}$, —NR$^{a4}$—W—OR$^{a5}$, —NR$^{a4}$—W—SO$_2$NR$^{a5}$R$^{a12}$,
  wherein R$^{a4}$, R$^{a5}$, R$^{a6}$ and R$^{a12}$ are as defined in the above-mentioned (4), or
a C$_{1-10}$ alkyl group optionally substituted by 1 to 3 substituents selected from a halogen atom and the group B (the group B is as defined in the above-mentioned (4)),
or a pharmaceutically acceptable salt thereof.

(24) The quinolizinone compound of the above-mentioned (4), wherein R$^2$ is a hydrogen atom, or a pharmaceutically acceptable salt thereof.

(25) The quinolizinone compound of the above-mentioned (4), which is represented by the following formula [II-1] or [II-2],

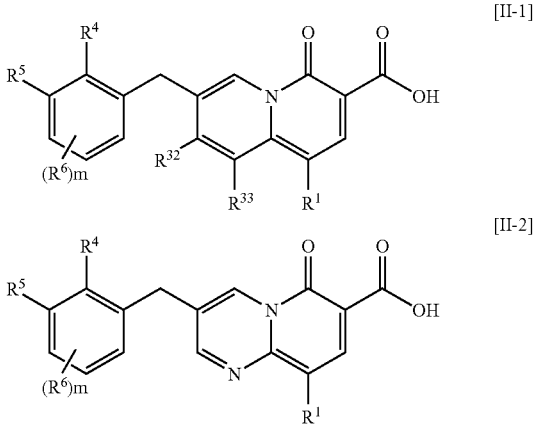

wherein R$^{32}$ and R$^{33}$ are the same or different and each is a hydrogen atom or —OR$^{a7}$ (R$^{a7}$ is as defined in the above-mentioned (4)), and the other symbols are as defined in the above-mentioned (4), or a pharmaceutically acceptable salt thereof.

(26) The quinolizinone compound of the above-mentioned (4), which is selected from the group consisting of
7-(3-chloro-2-fluorobenzyl)-4-oxo-4H-quinolizine-3-carboxylic acid (Example 2),
7-(3-chloro-2-fluorobenzyl)-1-ethyl-4-oxo-4H-quinolizine-3-carboxylic acid (Example 4),
7-(3-chloro-2-fluorobenzyl)-1-(2-hydroxyethyl)-4-oxo-4H-quinolizine-3-carboxylic acid (Example 7),
7-(3-chloro-2-fluorobenzyl)-1-((R)-1-hydroxymethyl-2-methylpropyl)-8-methoxy-4-oxo-4H-quinolizine-3-carboxylic acid (Example 10),
7-benzyl-4-oxo-4H-quinolizine-3-carboxylic acid (Example 11),
7-(3-chloro-2-fluorobenzyl)-4-oxo-1-propyl-4H-quinolizine-3-carboxylic acid (Example 12),
7-(3-chloro-2-fluorobenzyl)-1-isopropyl-4-oxo-4H-quinolizine-3-carboxylic acid (Example 13),
7-(3-chloro-2-fluorobenzyl)-1-((R)-2-hydroxy-1-methylethyl)-4-oxo-4H-quinolizine-3-carboxylic acid (Example 14),
7-(3-chloro-2-fluorobenzyl)-1-(1-hydroxymethyl-2-methylpropyl)-4-oxo-4H-quinolizine-3-carboxylic acid (Example 15),
7-(3-chloro-2-fluorobenzyl)-1-((R)-1-hydroxymethyl-2,2-dimethylpropyl)-4-oxo-4H-quinolizine-3-carboxylic acid (Example 16),
7-(3-chloro-2-fluorobenzyl)-1-((R)-1-hydroxymethyl-2,2-dimethylpropyl)-8-methoxy-4-oxo-4H-quinolizine-3-carboxylic acid (Example 17),
7-(3-chloro-2-fluorobenzyl)-1-hydroxymethyl-4-oxo-4H-quinolizine-3-carboxylic acid (Example 18),
7-(3-chloro-2-fluorobenzyl)-1-methoxymethyl-4-oxo-4H-quinolizine-3-carboxylic acid (Example 19),
1-aminomethyl-7-(3-chloro-2-fluorobenzyl)-4-oxo-4H-quinolizine-3-carboxylic acid hydrochloric acid (Example 20),
7-(3-chloro-2-fluorobenzyl)-1-methylaminomethyl-4-oxo-4H-quinolizine-3-carboxylic acid (Example 21),
1-(acetylaminomethyl)-7-(3-chloro-2-fluorobenzyl)-4-oxo-4H-quinolizine-3-carboxylic acid (Example 22),
7-(3-chloro-2-fluorobenzyl)-1-(methylsulfonylaminomethyl)-4-oxo-4H-quinolizine-3-carboxylic acid (Example 23),
7-(3-chloro-2-fluorobenzyl)-1-(methoxycarbonylaminomethyl)-4-oxo-4H-quinolizine-3-carboxylic acid (Example 24),
1-(aminocarbonyl)methyl-7-(3-chloro-2-fluorobenzyl)-4-oxo-4H-quinolizine-3-carboxylic acid (Example 26),
7-(3-chloro-2-fluorobenzyl)-1-(2-hydroxyethylamino)-4-oxo-4H-quinolizine-3-carboxylic acid (Example 27),
7-(3-chloro-2-fluorobenzyl)-1-methylsulfonylamino-4-oxo-4H-quinolizine-3-carboxylic acid (Example 29),
7-(3-chloro-2-fluorobenzyl)-1-cyano-4-oxo-4H-quinolizine-3-carboxylic acid (Example 33),
3-(3-chloro-2-fluorobenzyl)-9-(2-hydroxyethyl)-6-oxo-6H-pyrido[1,2-a]pyrimidine-7-carboxylic acid (Example 34),
1-(tert-butoxycarbonylaminomethyl)-7-(3-chloro-2-fluorobenzyl)-4-oxo-4H-quinolizine-3-carboxylic acid (Example 35),
1-carboxymethyl-7-(3-chloro-2-fluorobenzyl)-4-oxo-4H-quinolizine-3-carboxylic acid (Example 36),
7-(3-chloro-2-fluorobenzyl)-1-[(2,2-dimethylpropionylamino)methyl]-4-oxo-4H-quinolizine-3-carboxylic acid (Example 37),
7-(3-chloro-2-fluorobenzyl)-1-dimethylaminomethyl-4-oxo-4H-quinolizine-3-carboxylic acid (Example 38),
7-(3-chloro-2-fluorobenzyl)-1-[(2-hydroxyacetylamino)methyl]-4-oxo-4H-quinolizine-3-carboxylic acid (Example 39),
7-(3-chloro-2-fluorobenzyl)-1-[(2-methoxyacetylamino)methyl]-4-oxo-4H-quinolizine-3-carboxylic acid (Example 40),
1-[(N-(tert-butoxycarbonyl)-N-methylamino)methyl]-7-(3-chloro-2-fluorobenzyl)-4-oxo-4H-quinolizine-3-carboxylic acid (Example 41),
7-(3-chloro-2-fluorobenzyl)-4-oxo-1-(propionylaminomethyl)-4H-quinolizine-3-carboxylic acid (Example 42), 1-(butyrylaminomethyl)-7-(3-chloro-2-fluorobenzyl)-4-oxo-4H-quinolizine-3-carboxylic acid (Example 43),
7-(3-chloro-2-fluorobenzyl)-1-(isobutyrylaminomethyl)-4-oxo-4H-quinolizine-3-carboxylic acid (Example 44),
1-(benzoylaminomethyl)-7-(3-chloro-2-fluorobenzyl)-4-oxo-4H-quinolizine-3-carboxylic acid (Example 45),
7-(3-chloro-2-fluorobenzyl)-1-(ethoxycarbonylaminomethyl)-4-oxo-4H-quinolizine-3-carboxylic acid (Example 46),
7-(3-chloro-2-fluorobenzyl)-1-{[(morpholinocarbonyl)amino]methyl}-4-oxo-4H-quinolizine-3-carboxylic acid (Example 47),
7-(3-chloro-2-fluorobenzyl)-1-[(3-ethylureido)methyl]-4-oxo-4H-quinolizine-3-carboxylic acid (Example 48),
7-(3-chloro-2-fluorobenzyl)-4-oxo-1-(phenylacetylaminomethyl)-4H-quinolizine-3-carboxylic acid (Example 49),
7-(3-chloro-2-fluorobenzyl)-1-[(oxalylamino)methyl]-4-oxo-4H-quinolizine-3-carboxylic acid (Example 50),
7-(3-chloro-2-fluorobenzyl)-4-oxo-1-[(2-phenoxyacetylamino)methyl]-4H-quinolizine-3-carboxylic acid (Example 51),
7-(3-chloro-2-fluorobenzyl)-1-[((S)-2-methoxypropionylamino)methyl]-4-oxo-4H-quinolizine-3-carboxylic acid (Example 52),
7-(3-chloro-2-fluorobenzyl)-1-[((R)-2-methoxypropionylamino)methyl]-4-oxo-4H-quinolizine-3-carboxylic acid (Example 53),
1-[(3-carboxypropionylamino)methyl]-7-(3-chloro-2-fluorobenzyl)-4-oxo-4H-quinolizine-3-carboxylic acid (Example 54),
7-(3-chloro-2-fluorobenzyl)-1-[(2-ethoxyacetylamino)methyl]-4-oxo-4H-quinolizine-3-carboxylic acid (Example 55),
7-(3-chloro-2-fluorobenzyl)-1-[(2-methoxy-2-methylpropionylamino)methyl]-4-oxo-4H-quinolizine-3-carboxylic acid (Example 56),
1-[(2-acetylaminoacetylamino)methyl]-7-(3-chloro-2-fluorobenzyl)-4-oxo-4H-quinolizine-3-carboxylic acid (Example 57),
7-(3-chloro-2-fluorobenzyl)-1-methoxymethoxy-4-oxo-4H-quinolizine-3-carboxylic acid (Example 58),
1-(tert-butoxycarbonylamino)-7-(3-chloro-2-fluorobenzyl)-4-oxo-4H-quinolizine-3-carboxylic acid (Example 59),
1-acetylamino-7-(3-chloro-2-fluorobenzyl)-4-oxo-4H-quinolizine-3-carboxylic acid (Example 61),
7-(3-chloro-2-fluorobenzyl)-4-oxo-4H-quinolizine-1,3-dicarboxylic acid 1-tert-butyl ester (Example 62),
7-(2,3-dichlorobenzyl)-1-((R)-1-hydroxymethyl-2-methylpropyl)-4-oxo-4H-quinolizine-3-carboxylic acid (Example 63),
7-(2,3-dichlorobenzyl)-1-((R)-1-hydroxymethyl-2,2-dimethylpropyl)-4-oxo-4H-quinolizine-3-carboxylic acid (Example 64), and
7-(3-chloro-2-fluorobenzyl)-1-((R)-1-hydroxymethyl-2,2-dimethylpropyl)-9-methoxy-4-oxo-4H-quinolizine-3-carboxylic acid (Example 65),
or a pharmaceutically acceptable salt thereof.

(27) A pharmaceutical composition comprising a quinolizinone compound of any of the above-mentioned (4) to (26) or a pharmaceutically acceptable salt thereof, and a pharmaceutically acceptable carrier.

(28) An integrase inhibitor comprising a quinolizinone compound of any of the above-mentioned (1) to (26) or a pharmaceutically acceptable salt thereof, as an active ingredient.

(29) An antiviral agent comprising a quinolizinone compound of any of the above-mentioned (4) to (26) or a pharmaceutically acceptable salt thereof, as an active ingredient.

(30) An anti-HIV agent comprising a quinolizinone compound of any of the above-mentioned (4) to (26) or a pharmaceutically acceptable salt thereof, as an active ingredient.

(31) An anti-HIV composition comprising, as active ingredients, a quinolizinone compound of any of the above-mentioned (1) to (26) or a pharmaceutically acceptable salt thereof, and one or more other kinds of anti-HIV active substances.

(32) An anti-HIV agent comprising a quinolizinone compound of any of the above-mentioned (1) to (26) or a pharmaceutically acceptable salt thereof, as an active ingredient, for multiple drug combination therapy with other anti-HIV agent(s).

(33) Use of a quinolizinone compound of any of the above-mentioned (4) to (26) or a pharmaceutically acceptable salt thereof, for the production of an anti-HIV agent.

(34) Use of a quinolizinone compound of any of the above-mentioned (1) to (26) or a pharmaceutically acceptable salt thereof, for the production of an integrase inhibitor.

(35) Use of a quinolizinone compound of any of the above-mentioned (4) to (26) or a pharmaceutically acceptable salt thereof, for the production of an antiviral agent.

(36) A method for the prophylaxis or treatment of an HIV infectious disease in a mammal, which comprises administering an effective amount of a quinolizinone compound of any of the above-mentioned (4) to (26) or a pharmaceutically acceptable salt thereof to said mammal.

(37) The method for the prophylaxis or treatment of an HIV infectious disease according to the above-mentioned (36), which further comprises administering an effective amount of one or more other kinds of anti-HIV active substances to said mammal.

(38) A method for inhibiting integrase in a mammal, which comprises administering an effective amount of a quinolizinone compound of any of the above-mentioned (1) to (26) or a pharmaceutically acceptable salt thereof to said mammal.

(39) A method for the prophylaxis or treatment of a virus infectious disease in a mammal, which comprises administering an effective amount of a quinolizinone compound of any of the above-mentioned (4) to (26) or a pharmaceutically acceptable salt thereof to said mammal.

(40) An anti-HIV composition comprising a quinolizinone compound of any of the above-mentioned (4) to (26) or a pharmaceutically acceptable salt thereof, and a pharmaceutically acceptable carrier.

(41) A composition for inhibiting integrase, which comprises a quinolizinone compound of any of the above-mentioned (1) to (26) or a pharmaceutically acceptable salt thereof, and a pharmaceutically acceptable carrier.

(42) An antiviral composition comprising a quinolizinone compound of any of the above-mentioned (4) to (26) or a pharmaceutically acceptable salt thereof, and a pharmaceutically acceptable carrier.

(43) A commercial package comprising the composition of the above-mentioned (40) and a written matter associated therewith, the written matter stating that the composition can or should be used for the prophylaxis or treatment of an HIV infectious disease.

(44) A commercial package comprising the composition of the above-mentioned (41) and a written matter associated therewith, the written matter stating that the composition can or should be used for inhibiting integrase.

(45) A commercial package comprising the composition of the above-mentioned (42) and a written matter associated therewith, the written matter stating that the composition can or should be used for the prophylaxis or treatment of a viral infectious disease.

(46) An anti-HIV agent comprising a quinolizinone compound of any of the above-mentioned (1) to (26) or a pharmaceutically acceptable salt thereof, and other antiviral agent, in combination.

The compounds of the present invention can be effective pharmaceutical agents for the prophylaxis or therapy of AIDS, as anti-HIV agents having HIV integrase inhibitory activity. Moreover, by a combined use with other anti-HIV agents such as protease inhibitors, reverse transcriptase inhibitors and the like, the compounds can become more effective anti-HIV agents. Since the compounds have high inhibitory activity specific for integrases, they can provide safe pharmaceutical agents for human with a fewer side effects.

BEST MODE FOR CARRYING OUT THE INVENTION

The definitions of each substituent and each moiety used in the present specification are as follows.

The "halogen atom" is fluorine atom, chlorine atom, bromine atom or iodine atom, preferably fluorine atom, chlorine atom or bromine atom.

For $R^{31}$, $R^{32}$, $R^{33}$, $R^4$, $R^5$, $R^6$, $R^{6'}$, $R^{6''}$, $R^{6'''}$ ($R^{6'}$, $R^{6''}$ and $R^{6'''}$ to be mentioned later) or group A, fluorine atom and chlorine atom are particularly preferable, for $R^{32}$ or $R^5$, chlorine atom is more preferable, and for $R^{31}$, $R^{33}$, $R^4$, $R^6$, $R^{6'}$, $R^{6''}$, $R^{6'''}$ or the halogen atom of the "$C_{1-10}$ alkyl group optionally substituted by 1 to 3 substituents selected from halogen atom and group B", fluorine atom is more preferable.

The "$C_{1-4}$ alkyl group" is a straight chain or branched chain alkyl group having 1 to 4 carbon atoms, and specific examples thereof include methyl group, ethyl group, propyl group, isopropyl group, butyl group, isobutyl group, sec-butyl group and tert-butyl group.

For $R^2$, $R^{31}$ or $R^{a6}$, methyl group, ethyl group, propyl group, isopropyl group and tert-butyl group are preferable, for $R^4$, $R^5$, $R^6$, $R^{6'}$, $R^{6''}$, $R^{6'''}$ or group A, methyl group, ethyl group and isopropyl group are preferable, methyl group is more preferable, for $R^{a1}$ or $R^{a2}$, methyl group, ethyl group, propyl group and isopropyl group are preferable, methyl group is more preferable, for $R^{a3}$, $R^{a9}$, $R^{a10}$ or $R^{a11}$, methyl group is preferable, and for $R^{a4}$, $R^{a5}$ or $R^{a12}$, methyl group, ethyl group and tert-butyl group are preferable.

The "halo $C_{1-4}$ alkyl group" is a "$C_{1-4}$ alkyl group" defined above, which is substituted by 1 to 9, preferably 1 to 3, "halogen atom" defined above.

Specific examples thereof include 2-fluoroethyl group, 2-chloroethyl group, 2-bromoethyl group, 3-fluoropropyl group, 3-chloropropyl group, 4-fluorobutyl group, 4-chlorobutyl group, trifluoromethyl group, 2,2,2-trifluoroethyl group, 3,3,3-trifluoropropyl group, 4,4,4-trifluorobutyl group, pentafluoroethyl group, 2,2,2-trifluoro-1-trifluoromethyl-ethyl group and the like.

For $R^{31}$, $R^4$, $R^5$, $R^6$, $R^{6'}$, $R^{6''}$, $R^{6'''}$ or group A, trifluoromethyl group is preferable.

The "$C_{1-4}$ alkoxy group" is an alkyloxy group wherein its alkyl moiety is "$C_{1-4}$ alkyl group" defined above, and specific examples thereof include methoxy group, ethoxy group, propoxy group, isopropoxy group, butoxy group, isobutoxy group, tert-butoxy group and the like.

For $R^{31}$, methoxy group is preferable.

The "$C_{1-4}$ alkylsulfanyl group" is an alkylsulfanyl group wherein its alkyl moiety is "$C_{1-4}$ alkyl group" defined above. Specific examples thereof include methylsulfanyl group, ethylsulfanyl group, propylsulfanyl group, isopropylsulfanyl group, butylsulfanyl group, isobutylsulfanyl group, tert-butylsulfanyl group and the like.

For $R^{31}$, methylsulfanyl group is preferable.

The "halo $C_{1-4}$ alkyloxy group" is a halo $C_{1-4}$ alkyloxy group wherein its haloalkyl moiety is "halo $C_{1-4}$ alkyl group" defined above.

Specific examples thereof include 2-fluoroethyloxy group, 2-chloroethyloxy group, 2-bromoethyloxy group, 3-fluoropropyloxy group, 3-chloropropyloxy group, 4-fluorobutyloxy group, 4-chlorobutyloxy group, trifluoromethyloxy group, 2,2,2-trifluoroethyloxy group, 3,3,3-trifluoropropyloxy group, 4,4,4-trifluorobutyloxy group, pentafluoroethyloxy group, 2,2,2-trifluoro-1-trifluoromethyl-ethyloxy group and the like.

For $R^{31}$, $R^4$, $R^5$, $R^6$, $R^{6'}$, $R^{6''}$, $R^{6'''}$ or group A, trifluoromethyloxy group is preferable.

The "$C_{3-10}$ carbon ring group" means a saturated or unsaturated cyclic hydrocarbon group having 3 to 10 carbon atoms, and specific examples thereof include an aryl group, a cycloalkyl group, a cycloalkenyl group and a fused ring thereof.

Specific examples of the "aryl group" include phenyl group, naphthyl group, pentalenyl group, azulenyl group and the like, preferably phenyl group and naphthyl group, particularly preferably phenyl group.

Specific examples of the "cycloalkyl group" include cyclopropyl group, cyclobutyl group, cyclopentyl group, cyclohexyl group, cycloheptyl group, cyclooctyl group, adamantyl group, norbornanyl group and the like, preferably cyclopropyl group, cyclobutyl group, cyclopentyl group and cyclohexyl group.

The "cycloalkenyl group" contains at least one, preferably 1 or 2 double bonds, and specific examples thereof include cyclopropenyl group, cyclobutenyl group, cyclopentenyl group, cyclopentadienyl group, cyclohexenyl group, cyclohexadienyl group (2,4-cyclohexadien-1-yl group, 2,5-cyclohexadien-1-yl group and the like), cycloheptenyl group, cyclooctenyl group and the like.

Specific examples of the fused ring of these "aryl group", "cycloalkyl group" or "cycloalkenyl group" include indenyl group, indanyl group, 1,4-dihydronaphthyl group, 1,2,3,4-tetrahydronaphthyl group (1,2,3,4-tetrahydro-2-naphthyl group, 5,6,7,8-tetrahydro-2-naphthyl group and the like), perhydronaphthyl group and the like. Preferably, it is a fused ring of a phenyl group and a different ring, and specific examples thereof include indenyl group, indanyl group, 1,4-dihydronaphthyl group, 1,2,3,4-tetrahydronaphthyl group and the like, and indanyl group is particularly preferable.

The "$C_{3-10}$ carbon ring group optionally substituted by 1 to 5 substituents selected from group A" is a "$C_{3-10}$ carbon ring group" defined above, which is optionally substituted by 1 to 5, preferably 1 to 3, substituents selected from the following group A, and includes a non-substituted "$C_{3-10}$ carbon ring group".

The "group A" is a group constituting of a cyano group, a phenyl group, a nitro group, a "halogen atom" defined above, a "$C_{1-4}$ alkyl group" defined above, a "halo $C_{1-4}$ alkyl group" defined above, a "halo $C_{1-4}$ alkyloxy group" defined above, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$, wherein $R^{a1}$ and $R^{a2}$ are the same or different and each is a hydrogen atom, a "$C_{1-4}$ alkyl group" defined above or a benzyl group, and $R^{a3}$ is a "$C_{1-4}$ alkyl group" defined above.

Specific examples of "—$OR^{a1}$" include hydroxy group, methoxy group, ethoxy group, propoxy group, isopropoxy group, tert-butoxy group and the like.

Specific examples of "—$SR^{a1}$" include mercapto group, methylsulfanyl group, ethylsulfanyl group, propylsulfanyl group, isopropylsulfanyl group, tert-butylsulfanyl group and the like.

Specific examples of "—$NR^{a1}R^{a2}$" include amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group, N-benzyl-N-methylamino group and the like.

Specific examples of "—$CONR^{a1}R^{a2}$" include carbamoyl group, methylcarbamoyl group, ethylcarbamoyl group, propylcarbamoyl group, isopropylcarbamoyl group, tert-butylcarbamoyl group, dimethylcarbamoyl group, diethylcarbamoyl group, N-methyl-N-ethylcarbamoyl group and the like.

Specific examples of "—$SO_2NR^{a1}R^{a2}$" include sulfamoyl group, methylsulfamoyl group, ethylsulfamoyl group, propylsulfamoyl group, isopropylsulfamoyl group, tert-butylsulfamoyl group, dimethylsulfamoyl group, diethylsulfamoyl group, N-methyl-N-ethylsulfamoyl group and the like.

Specific examples of "—$COR^{a3}$" include acetyl group, propionyl group, butyryl group, isobutyryl group, 2,2-dimethylpropionyl group and the like.

Specific examples of "—$NR^{a1}COR^{a3}$" include acetylamino group, propionylamino group, butyrylamino group, isobutyrylamino group, 2,2-dimethylpropionylamino group, N-acetyl-N-methylamino group and the like.

Specific examples of "—$SO_2R^{a3}$" include methylsulfonyl group, ethylsulfonyl group, propylsulfonyl group, isopropylsulfonyl group, tert-butylsulfonyl group and the like.

Specific examples of "—$NR^{a1}SO_2R^{a3}$" include methylsulfonylamino group, ethylsulfonylamino group, propylsulfonylamino group, isopropylsulfonylamino group, tert-butylsulfonylamino group, N-methyl-N-(methylsulfonyl)amino group and the like.

Specific examples of "—$COOR^{a1}$" include carboxyl group, methoxycarbonyl group, ethoxycarbonyl group, propoxycarbonyl group, isopropoxycarbonyl group, tert-butoxycarbonyl group and the like.

Specific examples of "—$NR^{a2}COOR^{a3}$" include methoxycarbonylamino group, ethoxycarbonylamino group, propoxycarbonylamino group, isopropoxycarbonylamino group, tert-butoxycarbonylamino group and the like.

For group A, cyano group, phenyl group, nitro group, fluorine atom, chlorine atom, bromine atom, methyl group, ethyl group, isopropyl group, trifluoromethyl group, trifluoromethyloxy group, hydroxy group, methoxy group, ethoxy group, propoxy group, methylsulfanyl group, amino group, methylamino group, ethylamino group, isopropylamino group, dimethylamino group, diethylamino group, N-ethyl-N-methylamino group, N-methyl-N-propylamino group, N-isopropyl-N-methylamino group, N-benzyl-N-methylamino group, carbamoyl group, methylcarbamoyl group, dimethylcarbamoyl group, sulfamoyl group, methylsulfamoyl group, dimethylsulfamoyl group, acetyl group, acetylamino group, N-acetyl-N-methylamino group, methylsulfonyl group, methylsulfonylamino group, N-methyl-N-(methylsulfonyl)amino group, carboxyl group, methoxycarbonyl group, carboxyamino group and methoxycarbonylamino group are preferable.

For group A, cyano group, phenyl group, nitro group, fluorine atom, chlorine atom, bromine atom, methyl group, trifluoromethyl group, trifluoromethyloxy group, hydroxy group, methoxy group, ethoxy group, methylsulfanyl group, amino group, methylamino group, dimethylamino group, diethylamino group, N-ethyl-N-methylamino group, N-methyl-N-propylamino group, N-isopropyl-N-methylamino group, N-benzyl-N-methylamino group, dimethylcarbamoyl group, methylsulfamoyl group, dimethylsulfamoyl group, acetylamino group, N-acetyl-N-methylamino group, methylsulfonyl group, N-methyl-N-(methylsulfonyl)amino group and carboxyl group are particularly preferable, and fluorine atom and chlorine atom are more preferable.

The number of substituents is preferably 1 to 3, and when "$C_{3-10}$ carbon ring group" is phenyl group, ring Cy is preferably monosubstituted at the 2-position, monosubstituted at the 3-position, disubstituted at the 2,3-positions, disubstituted at the 2,4-positions, disubstituted at the 2,5-positions, disubstituted at the 2,6-positions, trisubstituted at the 2,3,4-positions, trisubstituted at the 2,3,5-positions, or trisubstituted at the 2,3,6-positions, particularly preferably disubstituted at the 2,3-positions.

Specific examples of the "$C_{3-10}$ carbon ring group optionally substituted by 1 to 5 substituents selected from group A" include phenyl group, naphthyl group, 2-fluorophenyl group, 2-chlorophenyl group, 2-bromophenyl group, 3-fluorophenyl group, 3-chlorophenyl group, 3-bromophenyl group, 4-fluorophenyl group, 2-nitrophenyl group, 3-nitrophenyl group, 2-cyanophenyl group, 3-cyanophenyl group, 2-methylphenyl group, 3-methylphenyl group, 4-methylphenyl group, 2-ethylphenyl group, 3-ethylphenyl group, 2-isopropylphenyl group, 3-isopropylphenyl group, 2-trifluoromethylphenyl group, 3-trifluoromethylphenyl group, 2-hydroxyphenyl group, 3-hydroxyphenyl group, 4-hydroxyphenyl group, 2-methoxyphenyl group, 3-methoxyphenyl group, 2-ethoxyphenyl group, 3-ethoxyphenyl group, 2-propoxyphenyl group, 3-propoxyphenyl group, 2-(trifluoromethyloxy)phenyl group, 3-(trifluoromethyloxy)phenyl group, 2-(methylsulfanyl)phenyl group, 3-(methylsulfanyl)phenyl group, 2-aminophenyl group, 3-aminophenyl group, 2-(methylamino)phenyl group, 3-(methylamino)phenyl group, 2-(dimethylamino)phenyl group, 3-(dimethylamino)phenyl group, 2-(diethylamino)phenyl group, 2-(N-ethyl-N-methylamino)phenyl group, 2-(N-isopropyl-N-methylamino)phenyl group, 2-(N-benzyl-N-methylamino)phenyl group, 2-(N-acetyl-N-methylamino)phenyl group, 2-carboxyphenyl group, 2-(acetylamino)phenyl group, 3-(acetylamino)phenyl group, 2-biphenyl group, 3-biphenyl group, 2-(methylsulfonyl)phenyl group, 3-(methylsulfonyl)phenyl group, 2-(sulfamoyl)phenyl group, 3-(sulfamoyl)phenyl group, 2-(methylsulfamoyl)phenyl group, 3-(methylsulfamoyl)phenyl group, 2-(dimethylsulfamoyl)phenyl group, 3-(dimethylsulfamoyl)phenyl group, 2-(methylsulfonylamino)phenyl group, 3-(methylsulfonylamino)phenyl group, 2-(N-methyl-N-methylsulfonyl)phenyl group, 2-(carbamoyl)phenyl group, 3-(carbamoyl)phenyl group, 2-(methylcarbamoyl)phenyl group, 3-(methylcarbamoyl) phenyl group, 2-(dimethylcarbamoyl)phenyl group, 3-(dimethylcarbamoyl)phenyl group, 2,3-difluorophenyl group, 2,3-dichlorophenyl group, 3,4-dichlorophenyl group, 2,3-dibromophenyl group, 2,4-difluorophenyl group, 2,4-dichlorophenyl group, 2,5-dichlorophenyl group, 2,6-dichlorophenyl group, 2-chloro-3-fluorophenyl group, 2-chloro-4-fluorophenyl group, 2-chloro-5-fluorophenyl group, 2-chloro-6-fluorophenyl group, 3-chloro-2-fluorophenyl group, 5-chloro-2-fluorophenyl group, 5-bromo-2-chlorophenyl group, 2-chloro-5-nitrophenyl group, 2-chloro-3-methylphenyl group, 2-chloro-5-methylphenyl group, 3-chloro-2-methylphenyl group, 2-chloro-3-(trifluoromethyl)phenyl group, 2-chloro-5-(trifluoromethyl)phenyl group, 2-chloro-3-hydroxyphenyl group, 2-chloro-5-hydroxyphenyl group, 2-chloro-3-methoxyphenyl group, 2-chloro-5-methoxyphenyl group, 3-chloro-2-methoxyphenyl group, 2-chloro-3-(methylsulfamoyl)phenyl group, 2-chloro-5-(methylsulfamoyl)phenyl group, 2-chloro-3-aminophenyl group, 2-chloro-5-aminophenyl group, 2-chloro-3-(methylamino) phenyl group, 2-chloro-5-(methylamino)phenyl group, 2-chloro-3-(dimethylamino)phenyl group, 2-chloro-5-(dimethylamino)phenyl group, 2-chloro-3-(acetylamino)phenyl group, 2-chloro-5-(acetylamino)phenyl group, 2-chloro-3-(methylsulfonyl) phenyl group, 2-chloro-5-(methylsulfonyl)phenyl group, 2-chloro-3-(methylsulfonylamino)phenyl group, 2-chloro-5-(methylsulfonylamino)phenyl group, 2-chloro-5-methylsulfanylphenyl group, 2,3,4-trifluorophenyl group, 2-chloro-3,4-difluorophenyl group, 2-chloro-3,5-difluorophenyl group, 2-chloro-3,6-difluorophenyl group, 2-chloro-4,5-difluorophenyl group, 2-chloro-4,6-difluorophenyl group, 3-chloro-2,4-difluorophenyl group, 3-chloro-2,5-difluorophenyl group, 3-chloro-2,6-difluorophenyl group, 2,3-dichloro-4-fluorophenyl group, 3-chloro-2-fluoro-5-trifluoromethylphenyl group, 2-chloro-3,5,6-trifluorophenyl group, 3-chloro-2,4,5-trifluorophenyl group, 3-chloro-2,4,6-trifluorophenyl group, 2,3-dichloro-4,5,6-trifluorophenyl group, 3,5-dichloro-3,4,6-trifluorophenyl group, 2,6-dichloro-3,4,5-trifluorophenyl group, perfluorophenyl group, cyclopropyl group, cyclobutyl group, cyclopentyl group, cyclohexyl group, 2-hydroxycyclopropyl group, 2-hydroxycyclobutyl group, 3-hydroxycyclobutyl group, 2-hydroxycyclopentyl group, 3-hydroxycyclopentyl group, 2-hydroxycyclohexyl group, 3-hydroxycyclohexyl group, 4-hydroxycyclohexyl group, 4-indanyl group, 1H-inden-4-yl group and the like.

For ring Cy, phenyl group, naphthyl group, 2-chlorophenyl group, 3-chlorophenyl group, 2-bromophenyl group, 3-bromophenyl group, 2-ethylphenyl group, 3-ethylphenyl group, 2-hydroxyphenyl group, 2-ethoxyphenyl group, 3-(trifluoromethyloxy)phenyl group, 3-(methylsulfonyl)phenyl group, 2,3-difluorophenyl group, 2,3-dichlorophenyl group, 2-chloro-3-fluorophenyl group, 2-chloro-4-fluorophenyl group, 2-chloro-5-fluorophenyl group, 2-chloro-6-fluorophenyl group, 3-chloro-2-fluorophenyl group, 5-bromo-2-chlorophenyl group, 2-chloro-5-methylphenyl group, 2-chloro-5-hydroxyphenyl group, 2-chloro-5-(methylsulfonyl)phenyl group, 2-chloro-3,6-difluorophenyl group, 3-chloro-2,4-difluorophenyl group, 3-chloro-2,6-difluorophenyl group, 2-chloro-3-methylphenyl group, 3-chloro-2-methylphenyl group, 2-chloro-3-methoxyphenyl group, 3-chloro-2-methoxyphenyl group, 3-nitrophenyl group, 3-cyanophenyl group, 4-methylphenyl group, 2-trifluoromethylphenyl group, 3-trifluoromethylphenyl group, 2-(trifluoromethyloxy)phenyl group, 3-hydroxyphenyl group, 3-ethoxyphenyl group, 3-aminophenyl group, 2-(methylamino)phenyl group, 2-(dimethylamino)phenyl group, 2-(diethylamino)phenyl group, 2-(N-ethyl-N-methylamino)phenyl group, 2-(N-isopropyl-N-methylamino)phenyl group, 2-(N-benzyl-N-methylamino)phenyl group, 2-(N-acetyl-N-methylamino)phenyl group, 2-(N-methyl-N-methylsulfonylamino)phenyl group, 3-(methylamino)phenyl group, 2-carboxyphenyl group, 3-(dimethylcarbamoyl)phenyl group, 2-(acetylamino)phenyl group, 2-biphenyl group, 2-(methylsulfonyl)phenyl group, 2-chloro-5-methylsulfanylphenyl group, 2-chloro-5-methylphenyl group, 2-(methylsulfamoyl)phenyl group, 2-(dimethylsulfamoyl)phenyl group and 3-(dimethylaminosulfonyl)phenyl group are preferable.

For ring Cy, phenyl group, 2-chlorophenyl group, 2-bromophenyl group, 2-ethylphenyl group, 2-hydroxyphenyl group, 2-ethoxyphenyl group, 2,3-difluorophenyl group, 2,3-dichlorophenyl group, 2-chloro-3-fluorophenyl group, 3-chloro-2-fluorophenyl group, 2-chloro-4-fluorophenyl group, 2-chloro-5-fluorophenyl group, 2-chloro-6-fluorophenyl group, 5-bromo-2-chlorophenyl group, 2-chloro-5-hydroxyphenyl group, 2-chloro-5-(methylsulfonyl)phenyl group, 2-chloro-3,6-difluorophenyl group, 3-chloro-2,6-difluorophenyl group, 2-chloro-3-methylphenyl group, 2-chloro-3-methoxyphenyl group, 2-trifluoromethylphenyl group, 2-(methylsulfonyl)phenyl group, 2-chloro-5-methylsulfanylphenyl group, 2-chloro-5-methylphenyl group and 2-(dimethylaminosulfonyl)phenyl group are more preferable.

For ring Cy, phenyl group, 2,3-dichlorophenyl group, 2,3-difluorophenyl group, 2-chloro-3-fluorophenyl group and 3-chloro-2-fluorophenyl group are particularly preferable.

For $R^1$ or group B, phenyl group, 3,4-dichlorophenyl group, 2-biphenyl group, cyclopropyl group, 2-hydroxycyclopropyl group, cyclobutyl group, 2-hydroxycyclobutyl group, 3-hydroxycyclobutyl group, cyclopentyl group, 2-hydroxycyclopentyl group, 3-hydroxycyclopentyl group, cyclohexyl group, 2-hydroxycyclohexyl group, 3-hydroxycyclohexyl group and 4-hydroxycyclohexyl group are preferable, and phenyl group, 3,4-dichlorophenyl group, 2-biphenyl group, cyclopropyl group, cyclobutyl group, cyclopentyl group and cyclohexyl group are particularly preferable.

For $R^{a4}$, $R^{a5}$ or $R^{a12}$, phenyl group is preferable, and for $R^{a6}$, phenyl group is preferable.

For $R^{32}$ or $R^{33}$, phenyl group and cyclohexyl group are preferable.

The "heterocyclic group" means a saturated or unsaturated (inclusive of partially unsaturated and completely unsaturated ones) monocyclic 5- or 6-membered heterocyclic group containing, besides carbon atom(s), at least one, preferably 1 to 4, hetero atoms selected from a nitrogen atom, an oxygen atom and a sulfur atom, a fused ring of these heterocycles, or a fused ring of $C_{3-10}$ carbon ring and these heterocycle, wherein the carbon ring is selected from benzene, cyclopentane and cyclohexane.

Examples of the "saturated monocyclic heterocyclic group" include pyrrolidinyl group, tetrahydrofuryl group, tetrahydrothienyl group, imidazolidinyl group, pyrazolidinyl group, 1,3-dioxolanyl group, 1,3-oxathiolanyl group, oxazolidinyl group, thiazolidinyl group, piperidinyl group, piperazinyl group, tetrahydropyranyl group, tetrahydrothiopyranyl group, dioxanyl group, morpholinyl group, thiomorpholinyl group, 2-oxopyrrolidinyl group, 2-oxopiperidinyl group, 4-oxopiperidinyl group, 2,6-dioxopiperidinyl group and the like. Preferably, it is pyrrolidinyl group, piperidinyl group, morpholinyl group or tetrahydropyranyl group.

Examples of the "unsaturated monocyclic heterocyclic group" include pyrrolyl group, furyl group, thienyl group, imidazolyl group, 1,2-dihydro-2-oxoimidazolyl group, pyrazolyl group, oxazolyl group, isoxazolyl group, thiazolyl group, isothiazolyl group, 1,2,4-triazolyl group, 1,2,3-triazolyl group, tetrazolyl group, 1,3,4-oxadiazolyl group, 1,2,4-oxadiazolyl group, 1,3,4-thiadiazolyl group, 1,2,4-thiadiazolyl group, furazanyl group, pyridyl group, pyrimidinyl group, 3,4-dihydro-4-oxopyrimidinyl group, pyridazinyl group, pyrazinyl group, 1,3,5-triazinyl group, imidazolinyl group, pyrazolinyl group, oxazolinyl group (2-oxazolinyl group, 3-oxazolinyl group, 4-oxazolinyl group), isoxazolinyl group, thiazolinyl group, isothiazolinyl group, pyranyl group, 2-oxopyranyl group, 2-oxo-2,5-dihydrofuranyl group and 1,1-dioxo-1H-isothiazolyl group. Preferable examples include pyrrolyl group, furyl group, thienyl group, imidazolyl group, pyrazolyl group, oxazolyl group, isoxazolyl group, thiazolyl group, isothiazolyl group, pyridyl group, 2-oxo-2,5-dihydrofuranyl group and 1,1-dioxo-1H-isothiazolyl group.

Examples of the "heterocyclic group, which is a fused ring" include indolyl group (e.g., 2-indolyl group, 3-indolyl group, 4-indolyl group, 7-indolyl group and the like), isoindolyl group, 1,3-dihydro-1,3-dioxoisoindolyl group, benzofuranyl group (e.g., 2-benzofuranyl group, 4-benzofuranyl group, 7-benzofuranyl group and the like), indazolyl group, isobenzofuranyl group, benzothiophenyl group (e.g., 2-benzothiophenyl group, 4-benzothiophenyl group, 7-benzothiophenyl group and the like), benzoxazolyl group (e.g., 2-benzoxazolyl group, 4-benzoxazolyl group, 7-benzoxazolyl group and the like), benzimidazolyl group (e.g., 2-benzimidazolyl group, 4-benzimidazolyl group, 7-benzimidazolyl group and the like), benzothiazolyl group (e.g., 2-benzothiazolyl group, 4-benzothiazolyl group, 7-benzothiazolyl group and the like), indolizinyl group, quinolyl group, isoquinolyl group, 1,2-dihydro-2-oxoquinolyl group, quinazolinyl group, quinoxalinyl group, cinnolinyl group, phthalazinyl group, quinolizinyl group, puryl group, pteridinyl group, indolinyl group, isoindolinyl group, 5,6,7,8-tetrahydroquinolyl group, 1,2,3,4-tetrahydroquinolyl group, 2-oxo-1,2,3,4-tetrahydroquinolyl group, benzo[1,3]dioxolyl group, 3,4-methylenedioxypyridyl group, 4,5-ethylenedioxypyrimidinyl group, chromenyl group, chromanyl group, isochromanyl group and the like. It is preferably a fused ring of monocyclic 5- or 6-membered heterocycle and benzene ring. Specific examples thereof include indolyl group, benzofuranyl group, benzothiophenyl group, benzimidazolyl group, benzoxazolyl group, benzothiazolyl group, benzo[1,3]dioxolyl group and the like.

The "heterocyclic group optionally substituted by 1 to 5 substituents selected from group A" is a "heterocyclic group" defined above, which is optionally substituted by 1 to 5, preferably 1 to 3, substituents selected from the "group A" defined above and includes a non-substituted "heterocyclic group".

The "heterocyclic group" is preferably a monocyclic heterocyclic group containing 1 or 2 hetero atoms, or a heterocyclic group which is a fused ring thereof with a benzene ring.

Specific examples of "heterocyclic group optionally substituted by 1 to 5 substituents selected from group A" include 1-pyrrolidinyl group, 2-pyrrolidinyl group, 3-pyrrolidinyl group, 1-piperidinyl group, 2-piperidinyl group, 3-piperidinyl group, 4-piperidinyl group, morpholino group, 1-pyrrolyl group, 2-pyrrolyl group, 3-pyrrolyl group, 2-furyl group, 3-furyl group, 2-thienyl group, 3-thienyl group, 4,5-dichlorothiophen-3-yl group, 2-oxo-2,5-dihydrofuran-3-yl group, 1,1-dioxo-1H-isothiazol-5-yl group, 4-methylthiazol-5-yl group, 1-imidazolyl group, 2-imidazolyl group, 3-imidazolyl group, 4-imidazolyl group, 1-pyrazolyl group, 3-pyrazolyl group, 4-pyrazolyl group, 2-oxazolyl group, 3-isoxazolyl group, 2-thiazolyl group, 3-isothiazolyl group, 3-fluoropyridin-2-yl group, 3-chloropyridin-2-yl group, 3-chloro-4-fluoropyridin-2-yl group, 3,5-dichloropyridin-2-yl group, 3-pyridyl group, 2-fluoropyridin-3-yl group, 2-chloropyridin-3-yl group, 2-chloro-4-fluoropyridin-3-yl group, 2-chloro-5-fluoropyridin-3-yl group, 2,5-dichloropyridin-3-yl group, 2-chloro-6-fluoropyridin-3-yl group, 2,6-dichloropyridin-3-yl group, 4-pyridyl group, 2-fluoropyridin-4-yl group, 2-chloropyridin-4-yl group, 2-chloro-3-fluoropyridin-4-yl group, 2,3-difluoropyridin-4-yl group, 2,3-dichloropyridin-4-yl group, 2,5-dichloropyridin-4-yl group, 2-chloro-6-fluoropyridin-4-yl group, 2,6-dichloropyridin-4-yl group, 2-chloro-3,6-difluoropyridin-4-yl group, 2-chloro-3,5-difluoropyridin-4-yl group, 2,3,6-trifluoropyridin-4-yl group, 2,3,5,6-tetrafluoropyridin-4-yl group, 2-indolyl group, 3-indolyl group, 4-indolyl group, 7-indolyl group, 2-benzofuranyl group, 4-benzofuranyl group, 7-benzofuranyl group, 2-benzothiophenyl group, 4-benzothiophenyl group, 7-benzothiophenyl group, 2-benzimidazolyl group, 4-benzimidazolyl group, 2-benzoxazolyl group, 4-benzoxazolyl group, 7-benzoxazolyl group, 2-benzothiazolyl group, 4-benzothiazolyl group, 7-benzothiazolyl group, 2-benzo[1,3]dioxolyl group, 4-benzo[1,3]dioxolyl group, 5-benzo[1,3]dioxolyl group, 2-pyridyl group, tetrahydropyran-2-yl group and the like.

For ring Cy, 2-pyridyl group and 4-pyridyl group are preferable.

For $R^1$ or group B, 1-imidazolyl group, 2-pyridyl group, 2-benzothiophenyl group, morpholino group and 4-methylthiazol-5-yl group are preferable.

For $R^{a4}$, $R^{a5}$ or $R^{a12}$, tetrahydropyran-2-yl group is preferable, and for $R^{a6}$, morpholino group is preferable.

For $R^{32}$ or $R^{33}$, 1-pyrrolidinyl group is preferable.

The "$C_{1-10}$ alkyl group optionally substituted by 1 to 3 substituents selected from halogen atom and group B" is a $C_{1-10}$ alkyl group optionally substituted by the substituent group selected from the "halogen atom" defined above and the "group B" defined below, and may be a non-substituted alkyl group. The alkyl moiety is a straight chain or branched chain alkyl group having 1 to 10 carbon atoms. Specific examples thereof include methyl group, ethyl group, propyl group, isopropyl group, butyl group, isobutyl group, sec-butyl group, tert-butyl group, pentyl group, isopentyl group, 1-methylbutyl group, 1-ethylpropyl group, 2-ethylpropyl group, 1,1-dimethylpropyl group, 1,2-dimethylpropyl group, tert-pentyl group, hexyl group, isohexyl group, 1-methylpentyl group, 1,1-dimethylbutyl group, 1,2-dimethylbutyl group, 1,3-dimethylbutyl group, 1-ethylbutyl group, 1-ethyl-1-methylpropyl group, 1-ethyl-2-methylpropyl group, 1,1,2-trimethylpropyl group, 1,2,2-trimethylpropyl group, 1-ethyl-1-methylpropyl group, heptyl group, isoheptyl group, 1-methylhexyl group, 1,1-dimethylpentyl group, 1,2-dimethylpentyl group, 1,3-dimethylpentyl group, 1,4-dimethylpentyl group, 1,1,2-trimethylbutyl group, 1,1,3-trimethylbutyl group, 1,2,2-trimethylbutyl group, 1,2,3-trimethylbutyl group, 1,3,3-trimethylbutyl group, 1-ethylpentyl group, 1-ethyl-2-methylbutyl group, 1-ethyl-3-methylbutyl group, 2-ethyl-1-methylbutyl group, 1-propylbutyl group, 1-ethyl-2,2-dimethylpropyl group, 1-isopropyl-2-methylpropyl group, 1-isopropyl-1-methylpropyl group, 1,1-diethylpropyl group, 1,1,2,2-tetramethylpropyl group, 1-isopropylbutyl group, 1-ethyl-1-methylbutyl group, octyl group, nonyl group, decyl group and the like, with preference given to straight chain or branched chain alkyl group having 1 to 6 carbon atoms, particularly preferably branched chain alkyl group having 1 to 6 carbon atoms.

The "group B" is a group consisting of the "$C_{3-10}$ carbon ring group optionally substituted by 1 to 5 substituents selected from group A" defined above, the "heterocyclic group optionally substituted by 1 to 5 substituents selected from group A" defined above, a cyano group, —OR$^{a4}$, —SR$^{a4}$, —NR$^{a4}$R$^{a5}$, —CONR$^{a4}$R$^{a5}$, —SO$_2$NR$^{a4}$R$^{a5}$, —COR$^{a6}$, —NR$^{a4}$COR$^{a6}$, —SO$_2$R$^{a6}$, —NR$^{a4}$SO$_2$R$^{a6}$, —COOR$^{a4}$, —NR$^{a5}$COOR$^{a6}$, —NR$^{a4}$CO—NR$^{a5}$R$^{a12}$, —NR$^{a4}$CO—COOR$^{a5}$, —O—W—OR$^{a5}$, —NR$^{a4}$—W—OR$^{a5}$, —NR$^{a4}$—W—SO$_2$NR$^{a5}$R$^{a12}$, —NR$^{a4}$CO—W—R$^{a5}$, —NR$^{a4}$CO—W—OR$^{a5}$, —NR$^{a4}$CO—W—COOR$^{a5}$ and —NR$^{a4}$CO—W—NR$^{a5}$COR$^{a6}$.

As used herein, R$^{a4}$, R$^{a5}$ and R$^{a12}$ are the same or different and each is a hydrogen atom, the "C$_{1-4}$ alkyl group" defined above, the "C$_{3-10}$ carbon ring group optionally substituted by 1 to 5 substituents selected from group A" defined above or the "heterocyclic group optionally substituted by 1 to 5 substituents selected from group A" defined above, and R$^{a6}$ is the "C$_{1-4}$ alkyl group" defined above, the "C$_{3-10}$ carbon ring group optionally substituted by 1 to 5 substituents selected from group A" defined above or the "heterocyclic group optionally substituted by 1 to 5 substituents selected from group A" defined above, and W is a C$_{1-10}$ alkylene group.

The "C$_{1-10}$ alkylene group" is a straight chain or branched chain alkylene group having 1 to 10 carbon atoms, and specific examples thereof include methylene group, ethylene group, trimethylene group, tetramethylene group,

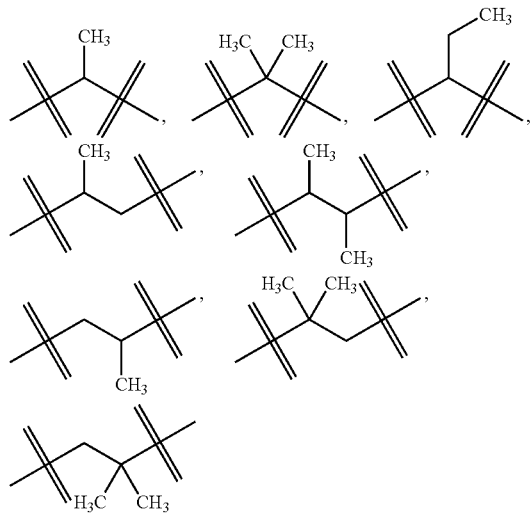

and the like, with preference given to straight chain or branched chain alkylene group having 1 to 6 carbon atoms, particularly preferably straight chain or branched chain alkylene group having 1 to 4 carbon atoms.

Specific examples of "—OR$^{a4}$" include hydroxy group, methoxy group, ethoxy group, propoxy group, isopropoxy group, tert-butoxy group, tetrahydropyran-2-yloxy group and the like.

Specific examples of "—SR$^{a4}$" include mercapto group, methylsulfanyl group, ethylsulfanyl group, propylsulfanyl group, isopropylsulfanyl group, tert-butylsulfanyl group and the like.

Specific examples of "—NR$^{a4}$R$^{a5}$" include amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group, N-benzyl-N-methylamino group and the like.

Specific examples of "—CONR$^{a4}$R$^{a5}$" include carbamoyl group, methylcarbamoyl group, ethylcarbamoyl group, propylcarbamoyl group, isopropylcarbamoyl group, tert-butylcarbamoyl group, dimethylcarbamoyl group, diethylcarbamoyl group, N-methyl-N-ethylcarbamoyl group, phenylcarbamoyl group and the like.

Specific examples of "—SO$_2$NR$^{a4}$R$^{a5}$" include sulfamoyl group, methylsulfamoyl group, ethylsulfamoyl group, propylsulfamoyl group, isopropylsulfamoyl group, tert-butylsulfamoyl group, dimethylsulfamoyl group, diethylsulfamoyl group, N-methyl-N-ethylsulfamoyl group and the like.

Specific examples of "—COR$^{a6}$" include acetyl group, propionyl group, butyryl group, isobutyryl group, 2,2-dimethylpropionyl group and the like.

Specific examples of "—NR$^{a4}$COR$^{a6}$" include acetylamino group, propionylamino group, butyrylamino group, isobutyrylamino group, 2,2-dimethylpropionylamino group, N-acetyl-N-methylamino group, benzoylamino group, morpholinocarbonylamino group and the like.

Specific examples of "—SO$_2$R$^{a6}$" include methylsulfonyl group, ethylsulfonyl group, propylsulfonyl group, isopropylsulfonyl group, tert-butylsulfonyl group and the like.

Specific examples of "—NR$^{a4}$SO$_2$R$^{a6}$" include methylsulfonylamino group, ethylsulfonylamino group, propylsulfonylamino group, isopropylsulfonylamino group, tert-butylsulfonylamino group, N-methyl-N-(methylsulfonyl)amino group and the like.

Specific examples of "—COOR$^{a4}$" include carboxyl group, methoxycarbonyl group, ethoxycarbonyl group, propoxycarbonyl group, isopropyloxycarbonyl group, tert-butoxycarbonyl group and the like.

Specific examples of "—NR$^{a5}$COOR$^{a6}$" include methoxycarbonylamino group, ethoxycarbonylamino group, propoxycarbonylamino group, isopropoxycarbonylamino group, tert-butoxycarbonylamino group, N-(tert-butoxycarbonyl)-N-methylamino group and the like.

Specific examples of "—NR$^{a4}$CO—NR$^{a5}$R$^{a12}$" include 3-methylureido group, 3-ethylureido group and the like.

Specific examples of "—NR$^{a4}$CO—COOR$^{a5}$" include oxalylamino group and the like.

Specific examples of "—O—W—OR$^{a5}$" include methoxymethoxy group and the like.

Specific examples of "—NR$^{a4}$—W—OR$^{a5}$" include 2-hydroxyethylamino group, N-(2-hydroxyethyl)-N-methylamino group and the like.

Specific examples of "—NR$^{a4}$—W—SO$_2$NR$^{a5}$R$^{a12}$" include (sulfamoylmethyl)amino group, N-methyl-N-(sulfamoylmethyl)amino group and the like.

Specific examples of "—NR$^{a4}$CO—W—R$^{a5}$" include phenylacetylamino group and the like.

Specific examples of "—NR$^{a4}$CO—W—OR$^{a5}$" include 2-hydroxyacetylamino group, 2-methoxyacetylamino group, 2-ethoxyacetylamino group, 2-phenoxyacetylamino group, (R)-2-methoxypropionylamino group, (S)-2-methoxypropionylamino group, 2-methoxy-2-methylpropionylamino group and the like.

Specific examples of "—NR$^{a4}$CO—W—COOR$^{a5}$" include 3-carboxypropionylamino group and the like.

Specific examples of "—NR$^{a4}$CO—W—NR$^{a5}$COR$^{a6}$" include 2-acetylaminoacetylamino group and the like.

Specific examples of "C$_{1-10}$ alkyl group optionally substituted by 1 to 3 substituents selected from halogen atom and group B" include methyl group, ethyl group, propyl group, isopropyl group, butyl group, isobutyl group, sec-butyl group, tert-butyl group, pentyl group, isopentyl group, 1-methylbutyl group, 1-ethylpropyl group, 2-ethylpropyl group, 1,1-dimethylpropyl group, 1,2-dimethylpropyl group, tert-pentyl group, hexyl group, isohexyl group, 1-methylpentyl group, 1,1-dimethylbutyl group, 1,2-dimethylbutyl group, 1,3-dimethylbutyl group, 1-ethylbutyl group, 1-ethyl-1-methylpropyl group, 1-ethyl-2-methylpropyl group, 1,1,2-trimethylpropyl group, 1,2,2-trimethylpropyl group, 1-ethyl-1-methylpropyl group, heptyl group, isoheptyl group, 1-methylhexyl group, 1,1-dimethylpentyl group, 1,2-dimethylpentyl group, 1,3-dimethylpentyl group, 1,4-dimethylpentyl group, 1,1,2-trimethylbutyl group, 1,1,3-trimethylbutyl group, 1,2,2-trimethylbutyl group, 1,2,3-trimethylbutyl group, 1,3,3-trimethylbutyl group, 1-ethylpentyl group, 1-ethyl-2-methylbutyl group, 1-ethyl-3-methylbutyl group, 2-ethyl-1-methylbutyl group, 1-propylbutyl group, 1-ethyl-2,2-dimethylpropyl group, 1-isopropyl-2-methylpropyl group, 1-isopropyl-1-methylpropyl group, 1,1-diethylpropyl group, 1,1,2,2-tetramethylpropyl group, 1-isopropylbutyl group, 1-ethyl-1-methylbutyl group, fluoromethyl group, trifluoromethyl group, chloroethyl group, 2-fluoroethyl group, 2-chloroethyl group, 3-fluoropropyl group, 2-chloropropyl group, 2,2,2-trifluoroethyl group, 2-hydroxyethyl group, 2-hydroxypropyl group, 2-hydroxy-1-methylethyl group, 2-hydroxy-1,1-dimethylethyl group, 1-(hydroxymethyl)propyl group, 3-hydroxypropyl group, 2-hydroxybutyl group, 4-hydroxybutyl group, 2-hydroxypentyl group, 5-hydroxypentyl group, 2,3-dihydroxypropyl group, 2,3-dihydroxybutyl group, 2-hydroxy-1-(hydroxymethyl)ethyl group, 2-hydroxy-2-methylpropyl group, 1-(hydroxymethyl)butyl group, 1-(hydroxymethyl)-2-methylpropyl group, 1-(hydroxymethyl)-2,2-dimethylpropyl group, 1-(hydroxymethyl)-2-methylbutyl group, 2-hydroxy-1-phenylethyl group, 2-hydroxy-2-phenylethyl group, 1-(hydroxymethyl)-2-phenylethyl group, 1-(hydroxymethyl)-3-methylbutyl group, 2-ethyl-1-(hydroxymethyl)butyl group, 3-hydroxy-1-methylpropyl group, 1,1-dimethyl-3-hydroxypropyl group, 1,2-dimethyl-3-hydroxypropyl group, 1-isopropyl-3-hydroxypropyl group, 2,2-dimethyl-1-(2-hydroxyethyl)propyl group, 1-ethyl-3-hydroxypropyl group, 2-hydroxy-1-isopropylpropyl group, 1-ethyl-1-(hydroxymethyl)propyl group, 1,1-dimethyl-2-hydroxypropyl group, 1,2-dimethyl-2-hydroxypropyl group, 1-ethyl-2-hydroxypropyl group, 4-hydroxy-1-methylbutyl group, 2-ethyl-1-(hydroxymethyl)-2-methylbutyl group, 3,3-dimethyl-1-(hydroxymethyl)butyl group, 1-(hydroxymethyl)pentyl group, 4-methyl-1-(hydroxymethyl)pentyl group, methoxymethyl group, 2-methoxyethyl group, methylsulfanylmethyl group, 2-(methylsulfanyl)ethyl group, 2-aminoethyl group, 2-(dimethylamino)ethyl group, carboxymethyl group, 2-carboxyethyl group, 2-carboxypropyl group, 3-carboxypropyl group, carbamoylmethyl group, 2-(carbamoyl)ethyl group, methylcarbamoylmethyl group, dimethylcarbamoylmethyl group, 2-(phenylcarbamoyl)ethyl group, 2-oxopropyl group, methylsulfonylmethyl group, 2-(methylsulfonyl)ethyl group, sulfamoylmethyl group, methylsulfamoylmethyl group, dimethylsulfamoylmethyl group, tert-butylsulfamoylmethyl group, 2-(acetylamino)ethyl group, 2-(methylsulfonylamino)ethyl group, 2-(ethoxycarbonylamino)ethyl group, benzyl group, phenethyl group, 3-phenylpropyl group, 4-phenylbutyl group, 2-biphenylmethyl group, 3,4-dichlorobenzyl group, 2-hydroxy-2-phenylethyl group, cyclopentylmethyl group, cyclohexylmethyl group, 2-cyclohexylethyl group, 1-cyclohexyl-2-hydroxyethyl group, 1-cyclohexylmethyl-2-hydroxyethyl group, phenylcarbamoylmethyl group, 2-pyridin-2-ylethyl group, 2-imidazol-1-ylethyl group, 2-benzothiophen-2-ylethyl group, 2-morpholinoethyl group, 2-(4-methylthiazolin-5-yl)ethyl group, 1-carboxyethyl group, 1-(carbamoyl)ethyl group, 1-carboxy-2-methylpropyl group, 1-(carbamoyl)-2-methylpropyl group, 2-hydroxy-1-(hydroxymethyl)propyl group, 1-(hydroxymethyl)-2-mercaptoethyl group, 1-(hydroxymethyl)-3-(methylsulfanyl)propyl group, 2-carboxy-1-(hydroxymethyl)ethyl group, 2-carbamoyl-1-(hydroxymethyl)ethyl group, 2-(indol-3-yl)-1-(hydroxymethyl)ethyl group, 2-(imidazol-4-yl)-1-(hydroxymethyl)ethyl group, 2-(4-hydroxyphenyl)-1-(hydroxymethyl)ethyl group, 3-carbamoyl-1-(hydroxymethyl)propyl group, 5-amino-1-(hydroxymethyl)pentyl group, 2-(tetrahydropyran-2-yloxy)ethyl group, 1-(methoxymethoxymethyl)-2-methylpropyl group, hydroxymethyl group, aminomethyl group, methylaminomethyl group, acetylaminomethyl group, methylsulfonylaminomethyl group, methoxycarbonylaminomethyl group, sulfamoylmethyl group, (tert-butoxycarbonylamino)methyl group, (2,2-dimethylpropionylamino)methyl group, dimethylaminomethyl group, (2-hydroxyacetylamino)methyl group, (2-methoxyacetylamino)methyl group, (N-tert-butoxycarbonyl-N-methylamino)methyl group, propionylaminomethyl group, butyrylaminomethyl group, isobutyrylaminomethyl group, benzoylaminomethyl group, ethoxycarbonylaminomethyl group, (morpholinocarbonylamino)methyl group, (3-methylureido)methyl group, (3-ethylureido)methyl group, phenylacetylaminomethyl group, (oxalylamino)methyl group, (2-phenoxyacetylamino)methyl group, (2-methoxypropionylamino)methyl group, (3-carboxypropionylamino)methyl group, (2-ethoxyacetylamino)methyl group, (2-methoxy-2-methylpropionylamino)methyl group and (2-acetylaminoacetylamino)methyl group.

For $R^1$, methyl group, ethyl group, propyl group, isopropyl group, butyl group, isobutyl group, tert-butyl group, 2-fluoroethyl group, 2,2,2-trifluoroethyl group, 2-hydroxyethyl group, 2-hydroxypropyl group, 3-hydroxypropyl group, 4-hydroxybutyl group, 5-hydroxypentyl group, 2,3-dihydroxypropyl group, 2-hydroxy-1-methylethyl group, 2-hydroxy-1,1-dimethylethyl group, 2-hydroxy-1-(hydroxymethyl)ethyl group, 1-(hydroxymethyl)propyl group, 2-hydroxy-2-methylpropyl group, 1-(hydroxymethyl)butyl group, 1-(hydroxymethyl)-2-methylpropyl group, 1-(hydroxymethyl)-2,2-dimethylpropyl group, 1-(hydroxymethyl)-2-methylbutyl group, 1-(hydroxymethyl)-3-methylbutyl group, 2-hydroxy-1-phenylethyl group, 2-hydroxy-2-phenylethyl group, 1-(hydroxymethyl)-2-phenylethyl group, methoxymethyl group, 2-methoxyethyl group, methylsulfanylmethyl group, 2-(methylsulfanyl)ethyl group, 2-aminoethyl group, 2-(dimethylamino)ethyl group, carboxymethyl group, 2-carboxyethyl group, 3-carboxypropyl group, (carbamoyl)methyl group, 2-(carbamoyl)ethyl group, methylcarbamoylmethyl group, dimethylcarbamoylmethyl group, 2-(phenylcarbamoyl)ethyl group, 2-oxopropyl group, methylsulfonylmethyl group, 2-(methylsulfonyl)ethyl group, sulfamoylmethyl group, methylsulfamoylmethyl group, dimethylsulfamoylmethyl group, tert-butylsulfamoylmethyl group, 2-(acetylamino)ethyl group, 2-(methylsulfonylamino)ethyl group, 2-(ethoxycarbonylamino)ethyl group, benzyl group, phenethyl group, 3-phenylpropyl group, 4-phenylbutyl group, 2-biphenylmethyl group, 3,4-dichlorobenzyl group, cyclopentylmethyl group, cyclohexylmethyl group, 1-cyclohexyl-2-hydroxyethyl group, 1-cyclohexylmethyl-2-hydroxyethyl group, 2-pyridin-2-ylethyl group, 2-imidazol-1-ylethyl group, 2-morpholinoethyl group, 2-(4-methylthiazolin-5-yl)ethyl group, 2-benzothiophen-2-ylmethyl group, 2-(tetrahydropyran-2-yloxy)ethyl group, 1-(methoxymethoxymethyl)-2-methylpropyl group, hydroxymethyl group, aminomethyl group, methylaminomethyl group, acetylaminomethyl group, methylsulfonylaminomethyl group, methoxycarbonylaminomethyl group, sulfamoylmethyl group, (tert-butoxycarbonylamino)methyl group, (2,2-dimethylpropionylamino)methyl group, dimethylaminomethyl group, (2-hydroxyacetylamino)methyl group, (2-methoxyacetylamino)methyl group, (N-tert-butoxycarbonyl-N-methylamino)methyl group, propionylaminomethyl group, butyrylaminomethyl group, isobutyrylaminomethyl group, benzoylaminomethyl group, ethoxycarbonylaminomethyl group, (morpholinocarbonylamino)methyl group, (3-methylureido)methyl group, (3-ethylureido)methyl group, phenylacetylaminomethyl group, (oxalylamino)methyl group, (2-phenoxyacetylamino)methyl group, (2-methoxypropionylamino)methyl group, (3-carboxypropionylamino)methyl group, (2-ethoxyacetylamino)methyl group, (2-methoxy-2-methylpropionylamino)methyl group and (2-acetylaminoacetylamino)methyl group are preferable, and ethyl group, propyl group, isopropyl group, 2-hydroxyethyl group, 2-hydroxy-1-methylethyl group, 1-(hydroxymethyl)-2-methylpropyl group, 1-(hydroxymethyl)-2,2-dimethylpropyl group, methoxymethyl group, carboxymethyl group, (carbamoyl)methyl group, 2-(tetrahydropyran-2-yloxy)ethyl group, 1-(methoxymethoxymethyl)-2-methylpropyl group, hydroxymethyl group, aminomethyl group, methylaminomethyl group, acetylaminomethyl group, methylsulfonylaminomethyl group, methoxycarbonylaminomethyl group, (tert-butoxycarbonylamino)methyl group, (2,2-dimethylpropionylamino)methyl group, dimethylaminomethyl group, (2-hydroxyacetylamino) methyl group, (2-methoxyacetylamino) methyl group, (N-tert-butoxycarbonyl-N-methylamino)methyl group, propionylaminomethyl group, butyrylaminomethyl group, isobutyrylaminomethyl group, benzoylaminomethyl group, ethoxycarbonylaminomethyl group, (morpholinocarbonylamino)methyl group, (3-ethylureido) methyl group, phenylacetylaminomethyl group, (oxalylamino)methyl group, (2-phenoxyacetylamino)methyl group, (2-methoxypropionylamino)methyl group, (3-carboxypropionylamino)methyl group, (2-ethoxyacetylamino)methyl group, (2-methoxy-2-methylpropionylamino)methyl group and (2-acetylaminoacetylamino)methyl group are more preferable.

Particularly preferably, it is alkyl group branched at the 1-position and/or alkyl group substituted by hydroxy group. Specific examples thereof include 2-hydroxy-1-methylethyl group, 1-(hydroxymethyl)-2-methylpropyl group, 1-(hydroxymethyl)-2,2-dimethylpropyl group, 1-(hydroxymethyl)-2-methylbutyl group, 2-hydroxy-1-(hydroxymethyl) ethyl group and 2-phenyl-1-(hydroxymethyl)ethyl group. When these particularly preferable substituents are in optically active forms, S form is more preferable.

For $R^{32}$ or $R^{33}$, methyl group, ethyl group and trifluoromethyl group are preferable.

For $R^{a7}$ or $R^{a8}$, methyl group, ethyl group, propyl group, isopropyl group, 2-hydroxyethyl group, 3-hydroxypropyl group and cyclohexylmethyl group are preferable, methyl group, ethyl group and isopropyl group are more preferable, and methyl group is particularly preferable.

The "fused ring formed together with a benzene ring" is a ring wherein the benzene ring is condensed with $C_{3-10}$ carbon ring or heterocycle.

The "$C_{3-10}$ carbon ring" is a ring constituting the "$C_{3-10}$ carbon ring group" defined above.

The "heterocycle" is a ring constituting the "heterocyclic group" defined above.

The fused ring which is formed by $R^4$ and $R^5$ together with a benzene ring is preferably a ring wherein the benzene ring is condensed with $C_{3-6}$ cycloalkane or $C_{3-6}$ cycloalkene, or a ring wherein the benzene ring is condensed with monocyclic 5- or 6-membered heterocycle. Specifically, of those defined for "$C_{3-10}$ carbon ring group" and "heterocyclic group", the ring constituting a fused ring group including benzene ring can be mentioned.

Specific examples of "—$OR^{a7}$" include hydroxy group, methoxy group, ethoxy group, propoxy group, isopropoxy group, tert-butoxy group, tetrahydropyran-2-yloxy group and the like.

Specific examples of "—$SR^{a7}$" include mercapto group, methylsulfanyl group, ethylsulfanyl group, propylsulfanyl group, isopropylsulfanyl group, tert-butylsulfanyl group and the like.

Specific examples of "—$NR^{a7}R^{a8}$" include amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group, N-benzyl-N-methylamino group and the like.

Specific examples of "—$NR^{a7}COR^{a9}$" include acetylamino group, propionylamino group, butyrylamino group, isobutyrylamino group, 2,2-dimethylpropionylamino group, N-acetyl-N-methylamino group and the like.

Specific examples of "—$COOR^{a10}$" include carboxyl group, methoxycarbonyl group, ethoxycarbonyl group, propoxycarbonyl group, isopropyloxycarbonyl group, tert-butoxycarbonyl group and the like.

Specific examples of "—N=CH—$NR^{a10}R^{a11}$" include aminomethyleneamino group, dimethylaminomethyleneamino group and the like.

The ring Cy in the formula [I] is preferably a "$C_{3-10}$ carbon ring group optionally substituted by 1 to 5 substituents selected from group A" defined above, more preferably a group represented by the formula:

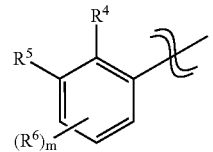

wherein $R^4$, $R^5$, $R^6$ and m are as defined above; namely, a quinolizinone compound represented by the following formula [II]:

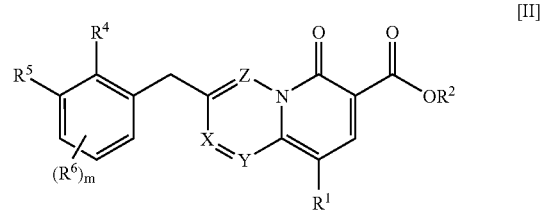

wherein each symbol is as defined above, is preferable.

The group A for ring Cy is preferably cyano group, phenyl group, nitro group,

"halogen atom" defined above, "$C_{1-4}$ alkyl group" defined above,

"halo $C_{1-4}$ alkyl group" defined above,

"halo $C_{1-4}$ alkyloxy group" defined above,

"—$OR^{a1}$" defined above, "—$SR^{a1}$" defined above,

"—$NR^{a1}R^{a2}$" defined above, "—$CONR^{a1}R^{a2}$" defined above,

"—$SO_2NR^{a1}R^{a2}$" defined above, "—$NR^{a1}COR^{a3}$" defined above,

"—$SO_2R^{a3}$" defined above, "—$NR^{a1}SO_2R^{a3}$" defined above,

"—$COOR^{a1}$" defined above or "—$NR^{a2}COOR^{a3}$" defined above, more preferably cyano group, phenyl group, nitro group, "halogen atom" defined above, "$C_{1-4}$ alkyl group" defined above, "halo $C_{1-4}$ alkyl group" defined above, "halo $C_{1-4}$ alkyloxy group" defined above, "—$OR^{a1}$" defined above, "—$SR^{a1}$" defined above, "—$NR^{a1}R^{a2}$" defined above, "—$SO_2NR^{a1}R^{a2}$" defined above, "—$NR^{a1}COR^{a3}$" defined above or "—$SO_2R^{a3}$" defined above, and particularly preferably "halogen atom" defined above.

The ring Cy is more preferably group represented by the formula:

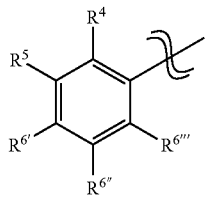

wherein $R^6$, $R^{6'}$ and $R^{6'''}$ are substituents selected from hydrogen atom and "group A" defined above, and $R^4$ and $R^5$ are as defined above.

$R^4$ and $R^5$ are preferably the same or different and each is hydrogen atom, cyano group, phenyl group, nitro group, "halogen atom" defined above, "$C_{1-4}$ alkyl group" defined above, "halo $C_{1-4}$ alkyl group" defined above, "halo $C_{1-4}$ alkyloxy group" defined above, "—$OR^{a1}$" defined above, "—$SR^{a1}$" defined above, "—$NR^{a1}R^{a2}$" defined above, "—$CONR^{a1}R^{a2}$" defined above, "—$SO_2NR^{a1}R^{a2}$" defined above, "—$NR^{a1}COR^{a3}$" defined above, "—$SO_2R^{a3}$" defined above, "—$NR^{a1}SO_2R^{a3}$" defined above, "—$COOR^{a1}$" defined above or "—$NR^{a2}COOR^{a3}$" defined above.

$R^4$ is preferably hydrogen atom, phenyl group,

"halogen atom" defined above, "$C_{1-4}$ alkyl group" defined above,

"halo $C_{1-4}$ alkyloxy group" defined above,

"—$OR^{a1}$" defined above, "—$NR^{a1}R^{a2}$" defined above,

"—$CONR^{a1}R^{a2}$" defined above, "—$SO_2NR^{a1}R^{a2}$" defined above,

"—$NR^{a1}COR^{a3}$" defined above, "—$SO_2R^{a3}$" defined above,

"—$NR^{a1}SO_2R^{a3}$" defined above or "—$COOR^{a1}$" defined above, more preferably hydrogen atom, "halogen atom" defined above, "$C_{1-4}$ alkyl group" defined above, "halo $C_{1-4}$ alkyloxy group" defined above, "—$OR^{a1}$" defined above or "—$NR^{a1}R^{a2}$" defined above, and particularly preferably hydrogen atom or "halogen atom" defined above.

$R^5$ is preferably hydrogen atom, cyano group, phenyl group, nitro group,

"halogen atom" defined above, "$C_{1-4}$ alkyl group" defined above,

"halo $C_{1-4}$ alkyl group" defined above,

"—$OR^{a1}$" defined above, "—$SR^{a1}$" defined above,

"—$NR^{a1}R^{a2}$" defined above, "—$CONR^{a1}R^{a2}$" defined above,

"—$SO_2NR^{a1}R^{a2}$" defined above or "—$NR^{a1}COR^{a3}$" defined above, more preferably hydrogen atom, "halogen atom" defined above or "$C_{1-4}$ alkyl group" defined above, and particularly preferably hydrogen atom or "halogen atom" defined above.

$R^6$ is preferably

"halogen atom" defined above, "$C_{1-4}$ alkyl group" defined above,

"—$OR^{a1}$" defined above, "—$SR^{a1}$" defined above or

"—$SO_2R^{a3}$" defined above, and more preferably "halogen atom" defined above.

"m" is preferably 0 or 1, and more preferably 0.

$R^{6'}$ and $R^{6'''}$ are preferably the same or different and each is hydrogen atom or "halogen atom" defined above.

$R^{6''}$ is preferably hydrogen atom, "halogen atom" defined above, "$C_{1-4}$ alkyl group" defined above, "—$SO_2R^{a3}$" defined above, "—$OR^{a1}$" defined above or "—$SR^{a1}$" defined above, more preferably hydrogen atom, "halogen atom" defined above, "$C_{1-4}$ alkyl group" defined above or "—$SR^{a1}$" defined above, and particularly preferably hydrogen atom.

$R^1$ is preferably hydrogen atom,

"$C_{3-10}$ carbon ring group optionally substituted by 1 to 5 substituents selected from group A" defined above, "heterocyclic group optionally substituted by 1 to 5 substituents selected from group A" defined above, cyano group, "—$OR^{a4}$" defined above (here, it is concretely preferably methoxy group), "—$NR^{a4}R^{a5}$" defined above (here, it is concretely preferably amino group, methylamino group, ethylamino group or dimethylamino group), "—$NR^{a4}COR^{a6}$" defined above (here, it is concretely preferably acetylamino group), "—$NR^{a4}SO_2R^{a6}$" defined above (here, it is concretely preferably methylsulfonylamino group or N-methyl-N-(methylsulfonyl)amino group), "—$COOR^{a4}$" defined above (here, it is concretely preferably tert-butoxycarbonyl group), "—$NR^{a5}COOR^{a6}$" defined above (here, it is concretely preferably methoxycarbonylamino group or tert-butoxycarbonylamino group), "—O—W—$OR^{a5}$" defined above (here, it is concretely preferably methoxymethoxy group), "—$NR^{a4}$—W—$OR^{a5}$" defined above (here, it is concretely preferably 2-hydroxyethylamino group or N-methyl-N-(2-hydroxyethyl)amino group), "—$NR^{a4}$—W—$SO_2NR^{a5}R^{a12}$" defined above (here, it is concretely preferably (sulfamoylmethyl)amino group or N-methyl-N-(sulfamoylmethyl)amino group) or "$C_{1-10}$ alkyl group optionally substituted by 1 to 3 substituents selected from halogen atom and group B" defined above, more preferably hydrogen atom, "$C_{3-10}$ carbon ring group optionally substituted by 1 to 5 substituents selected from group A" defined above, cyano group, "—$NR^{a4}R^{a5}$" defined above, "—$NR^{a4}COR^{a6}$" defined above, "—$NR^{a4}SO_2R^{a6}$" defined above, "—$COOR^{a4}$" defined above, "—$NR^{a5}COOR^{a6}$" defined above, "—O—W—$OR^{a5}$" defined above, "—$NR^{a4}$—W—$OR^{a5}$" defined above, "—$NR^{a4}$—W—$SO_2NR^{a5}R^{a12}$" defined above or "$C_{1-10}$ alkyl group optionally substituted by 1 to 3 substituents selected from halogen atom and group B" defined above, and particularly preferably hydrogen atom, cyano group, "—$NR^{a4}COR^{a6}$" defined above, "—$NR^{a4}SO_2R^{a6}$" defined above, "—$COOR^{a4}$" defined above, "—$NR^{a5}COOR^{a6}$" defined above, "—O—W—$OR^{a5}$" defined above, "—$NR^{a4}$—W—$OR^{a5}$" defined above, "—$NR^{a4}$—W—$SO_2NR^{a5}R^{a12}$" defined above or "$C_{1-10}$ alkyl group optionally substituted by 1 to 3 substituents selected from halogen atom and group B" defined above.

Here, group B of the "$C_{1-10}$ alkyl group optionally substituted by 1 to 3 substituents selected from halogen atom and group B" is preferably "—$OR^{a4}$" defined above, "—$NR^{a4}R^{a5}$" defined above, "—$CONR^{a4}R^{a5}$" defined above, "—$SO_2NR^{a4}R^{a5}$" defined above, "—$NR^{a4}COR^{a6}$" defined above, "—$NR^{a4}SO_2R^{a6}$" defined above, "—$COOR^{a4}$" defined above, "—$NR^{a5}COOR^{a6}$" defined above, "—$NR^{a4}CO$—$NR^{a5}R^{a12}$" defined above, "—$NR^{a4}CO$—$COOR^{a5}$" defined above, "—O—W—$OR^{a5}$" defined above, "—$NR^{a4}$—W—$SO_2NR^{a5}R^{a12}$" defined above, "—$NR^{a4}CO$—W—$R^{a5}$" defined above, "—$NR^{a4}CO$—W—$OR^{a5}$" defined above, "—$NR^{a4}CO$—W—$COOR^{a5}$" defined above and "—$NR^{a4}CO$—W—$NR^{a5}COR^{a6}$" defined above.

$R^2$ is preferably hydrogen atom.
X is preferably C—$R^{32}$.
Y is preferably C—$R^{33}$
Z is preferably C—$R^{31}$
$R^{31}$ is preferably hydrogen atom, cyano group, hydroxy group, "halogen atom" defined above or "$C_{1-4}$ alkoxy group" defined above, more preferably hydrogen atom, cyano group, hydroxy group or "$C_{1-4}$ alkoxy group" defined above, and particularly preferably hydrogen atom.

$R^{32}$ is preferably hydrogen atom, cyano group, "halogen atom" defined above, "heterocyclic group optionally substituted by 1 to 5 substituents selected from group A" defined above, "$C_{1-10}$ alkyl group optionally substituted by 1 to 3 substituents selected from halogen atom and group B" defined above, "—$OR^{a7}$" defined above (here, it is concretely preferably methoxy group), "—$SR^{a7}$" defined above, "—$NR^{a7}R^{a8}$" defined above, "—$NR^{a7}COR^{a9}$" defined above, "—$COOR^{a10}$" defined above or "—N=CH—$NR^{a10}R^{a11}$" defined above, more preferably hydrogen atom, cyano group, "halogen atom" defined above, "$C_{1-10}$ alkyl group optionally substituted by 1 to 3 substituents selected from halogen atom and group B" defined above, "—OR$^{a7}$" defined above, "—SR$^{a7}$" defined above, "—NR$^{a7}$R$^{a8}$" defined above, "—NR$^{a7}$COR$^{a9}$" defined above or "—COOR$^{a10}$" defined above, particularly preferably hydrogen atom, "—OR$^{a7}$" defined above, "—SR$^{a7}$" defined above or "—NR$^{a7}$R$^{a8}$" defined above, and most preferably hydrogen atom or "—OR$^{a7}$" defined above.

R$^{33}$ is preferably hydrogen atom, cyano group, "halogen atom" defined above, "heterocyclic group optionally substituted by 1 to 5 substituents selected from group A" defined above, "C$_{1-10}$ alkyl group optionally substituted by 1 to 3 substituents selected from halogen atom and group B" defined above, "—OR$^{a7}$" defined above (here, it is concretely preferably methoxy group), "—SR$^{a7}$" defined above, "—NR$^{a7}$R$^{a8}$" defined above, "—NR$^{a7}$COR$^{a9}$" defined above, "—COOR$^{a10}$" defined above or "—N=CH—NR$^{a10}$R$^{a11}$" defined above, more preferably hydrogen atom, "C$_{1-10}$ alkyl group optionally substituted by 1 to 3 substituents selected from halogen atom and group B" defined above, "—OR$^{a7}$" defined above or "—NR$^{a7}$R$^{a8}$" defined above, particularly preferably hydrogen atom, "—OR$^{a7}$" defined above or "—NR$^{a7}$R$^{a8}$" defined above, and most preferably hydrogen atom or "—OR$^{a7}$" defined above.

It is preferable that one of R$^{32}$ and R$^{33}$ be hydrogen atom, and the other be "—OR$^{a7}$" defined above.

It is preferable that R$^{31}$ be hydrogen atom and R$^{32}$ or R$^{33}$ be other than hydrogen atom.

R$^{a7}$ and R$^{a8}$ are preferably the same or different and each is "C$_{1-10}$ alkyl group optionally substituted by 1 to 3 substituents selected from halogen atom and group B" defined above.

Compound [II] is preferably a quinolizinone compound represented by the following formula [II-1] or [II-2]:

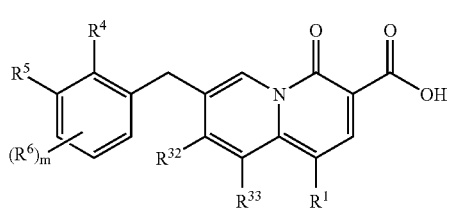

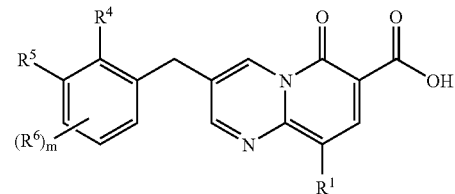

wherein each symbol is as defined above.

The compound represented by the formula [I] or a pharmaceutically acceptable salt thereof is preferably ethyl 7-(3-chloro-2-fluorobenzyl)-4-oxo-4H-quinolizine-3-carboxylate (Example 1), 7-(3-chloro-2-fluorobenzyl)-4-oxo-4H-quinolizine-3-carboxylic acid (Example 2), ethyl 7-(3-chloro-2-fluorobenzyl)-1-ethyl-4-oxo-4H-quinolizine-3-carboxylate (Example 3), 7-(3-chloro-2-fluorobenzyl)-1-ethyl-4-oxo-4H-quinolizine-3-carboxylic acid (Example 4), ethyl 7-(3-chloro-2-fluorobenzyl)-1-[2-(tetrahydropyran-2-yloxy)ethyl]-4-oxo-4H-quinolizine-3-carboxylate (Example 5), ethyl 7-(3-chloro-2-fluorobenzyl)-1-(2-hydroxyethyl)-4-oxo-4H-quinolizine-3-carboxylate (Example 6), 7-(3-chloro-2-fluorobenzyl)-1-(2-hydroxyethyl)-4-oxo-4H-quinolizine-3-carboxylic acid (Example 7), ethyl 7-(3-chloro-2-fluorobenzyl)-1-((R)-1-methoxymethoxymethyl-2-methylpropyl)-8-methoxy-4-oxo-4H-quinolizine-3-carboxylate (Example 8), ethyl 7-(3-chloro-2-fluorobenzyl)-1-((R)-1-hydroxymethyl-2-methylpropyl)-8-methoxy-4-oxo-4H-quinolizine-3-carboxylate (Example 9), 7-(3-chloro-2-fluorobenzyl)-1-((R)-1-hydroxymethyl-2-methylpropyl)-8-methoxy-4-oxo-4H-quinolizine-3-carboxylic acid (Example 10), 7-benzyl-4-oxo-4H-quinolizine-3-carboxylic acid (Example 11), 7-(3-chloro-2-fluorobenzyl)-4-oxo-1-propyl-4H-quinolizine-3-carboxylic acid (Example 12), 7-(3-chloro-2-fluorobenzyl)-1-isopropyl-4-oxo-4H-quinolizine-3-carboxylic acid (Example 13), 7-(3-chloro-2-fluorobenzyl)-1-((R)-2-hydroxy-1-methylethyl)-4-oxo-4H-quinolizine-3-carboxylic acid (Example 14), 7-(3-chloro-2-fluorobenzyl)-1-(1-hydroxymethyl-2-methylpropyl)-4-oxo-4H-quinolizine-3-carboxylic acid (Example 15), 7-(3-chloro-2-fluorobenzyl)-1-((R)-1-hydroxymethyl-2,2-dimethylpropyl)-4-oxo-4H-quinolizine-3-carboxylic acid (Example 16), 7-(3-chloro-2-fluorobenzyl)-1-((R)-1-hydroxymethyl-2,2-dimethylpropyl)-8-methoxy-4-oxo-4H-quinolizine-3-carboxylic acid (Example 17), 7-(3-chloro-2-fluorobenzyl)-1-hydroxymethyl-4-oxo-4H-quinolizine-3-carboxylic acid (Example 18), 7-(3-chloro-2-fluorobenzyl)-1-methoxymethyl-4-oxo-4H-quinolizine-3-carboxylic acid (Example 19), 1-aminomethyl-7-(3-chloro-2-fluorobenzyl)-4-oxo-4H-quinolizine-3-carboxylic acid hydrochloric acid (Example 20), 7-(3-chloro-2-fluorobenzyl)-1-methylaminomethyl-4-oxo-4H-quinolizine-3-carboxylic acid (Example 21), 1-(acetylaminomethyl)-7-(3-chloro-2-fluorobenzyl)-4-oxo-4H-quinolizine-3-carboxylic acid (Example 22), 7-(3-chloro-2-fluorobenzyl)-1-(methylsulfonylaminomethyl)-4-oxo-4H-quinolizine-3-carboxylic acid (Example 23), 7-(3-chloro-2-fluorobenzyl)-1-(methoxycarbonylaminomethyl)-4-oxo-4H-quinolizine-3-carboxylic acid (Example 24), 7-(3-chloro-2-fluorobenzyl)-1-sulfamoylmethyl-4-oxo-4H-quinolizine-3-carboxylic acid (Example 25), 1-carbamoylmethyl-7-(3-chloro-2-fluorobenzyl)-4-oxo-4H-quinolizine-3-carboxylic acid (Example 26), 7-(3-chloro-2-fluorobenzyl)-1-(2-hydroxyethylamino)-4-oxo-4H-quinolizine-3-carboxylic acid (Example 27), 7-(3-chloro-2-fluorobenzyl)-1-sulfamoylmethylamino-4-oxo-4H-quinolizine-3-carboxylic acid (Example 28), 7-(3-chloro-2-fluorobenzyl)-1-methylsulfonylamino-4-oxo-4H-quinolizine-3-carboxylic acid (Example 29), 7-(3-chloro-2-fluorobenzyl)-1-[N-(2-hydroxyethyl)-N-methylamino]-4-oxo-4H-quinolizine-3-carboxylic acid (Example 30), 7-(3-chloro-2-fluorobenzyl)-1-[N-methyl-N-(sulfamoylmethyl)amino]-4-oxo-4H-quinolizine-3-carboxylic acid (Example 31), 7-(3-chloro-2-fluorobenzyl)-1-[N-methyl-N-methylsulfonylamino]-4-oxo-4H-quinolizine-3-carboxylic acid (Example 32), 7-(3-chloro-2-fluorobenzyl)-1-cyano-4-oxo-4H-quinolizine-3-carboxylic acid (Example 33), 3-(3-chloro-2-fluorobenzyl)-9-(2-hydroxyethyl)-6-oxo-6H-pyrido[1,2-a]pyrimidine-7-carboxylic acid (Example 34), 1-(tert-butoxycarbonylamino)methyl-7-(3-chloro-2-fluorobenzyl)-4-oxo-4H-quinolizine-3-carboxylic acid (Example 35), 1-carboxymethyl-7-(3-chloro-2-fluorobenzyl)-4-oxo-4H-quinolizine-3-carboxylic acid (Example 36), 7-(3-chloro-2-fluorobenzyl)-1-(2,2-dimethylpropionylamino)methyl-4-oxo-4H-quinolizine-3-carboxylic acid (Example 37), 7-(3-chloro-2-fluorobenzyl)-1-dimethylaminomethyl-4-oxo-4H-quinolizine-3-carboxylic acid (Example 38), 7-(3-chloro-2-fluorobenzyl)-1-[(2-hydroxyacetylamino)methyl]-4-oxo-4H-quinolizine-3-carboxylic acid (Example 39), 7-(3-chloro-2-fluorobenzyl)-1-[(2-methoxyacetylamino)methyl]-4-oxo-4H-quinolizine-3-carboxylic acid (Example 40), 1-[(N-(tert-butoxycarbonyl)-N-methylamino)methyl]-7-(3-chloro-2-fluorobenzyl)-4-oxo-4H-quinolizine-3-carboxylic acid (Example 41), 7-(3-chloro-2-fluorobenzyl)-4-oxo-1-(propionylaminomethyl)-4H-quinolizine-3-carboxylic acid (Example 42), 1-(butyrylaminomethyl)-7-(3-chloro-2-fluorobenzyl)-4-oxo-4H-quinolizine-3-carboxylic acid (Example 43), 7-(3-chloro-2-fluorobenzyl)-1-(isobutyrylaminomethyl)-4-oxo-4H-quinolizine-3-carboxylic acid (Example 44), 1-(benzoylaminomethyl)-7-(3-chloro-2-fluorobenzyl)-4-oxo-4H-quinolizine-3-carboxylic acid (Example 45), 7-(3-chloro-2-fluorobenzyl)-1-(ethoxycarbonylaminomethyl)-4-oxo-4H-quinolizine-3-carboxylic acid (Example 46), 7-(3-chloro-2-fluorobenzyl)-1-({[(morpholinocarbonyl)amino]methyl})-4-oxo-4H-quinolizine-3-carboxylic acid (Example 47), 7-(3-chloro-2-fluorobenzyl)-1-[(3-ethylureido)methyl]-4-oxo-4H-quinolizine-3-carboxylic acid (Example 48), 7-(3-chloro-2-fluorobenzyl)-4-oxo-1-(phenylacetylaminomethyl)-4H-quinolizine-3-carboxylic acid (Example 49), 7-(3-chloro-2-fluorobenzyl)-1-[(oxalylamino)methyl]-4-oxo-4H-quinolizine-3-carboxylic acid (Example 50), 7-(3-chloro-2-fluorobenzyl)-4-oxo-1-[(2-phenoxyacetylamino)methyl]-4H-quinolizine-3-carboxylic acid (Example 51), 7-(3-chloro-2-fluorobenzyl)-1-[((S)-2-methoxypropionylamino)methyl]-4-oxo-4H-quinolizine-3-carboxylic acid (Example 52), 7-(3-chloro-2-fluorobenzyl)-1-[((R)-2-methoxypropionylamino)methyl]-4-oxo-4H-quinolizine-3-carboxylic acid (Example 53), 1-[(3-carboxypropionylamino)methyl]-7-(3-chloro-2-fluorobenzyl)-4-oxo-4H-quinolizine-3-carboxylic acid (Example 54), 7-(3-chloro-2-fluorobenzyl)-1-[(2-ethoxyacetylamino)methyl]-4-oxo-4H-quinolizine-3-carboxylic acid (Example 55), 7-(3-chloro-2-fluorobenzyl)-1-[(2-methoxy-2-methylpropionylamino)methyl]-4-oxo-4H-quinolizine-3-carboxylic acid (Example 56), 1-[(2-acetylaminoacetylamino)methyl]-7-(3-chloro-2-fluorobenzyl)-4-oxo-4H-quinolizine-3-carboxylic acid (Example 57), 7-(3-chloro-2-fluorobenzyl)-1-methoxymethoxy-4-oxo-4H-quinolizine-3-carboxylic acid (Example 58), 1-(tert-butoxycarbonylamino)-7-(3-chloro-2-fluorobenzyl)-4-oxo-4H-quinolizine-3-carboxylic acid (Example 59), ethyl 1-(tert-butoxycarbonylamino)-7-(3-chloro-2-fluorobenzyl)-4-oxo-4H-quinolizine-3-carboxylate (Example 60), 1-acetylamino-7-(3-chloro-2-fluorobenzyl)-4-oxo-4H-quinolizine-3-carboxylic acid (Example 61), 7-(3-chloro-2-fluorobenzyl)-4-oxo-4H-quinolizine-1,3-dicarboxylic acid 1-tert-butyl ester (Example 62), 7-(2,3-dichlorobenzyl)-1-((R)-1-hydroxymethyl-2-methylpropyl)-4-oxo-4H-quinolizine-3-carboxylic acid (Example 63), 7-(2,3-dichlorobenzyl)-1-((R)-1-hydroxymethyl-2,2-dimethylpropyl)-4-oxo-4H-quinolizine-3-carboxylic acid (Example 64), or 7-(3-chloro-2-fluorobenzyl)-1-((R)-1-hydroxymethyl-2,2-dimethylpropyl)-9-methoxy-4-oxo-4H-quinolizine-3-carboxylic acid (Example 65).

It is more preferably 7-(3-chloro-2-fluorobenzyl)-4-oxo-4H-quinolizine-3-carboxylic acid (Example 2), 7-(3-chloro-2-fluorobenzyl)-1-ethyl-4-oxo-4H-quinolizine-3-carboxylic acid (Example 4), 7-(3-chloro-2-fluorobenzyl)-1-(2-hydroxyethyl)-4-oxo-4H-quinolizine-3-carboxylic acid (Example 7), 7-(3-chloro-2-fluorobenzyl)-1-((R)-1-hydroxymethyl-2-methylpropyl)-8-methoxy-4-oxo-4H-quinolizine-3-carboxylic acid (Example 10), 7-benzyl-4-oxo-4H-quinolizine-3-carboxylic acid (Example 11), 7-(3-chloro-2-fluorobenzyl)-4-oxo-1-propyl-4H-quinolizine-3-carboxylic acid (Example 12), 7-(3-chloro-2-fluorobenzyl)-1-isopropyl-4-oxo-4H-quinolizine-3-carboxylic acid (Example 13), 7-(3-chloro-2-fluorobenzyl)-1-((R)-2-hydroxy-1-methylethyl)-4-oxo-4H-quinolizine-3-carboxylic acid (Example 14), 7-(3-chloro-2-fluorobenzyl)-1-(1-hydroxymethyl-2-methylpropyl)-4-oxo-4H-quinolizine-3-carboxylic acid (Example 15), 7-(3-chloro-2-fluorobenzyl)-1-((R)-1-hydroxymethyl-2,2-dimethylpropyl)-4-oxo-4H-quinolizine-3-carboxylic acid (Example 16), 7-(3-chloro-2-fluorobenzyl)-1-((R)-1-hydroxymethyl-2,2-dimethylpropyl)-8-methoxy-4-oxo-4H-quinolizine-3-carboxylic acid (Example 17), 7-(3-chloro-2-fluorobenzyl)-1-hydroxymethyl-4-oxo-4H-quinolizine-3-carboxylic acid (Example 18), 7-(3-chloro-2-fluorobenzyl)-1-methoxymethyl-4-oxo-4H-quinolizine-3-carboxylic acid (Example 19), 1-aminomethyl-7-(3-chloro-2-fluorobenzyl)-4-oxo-4H-quinolizine-3-carboxylic acid hydrochloric acid (Example 20), 7-(3-chloro-2-fluorobenzyl)-1-methylaminomethyl-4-oxo-4H-quinolizine-3-carboxylic acid (Example 21), 1-(acetylaminomethyl)-7-(3-chloro-2-fluorobenzyl)-4-oxo-4H-quinolizine-3-carboxylic acid (Example 22), 7-(3-chloro-2-fluorobenzyl)-1-(methylsulfonylaminomethyl)-4-oxo-4H-quinolizine-3-carboxylic acid (Example 23), 7-(3-chloro-2-fluorobenzyl)-1-(methoxycarbonylaminomethyl)-4-oxo-4H-quinolizine-3-carboxylic acid (Example 24), 1-carbamoylmethyl-7-(3-chloro-2-fluorobenzyl)-4-oxo-4H-quinolizine-3-carboxylic acid (Example 26), 7-(3-chloro-2-fluorobenzyl)-1-(2-hydroxyethylamino)-4-oxo-4H-quinolizine-3-carboxylic acid (Example 27), 7-(3-chloro-2-fluorobenzyl)-1-methylsulfonylamino-4-oxo-4H-quinolizine-3-carboxylic acid (Example 29), 7-(3-chloro-2-fluorobenzyl)-1-cyano-4-oxo-4H-quinolizine-3-carboxylic acid (Example 33), 3-(3-chloro-2-fluorobenzyl)-9-(2-hydroxyethyl)-6-oxo-6H-pyrido[1,2-a]pyrimidine-7-carboxylic acid (Example 34), 1-(tert-butoxycarbonylamino)methyl-7-(3-chloro-2-fluorobenzyl)-4-oxo-4H-quinolizine-3-carboxylic acid (Example 35), 1-carboxymethyl-7-(3-chloro-2-fluorobenzyl)-4-oxo-4H-quinolizine-3-carboxylic acid (Example 36), 7-(3-chloro-2-fluorobenzyl)-1-(2,2-dimethylpropionylamino)methyl-4-oxo-4H-quinolizine-3-carboxylic acid (Example 37), 7-(3-chloro-2-fluorobenzyl)-1-dimethylaminomethyl-4-oxo-4H-quinolizine-3-carboxylic acid (Example 38), 7-(3-chloro-2-fluorobenzyl)-1-[(2-hydroxyacetylamino)methyl]-4-oxo-4H-quinolizine-3-carboxylic acid (Example 39), 7-(3-chloro-2-fluorobenzyl)-1-[(2-methoxyacetylamino)methyl]-4-oxo-4H-quinolizine-3-carboxylic acid (Example 40), 1-[(N-(tert-butoxycarbonyl)-N-methylamino)methyl]-7-(3-chloro-2-fluorobenzyl)-4-oxo-4H-quinolizine-3-carboxylic acid (Example 41), 7-(3-chloro-2-fluorobenzyl)-4-oxo-1-(propionylaminomethyl)-4H-quinolizine-3-carboxylic acid (Example 42), 1-(butyrylaminomethyl)-7-(3-chloro-2-fluorobenzyl)-4-oxo-4H-quinolizine-3-carboxylic acid (Example 43), 7-(3-chloro-2-fluorobenzyl)-1-(isobutyrylaminomethyl)-4-oxo-4H-quinolizine-3-carboxylic acid (Example 44), 1-(benzoylaminomethyl)-7-(3-chloro-2-fluorobenzyl)-4-oxo-4H-quinolizine-3-carboxylic acid (Example 45), 7-(3-chloro-2-fluorobenzyl)-1-(ethoxycarbonylaminomethyl)-4-oxo-4H-quinolizine-3-carboxylic acid (Example 46), 7-(3-chloro-2-fluorobenzyl)-1-{[(morpholinocarbonyl)amino]methyl}-4-oxo-4H-quinolizine-3-carboxylic acid (Example 47), 7-(3-chloro-2-fluorobenzyl)-1-[(3-ethylureido)methyl]-4-oxo-4H-quinolizine-3-carboxylic acid (Example 48), 7-(3-chloro-2-fluorobenzyl)-4-oxo-1-(phenylacetylaminomethyl)-4H-quinolizine-3-carboxylic acid (Example 49), 7-(3-chloro-2-fluorobenzyl)-1-[(oxalylamino)methyl]-4-oxo-4H-quinolizine-3-carboxylic acid (Example 50), 7-(3-chloro-2-fluorobenzyl)-4-oxo-1-[(2-phenoxyacetylamino)methyl]-4H-quinolizine-3-carboxylic acid (Example 51), 7-(3-chloro-2-fluorobenzyl)-1-[((S)-2-methoxypropionylamino)methyl]-4-oxo-4H-quinolizine-3-carboxylic acid (Example 52), 7-(3-chloro-2-fluorobenzyl)-1-[((R)-2-methoxypropionylamino)methyl]-4-oxo-4H-quinolizine-3-carboxylic acid (Example 53), 1-[(3-carboxypropionylamino)methyl]-7-(3-chloro-2-fluorobenzyl)-4-oxo-4H-quinolizine-3-carboxylic acid (Example 54), 7-(3-chloro-2-fluorobenzyl)-1-[(2-ethoxyacetylamino)methyl]-4-oxo-4H-quinolizine-3-carboxylic acid (Example 55), 7-(3-chloro-2-fluorobenzyl)-1-[(2-methoxy-2-methylpropionylamino)methyl]-4-oxo-4H-quinolizine-3-carboxylic acid (Example 56), 1-[(2-acetylaminoacetylamino)methyl]-7-(3-chloro-2-fluorobenzyl)-4-oxo-4H-quinolizine-3-carboxylic acid (Example 57), 7-(3-chloro-2-fluorobenzyl)-1-methoxymethoxy-4-oxo-4H-quinolizine-3-carboxylic acid (Example 58), 1-(tert-butoxycarbonylamino)-7-(3-chloro-2-fluorobenzyl)-4-oxo-4H-quinolizine-3-carboxylic acid (Example 59), 1-acetylamino-7-(3-chloro-2-fluorobenzyl)-4-oxo-4H-quinolizine-3-carboxylic acid (Example 61), 7-(3-chloro-2-fluorobenzyl)-4-oxo-4H-quinolizine-1,3-dicarboxylic acid 1-tert-butyl ester (Example 62), 7-(2,3-dichlorobenzyl)-1-((R)-1-hydroxymethyl-2-methylpropyl)-4-oxo-4H-quinolizine-3-carboxylic acid (Example 63), 7-(2,3-dichlorobenzyl)-1-((R)-1-hydroxymethyl-2,2-dimethylpropyl)-4-oxo-4H-quinolizine-3-carboxylic acid (Example 64), or 7-(3-chloro-2-fluorobenzyl)-1-((R)-1-hydroxymethyl-2,2-dimethylpropyl)-9-methoxy-4-oxo-4H-quinolizine-3-carboxylic acid (Example 65).

The "pharmaceutically acceptable salt thereof" may be any as long as it forms a non-toxic salt with a compound of the above-mentioned formula [I], [II], [II-1] or [II-2]. For example, it can be obtained by reaction with an inorganic acid such as hydrochloric acid, sulfuric acid, phosphoric acid, hydrobromic acid and the like; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; an inorganic base such as sodium hydroxide, potassium hydroxide, calcium hydroxide, magnesium hydroxide, ammonium hydroxide and the like; an organic base such as methylamine, diethylamine, triethylamine, triethanolamine, ethylenediamine, tris(hydroxymethyl)methylamine, guanidine, choline, cinchonine and the like; or an amino acid such as lysin, arginine, alanine and the like. The present invention encompasses water-containing products, hydrates and solvates of each compound.

In addition, the compounds represented by the above-mentioned formulas [I], [II], [II-1] and [II-2] have various isomers. For example, E form and Z form are present as geometric isomers, and when an asymmetric carbon atom exists, enantiomer and diastereomer are present as stereoisomers based thereon, and tautomer can be present. Accordingly, the present invention encompasses all these isomers and mixtures thereof. The compound of the present invention is preferably isolated and purified from various isomers, by-products, metabolites or prodrugs, where one having a purity of 90% or above is preferable and one having a purity of 95% or above is more preferable.

The present invention also encompasses prodrugs and metabolites of each compound.

By the "prodrug" is meant a compound of the compound of the present invention, which has a chemically or metabolically decomposable group and which, after administration to a body, restores to the original compound to show its inherent efficacy, including a complex and a salt free of covalent bond.

The prodrug is utilized for, for example, improving absorption by oral administration or targeting of a target site.

As the site to be modified, highly reactive functional groups in the compound of the present invention, such as hydroxyl group, carboxyl group, amino group, thiol group and the like, are mentioned.

Specific examples of the hydroxyl-modifying group include acetyl group, propionyl group, isobutyryl group, pivaloyl group, benzoyl group, 4-methylbenzoyl group, dimethylcarbamoyl group, sulfo group and the like. Specific examples of the carboxyl-modifying group include ethyl group, pivaloyloxymethyl group, 1-(acetyloxy)ethyl group, 1-(ethoxycarbonyloxy)ethyl group, 1-(cyclohexyloxycarbonyloxy)ethyl group, carboxylmethyl group, (5-methyl-2-oxo-1,3-dioxol-4-yl)methyl group, phenyl group, o-tolyl group and the like. Specific examples of the amino-modifying group include hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like.

The compound of the present invention can be administered to a mammal (human, mouse, rat, hamster, rabbit, cat, dog, bovine, sheep, monkey and the like) as an anti-HIV agent, an integrase inhibitor, an antiviral agent and the like.

When the compound of the present invention is used as a pharmaceutical preparation, it is admixed with pharmaceutically acceptable carriers, excipients, diluents, extending agents, disintegrants, stabilizers, preservatives, buffers, emulsifiers, flavoring agents, coloring agents, sweetening agents, thickeners, correctives, dissolution aids, and other additives, that are generally known per se, such as water, vegetable oil, alcohol (e.g., ethanol, benzyl alcohol etc.), polyethylene glycol, glycerol triacetate, gelatin, carbohydrate (e.g., lactose, starch etc.), magnesium stearate, talc, lanolin, petrolatum and the like, formed into tablet, pill, powder, granule, suppository, injection, eye drop, liquid, capsule, troche, aerosol, elixir, suspension, emulsion, syrup and the like by a conventional method, and administered systemically or topically, and orally or parenterally.

While the dose varies depending on age, body weight, symptom, treatment effect, administration method and the like, it is generally 0.01 mg to 1 g per administration for an adult, which is given once to several times a day orally or in a dosage form of an injection such as intravenous injection and the like.

An anti-HIV agent is generally required to sustain its effect for a long time, so that can be effective not only for temporal suppression of viral growth but also for prohibition of viral re-growth. This means that a long-term administration is necessary and that a high single dose may be frequently inevitable to sustain effect for a longer period through the night. Such long term and high dose administration increases the risk of causing side effects.

In view of this, one of the preferable modes of the quinolizinone compound of the present invention is such compound permitting high absorption by oral administration, and such compound capable of maintaining blood concentration of the administered compound for an extended period of time.

By the "prophylaxis of AIDS" is meant, for example, administration of a pharmaceutical agent to an individual who tested HIV positive but has not yet developed the disease state of AIDS, administration of a pharmaceutical agent to an individual who shows an improved disease state of AIDS after treatment but who carries HIV still to be eradicated and whose relapse of AIDS is worried, and administration of a pharmaceutical agent before the infection of HIV out of a fear of possible infection.

Examples of the "other anti-HIV agents" and "other anti-HIV active substance" to be used for a multiple drug combination therapy include an anti-HIV antibody, an HIV vaccine, immunostimulants such as interferon and the like, a ribozyme against HIV, an HIV antisense drug, an HIV reverse transcriptase inhibitor, an HIV protease inhibitor, an HIV integrase inhibitor, an inhibitor of bond between a bond receptor (CD4, CXCR4, CCR5 and the like) of a host cell recognized by virus and the virus, and the like.

Specific examples of the HIV reverse transcriptase inhibitor include Retrovir(R) (zidovudine), Epivir(R) (lamivudine), Zerit(R) (sanilvudine), Videx(R) (didanosine), Hivid(R) (zalcitabine), Ziagen(R) (abacavir sulfate), Viramune(R) (nevirapine), Stocrin(R) (efavirenz), Rescriptor(R) (delavirdine mesylate), Combivir(R) (zidovudine+lamivudine), Trizivir (R) (abacavir sulfate+lamivudine+zidovudine), Coactinon (R) (emivirine), Phosphonovir(R), Coviracil(R), alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis (isopropoxycarbonyloxymethyl)ester fumarate), DPC-083 ((4S)-6-chloro-4-[(1E)-cyclopropylethenyl]-3,4-dihydro-4-trifluoromethyl-2(1H)-quinazolinone), DPC-961 ((4S)-6-chloro-4-(cyclopropylethynyl)-3,4-dihydro-4-(trifluoromethyl)-2(1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, UC-781, BCH-10618, DPC-083, Etravirine, BCH-13520, MIV-210, Abacavir sulfate/lamivudine, GW-5634, GW-695634 and the like, wherein (R) means a registered trademark (hereinafter the same) and the names of other pharmaceutical agents are general names.

Specific examples of the HIV protease inhibitor include Crixivan(R) (indinavir sulfate ethanolate), saquinavir, Invirase(R) (saquinavir mesylate), Norvir(R) (ritonavir), Viracept (R) (nelfinavir mesylate), lopinavir, Prozei(R) (amprenavir), Kaletra(R) (ritonavir+lopinavir), mozenavir dimesylate ([4R-(4α,5α,6β)]-1-3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy) phenylcarbonylamino]-1-oxabutyl]-4-[(2-methylphenyl) methylamino]carbonyl-4(R)-5,5-dimethyl-1,3-thiazole), BMS-232632 ((3S,8S,9S,12S)-3,12-bis(1,1-dimethylethyl)-8-hydroxy-4,11-dioxo-9-(phenylmethyl)-6-[[4-(2-pyridinyl) phenyl]methyl]-2,5,6,10,13-pentaazatetradecanedicarboxylic acid dimethyl ester), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir calcium, Darunavir, GW-0385, R-944, RO-033-4649, AG-1859 and the like.

The HIV integrase inhibitor is exemplified by S-1360, L-870810 and the like, the DNA polymerase inhibitor or DNA synthesis inhibitor is exemplified by Foscavir(R), ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β, 12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum alubm extract), Rubutecan and the like, the HIV antisense drug is exemplified by HGTV-43, GEM-92 and the like, the anti-HIV antibody or other antibody is exemplified by NM-01, PRO-367, KD-247, Cytolin(R), TNX-355 (CD4 antibody), AGT-1, PRO-140 (CCR5 antibody), Anti-CTLA-4 MAb and the like, the HIV vaccine or other vaccine is exemplified by ALVAC(R), AIDSVAX(R), Remune(R), HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, AntiTat, MVA-F6 Nef vaccine, HIV rev vaccine, C4-V3 peptide, p2249f, VIR-201, HGP-30W, TBC-3B, PARTICLE-3B and the like, Antiferon (interferon-α vaccine) and the like, the interferon or interferon agonist is exemplified by Sumiferon(R), MultiFeron(R), interferon-τ, Reticulose, Human leukocyte interferon alpha and the like, the CCR5 antagonist is exemplified by SCH-351125 and the like, the pharmaceutical agent acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl] naphthyl-2,5-dimethoxyphenyl-1,4-dihydrazone), T-1249, Synthetic Polymeric Construction No 3, pentafuside, FP-21399, PRO-542, Enfuvirtide and the like, the IL-2 agonist or antagonist is exemplified by interleukin-2, Imunace (R), Proleukin(R), Multikine(R), Ontak(R) and the like, the TNF-α antagonist is exemplified by Thalomid(R) (thalidomide), Remicade(R) (infliximab), curdlan sulfate and the like, the α-glucosidase inhibitor is exemplified by Bucast(R) and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z(R), Panavir(R), Coenzyme Q10 (2-deca(3-methyl-2-butenylene)-5,6-dimethoxy-3-methyl-p-benzoquinone) and the like, the cholinesterase inhibitor is exemplified by Cognex(R) and the like, and the immunomodulator is exemplified by Imunox(R), Prokine(R), Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602 and the like.

In addition, Neurotropin(R), Lidakol(R), Ancer 20(R), Ampligen(R), Anticort(R), Inactivin(R) and the like, PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (±)-FTC, Ushercell, D2S, BufferGel(R), VivaGel(R), Glyminox vaginal gel, sodium lauryl sulfate, 2F5, 2F5/2G12, VRX-496, Ad5gag2, BG-777, IGIV-C, BILR-255 and the like are exemplified.

As the "other anti-HIV agents" and "other anti-HIV active substance" to be used for a multiple drug combination therapy with the compound of the present invention, preferred are an HIV reverse transcriptase inhibitor and an HIV protease inhibitor. Two or three, or even a greater number of pharmaceutical agents can be used in combination, wherein a combination of pharmaceutical agents having different action mechanisms is one of the preferable embodiments. In addition, selection of pharmaceutical agents free of side effect duplication is preferable.

Specific combination of pharmaceutical agents include a combination of a group consisting of Efavirenz, Tenofovir, Emtricitabine, Indinavir, Nelfinavir, Atanazavir, Ritonavir+Indinavir, Ritonavir+Lopinavir, Ritonavir+Saquinavir, Didanosine+Lamivudine, Zidovudine+Didanosine, Stavudine+Didanosine, Zidovudine+Lamivudine, Stavudine+Lamivudine, and Emtriva and the quinolizinone compound [I] of the present invention (Guidelines for the Use of Anti-retroviral Agents in HIV-Infected Adults and Adolescents. Aug. 13, 2001). Particularly preferably, two drug therapy by the combination with Efavirenz, Indinavir, Nelfinavir, Tenofovir, Emtricitabine, Zidovudine and Lamivudine, and three drug therapy by the combination with Zidovudine+Lamivudine, Tenofovir+Lamivudine, Tenofovir+Zidovudine, Tenofovir+Efavirenz, Tenofovir+Nelfinavir, Tenofovir+Indinavir, Tenofovir+Emtricitabine, Emtricitabine+Lamivudine, Emtricitabine+Zidovudine, Emtricitabine+Efavirenz, Emtricitabine+Nelfinavir, Emtricitabine+Indinavir, Nelfinavir+Lamivudine, Nelfinavir+Zidovudine, Nelfinavir+Efavirenz, Nelfinavir+Indinavir, Efavirenz+Lamivudine, Efavirenz+Zidovudine, and Efavirenz+Indinavir can be mentioned.

Some examples of the production methods of the compounds used for embodiment of the present invention are shown in the following. However, the production method of the compounds of the present invention is not limited to these examples.

Even in the absence of description in the production method, efficient production can be afforded, where necessary, by introducing a protecting group into a functional group followed by deprotection in a subsequent step, by using a compound with a functional group as a precursor in each step and converting the group to a desired functional group in a suitable step, by exchanging the order of respective production methods and steps, or by other method.

The workup in each step can be applied by a typical method, wherein isolation and purification is performed by selecting or combining conventional methods as necessary, such as crystallization, recrystallization, distillation, partitioning, silica gel chromatography, preparative HPLC and the like.

Production Method 1
Production Method 1-1

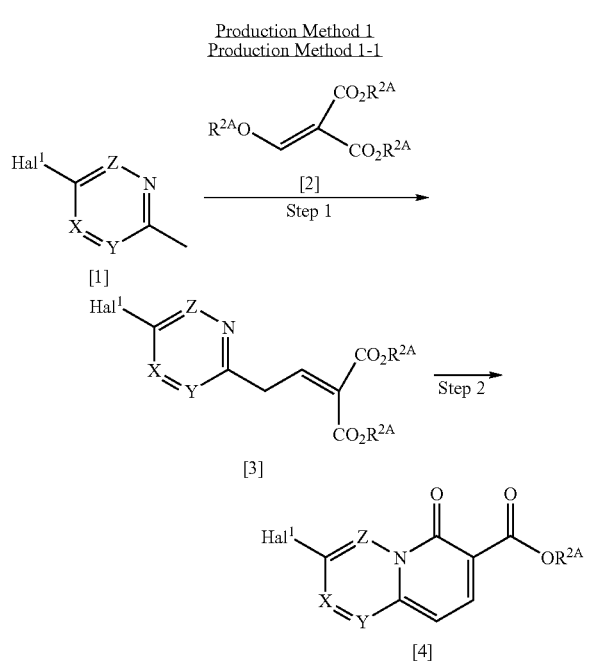

wherein $Hal^1$ is a halogen atom (e.g., bromine atom, iodine atom, chlorine atom etc.), preferably a bromine atom or an iodine atom, each $R^{2A}$ is independently the "$C_{1-4}$ alkyl group" defined above, preferably a methyl group or an ethyl group, and other symbols are as defined above.

<Step 1>

The compound [3] can be obtained by mixing compound [1] with a strong base (e.g., n-butyl lithium, lithium diisopropylamide, lithium hexamethyldisilazide, sodium hexamethyldisilazide etc.) in tetrahydrofuran under an argon or nitrogen atmosphere, under cooling to room temperature, and reacting the mixture with compound [2] under cooling to room temperature.

The respective compounds are preferably mixed gradually by dropwise addition under cooling.

<Step 2>

The compound [4] can be obtained by reacting compound [3] in a solvent under heating.

It is preferable to carry out the reaction in a solvent having a high boiling point, such as diphenyl ether, a mixture of diphenyl ether and biphenyl (e.g., Dowtherm A (trademark)), a mixed solvent thereof and the like, at 180-250° C.

The compound [4] can also be obtained by heating compound [3] in toluene under reflux.

Production Method 1-2

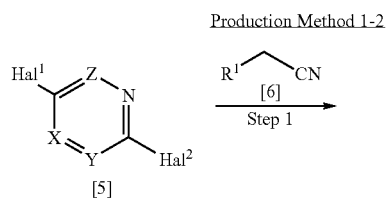

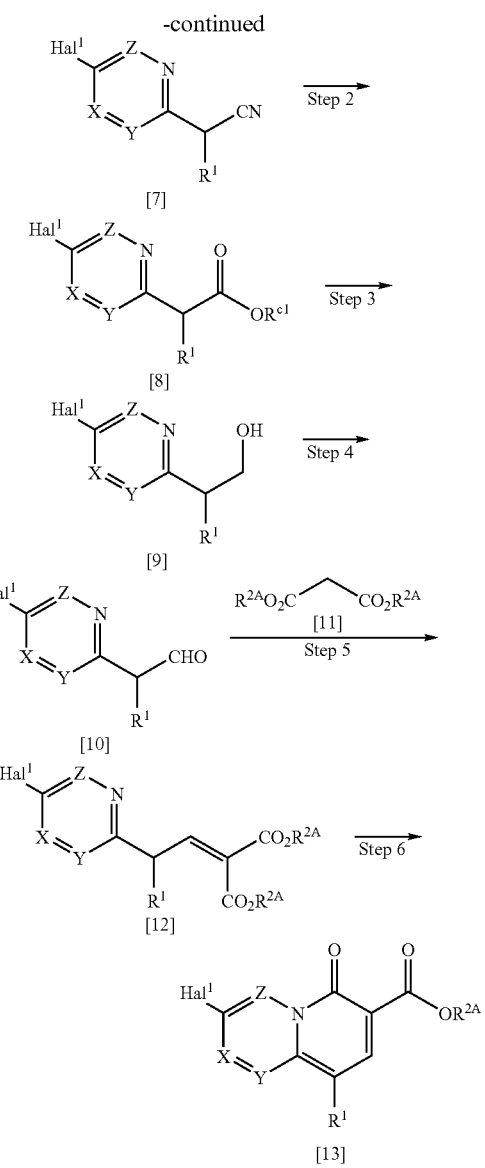

wherein $Hal^2$ is a halogen atom (e.g., fluorine atom, chlorine atom, bromine atom, iodine atom), preferably a fluorine atom or a chlorine atom (particularly fluorine atom), $R^{C1}$ is a hydrogen atom or an alkyl group, and other symbols are as defined above.

<Step 1>

The compound [7] can be obtained by mixing compound [6] with a strong base (e.g., n-butyl lithium, lithium diisopropylamide, lithium hexamethyldisilazide, sodium hexamethyldisilazide etc.) in tetrahydrofuran under an argon or nitrogen atmosphere, under cooling to room temperature, and reacting the mixture with compound [5] under cooling to room temperature.

The respective compounds are preferably mixed gradually by dropwise addition under cooling.

<Step 2>

The compound [8] can be obtained by converting the cyano group of compound [7] to carboxylic acid or a carboxylate by a conventional method.

For example, the compound [7] is heated under reflux in an alcohol (e.g., methanol, ethanol etc.) in the presence of an acid (e.g., concentrated sulfuric acid etc.) to give compound [8] ($R^{C1}$ is an alkyl group derived from the above-mentioned alcohol).

In addition, compound [8] ($R^{C1}$ is a hydrogen atom) can also be obtained by heating compound [7] in ethylene glycol at a high temperature in the presence of a base (e.g., sodium hydroxide, potassium hydroxide, lithium hydroxide etc.).

<Step 3>

The compound [9] can be obtained by reducing the —$CO_2R^{C1}$ group of compound [8] by a conventional method.

For example, compound [8] only needs to be reacted in a solvent under cooling to room temperature under an argon or nitrogen atmosphere in the presence of a reducing agent (e.g., diisobutylaluminum hydride, lithium aluminum hydride, lithium borohydride, sodium borohydride, diborane etc.).

As the solvent, ethers such as 1,4-dioxane, tetrahydrofuran and the like; alcohols such as methanol, ethanol and the like; halogenated solvents such as dichloromethane, chloroform and the like; hydrocarbons such as benzene, toluene and the like; a mixed solvent thereof; and the like can be mentioned.

When compound [8] is an carboxylic acid compound, for example, compound [9] can also be obtained by reacting compound [8] with a chloroformate (e.g., isobutyl chloroformate, isopropyl chloroformate etc.) in a halogenated solvent or tetrahydrofuran in the presence of triethylamine to give a mixed anhydride, and subjecting the mixed anhydride to the above-mentioned reaction.

<Step 4>

The compound [10] can be obtained by oxidizing the hydroxy group of compound [9] by a conventional method.

For example, compound [9] only needs to be oxidized using oxalyl chloride in dimethyl sulfoxide or a mixed solvent of dimethyl sulfoxide and dichloromethane, under cooling to room temperature, and then adding a tertiary amine (e.g., triethylamine etc.).

Dicyclohexylcarbodiimide, acid anhydride, sulfur trioxide, chlorine and the like may be used instead of oxalyl chloride.

<Step 5>

The compound [12] can be obtained by reacting compound [10] with compound [11] in a solvent under heating in the presence of a base or acid.

As the base, pyridine, piperidine, triethylamine, potassium carbonate, sodium carbonate, sodium hydroxide, potassium hydroxide, lithium hydroxide and the like can be mentioned, and as the acid, acetic acid, hydrochloric acid, nitric acid, sulfuric acid and the like can be mentioned.

As the solvent, alcohols such as methanol, ethanol, n-propanol, isopropanol and the like; hydrocarbons such as benzene, toluene, hexane, xylene and the like; halogenated solvents such as dichloromethane, chloroform, carbon tetrachloride, 1,2-dichloroethane and the like; ethers such as 1,4-dioxane, diethyl ether, 1,2-dimethoxyethane, tetrahydrofuran and the like; a mixed solvent thereof; and the like can be mentioned.

When piperidine is used as a base, acetic acid may be added to promote the reaction.

<Step 6>

The compound [13] can be obtained by reacting compound [12] in the same manner as in Production Method 1-1, Step 2.

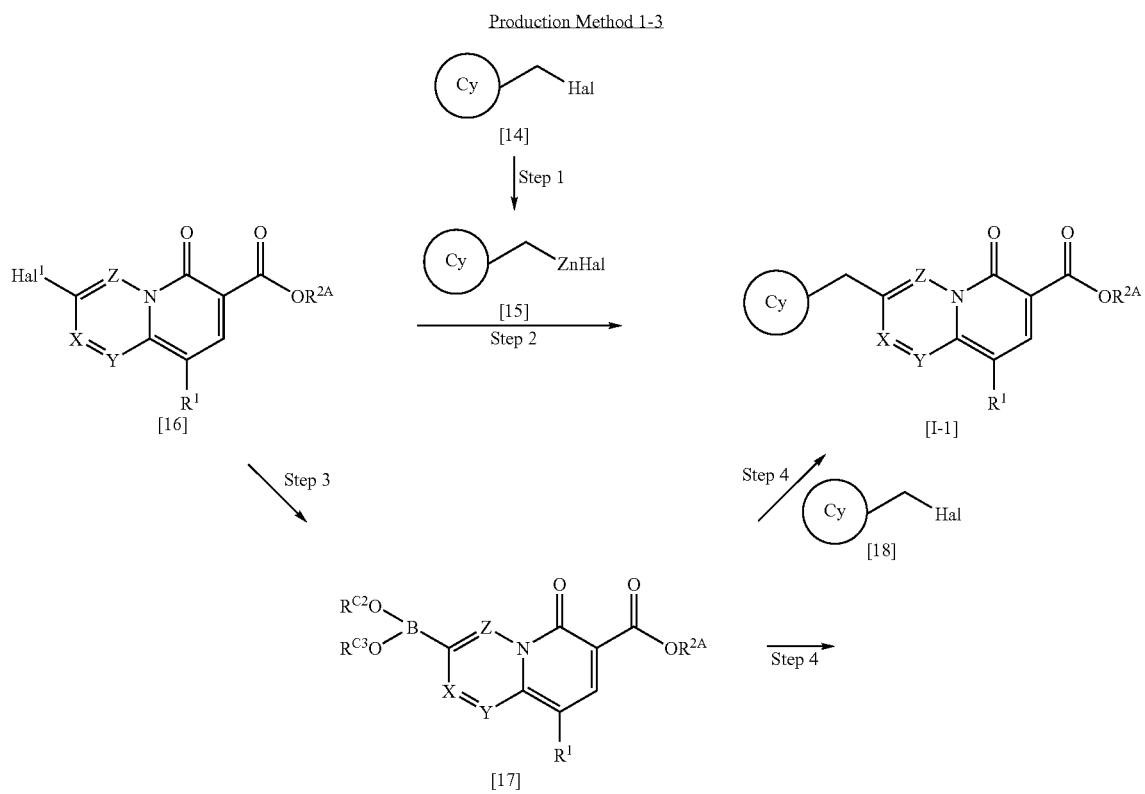

Production Method 1-3

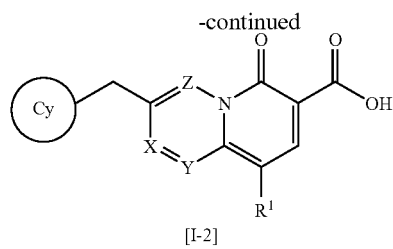

[I-2]

wherein Hal is a halogen atom (e.g., chlorine atom, bromine atom etc.), —B(OR^{C2})(OR^{C3}) is —B(OH)$_2$, —B(OMe)$_2$, —B(OiPro)$_2$, 4,4,5,5-tetramethyl-1,3,2-dioxaborolan-2-yl group and the like, and other symbols are as defined above.

<Step 1>

The compound [15] can be obtained by reacting a zinc powder and 1,2-dibromoethane in a solvent under heating under an argon or nitrogen atmosphere, reacting the resulting compound with trimethylsilyl chloride, and adding compound [14] solution to the reaction solution to allow reaction.

As the solvent, ethers such as 1,4-dioxane, 1,2-dimethoxyethane, tetrahydrofuran and the like; hydrocarbons such as benzene, toluene, hexane, xylene and the like; and the like can be mentioned.

<Step 2>

The compound [I-1] can be obtained by reacting compound [15] with compound [16] in a solvent in the presence of a catalyst, and where necessary, in the presence of a ligand (e.g., triphenylphosphine, tri(2-furyl)phosphine etc.), under an argon or nitrogen atmosphere under cooling to heating.

The compound [16] can be obtained in the same manner as in the above-mentioned Production Methods 1-1 and 1-2.

As the catalyst, palladium catalysts such as bis(dibenzylideneacetone) palladium, tris(dibenzylideneacetone) dipalladium, dichlorobis(triphenylphosphine) palladium, dichlorobis(benzonitrile) palladium, dichloroethylenediamine palladium, palladium acetate, tetrakis(triphenylphosphine) palladium and the like; nickel catalysts; and the like can be mentioned.

As the solvent, ethers such as 1,4-dioxane, 1,2-dimethoxyethane, tetrahydrofuran and the like; hydrocarbons such as benzene, toluene, hexane, xylene and the like; and the like can be mentioned.

<Step 3>

The compound [17] can be obtained by reacting compound [16] with boric acid or a borate under an argon or nitrogen atmosphere, under heating in the presence of a base and a catalyst.

As the borate, pinacolborane, bis(pinacolato)diboron and the like can be mentioned.

As the catalyst, palladium catalysts such as Pd(PPh$_3$)$_4$, PdCl$_2$(dppb), PdCl$_2$(dppf), PdCl$_2$(dppf)CH$_2$Cl$_2$, PdCl$_2$(PPh$_3$)$_2$, Pd(OAc)$_2$, PdCl$_2$, palladium black, palladium carbon and the like, and the like can be mentioned.

As the base, ethylenediamine, sodium carbonate, barium hydroxide, potassium phosphate, cesium carbonate, sodium hydrogencarbonate, sodium tert-butoxide, potassium tert-butoxide, triethylamine, potassium acetate and the like can be generally mentioned.

Furthermore, compound [16] may be reacted with a borate (e.g., triisopropyl borate, trimethyl borate etc.) in the presence of n-butyl lithium.

As the solvent, dimethyl sulfoxide, 1,4-dioxane, tetrahydrofuran, toluene, dimethoxyethane, water and the like can be mentioned.

<Step 4>

The compound [I-1] can be obtained by subjecting compound [17] and compound [18] to Suzuki reaction.

For example, compound [I-1] can be obtained by reacting compound [17] with compound [18] in a solvent (e.g., dimethylformamide, acetonitrile, an alcohol (methanol, ethanol), DME, tetrahydrofuran, toluene, water, a mixed solvent thereof etc.), in the presence of a palladium catalyst (e.g., tetrakistriphenylphosphine palladium, dichlorobistriphenylphosphine palladium (II), palladium acetate-triphenylphosphine etc.) or a nickel catalyst (e.g., nickel chloride, 1,3-bis(diphenylphosphino)propane nickel (II) chloride etc.) and a base (e.g., sodium carbonate, potassium carbonate, potassium hydrogencarbonate, sodium hydrogencarbonate, potassium phosphate, triethylamine, potassium fluoride, cesium fluoride, sodium hydrogenphosphate, cesium carbonate etc.) at room temperature to under heating.

The reactivity may be enhanced by the addition of lithium chloride and the like.

<Step 5>

The compound [I-2] can be obtained by subjecting compound [I-1] to hydrolysis in a solvent at room temperature to under heating under basic conditions with sodium hydroxide, potassium hydroxide, lithium hydroxide and the like, or acidic conditions with hydrochloric acid, sulfuric acid and the like.

As the solvent, alcohols such as methanol, ethanol, n-propanol, isopropanol and the like; hydrocarbons such as benzene, toluene, hexane, xylene and the like; ethers such as 1,4-dioxane, diethyl ether, 1,2-dimethoxyethane, tetrahydrofuran and the like; polar solvents such as dimethylformamide, dimethyl sulfoxide, acetonitrile and the like; water; a mixed solvent thereof; and the like can be mentioned.

Production Method 2

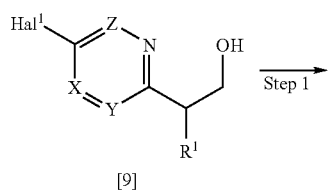

[9]

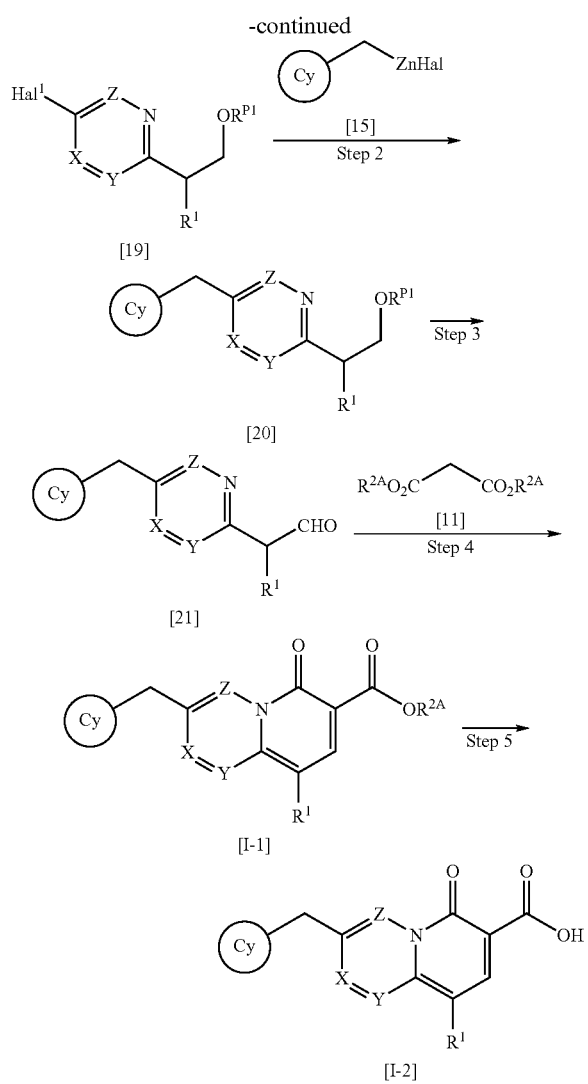

wherein $R^{P1}$ is a hydroxy-protecting group, and other symbols are as defined above.

<Step 1>

The compound [19] can be obtained by introducing a protecting group by a conventional method into the hydroxy group of compound [9] obtained in the same manner as in Production Method 1-2, Step 3.

As the hydroxy-protecting group, acetyl group, methoxycarbonyl group, methoxymethyl group, methoxyethoxymethyl group, trimethylsilyl group, tert-butyldimethylsilyl group, tert-butyldiphenylsilyl group, tetrahydropyran-2-yl group and the like can be mentioned.

When $R^{P1}$ is a tert-butyldimethylsilyl group, for example, compound [9] only needs to be reacted with tert-butyldimethylsilyl chloride in dimethylformamide or toluene at room temperature in the presence of imidazole.

When $R^{P1}$ is a methoxycarbonyl group, compound [9] only needs to be reacted with methyl chloroformate methyl in chloroform under cooling to room temperature in the presence of pyridine.

When $R^{P1}$ is a tetrahydropyran-2-yl group, compound [9] only needs to be reacted with dihydropyran in chloroform under cooling in the presence of pyridinium p-toluenesulfonate.

When $R^{P1}$ is a methoxymethyl group, dimethoxymethane and diphosphorus pentaoxide are added to compound [9] in chloroform under cooling, and the mixture only needs to be reacted at room temperature.

<Step 2>

The compound [20] can be obtained by reacting compound [15] obtained in the same manner as in Production Method 1-3, Step 1, with compound [19] in the same manner as in Production Method 1-3, Step 2.

<Step 3>

The compound [21] can be obtained by removing the hydroxy-protecting group from compound [20] by a conventional method and reacting the resulting compound in the same manner as in Production Method 1-2, Step 4.

For removal of the protecting group, for example, when $R^{P1}$ is a tert-butyldimethylsilyl group, the compound may be treated with tetrabutylammonium fluoride in tetrahydrofuran at room temperature, or may be treated with acetic acid-water-tetrahydrofuran at room temperature to under heating, or other method may be employed.

<Step 4>

The compound [I-1] can be obtained by reacting compound [21] with compound [11] in the same manner as in Production Method 1-2, Step 5.

Subsequently, a similar reaction as in Production Method 1-2, Step 6, may be carried out to promote the cyclization reaction.

<Step 5>

The compound [I-2] can be obtained by reacting compound [I-1] in the same manner as in Production Method 1-3, Step 5.

Production Method 3-1

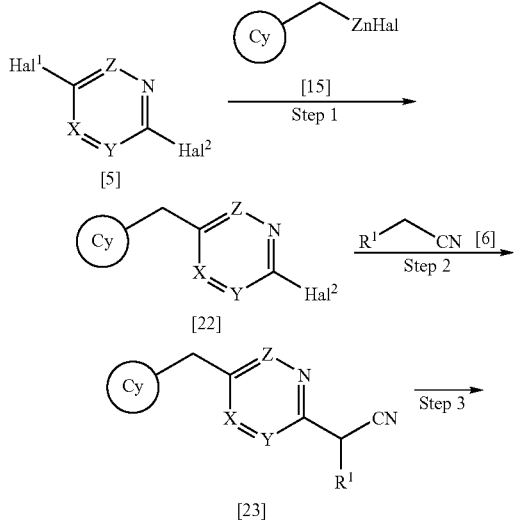

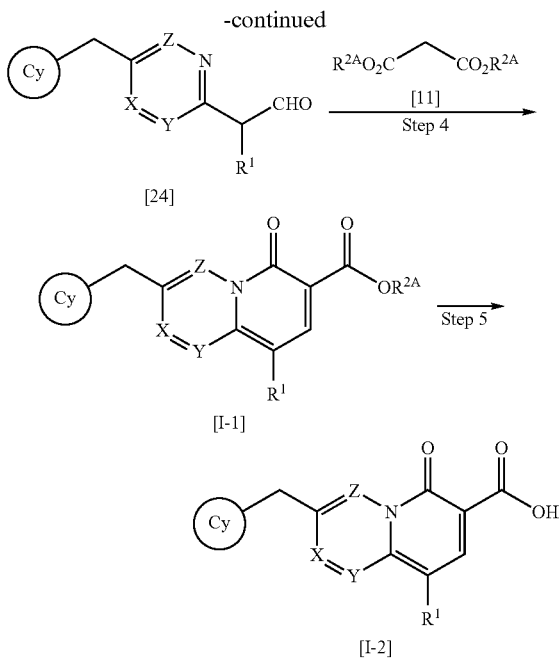

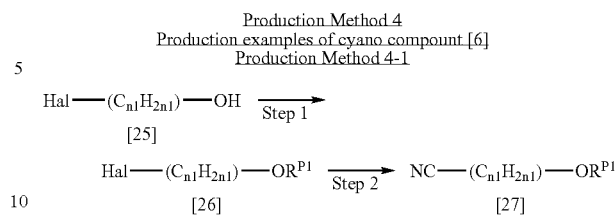

wherein each symbol is as defined above.

<Step 1>

The compound [22] can be obtained by reacting compound [15] obtained in the same manner as in Production Method 1-3, Step 1, with compound [5] in the same manner as in Production Method 1-3, Step 2.

<Step 2>

The compound [23] can be obtained by reacting compound [22] with compound [6] in the same manner as in Production Method 1-2, Step 1.

<Step 3>

The compound [24] can be obtained by converting the cyano group of compound [23] to a formyl group by a conventional method.

In this Step, conventional reduction methods such as reduction using a reducing agent (e.g., diisobutylaluminum hydride etc.), catalytic reduction with hydrogen gas in the presence of a metal catalyst (e.g., palladium carbon, Raney nickel etc.) at room temperature to refluxing temperature and the like can be employed.

For example, compound [24] can be obtained by reacting compound [23] by adding a metal catalyst (e.g., Raney nickel etc.) and sodium phosphinate under cooling in an organic solvent such as a mixed solvent of pyridine, water and acetic acid, and the like.

<Step 4>

The compound [I-1] can be obtained by reacting compound [24] with compound [11] in the same manner as in Production Method 1-2, Step 5.

A similar reaction as in Production Method 1-2, Step 6, may be carried out to promote the cyclization reaction.

<Step 5>

The compound [I-2] can be obtained by reacting compound [I-1] in the same manner as in Production Method 1-3, Step 5.

Production Method 4
Production examples of cyano compount [6]
Production Method 4-1 wherein n1 is an integer of 1 to 10, and other symbols are as defined above.

In the above-mentioned Production Method, the hydroxy-protecting group $R^{P1}$ can be removed by a conventional method at a suitable point in time.

For example, when $R^{P1}$ is a tetrahydropyran-2-yl group, it can be removed by a reaction with p-toluenesulfonic acid or hydrochloric acid in an alcohol (e.g., methanol, ethanol etc.) at room temperature to under heating.

<Step 1>

The compound [26] can be obtained by reacting compound [25] in the same manner as in Production Method 2, Step 1.

<Step 2>

The compound [27] can be obtained by cyanating compound [26] by a conventional method.

For example, the compound [27] can be obtained by reacting compound [26] with a cyanating agent (e.g., potassium cyanide, sodium cyanide etc.) or cyanotrimethylsilane and tetrabutylammonium fluoride in a solvent (e.g., acetonitrile, tetrahydrofuran, dimethylformamide, dimethyl sulfoxide etc.) under heating.

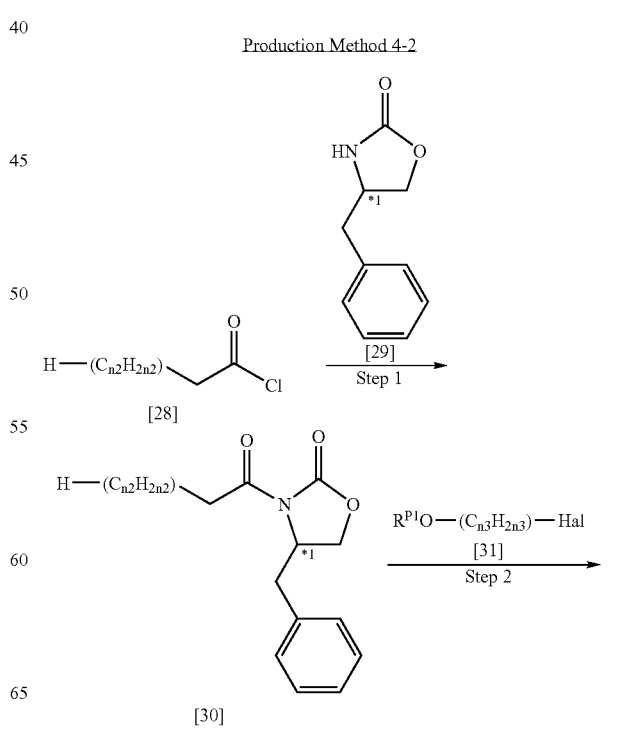

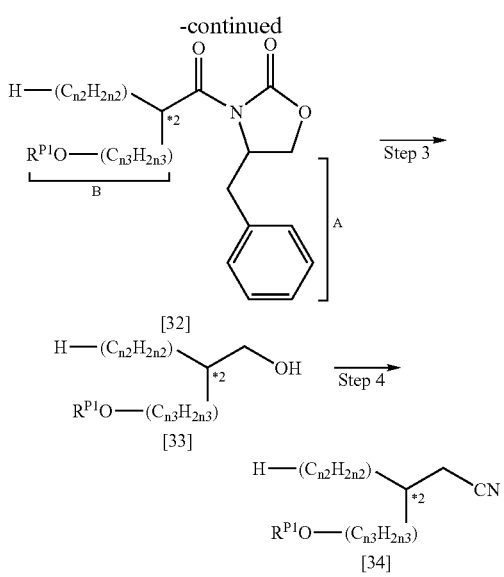

wherein n2 and n3 are each independently an integer of 1 or above, n2+n3 is an integer of 2 to 10, the moiety A (benzyl group) and moiety B (—($C_{n3}H_{2n3}$)—$OR^{P1}$) are inverse configurations to each other, and when, for example, compound [34] wherein the moiety B is down is to be obtained, the moiety A should be up (in this case, compound [29] is an R form), and other symbols are as defined above.

This Production Method can be performed in the same manner as the methods described in Helvetica Chimica Acta, 2003, 86, 2848; Journal of the American Chemical Society, 1990, 112, 5290; and Journal of the American Chemical Society, 1982, 104, 1737.

<Step 1>

The compound [30] can be obtained by mixing compound [29] with a strong base (e.g., n-butyl lithium, lithium diisopropylamide, lithium hexamethyldisilazide etc.) in tetrahydrofuran under an argon or nitrogen atmosphere, under cooling to room temperature, and reacting the mixture with compound [28] under cooling to room temperature.

The respective compounds are preferably mixed gradually by dropwise addition under cooling.

Moreover, compound [28] may be reacted with compound [29] in an ether (e.g., dioxane, tetrahydrofuran etc.) or a halogenated solvent (e.g., dichloromethane, chloroform etc.) under cooling to room temperature, in the presence of triethylamine and dimethylaminopyridine.

<Step 2>

The compound [32] can be obtained by reacting compound [30] with compound [31] in a solvent under cooling to room temperature in the presence of titanium tetrachloride and diisopropylethylamine.

The respective compounds are preferably mixed by dropwise addition under cooling.

As the solvent, hydrocarbons such as toluene, xylene and the like; halogenated solvents such as dichloromethane, chloroform, carbon tetrachloride, 1,2-dichloroethane and the like; and the like can be mentioned.

At this point, the hydroxy-protecting group of compound [32] may also be converted to a protecting group more suitable for the next and the following Steps by a conventional method.

<Step 3>

The compound [33] can be obtained by reducing compound [32] with lithium aluminum hydride in a solvent under cooling to room temperature, under an argon or nitrogen atmosphere.

As the solvent, ethers such as dioxane, tetrahydrofuran and the like; alcohols such as methanol, ethanol and the like; halogenated solvents such as dichloromethane, chloroform and the like; hydrocarbons such as benzene, toluene and the like; a mixed solvent thereof; and the like can be mentioned.

<Step 4>

The compound [34] can be obtained by converting the hydroxy group of compound [33] to a leaving group (e.g., methanesulfonyloxy group etc.) by a conventional method, and cyanating the resulting compound in the same manner as in Production Method 4-1, Step 2.

Production Method 5 Production examples of compound [5]

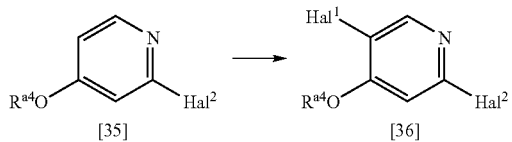

wherein each symbol is as defined above.

As used herein, $Hal^1$ is preferably bromine or iodine and compound [36] can be obtained by halogenating compound [35] by a conventional method.

For example, the compound [36] can be obtained by reacting compound [35] with a halogenating agent (e.g., N-bromosuccinimide, N-iodosuccinimide etc.) at room temperature to under heating in a solvent (e.g., trifluoromethanesulfonic acid, acetic acid, concentrated sulfuric acid, dimethylformamide etc.).

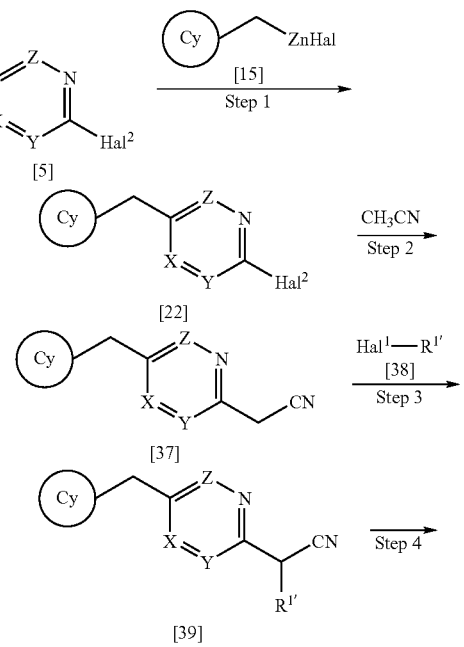

<Step 4>

The compound [40] can be obtained by reacting compound [39] in the same manner as in Production Method 3-1, Step 3.

<Step 5>

The compound [I-3] can be obtained by reacting compound [40] with compound [11] in the same manner as in Production Method 1-2, Step 5.

A similar reaction as in Production Method 1-2, Step 6, may be carried out to promote the cyclization reaction.

<Step 6>

The compound [I-4] can be obtained by reacting compound [I-3] in the same manner as in Production Method 1-3, Step 5.

wherein $R^{1'}$ is a $C_{1-10}$ alkyl group optionally substituted by 1 to 3 substituents selected from a halogen atom and the above-mentioned group B, and other symbols are as defined above.

<Step 1>

The compound [22] can be obtained by reacting compound [5] with compound [15] in the same manner as in Production Method 1-3, Step 2.

<Step 2>

The compound [37] can be obtained by reacting compound [22] with acetonitrile in the same manner as in Production Method 1-2, Step 1.

Alternatively, NC—CH$_2$—COOR$^{a13}$ (R$^{a13}$ is an alkyl group (e.g., methyl group, ethyl group, tert-butyl group etc.)) may be used for the reaction instead of acetonitrile and then the —COOR$^{a13}$ group may be removed.

<Step 3>

The compound [39] can be obtained by reacting compound [37] with compound [38] in a solvent under heating in the presence of a base.

As the base, potassium carbonate, sodium carbonate, sodium hydroxide, potassium hydroxide, lithium hydroxide and the like can be mentioned.

As the solvent, alcohols such as methanol, ethanol, n-propanol, isopropanol and the like; hydrocarbons such as benzene, toluene, hexane, xylene and the like; halogenated solvents such as dichloromethane, carbon tetrachloride, 1,2-dichloroethane and the like; ethers such as 1,4-dioxane, diethyl ether, 1,2-dimethoxyethane, tetrahydrofuran and the like; polar solvents such as dimethylformamide, dimethyl sulfoxide, acetonitrile and the like; water; a mixed solvent thereof; and the like can be mentioned.

wherein n4 is an integer of 1 to 10, and other symbols are as defined above.

The compound [I-6] can be obtained by reacting compound [I-5] obtained in the above-mentioned Production Method with compound [41] in a solvent such as ether (e.g., 1,4-dioxane, tetrahydrofuran etc.); hydrocarbon (e.g., toluene, xylene etc.) and the like, in the presence of triethylamine and diphenylphosphorylazide.

The compound [42] can also be obtained by isolation before complication of the reaction.

Production Method 6-2

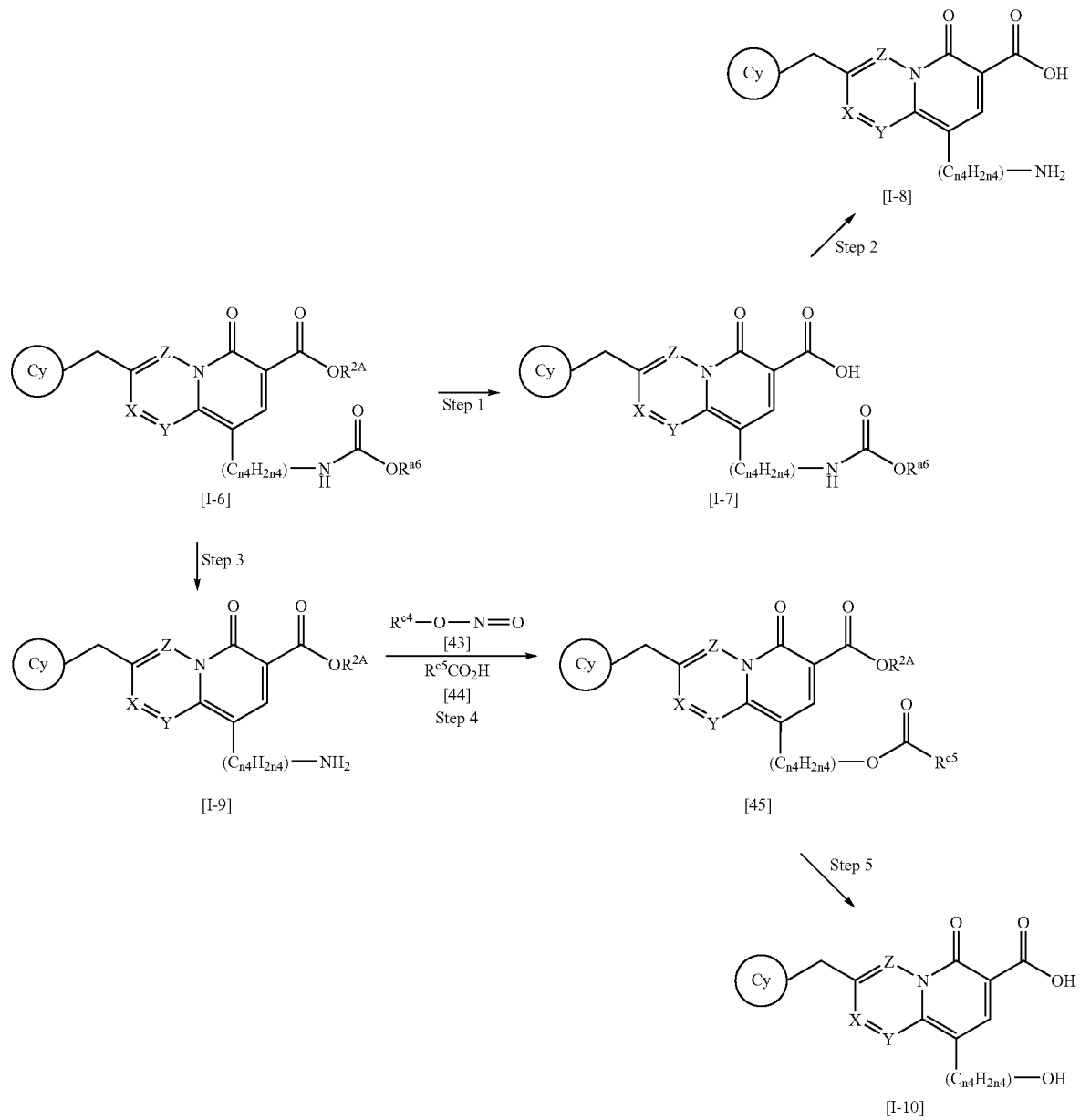

wherein $R^{C4}$ is an alkyl group (e.g., methyl group, ethyl group, tert-butyl group etc., preferably tert-butyl group), a —$COR^{C5}$ group is an acyl group (e.g., acetyl group, trifluoromethylcarbonyl group, benzoyl etc.) that can be removed from the hydroxy group, and other symbols are as defined above.

<Step 1>

The compound [I-7] can be obtained by reacting compound [I-6] in the same manner as in Production Method 1-3, Step 5.

<Step 2>

The compound [I-8] can be obtained by treating compound [I-7] by a conventional method.

When $R^{a6}$ is a tert-butyl group, for example, methods such as a treatment with trifluoroacetic acid at room temperature; a treatment with hydrogen chloride-ethyl acetate solution in ethyl acetate or methanol solution at room temperature; a treatment with hydrochloric acid in tetrahydrofuran at room temperature; a treatment with hydrogen chloride-dioxane in methanol at room temperature, and the like can be used.

<Step 3>

The compound [I-9] can be obtained by reacting compound [I-6] in the same manner as in Production Method 6-2, Step 2.

<Step 4>

The compound [45] can be obtained by reacting compound [I-9] with compound [43] and compound [44] in a solvent (e.g., toluene etc.) at room temperature to under heating.

<Step 5>

The compound [I-10] can be obtained by reacting compound [45] in the same manner as in Production Method 1-3, Step 5.

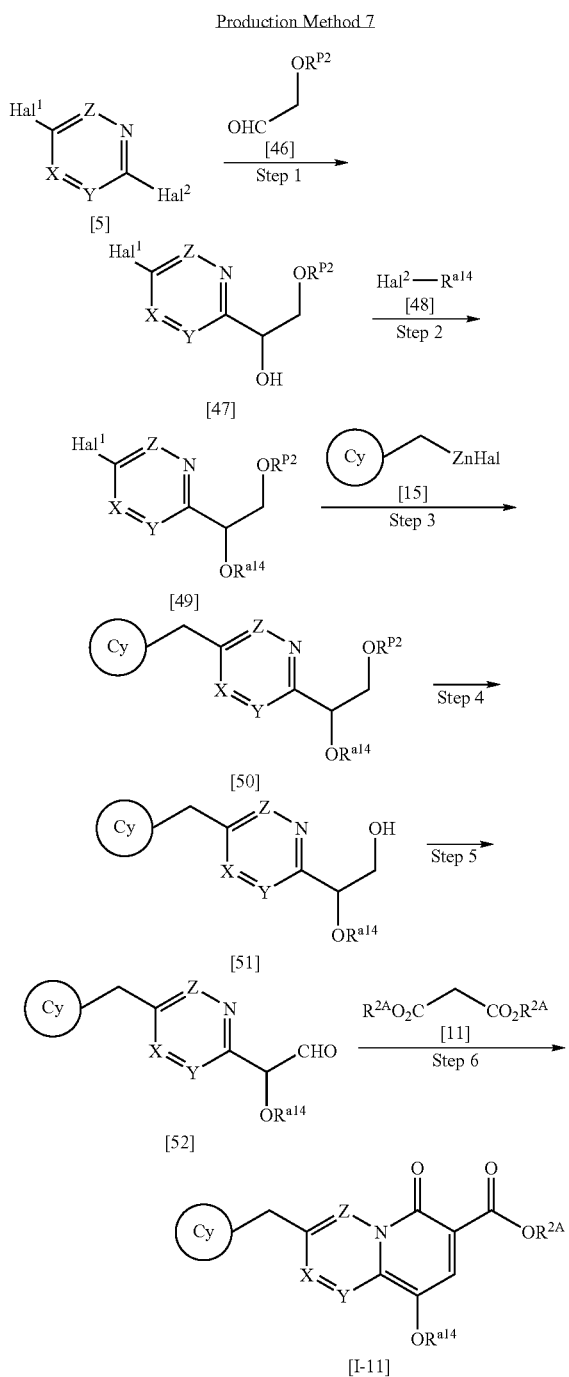

wherein $R^{P2}$ is a hydroxy-protecting group, $R^{a14}$ is —W—$OR^{a5}$ or —$R^{a4}$, and other symbols are as defined above.

<Step 1>

The compound [47] can be obtained by reacting compound [5] with compound [46] using a Grignard reagent (e.g., isopropyl magnesium chloride etc.) in a solvent under an argon or nitrogen atmosphere under cooling to room temperature.

As the solvent, ethers such as 1,4-dioxane, 1,2-dimethoxyethane, tetrahydrofuran and the like; hydrocarbons such as benzene, toluene, hexane, xylene and the like; and the like can be mentioned.

<Step 2>

The compound [49] can be obtained by reacting compound [47] with compound [48] in a solvent in the presence of a tertiary amine (e.g., triethylamine, diisopropylethylamine, N-methylmorpholine etc.), an inorganic base (e.g., potassium carbonate, sodium carbonate etc.) and the like under heating.

As the solvent, halogenated solvents such as dichloromethane, chloroform, carbon tetrachloride, tetrachloroethylene and the like; hydrocarbons such as benzene, toluene, hexane, xylene and the like; ethers such as 1,4-dioxane, diethyl ether, 1,2-dimethoxyethane, tetrahydrofuran and the like; polar solvents such as dimethylformamide, dimethyl sulfoxide, acetonitrile, acetone and the like; and the like can be mentioned.

<Step 3>

The compound [50] can be obtained by reacting compound [49] with compound [15] in the same manner as in Production Method 1-3, Step 2.

<Step 4>

The compound [51] can be obtained by removing the hydroxy-protecting group $R^{P2}$ from compound [50] by a conventional method as in Production Method 2, Step 3.

$R^{P2}$ is preferably one that does not show a marked effect on $R^{a14}$ and, for example, tert-butyldimethylsilyl group and the like can be mentioned.

<Step 5>

The compound [52] can be obtained by reacting compound [51] in the same manner as in Production Method 1-2, Step 4.

<Step 6>

The compound [I-11] can be obtained by reacting compound [52] with compound [11] in the same manner as in Production Method 3-1, Step 4.

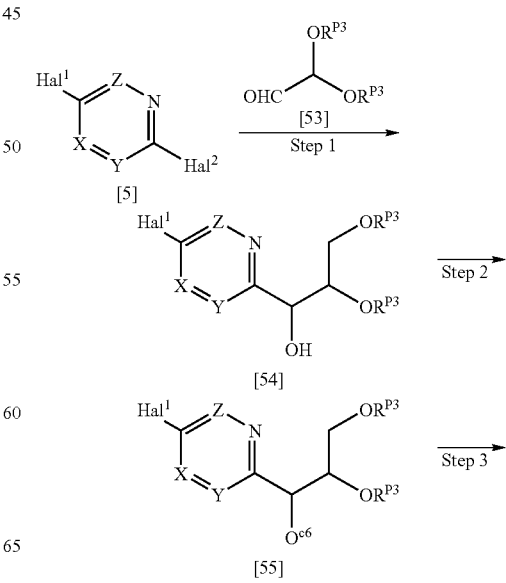

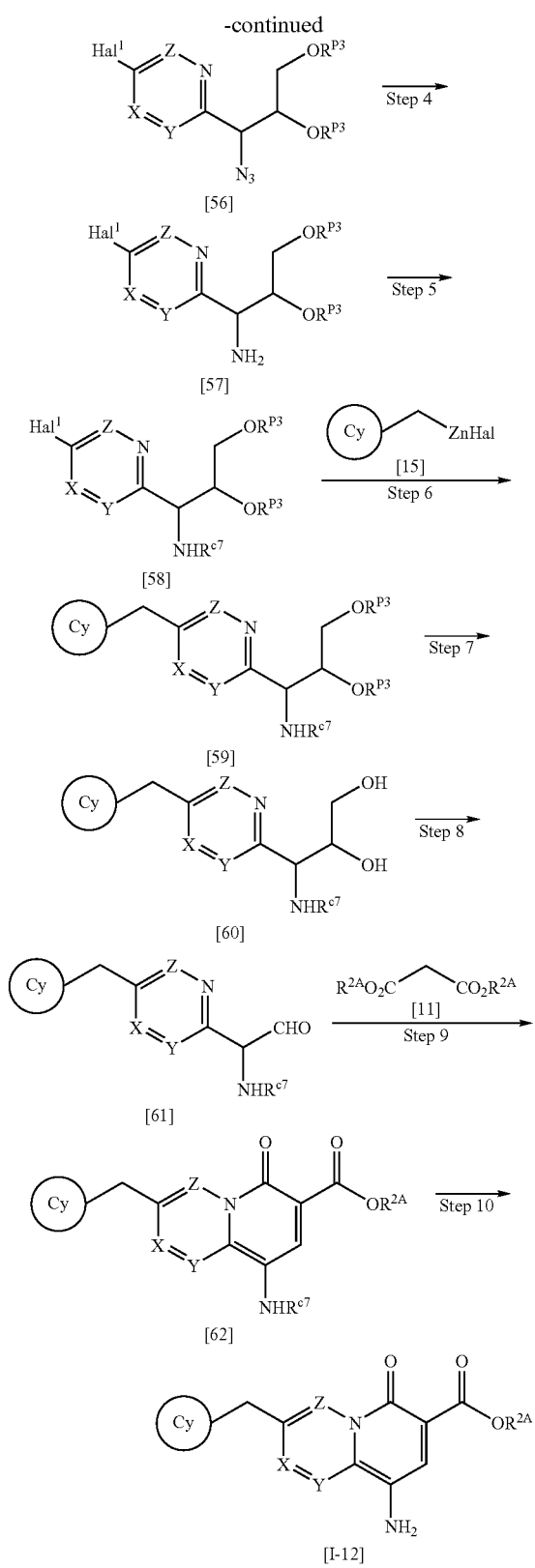

wherein $R^{P3}$ is a hydroxy-protecting group such as an alkyl group (e.g., methyl group, ethyl group etc.), or an acetonido group or methyleneacetal formed by two —$OR^{P3}$ in combination and the like, —$OR^{c6}$ is a leaving group (e.g., mesyloxy group etc.), $R^{c7}$ is an amino-protecting group, and other symbols are as defined above.

<Step 1>

The compound [54] can be obtained by reacting compound [5] with compound [53] in the same manner as in Production Method 7, Step 1.

<Step 2>

The compound [55] can be obtained by converting the hydroxy group of compound [54] to a leaving group by a conventional method.

When, for example, $R^{c6}$ is a mesyl group, methods such as a treatment with mesyl chloride in a solvent (e.g., tetrahydrofuran, chloroform etc.) under argon atmosphere in the presence of a base (e.g., triethylamine, pyridine, dimethylaminopyridine etc.), and the like can be employed.

<Step 3>

The compound [56] can be obtained by reacting compound [55] with metal azide (e.g., lithium azide etc.) in dimethyl sulfoxide under argon atmosphere.

<Step 4>

The compound [57] can be obtained by reacting compound [56] in an ether (e.g., 1,4-dioxane, tetrahydrofuran etc.) and water in the presence of triphenylphosphine resin.

<Step 5>

The compound [58] can be obtained by introducing a protecting group into the amino group of compound [57] by a conventional method.

As the amino-protecting group, tert-butoxycarbonyl group, benzyloxycarbonyl group, trifluoroacetyl group and the like can be mentioned. When, for example, $R^{c7}$ is a tert-butoxycarbonyl group, the compound may be treated with tert-butoxycarbonyl chloride or di-tert-butyl dicarbonate in tetrahydrofuran at room temperature to under cooling.

<Step 6>

The compound [59] can be obtained by reacting compound [58] with compound [15] in the same manner as in Production Method 1-3, Step 2.

<Step 7>

The compound [60] can be obtained by removing the hydroxy-protecting group from compound [59] by a conventional method.

When, for example, two —$OR^{P3}$ form an acetonido group in combination, the compound may be treated with trifluoroacetic acid in methanol and water under heating, or treated with acetic acid-water under heating.

<Step 8>

The compound [61] can be obtained by treating compound [60] with a periodate (e.g., sodium periodate, potassium periodate etc.) under cooling.

<Step 9>

The compound [62] can be obtained by reacting compound [61] with compound [11] in the same manner as in Production Method 1-2, Step 5.

A similar reaction as in Production Method 1-2, Step 6, may be carried out to promote the cyclyzing reaction.

<Step 10>

The compound [I-12] can be obtained by removing the amino-protecting group from compound [62] by a conventional method.

For example, when $R^{c7}$ is a tert-butoxycarbonyl group, the protecting group can be removed by methods such as a treat- Production Method 9

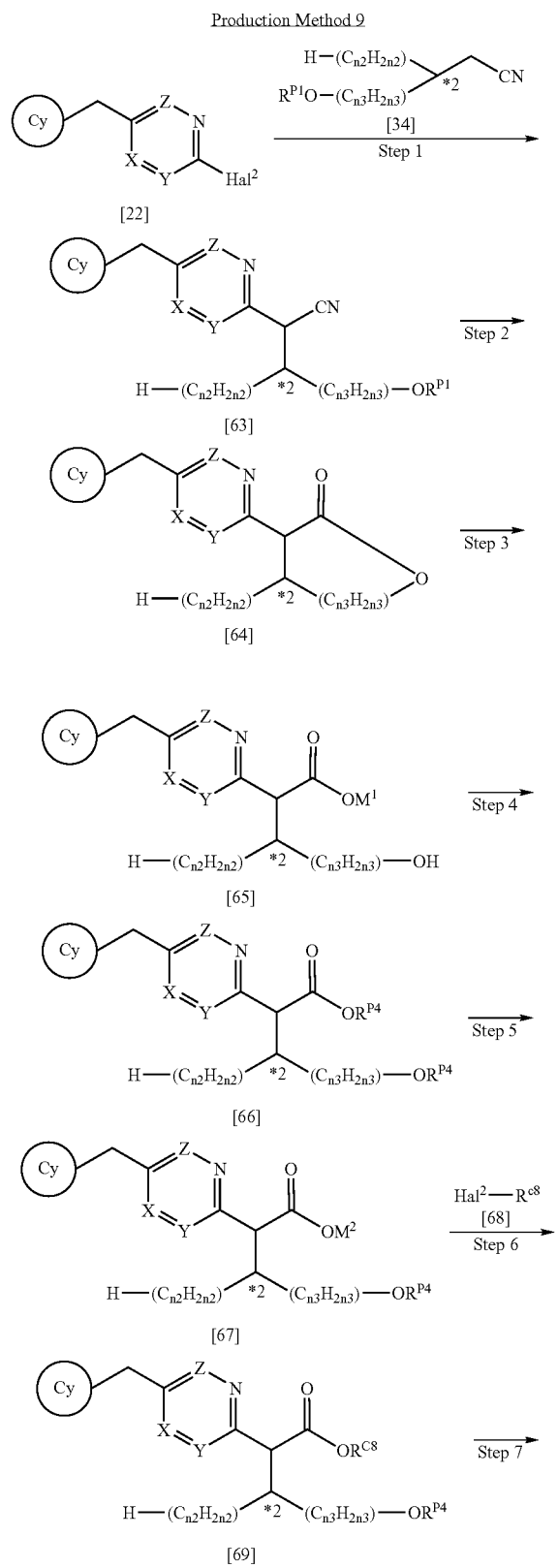

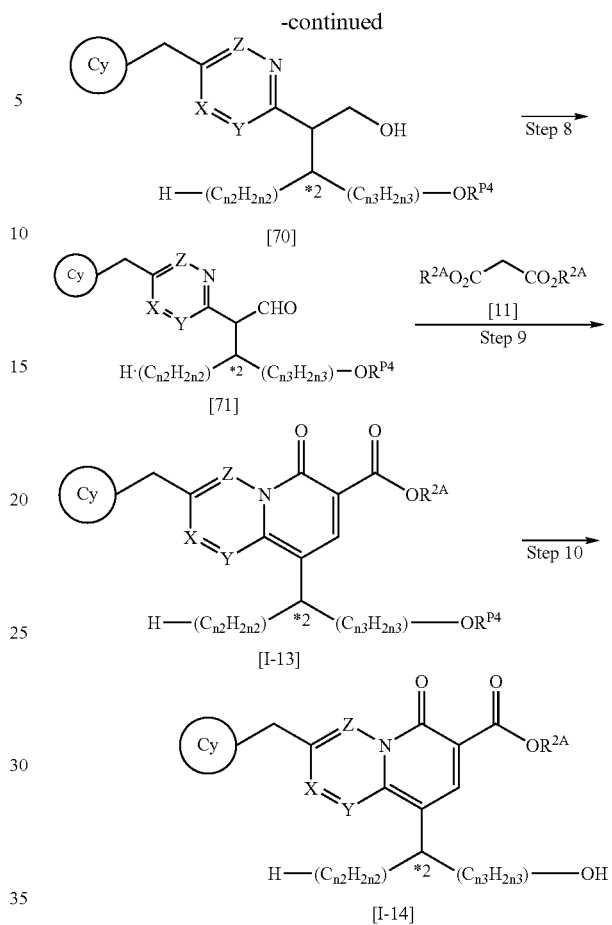

wherein $M^1$ is an alkali metal (e.g., sodium, potassium, lithium etc., preferably sodium), $M^2$ is an alkali metal (e.g., sodium, potassium, lithium etc., preferably lithium), $R^{P4}$ is a hydroxy-protecting group, $R^{c8}$ is an alkyl group (e.g., methyl group, ethyl group etc.), and other symbols are as defined above.

<Step 1>

The compound [63] can be obtained by reacting compound [22] with compound [34] in the same manner as in Production Method 1-2, Step 1.

<Step 2>

The compound [64] can be obtained by subjecting compound [63] to hydrolysis in an alcohol (e.g., methanol, ethanol etc.) under the acidic conditions with concentrated hydrochloric acid, concentrated sulfuric acid and the like.

By the hydrolysis using a base such as sodium hydroxide, potassium hydroxide, lithium hydroxide and the like in ethylene glycol, compound [65] or compound [65] wherein the hydroxy group is protected by $R^{P1}$ can also be obtained from compound [63].

<Step 3>

The compound [65] can be obtained by reacting compound [64] in a solvent in the presence of a base.

As the base, sodium hydrogencarbonate, potassium carbonate, sodium carbonate, sodium hydroxide, potassium hydroxide, lithium hydroxide and the like can be mentioned.

As the solvent, ethers such as dioxane, tetrahydrofuran and the like; alcohols such as methanol, ethanol and the like; water; a mixed solvent thereof; and the like can be mentioned.

<Step 4>

The compound [66] can be obtained by introducing a protecting group into the hydroxy group of compound [65] by a conventional method.

The protecting group to be introduced here is preferably one that can be removed by high load or under special conditions to give compound [70] and, for example, tert-butyldimethylsilyl group and the like can be mentioned.

<Step 5>

The compound [67] can be obtained by hydrolyzing, under basic conditions, the group introduced into the carboxyl group of compound [66] in Step 4.

For example, the reaction only needs to be carried out in the same manner as in Production Method 9, Step 3, and the conditions that do not affect $R^{P4}$ are preferable.

<Step 6>

The compound [69] can be obtained by reacting compound [67] with compound [68] in a solvent.

<Step 7>

The compound [70] can be obtained by reacting compound [69] in the same manner as in Production Method 1-2, Step 3.

<Step 8>

The compound [71] can be obtained by reacting compound [70] in the same manner as in Production Method 1-2, Step 4.

<Step 9>

The compound [I-13] can be obtained by reacting compound [71] with compound [11] in the same manner as in Production Method 1-2, Step 5.

Subsequently, a similar reaction as in Production Method 1-2, Step 6, may be carried out to promote the cyclyzing reaction.

<Step 10>

The compound [I-14] can be obtained by removing the hydroxy-protecting group from compound [I-13] by a conventional method.

Production Method 10

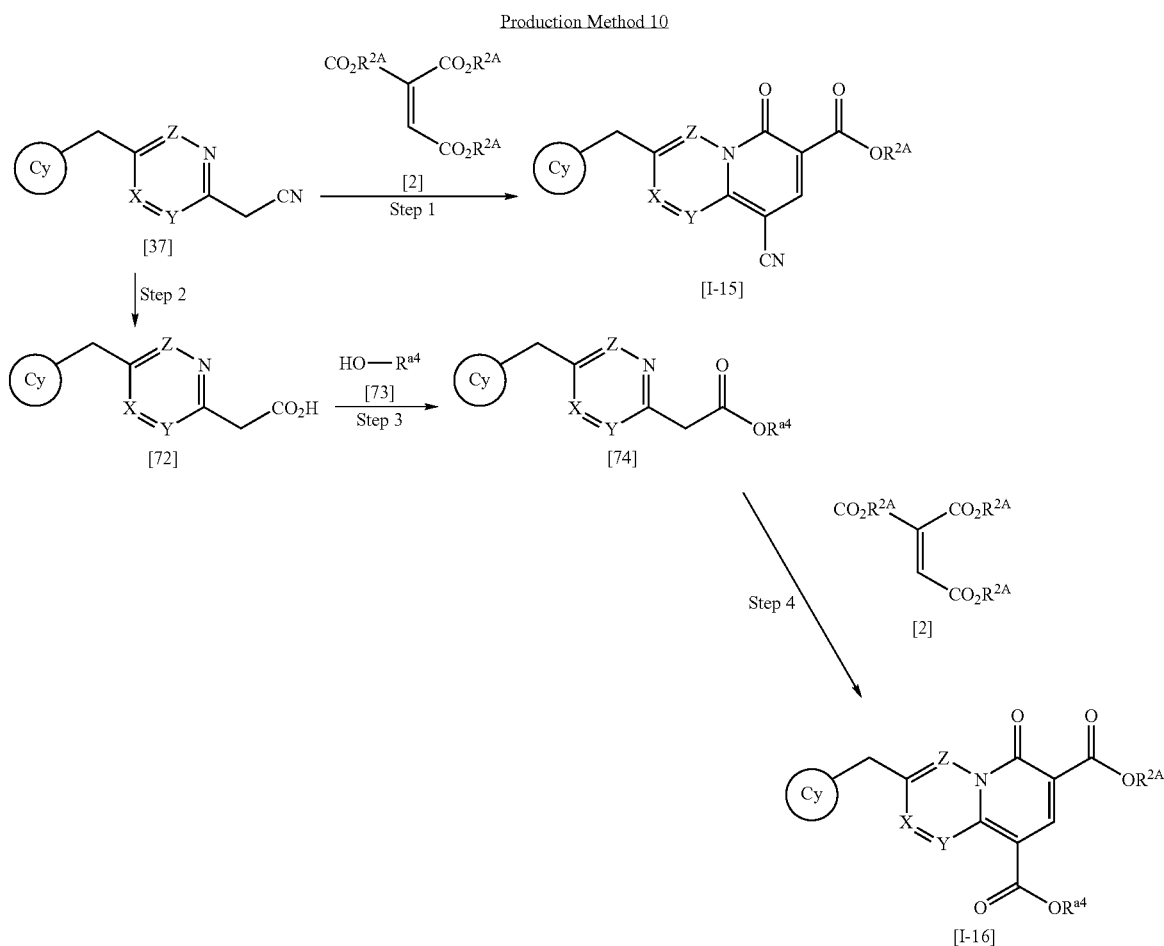

As the solvent, alcohols such as methanol, ethanol, n-propanol, isopropanol and the like; hydrocarbons such as benzene, toluene, hexane, xylene and the like; ethers such as 1,4-dioxane, diethyl ether, 1,2-dimethoxyethane, tetrahydrofuran and the like; polar solvents such as dimethylformamide, dimethyl sulfoxide, acetonitrile and the like; and the like can be mentioned.

wherein each symbol is as defined above.

<Step 1>

The compound [I-15] can be obtained by reacting compound [37] with compound [2] in the same manner as in Production Method 1-1.

<Step 2>

The compound [72] can be obtained by reacting compound [37] in the presence of a base under heating in the same manner as in Production Method 1-2, Step 2.

Alternatively, compound [74] can be directly obtained by reacting compound [37] in alcohol in the presence of an acid, in the same manner as in Production Method 1-2, Step 2.

<Step 3>

The compound [74] can be obtained by subjecting compound [72] and compound [73] to esterification by a conventional method.

For example, compound [72] is reacted with compound [73] in dichloromethane under cooling in the presence of 1,3-dicyclohexylcarbodiimide and 4-dimethylaminopyridine.

<Step 4>

The compound [I-16] can be obtained by reacting compound [74] with compound [2] in the same manner as in Production Method 1-1.

EXAMPLES

The quinolizinone compound represented by the formula [I] of the present invention, pharmaceutically acceptable salt thereof and production method thereof are concretely explained by referring to Examples, which are not to be construed as limitative.

Example 1

Step 1

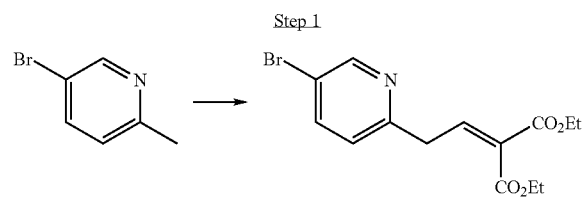

To a solution of lithium diisopropylamide mono (tetrahydrofuran) (1.5 M cyclohexane solution) (3.2 ml, 4.8 mmol) in tetrahydrofuran (2 ml) was added dropwise a solution of 5-bromo-2-methylpyridine (750 mg, 4.4 mmol) in tetrahydrofuran (8 ml) under an argon atmosphere at not more than −60° C. The mixture was stirred at the same temperature for 1 hr, and diethyl ethoxymethylenemalonate (881 μl, 4.4 mmol) was added dropwise at −60° C. The mixture was allowed to warm to −20° C. and stirred for 1 hr, and saturated brine and ethyl acetate were added to the mixture to partition the layers. The aqueous layer was extracted with ethyl acetate, the organic layer was washed with saturated brine, and dried over sodium sulfate. After filtration, the filtrate was concentrated under reduced pressure and the residue was roughly purified by silica gel chromatography (hexane:ethyl acetate=5:1) to give the object product as a yellow oil (536 mg).

Step 2

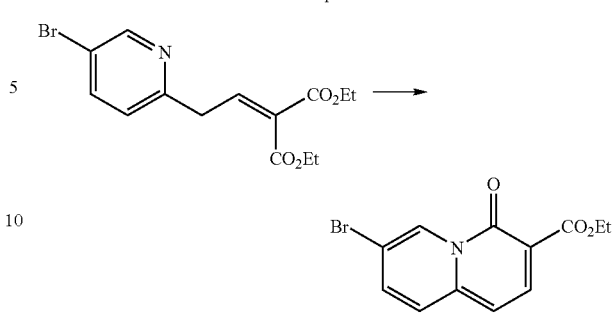

The compound (536 mg) obtained in Step 1 was dissolved in Dowtherm A (3 ml), and the mixture was stirred with heating at 200° C. for 2 hr. After cooling, hexane was added to the reaction mixture, and the mixture was stirred at room temperature for 20 min. After filtration, the solid was dried under reduced pressure to give the object product as a brown solid (23 mg, yield 18%, 2 steps).

$^1$H NMR (DMSO-$d_6$ 400 MHz) (δ) ppm: 1.42 (3H, t, J=7.1 Hz), 4.42 (2H, q, J=7.1 Hz), 6.65 (1H, d, J=8.4 Hz), 7.45 (1H, d, J=9.3 Hz), 7.61 (1H, dd, J=2.0, 9.2 Hz), 8.41 (1H, d, J=8.4 Hz), 9.50 (1H, s)

MS (ESI): M+ 296

Step 3

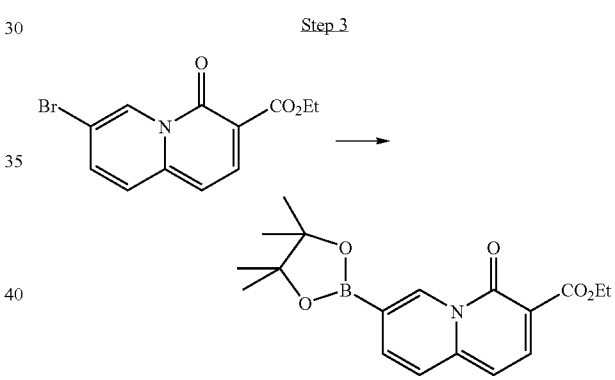

Under an argon atmosphere, to a mixture of bis(pinacolato) diboron (75 mg, 0.29 mmol), potassium acetate (79 mg, 0.80 mmol) and PdCl$_2$(dppf) (7 mg, 0.0086 mmol) were added dimethyl sulfoxide (1 ml) and the compound (79 mg, 0.27 mmol) obtained in Step 2, and the mixture was stirred with heating at 80° C. for 3 hr. Water and ethyl acetate were added to the reaction mixture to partition into layers. The organic layer was washed with water and saturated brine, and dried over magnesium sulfate. After filtration, the filtrate was concentrated under reduced pressure to give a crude product as a brown solid (76 mg).

Step 4

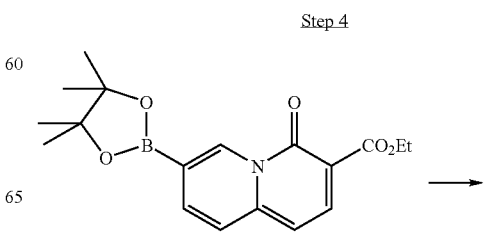

-continued

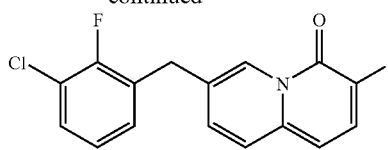

The compound (76 mg) obtained in Step 3 was dissolved in dimethoxyethane (0.76 ml), and under an argon atmosphere, 3-chloro-2-fluorobenzyl bromide (189 mg, 1.1 mmol), tetrakistriphenylphosphine palladium (8 mg, 0.0069 mmol), 1.2 M aqueous sodium hydrogencarbonate solution (1.1 ml, 0.92 mmol) and ethanol (0.38 ml) were added, and the mixture was stirred with heating at 80° C. for 30 min. Saturated aqueous ammonium chloride solution and ethyl acetate were added to the reaction mixture to partition into layers. The organic layer was washed with water and saturated brine, and dried over magnesium sulfate. After filtration, the filtrate was concentrated under reduced pressure and the residue was slurry-washed with hexane. The obtained solid was purified by PTLC to give the object product as a brown solid (14 mg, yield 15%, 2 steps).

$^1$H NMR (CDCl$_3$ 400 MHz) (δ) ppm: 1.43 (3H, t, J=6.8 Hz), 4.10 (2H, s), 4.43 (2H, q, J=6.8 Hz), 6.63 (1H, d, J=8.8 Hz), 7.02-7.13 (2H, m), 7.31-7.35 (1H, m), 7.46-7.54 (2H, m), 8.38 (1H, d, J=8.3 Hz), 9.28 (1H, s)

Example 2

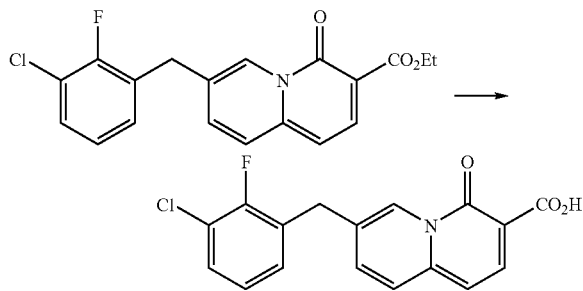

The compound (14 mg, 0.039 mmol) obtained in Example 1 was dissolved in tetrahydrofuran (2 ml), ethanol (1 ml) and water (1 ml), lithium hydroxide monohydrate (4 mg, 0.098 mmol) was added, and the mixture was stirred at room temperature for 3 hr. The reaction mixture was acidified with 1N hydrochloric acid, and extracted with ethyl acetate. The organic layer was washed with water and saturated brine, and dried over magnesium sulfate. After filtration, the filtrate was concentrated under reduced pressure and the residue was slurry-washed with a mixed solvent of hexane and acetone. After filtration, the solid was dried under reduced pressure to give the object product as a yellow solid (8 mg, yield 62%).

$^1$H NMR (DMSO-d$_6$ 400 MHz) (δ) ppm: 4.28 (2H, s), 7.18-7.26 (2H, m), 7.37-7.42 (1H, m), 7.48-7.53 (1H, m), 7.90 (1H, d, J=8.8 Hz), 8.09 (1H, d, J=9.3 Hz), 8.37 (1H, d, J=8.3 Hz), 9.17 (1H, s), 14.13 (1H, s)

MS (ESI): M+ 332

Example 3

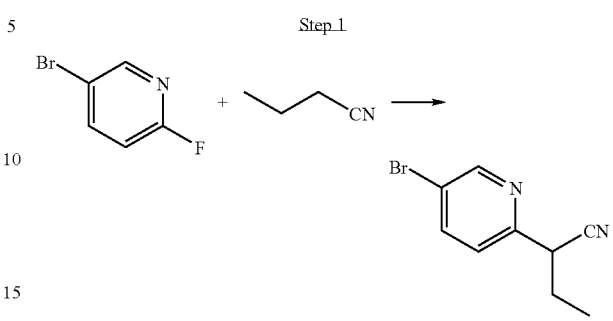

To a solution of butyronitrile (1.47 g, 21.31 mmol) in tetrahydrofuran (15 ml) was added dropwise lithium diisopropylamide (2.0M heptane/tetrahydrofuran/ethylbenzene solution) (11.37 ml, 22.74 mmol) under an argon atmosphere at −78° C., and the mixture was stirred for 15 min. Then a solution of 5-bromo-2-fluoropyridine (2.50 g, 14.21 mmol) in tetrahydrofuran (15 ml) was added dropwise at −78° C. The mixture was stirred for 1 hr, allowed to warm to room temperature and stirred for 1.5 hr. A saturated aqueous ammonium chloride solution was added to the reaction mixture, and the mixture was extracted with ethyl acetate. The organic layer was washed with water and saturated brine, and dried over sodium sulfate. After filtration, the filtrate was concentrated under reduced pressure and the residue was purified by silica gel chromatography (hexane:ethyl acetate=5:1) to give the object product as a pale-white yellow oil (2.11 g, yield 66%).

$^1$H NMR (CDCl$_3$ 400 MHz) (δ) ppm: 1.10 (3H, t, J=7.4 Hz), 1.97-2.14 (2H, m), 3.91 (1H, dd, J=6.0, 8.3 Hz), 7.36 (1H, d, J=8.3 Hz), 7.87 (1H, dd, J=2.3, 8.3 Hz), 8.65 (1H, d, J=2.3 Hz)

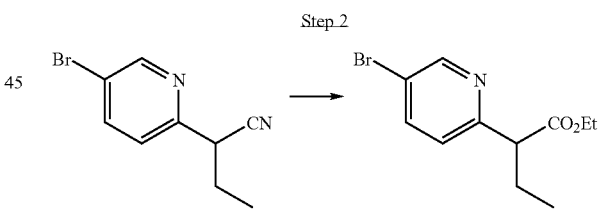

The compound (2.00 g, 8.89 mmol) obtained in Step 1 was dissolved in ethanol (18 ml), concentrated sulfuric acid (6 ml) was added, and the mixture was heated under reflux for 45 hr. The reaction mixture was poured into ice water and extracted with ethyl acetate. The organic layer was washed successively with water, saturated aqueous sodium hydrogencarbonate and saturated brine, and dried over sodium sulfate. After filtration, the filtrate was concentrated under reduced pressure to give the object product as a pale-yellow oily solid (2.12 g, yield 88%).

$^1$H NMR (CDCl$_3$ 400 MHz) (δ) ppm: 0.92 (3H, t, J=7.4 Hz), 1.22 (3H, t, J=7.0 Hz), 1.87-1.97 (1H, m), 2.08-2.18 (1H, m), 3.68 (1H, t, J=7.9 Hz), 4.09-4.21 (2H, m), 7.24 (1H, d, J=8.3 Hz), 7.78 (1H, dd, J=2.8, 8.3 Hz), 8.61 (1H, d, J=2.3 Hz)

Step 3

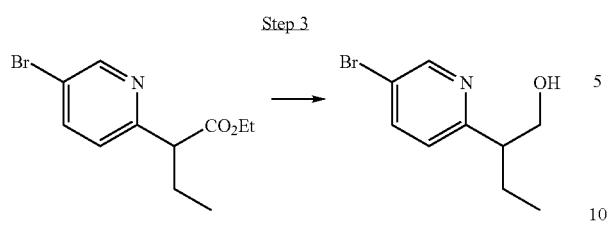

Lithium aluminum hydride (210 mg, 5.51 mmol) was suspended in tetrahydrofuran (7 ml) and, under an argon atmosphere, a solution of the compound (1.50 g, 5.51 mmol) obtained in Step 2 in tetrahydrofuran (7 ml) was added dropwise at −78° C. The mixture was allowed to warm to 0° C. and stirred for 40 min. Water (0.21 ml), 4N aqueous sodium hydroxide solution (0.21 ml) and water (0.63 ml) were successively added to the reaction mixture and the mixture was stirred at room temperature for 10 min. Ethyl acetate was added, and the mixture was filtered through celite. The filtrate was concentrated under reduced pressure and the residue was purified by silica gel chromatography (hexane:ethyl acetate=3:2) to give the object product as a colorless oil (713 mg, yield 56%).

$^1$H NMR (CDCl$_3$ 400 MHz) (δ) ppm: 0.90 (3H, t, J=7.4 Hz), 1.68-1.86 (2H, m), 2.73-2.79 (1H, m), 3.33 (1H, br), 3.86-3.98 (2H, m), 7.08 (1H, d, J=8.3 Hz), 7.76 (1H, dd, J=2.3, 8.3 Hz), 8.59 (1H, d, J=2.3 Hz)

Step 4

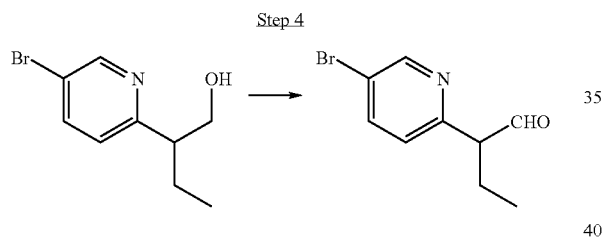

To a solution of dimethyl sulfoxide (414 μl, 5.83 mmol) in dichloromethane (2 ml) was added dropwise a solution of oxalyl chloride (254 μl, 2.91 mmol) in dichloromethane (2 ml), and the mixture was stirred at −78° C. for 10 min. Then, a solution of the compound (106 mg, 0.44 mmol) obtained in Step 3 in dichloromethane (1 ml) was added dropwise at −78° C., and the mixture was stirred for 10 min. Triethylamine (1.35 ml, 9.72 mmol) was further added dropwise at −78° C. and the mixture was stirred for 10 min. The mixture was allowed to warm to −10° C. and the mixture was stirred for 10 min. Water was added to the reaction mixture, and the mixture was extracted with ethyl acetate. The organic layer was washed with water and saturated brine, and dried over sodium sulfate. After filtration, the filtrate was concentrated under reduced pressure to give a crude product as a red-orange oil (426 mg).

Step 5

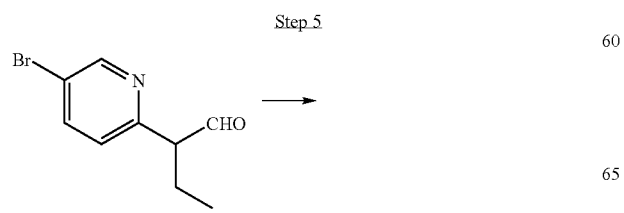

-continued

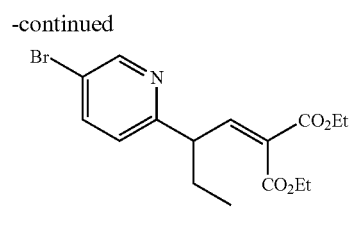

The compound (426 mg) obtained in Step 4 was dissolved in ethanol (13 ml) and acetic acid (0.45 ml), piperidine (0.45 ml) and diethyl malonate (1.47 ml, 9.72 mmol) were added. The mixture was heated under reflux for 4 hr. The reaction mixture was concentrated under reduced pressure and the residue was dissolved in ethyl acetate. The solution was washed with water and saturated brine, and dried over sodium sulfate. After filtration, the filtrate was concentrated under reduced pressure and the residue was roughly purified by silica gel chromatography (hexane:ethyl acetate=9:1) to give the object product as a clear pale-yellow oil (1.55 g).

Step 6

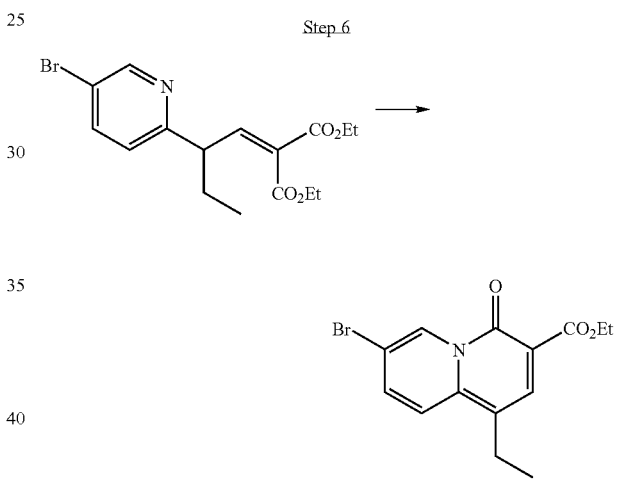

The compound (1.55 g) obtained in Step 5 was dissolved in diphenyl ether (2.5 ml), and this solution was added dropwise to diphenyl ether (7.5 ml) heated to 245° C. The mixture was stirred with heating at the same temperature for 1.5 hr, and purified by silica gel chromatography (hexane:ethyl acetate=1:1 to 1:2) to give the object product as a yellow solid (284 mg, yield 57%, 3 steps).

$^1$H NMR (CDCl$_3$ 300 MHz) (δ) ppm: 1.27 (3H, t, J=7.7 Hz), 1.41 (3H, t, J=7.0 Hz), 2.79 (2H, q, J=7.7 Hz), 4.41 (2H, q, J=7.0 Hz), 7.61 (2H, s), 8.30 (1H, s), 9.57 (1H, s)

Step 7

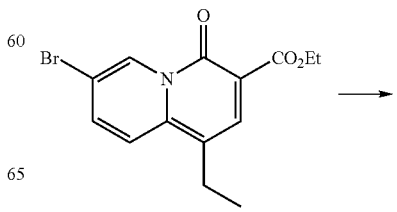

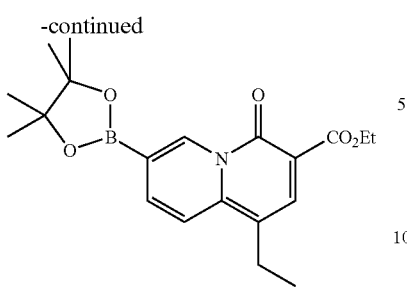

The compound (150 mg, 0.463 mmol) obtained in Step 6 was dissolved in dimethyl sulfoxide (3 ml) and, under an argon atmosphere, bis(pinacolato)diboron (129 mg, 0.51 mmol), potassium acetate (136 mg, 1.39 mmol) and $PdCl_2$ (dppf) (12 mg, 0.014 mmol) were added. The mixture was stirred with heating at 80° C. for 2 hr. Water was added to the reaction mixture, and the mixture was extracted with ethyl acetate. The organic layer was washed with water and saturated brine, and dried over magnesium sulfate. After filtration, the filtrate was concentrated under reduced pressure to give a crude product as a brown solid (207 mg).

Step 8

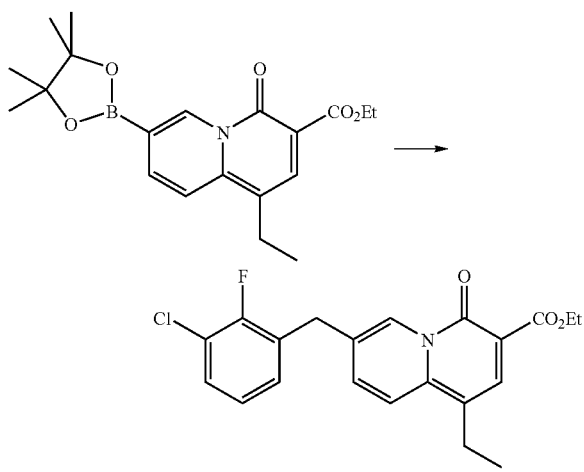

The compound (207 mg) obtained in Step 7 was dissolved in dimethoxyethane (2 ml) and, under an argon atmosphere, a solution of 3-chloro-2-fluorobenzyl bromide (517 mg, 2.32 mmol) in ethanol (1 ml) was added. Then, tetrakistriphenylphosphine palladium (27 mg, 0.023 mmol) and 1.2 M aqueous sodium hydrogencarbonate solution (2.30 ml, 2.78 mmol) were added, and the mixture was stirred with heating at 80° C. for 30 min. Water was added to the reaction mixture, and the mixture was extracted with ethyl acetate. The organic layer was washed with water and saturated brine, and dried over sodium sulfate. After filtration, the filtrate was concentrated under reduced pressure and the residue was roughly purified by silica gel chromatography (hexane:ethyl acetate=1:2) and further purified by PTLC to give the object product as a yellow solid (15 mg, yield 8%, 2 steps).

$^1$H NMR (CDCl$_3$ 400 MHz) (δ) ppm: 1.28 (3H, t, J=7.4 Hz), 1.43 (3H, t, J=7.0 Hz), 2.80 (2H, q, J=7.4 Hz), 4.11 (2H, s), 4.43 (2H, q, J=7.0 Hz), 7.05 (1H, dd, J=7.9, 7.9 Hz), 7.11 (1H, ddd, J=1.4, 7.0, 7.9 Hz), 7.31 (1H, ddd, J=1.4, 7.9, 8.3 Hz), 7.52 (1H, d, J=9.3 Hz), 7.70 (1H, d, J=9.3 Hz), 8.28 (1H, s), 9.38 (1H, s)

Example 4

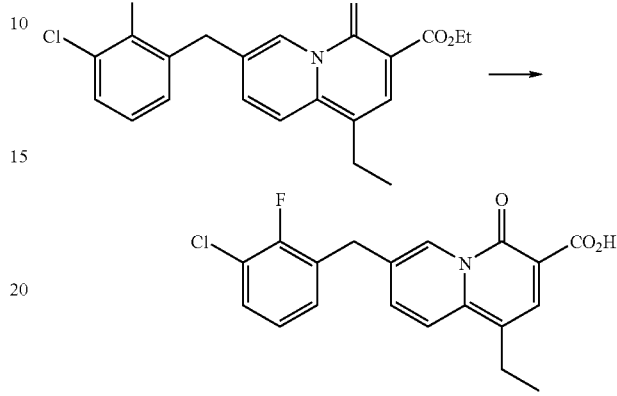

The compound (15 mg, 0.039 mmol) obtained in Example 3 was dissolved in tetrahydrofuran (2 ml) and ethanol (1 ml), and lithium hydroxide monohydrate (4 mg, 0.097 mmol) and water (1 ml) were added, and the mixture was stirred at room temperature for 15.5 hr. A 10% aqueous citric acid solution was added to the reaction mixture, and the mixture was extracted with ethyl acetate. The organic layer was washed with water and saturated brine, and dried over sodium sulfate. After filtration, the filtrate was concentrated under reduced pressure and purified by HPLC. The obtained solid was dissolved in ethyl acetate, and the solution was washed with water and saturated brine, and dried over sodium sulfate. After filtration, the filtrate was concentrated under reduced pressure to give the object product as a yellow solid (6 mg, yield 43%).

$^1$H NMR (CDCl$_3$ 400 MHz) (δ) ppm: 1.32 (3H, t, J=7.4 Hz), 2.89 (2H, q, J=7.4 Hz), 4.18 (2H, s), 7.09 (1H, dd, J=7.9, 7.9 Hz), 7.16 (1H, ddd, J=1.9, 6.0, 7.9 Hz), 7.36 (1H, ddd, J=1.9, 7.0, 7.9 Hz), 7.66 (1H, dd, J=1.9, 9.3 Hz), 7.87 (1H, d, J=9.3 Hz), 8.51 (1H, s), 9.31 (1H, s), 14.20 (1H, br)

MS (ESI): M+ 360

Example 5

Step 1

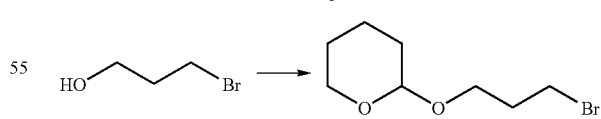

To a solution of 3-bromo-1-propanol (2.00 g, 14.39 mmol) in chloroform (20 ml) were added dihydropyran (1.44 ml, 15.83 mmol) and pyridinium p-toluenesulfonate (181 mg, 0.72 mmol) under ice-cooling, and the mixture was stirred at room temperature for 1.5 hr. A saturated aqueous sodium hydrogencarbonate solution was added to the reaction mixture, and the mixture was extracted with chloroform. The organic layer was washed with water and saturated brine, and dried over magnesium sulfate. After filtration, the filtrate was concentrated under reduced pressure and the residue was purified by silica gel chromatography (hexane:ethyl acetate=20:1) to give the object product as a pale-yellow oil (2.54 g, yield 79%).

$^1$H NMR (CDCl$_3$ 400 MHz) (δ) ppm: 1.50-1.61 (4H, m), 1.67-1.85 (2H, m), 2.10-2.17 (2H, m), 3.49-3.57 (4H, m), 3.83-3.91 (2H, m), 4.60-4.63 (1H, m)

Step 2

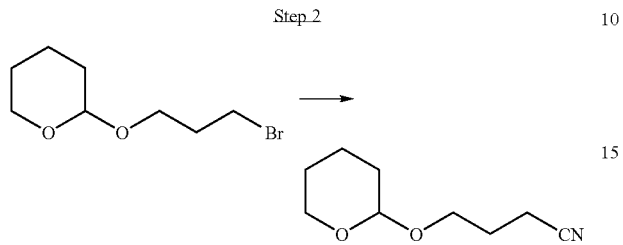

The compound (2.54 g, 11.40 mmol) obtained in Step 1 was dissolved in acetonitrile (23 ml), and cyanotrimethylsilane (3.00 ml, 22.80 mmol) and tetrabutylammonium fluoride (1M tetrahydrofuran solution) (22.80 ml, 22.80 mmol) were added. The mixture was stirred with heating at 80° C. for 3.5 hr. Water was added to the reaction mixture, and the mixture was extracted with ethyl acetate. The organic layer was washed with water and saturated brine, and dried over magnesium sulfate. After filtration, the filtrate was concentrated under reduced pressure and the obtained residue was purified by silica gel chromatography (hexane:ethyl acetate=2:1) to give the object product as a colorless oil (1.67 g, yield 87%).

$^1$H NMR (CDCl$_3$ 400 MHz) (δ) ppm: 1.51-1.61 (4H, m), 1.70-1.85 (2H, m), 1.92-1.99 (2H, m), 2.48-2.52 (2H, m), 3.48-3.56 (2H, m), 3.82-3.89 (2H, m), 4.59-4.61 (1H, m)

Step 3

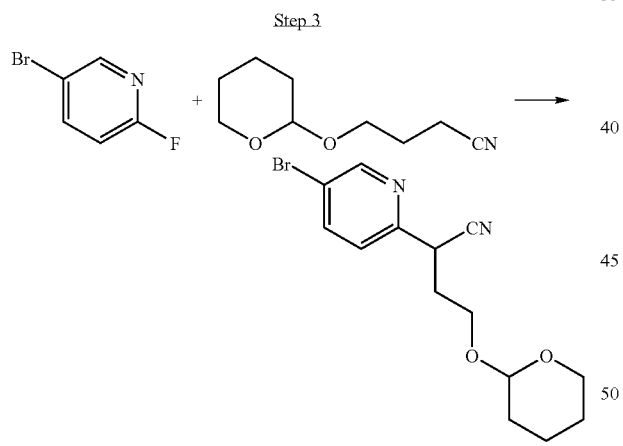

To a solution of the compound (1.67 g, 4.93 mmol) obtained in Step 2 in tetrahydrofuran (8 ml) was added dropwise n-butyl lithium (2.59M n-hexane solution) (3.8 ml, 9.86 mmol) at −60° C. or below under an argon atmosphere, and the mixture was stirred for 30 min. Then, a solution of 5-bromo-2-fluoropyridine (867 mg, 4.93 mmol) in tetrahydrofuran (8 ml) was added dropwise at −70° C. or below. After dropwise addition, and the mixture was allowed to warm to room temperature and stirred for 1.5 hr. Water was added to the reaction mixture, and the mixture was extracted with ethyl acetate. The organic layer was washed with water and saturated brine, and dried over magnesium sulfate. After filtration, the organic layer was dried under reduced pressure and the residue was roughly purified by silica gel chromatography (hexane:ethyl acetate=4:1) to give the object product as a yellow oil (1.67 g).

Step 4

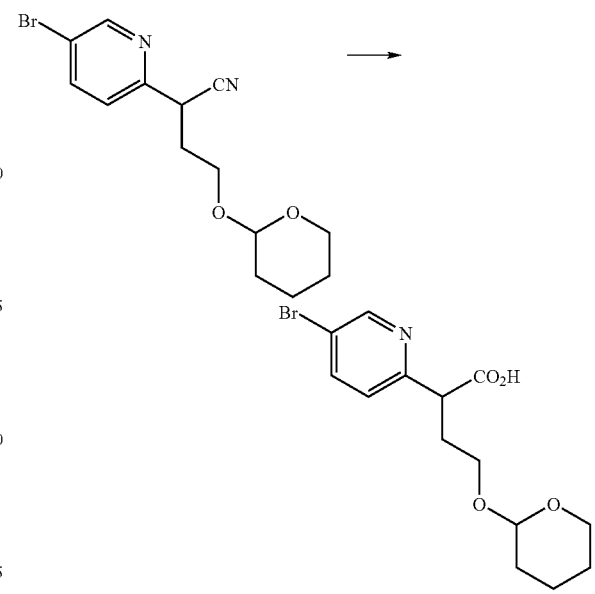

To a solution of the compound (1.67 g) obtained in Step 3 in ethylene glycol (17 ml) was added 8N aqueous potassium hydroxide solution (2.70 ml, 21.45 mmol), and the mixture was stirred with heating at 150° C. for 2 hr. A 10% aqueous citric acid solution was added to the reaction mixture, and the mixture was extracted with ethyl acetate. The organic layer was washed with water and saturated brine, and dried over magnesium sulfate. After filtration, the filtrate was concentrated under reduced pressure and the residue was roughly purified by silica gel chromatography (hexane:ethyl acetate=3:1 to 1:1) to give the object product as a pale-brown oil (898 mg).

Step 5

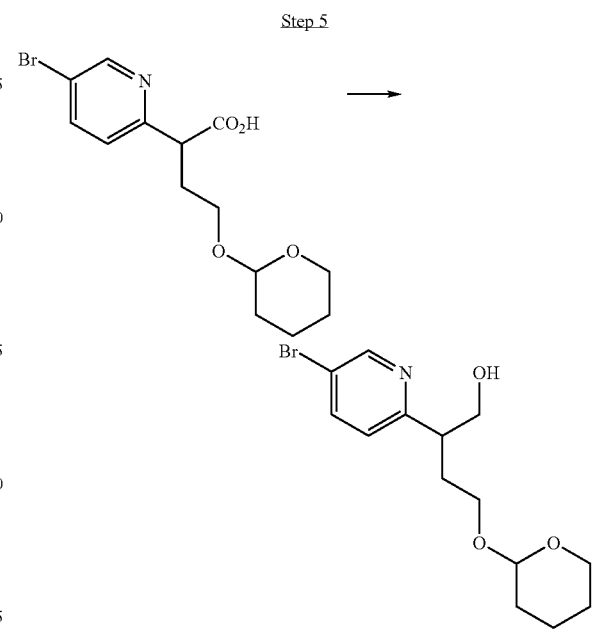

To a solution of the compound (898 mg) obtained in Step 4 in tetrahydrofuran (9 ml) were added isopropyl chloroformate (439 μl, 3.38 mmol) and triethylamine (471 μl, 3.38 mmol) under ice-cooling, and the mixture was stirred for 1 hr. The reaction mixture was filtered, and the filtrate was added dropwise to a solution of sodium borohydride (382 mg, 10.11 mmol) in water (2 ml). The mixture was stirred at room temperature for 1 hr. A saturated aqueous ammonium chloride solution was added to the reaction mixture, and the mixture was extracted with ethyl acetate. The organic layer was washed with water and saturated brine, and dried over magnesium sulfate. After filtration, the filtrate was concentrated under reduced pressure and the residue was purified by silica gel chromatography (hexane:ethyl acetate=4:1 to 1:1) to give the object product as a colorless oil (153 mg, yield 9%, 3 steps).

$^1$H NMR (CDCl$_3$ 400 MHz) (δ) ppm: 1.48-1.61 (4H, m), 1.65-1.85 (2H, m), 1.99-2.14 (2H, m), 3.06-3.14 (1H, m), 3.28-4.01 (6H, m), 4.50-4.57 (1H, m), 7.11-7.16 (1H, m), 7.75-7.77 (1H, m), 8.59 (1H, s)

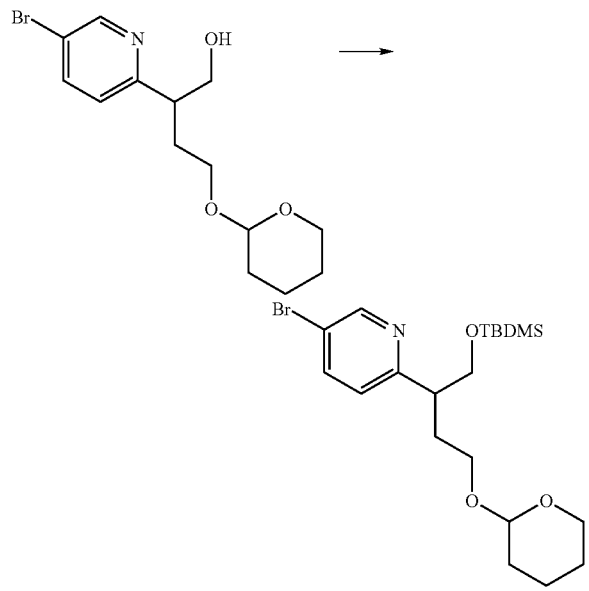

The compound (196 mg, 0.59 mmol) obtained in Step 5 was dissolved in dimethylformamide (2.4 ml), t-butyldimethylsilyl chloride (108 mg, 0.72 mmol) and imidazole (53 mg, 0.78 mmol) were added, and the mixture was stirred at room temperature for 10 min. Water was added to the reaction mixture, and the mixture was extracted with ethyl acetate. The organic layer was washed with water and saturated brine, and dried over magnesium sulfate. After filtration, the filtrate was concentrated under reduced pressure and the residue was purified by silica gel chromatography (hexane to hexane: ethyl acetate=20:1) to give the object product as a colorless oil (178 mg, yield 75%).

$^1$H NMR (CDCl$_3$ 400 MHz) (δ) ppm: −0.11 (3H, s), −0.07 (3H, s), 0.80 (9H, s), 1.44-1.82 (6H, m), 1.98-2.05 (2H, m), 3.04-3.83 (7H, m), 4.43-4.52 (1H, m), 7.08-7.11 (1H, m), 7.67-7.71 (1H, m), 8.60 (1H, s)

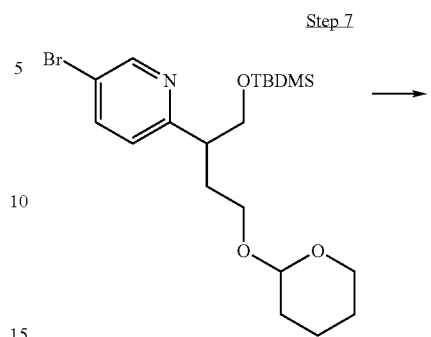

Preparation of 3-chloro-2-fluorobenzylzinc bromide tetrahydrofuran solution

Under an argon atmosphere, a zinc powder (11 g, 175 mmol) was suspended in tetrahydrofuran (30 ml), 1,2-dibromoethane (0.1 ml, 1.20 mmol) and trimethylsilyl chloride (0.29 ml, 2.4 mmol) were added at 60° C., and the mixture was stirred with heating for 30 min. A solution of 3-chloro-2-fluorobenzyl bromide (27 g, 119 mmol) in tetrahydrofuran (60 ml) was added dropwise at 60° C., and the mixture was stirred with heating for 1 hr, allowed cool and used for the main step.

(Main Step)

The compound (689 mg, 1.55 mmol) obtained in Step 6 was dissolved in tetrahydrofuran (5 ml) and, under an argon atmosphere, dichlorobis(triphenylphosphine) palladium (II) (55 mg, 0.078 mmol) and 1 M 3-chloro-2-fluorobenzylzinc bromide tetrahydrofuran solution (2.30 ml, 2.30 mmol) were added dropwise, and the mixture was heated under reflux for 30 min. A saturated aqueous ammonium chloride solution was added to the reaction mixture, and the mixture was extracted with ethyl acetate. The organic layer was washed successively with saturated aqueous ammonium chloride solution, saturated aqueous sodium hydrogencarbonate solution and saturated brine, and dried over magnesium sulfate. After filtration, the filtrate was concentrated under reduced pressure and the residue was roughly purified by silica gel chromatography (hexane:ethyl acetate=4:1) to give the object product as a yellow oil (859 mg).

Step 8

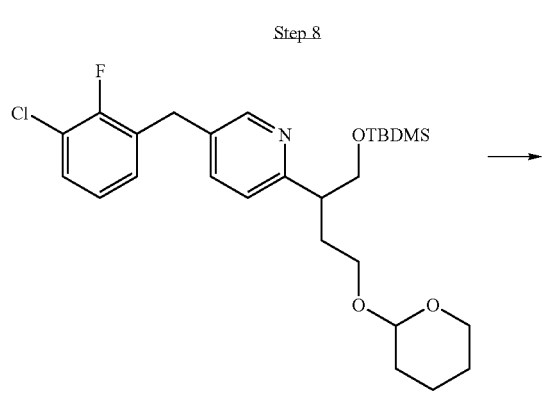

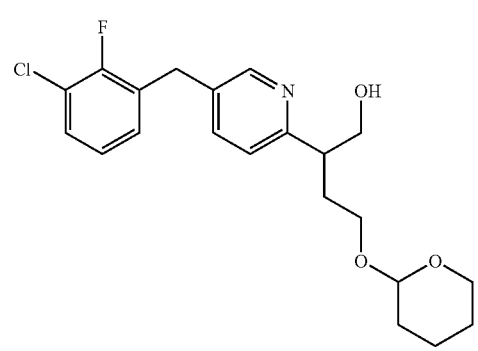

The compound (859 mg) obtained in Step 7 was dissolved in tetrahydrofuran (8 ml), tetrabutylammonium fluoride (1 M tetrahydrofuran solution) (2.54 ml, 2.54 mmol) was added, and the mixture was stirred with heating at 50° C. for 5 min. Water was added to the reaction mixture, and the mixture was extracted with ethyl acetate. The organic layer was washed with water and saturated brine, and dried over sodium sulfate. After filtration, the filtrate was concentrated under reduced pressure and the residue was purified by silica gel chromatography (hexane:ethyl acetate=4:1 to chloroform:acetone=4:1) to give the object product as a brown oil (402 mg, yield 66%, 2 steps).

$^1$H NMR (CDCl$_3$ 400 MHz) (δ) ppm: 1.47-1.60 (4H, m), 1.64-1.84 (2H, m), 2.06-2.10 (2H, m), 3.04-3.11 (1H, m), 3.28-4.06 (6H, m), 3.98 (2H, s), 4.51-4.56 (1H, m), 7.01-7.16 (3H, m), 7.23-7.32 (1H, m), 7.44-7.47 (1H, m), 8.41 (1H, s)

Step 9

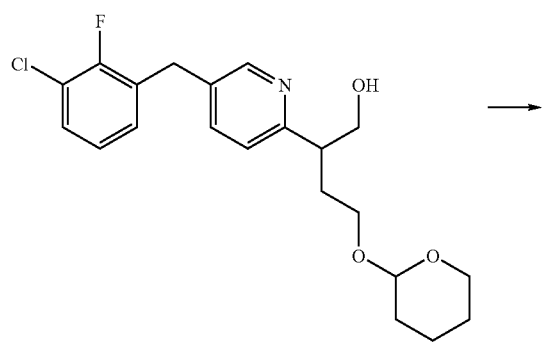

-continued

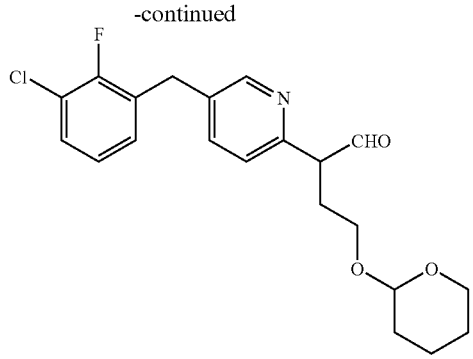

To a solution of dimethyl sulfoxide (108 μl, 1.52 mmol) in dichloromethane (2 ml) was added dropwise a solution of oxalyl chloride (66 μl, 0.76 mmol) in dichloromethane (1 ml) at −70° C. or below and the mixture was stirred for 10 min. Then, a solution of the compound (200 mg, 0.51 mmol) obtained in Step 8 in dichloromethane (3 ml) was added dropwise at −70° C. or below, and the mixture was stirred for 15 min. Triethylamine (354 μl, 2.54 mmol) was further added dropwise, and the mixture was stirred for 5 min, and allowed to warm to −10° C. and stirred for 20 min. Water was added to the reaction mixture, and the mixture was extracted with ethyl acetate. The organic layer was washed with water and saturated brine, and dried over magnesium sulfate. After filtration, the filtrate was concentrated under reduced pressure to give a crude product as a yellow gum (201 mg).

Step 10

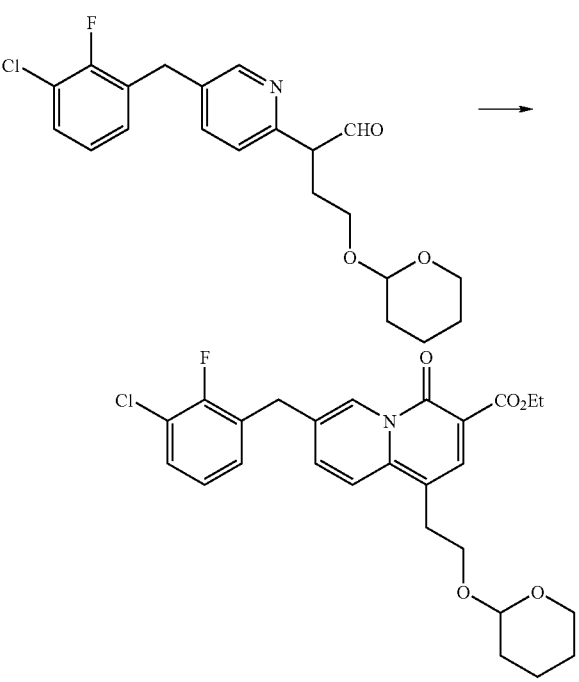

The compound (201 mg) obtained in Step 9 was dissolved in ethanol (6 ml), piperidine (0.11 ml) and diethyl malonate (386 μl, 2.54 mmol) were added, and the mixture was heated under reflux for 3 hr. The reaction mixture was concentrated under reduced pressure and the residue was dissolved in toluene (6 ml) and heated under reflux for 3 hr. The reaction mixture was concentrated under reduced pressure and the residue was dissolved in ethyl acetate. The solution was washed with water and saturated brine, and dried over magnesium sulfate. After filtration, the filtrate was concentrated under reduced pressure and the residue was purified by silica gel chromatography (hexane:ethyl acetate=3:1 to 1:1, then chloroform:acetone=3:1) to give the object product as a yellow gum (97 mg, yield 39%).

¹H NMR (CDCl₃ 400 MHz) (δ) ppm: 1.40-1.73 (6H, m), 1.43 (3H, t, J=6.8 Hz), 3.07 (2H, t, J=6.8 Hz), 3.40-3.46 (1H, m), 3.62 (1H, dt, J=6.8, 9.6 Hz), 3.62-3.69 (1H, m), 3.95 (1H, dt, J=6.8, 9.6 Hz), 4.11 (2H, s), 4.43 (2H, q, J=6.8 Hz), 4.55-4.57 (1H, m), 7.03-7.12 (2H, m), 7.30-7.35 (1H, m), 7.49-7.52 (1H, m), 7.84 (1H, d, J=9.6 Hz), 8.32 (1H, s), 9.37 (1H, s)

Example 6

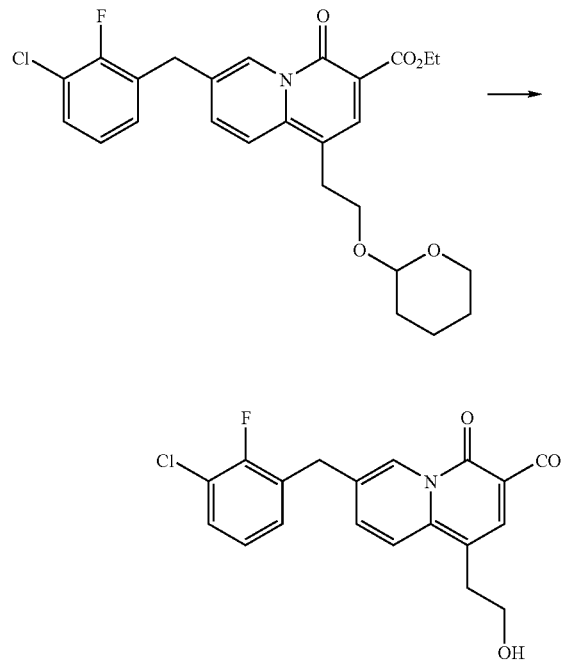

The compound (97 mg, 0.20 mmol) obtained in Example 5 was dissolved in ethanol (2 ml), p-toluenesulfonic acid monohydrate (2 mg, 0.010 mmol) was added, and the mixture was stirred with heating at 50° C. for 1.5 hr. Water and chloroform were added to the reaction mixture to partition into layers. The organic layer was washed with saturated aqueous sodium hydrogencarbonate solution and saturated brine, and dried over magnesium sulfate. After filtration, the filtrate was concentrated under reduced pressure to give the object product as a yellow solid (49 mg, yield 61%).

¹H NMR (CDCl₃ 400 MHz) (δ) ppm: 1.43 (3H, t, J=6.8 Hz), 3.05 (2H, t, J=6.8 Hz), 3.88-3.93 (2H, m), 4.11 (2H, s), 4.43 (2H, q, J=6.8 Hz), 7.03-7.14 (2H, m), 7.31-7.35 (1H, m), 7.51-7.55 (1H, m), 7.79-7.82 (1H, m), 8.30 (1H, s), 9.37 (1H, s)

Example 7

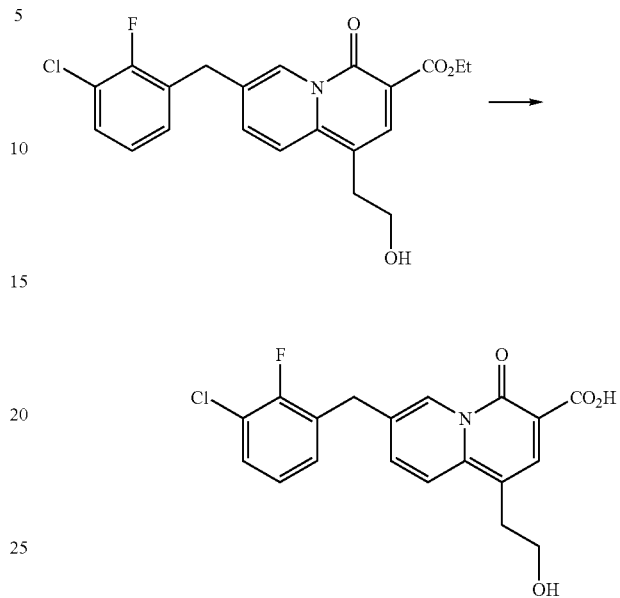

The compound (49 mg, 0.12 mmol) obtained in Example 6 was dissolved in tetrahydrofuran (3 ml), ethanol (1 ml) and water (1 ml), lithium hydroxide monohydrate (25 mg, 0.60 mmol) was added, and the mixture was stirred at room temperature for 6 hr. The reaction mixture was acidified with 1N hydrochloric acid, and extracted with ethyl acetate. The organic layer was washed with water and saturated brine, and dried over magnesium sulfate. After filtration, the filtrate was concentrated under reduced pressure, diethyl ether was added to the residue and the residue was sonicated. After filtration, the solid was dried under reduced pressure to give the object product as a yellow solid (40 mg, yield 88%).

¹H NMR (DMSO-d₆ 400 MHz) (δ) ppm: 3.03 (2H, t, J=6.8 Hz), 3.64 (2H, dt, J=5.6, 6.8 Hz), 4.30 (2H, s), 4.62 (1H, t, J=5.6 Hz), 7.19-7.23 (1H, m), 7.39-7.43 (1H, m), 7.49-7.53 (1H, m), 7.90-7.93 (1H, m), 8.21-8.23 (1H, m), 8.28 (1H, s), 9.24 (1H, s), 14.28 (1H, s)

MS (ESI): M+ 376

Example 8

Step 1

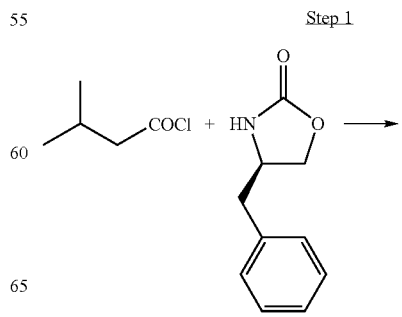

-continued

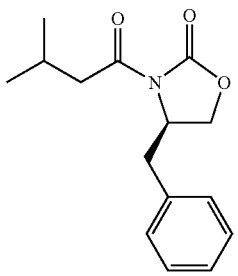

(R)-(+)-4-Benzyl-2-oxazolidinone (7.00 g, 39.50 mmol) was dissolved in tetrahydrofuran (70 ml) and, under an argon atmosphere, n-butyl lithium (2.6 M n-hexane solution) (15.20 ml, 39.50 mmol) was added dropwise at −60° C. or below, and the mixture was stirred for 20 min. Then isovaleryl chloride (5.40 ml, 43.45 mmol) was added dropwise at −60° C. or below, and the mixture was stirred for 30 min, allowed to warm to room temperature, and stirred for 19 hr. Methanol was added to the reaction mixture and the mixture was concentrated under reduced pressure. The residue was dissolved in ethyl acetate, washed with water, 1N hydrochloric acid and saturated brine, and dried over sodium sulfate. After filtration, the filtrate was concentrated under reduced pressure and the residue was purified by silica gel chromatography (hexane:ethyl acetate=4:1) to give the object product as a white solid (10.34 g, yield quantitative).

$^1$H NMR (CDCl$_3$ 300 MHz) (δ) ppm: 1.00 (3H, d, J=4.8 Hz), 1.02 (3H, d, J=4.8 Hz), 2.22 (1H, m), 2.71-2.93 (3H, m), 3.29-3.34 (1H, m), 4.09-4.22 (2H, m), 4.66-4.71 (1H, m), 7.20-7.36 (5H, m)

Step 2

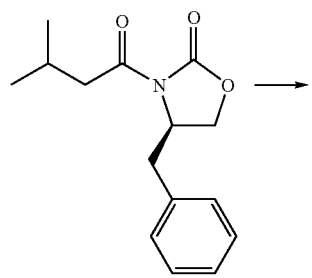

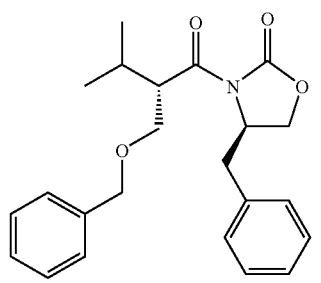

The compound (10.00 g, 38.27 mmol) obtained in Step 1 was dissolved in dichloromethane (150 ml), titanium tetrachloride (4.41 ml, 40.17 mmol) was added dropwise at 0° C., and the mixture was stirred for 10 min. Then, diisopropylethylamine (6.92 ml, 40.17 mmol) was added dropwise at 0° C., and the mixture was stirred for 1 hr. Then benzyl chloromethyl ether (10.61 ml, 76.52 mmol) was further added dropwise, and the mixture was stirred for 16 hr. A saturated aqueous ammonium chloride solution was added to the reaction mixture, and the mixture was extracted with chloroform. The organic layer was washed with water, and dried over magnesium sulfate. After filtration, the organic layer was dried under reduced pressure and the residue was purified by silica gel chromatography (hexane:ethyl acetate=4:1) and the resulting solid was dissolved in diethyl ether. Hexane was added to allow recrystallization to give the object product as a white solid (9.48 g, yield 65%).

$^1$H NMR (CDCl$_3$ 300 MHz) (δ) ppm: 0.97 (3H, d, J=8.1 Hz), 1.00 (3H, d, J=8.1 Hz), 2.02 (1H, m), 2.63-2.69 (1H, m), 3.21-3.24 (1H, m), 3.72 (1H, m), 3.85-3.87 (1H, m), 4.11-4.20 (3H, m), 4.49-4.57 (2H, m), 4.73-4.75 (1H, m), 7.20-7.31 (10H, m)

Step 3

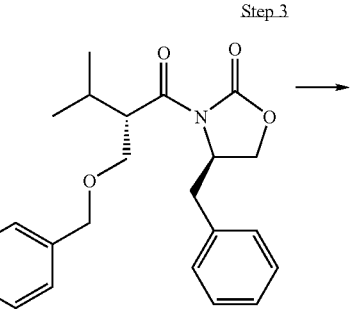

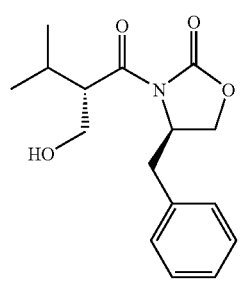

The compound (9.18 g, 24.06 mmol) obtained in Step 2 was dissolved in tetrahydrofuran (30 ml) and methanol (30 ml), palladium hydroxide (20 wt % palladium-carbon, containing water) (900 mg) was added. Hydrogen was added at 3 atm and the mixture was stirred at room temperature for 2.5 hr. The reaction mixture was filtered through celite. The filtrate was concentrated under reduced pressure to give the object product as a white solid (7.09 g).

Step 4

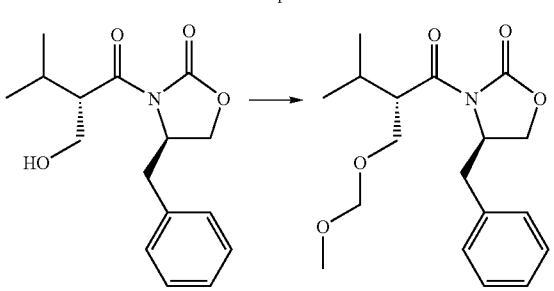

The compound (7.09 g) obtained in Step 3 was dissolved in chloroform (120 ml), dimethoxymethane (40 ml, 452 mmol) and diphosphorus pentaoxide (28 g, 197 mmol) were added under ice-cooling, and the mixture was stirred at room temperature for 30 min. The reaction mixture was added dropwise to saturated aqueous sodium carbonate solution (150 ml) and stirred. Water was added and the mixture was extracted with chloroform. The organic layer was washed with water and saturated brine, and dried over magnesium sulfate. After filtration, the filtrate was concentrated under reduced pressure and the residue was purified by silica gel chromatography (hexane:ethyl acetate=3:1) to give the object product as a colorless oil (6.85 g, yield 85%, 2 steps).

$^1$H NMR (CDCl$_3$ 300 MHz) (δ) ppm: 0.97 (3H, d, J=6.6 Hz), 1.00 (3H, d, J=6.6 Hz), 2.05 (1H, m), 2.77-2.85 (1H, m), 3.24-3.29 (1H, m), 3.35 (3H, s), 3.74-3.79 (1H, m), 3.93 (1H, m), 4.09-4.18 (3H, m), 4.62 (2H, m), 4.72-4.77 (1H, m), 7.24-7.35 (5H, m)

Step 5

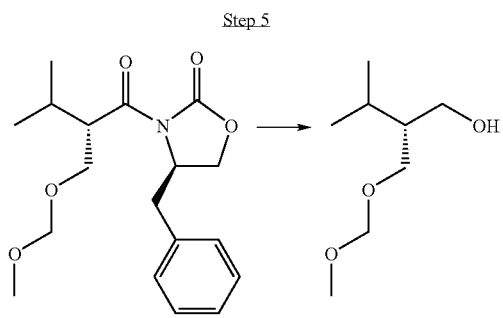

Lithium aluminum hydride (2.12 g, 55.87 mmol) was suspended in tetrahydrofuran (20 ml) and, under an argon atmosphere, a solution of the compound (6.24 g, 18.62 mmol) obtained in Step 4 in tetrahydrofuran (30 ml) was added dropwise at 0° C., and the mixture was stirred for 30 min. Water (2.2 ml), 4N aqueous sodium hydroxide solution (2.2 ml), water (6.6 ml) and diethyl ether (50 ml) were successively added to the reaction mixture, and the mixture was stirred at room temperature for 1 hr. The mixture was filtered through celite. The filtrate was concentrated under reduced pressure and the residue was purified by silica gel chromatography (hexane:ethyl acetate=1:1) to give the object product as a colorless oil (2.20 g, yield 73%).

$^1$H NMR (CDCl$_3$ 300 MHz) (δ) ppm: 0.93 (3H, d, J=2.5 Hz), 0.96 (3H, d, J=2.5 Hz), 1.58-1.67 (1H, m), 1.73-1.84 (1H, m), 2.36-2.40 (1H, m), 3.40 (3H, s), 3.61-3.79 (4H, m), 4.63 (2H, s)

Step 6

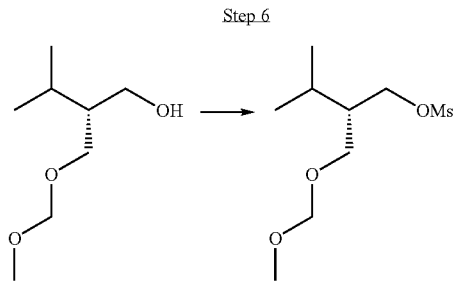

The compound (2.38 g, 14.70 mmol) obtained in Step 5 was dissolved in tetrahydrofuran (15 ml), triethylamine (2.46 ml, 17.64 mmol) was added dropwise at 0° C., a solution of methanesulfonyl chloride (1.25 ml, 16.16 mmol) in tetrahydrofuran (10 ml) was further added dropwise, and the mixture was stirred at room temperature for 30 min. Water was added to the reaction mixture, and the mixture was extracted with ethyl acetate. The organic layer was washed with water and saturated brine, and dried over sodium sulfate. After filtration, the filtrate was concentrated under reduced pressure to give the object product as a colorless oil (2.90 g).

Step 7

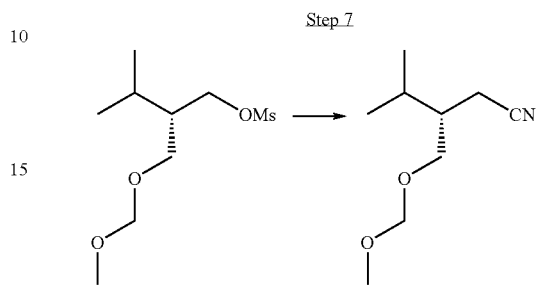

The compound (2.90 g) obtained in Step 6 was dissolved in acetonitrile (25 ml), cyanotrimethylsilane (3.22 ml, 24.12 mmol) and tetrabutylammonium fluoride (1 M tetrahydrofuran solution) (24.12 ml, 24.12 mmol) were added dropwise, and the mixture was stirred with heating at 80° C. for 13 hr. Water was added to the reaction mixture, and the mixture was extracted with diethyl ether. The organic layer was washed with water and saturated brine, and dried over sodium sulfate. After filtration, the filtrate was concentrated under reduced pressure and the obtained residue was purified by silica gel chromatography (hexane:ethyl acetate=4:1) to give the object product as a colorless oil (1.82 g, yield 72%, 2 steps).

$^1$H NMR (CDCl$_3$ 300 MHz) (δ) ppm: 0.98 (3H, d, J=1.8 Hz), 0.99 (3H, d, J=1.8 Hz), 1.73-1.91 (2H, m), 2.49-2.52 (2H, m), 3.38 (3H, s), 3.47-3.53 (1H, m), 3.61-3.69 (1H, m), 4.63 (2H, s)

Step 8

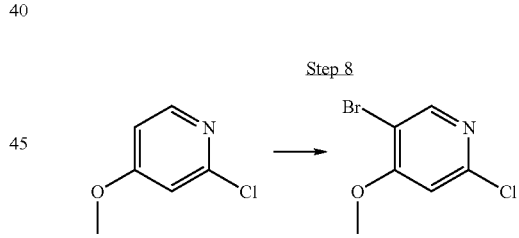

2-Chloro-4-methoxypyridine (13.3 g, 92.6 mmol) was dissolved in concentrated sulfuric acid (65 ml), N-bromosuccinimide (16.5 g, 92.6 mmol) was added under ice-cooling, and the mixture was stirred with heating at 55° C. for 3 hr. The reaction mixture was poured into ice water, alkalified with 8N aqueous sodium hydroxide solution, and extracted with chloroform. The organic layer was washed with saturated brine, and dried over sodium sulfate. After filtration, the filtrate was concentrated under reduced pressure and the residue was purified by silica gel chromatography (hexane:ethyl acetate=9:1 to 5:1) to give the object product as a white solid (9.3 g, yield 45%).

$^1$H NMR (CDCl$_3$ 300 MHz) (δ) ppm: 3.97 (3H, s), 6.84 (1H, s), 8.34 (1H, s)

Step 9

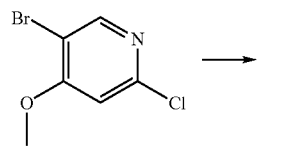

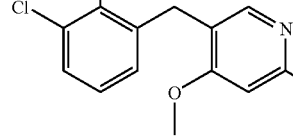

The compound (2.82 g, 12.68 mmol) obtained in Step 8 was dissolved in tetrahydrofuran (10 ml) and, under an argon atmosphere, dichlorobis(triphenylphosphine) palladium(II) (445 mg, 0.63 mmol) and 1 M 3-chloro-2-fluorobenzylzinc bromide tetrahydrofuran solution (17.75 ml, 17.75 mmol) were added dropwise, and the mixture was heated under reflux at 80° C. for 2 hr. A saturated aqueous ammonium chloride solution was added to the reaction mixture, and the mixture was extracted with ethyl acetate. The organic layer was washed with saturated aqueous ammonium chloride solution and saturated brine, and dried over sodium sulfate. After filtration, the filtrate was concentrated under reduced pressure and the residue was purified by silica gel chromatography (hexane:ethyl acetate=5:1) to give the object product as a white solid (2.19 g, yield 60%).

$^1$H NMR (CDCl$_3$ 300 MHz) (δ) ppm: 3.86 (3H, s), 3.91 (2H, s), 6.79 (1H, s), 6.94-7.01 (2H, m), 7.23-7.28 (1H, m), 8.03 (1H, s)

Step 10

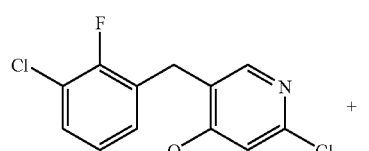

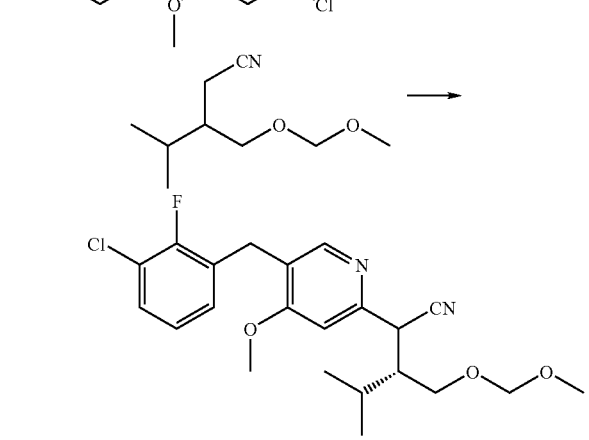

To sodium bistrimethylsilylamide (1.1 M tetrahydrofuran solution) (8.00 ml, 8.80 mmol) was added dropwise at 0° C. a solution of the compound (840 mg, 2.94 mmol) obtained in Step 9 and compound (500 mg, 2.94 mmol) obtained in Step 7 in tetrahydrofuran (9 ml), and the mixture was stirred at room temperature for 2.5 hr. A saturated aqueous ammonium chloride solution was added to the reaction mixture, and the mixture was extracted with ethyl acetate. The organic layer was washed with water and saturated brine, and dried over sodium sulfate. After filtration, the filtrate was concentrated under reduced pressure and the residue was roughly purified by silica gel chromatography (hexane:ethyl acetate=5:2) to give the object product as a pale-orange oil (890 mg).

Step 11

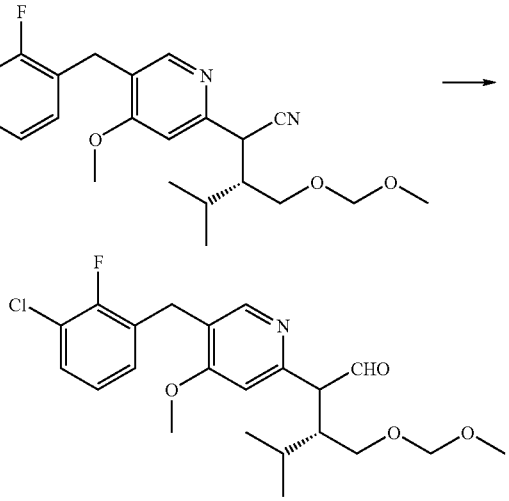

The compound (400 mg, 0.95 mmol) obtained in Step 10 was dissolved in pyridine (4 ml), acetic acid (2 ml) and water (2 ml), sodium phosphinate monohydrate (504 mg, 4.75 mmol) and Raney nickel (1 ml) were added, and the mixture was stirred with heating at 60° C. for 2.5 hr. The supernatant was filtered through celite. The filtrate was concentrated under reduced pressure and the residue was dissolved in ethyl acetate, and the solution was washed successively with water, diluted hydrochloric acid, water, saturated aqueous sodium hydrogencarbonate solution and saturated brine, and dried over sodium sulfate. After filtration, the filtrate was concentrated under reduced pressure to give the object product as a bright orange oil (314 mg).

Step 12

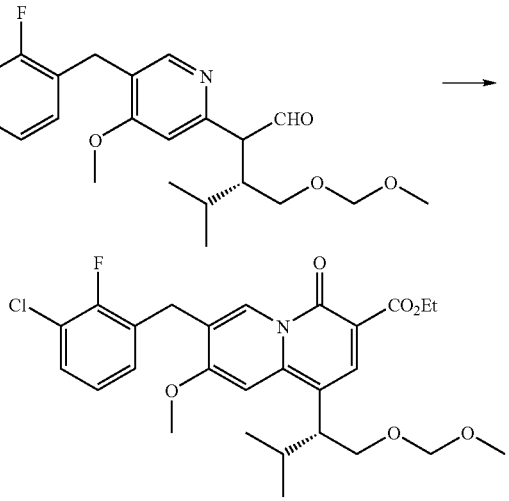

The compound (314 mg) obtained in Step 11 was dissolved in ethanol (8 ml), piperidine (0.11 ml), acetic acid (0.17 ml) and diethyl malonate (386 µl, 2.54 mmol) were added, and the mixture was heated under reflux for 4 hr. The reaction mixture was concentrated under reduced pressure and the residue was dissolved in toluene (8 ml). The mixture was heated under reflux for 2 hr. The reaction mixture was concentrated under reduced pressure and the residue was dissolved in ethyl acetate, and the solution was washed with water and saturated brine, and dried over magnesium sulfate. After filtration, the filtrate was concentrated under reduced pressure and roughly purified by silica gel chromatography (hexane:ethyl acetate=1:1 to 1:3, then chloroform:methanol=20:1) to give the object product as a yellow oil (219 mg).

Example 9

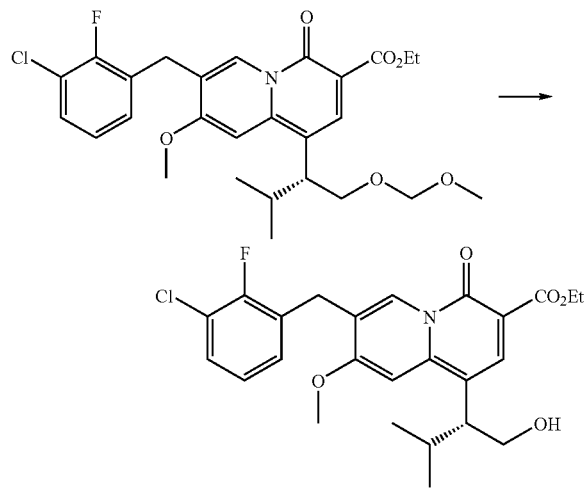

The compound (219 mg) obtained in Example 8 was dissolved in ethanol (2 ml), 4N hydrochloric acid-dioxane solution (1.00 ml, 0.25 mmol) was added, and the mixture was stirred at room temperature for 1.5 hr. Water was added to the reaction mixture, and the mixture was extracted with ethyl acetate. The organic layer was washed with water and saturated brine, and dried over sodium sulfate. After filtration, the filtrate was concentrated under reduced pressure, ethyl acetate (1 ml) and hexane (2 ml) were added to the residue, and the residue was sonicated. After filtration, the solid was dried under reduced pressure to give the object product as a yellow solid (110 mg, yield 17%, 4 steps).

$^1$H NMR (CDCl$_3$ 300 MHz) (δ) ppm: 0.81 (3H, d, J=6.6 Hz), 1.07 (3H, d, J=6.6 Hz), 1.41 (3H, t, J=7.3 Hz), 1.98-2.11 (1H, m), 2.84-2.93 (1H, m), 3.90 (1H, dd, J=8.8, 10.3 Hz), 4.00-4.09 (1H, m), 4.01 (3H, s), 4.04 (2H, s), 4.40 (2H, q, J=7.3 Hz), 7.01 (1H, dd, J=8.1, 8.1 Hz), 7.07 (1H, s), 7.11 (1H, ddd, J=1.8, 5.9, 8.1 Hz), 7.30 (1H, ddd, J=1.8, 6.6, 8.1 Hz), 8.22 (1H, s), 9.22 (1H, s)

Example 10

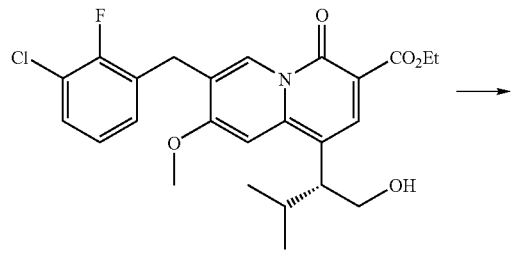

-continued

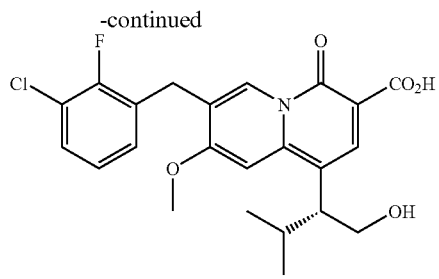

The compound (100 mg, 0.21 mmol) obtained in Example 9 was dissolved in tetrahydrofuran (2 ml), methanol (1 ml) and water (0.5 ml), lithium hydroxide monohydrate (18 mg, 0.42 mmol) was added, and the mixture was stirred at room temperature for 15 hr. A 1N aqueous potassium hydrogensulfate solution was added to the reaction mixture and the mixture was extracted with ethyl acetate. The organic layer was washed with water and saturated brine, and dried over sodium sulfate. After filtration, the filtrate was concentrated under reduced pressure and the residue was dissolved in ethyl acetate (1 ml). Hexane (3 ml) was added to allow recrystallization to give the object product as a bright yellow solid (84 mg, yield 89%).

$^1$H NMR (CDCl$_3$ 300 MHz) (δ) ppm: 0.80 (3H, d, J=6.5 Hz), 1.08 (3H, d, J=6.5 Hz), 1.83 (1H, br), 2.03-2.13 (1H, m), 2.92-2.98 (1H, m), 3.90-3.96 (1H, m), 4.06-4.12 (1H, m), 4.07 (3H, s), 4.11 (2H, s), 7.06 (1H, dd, J=7.9, 7.9 Hz), 7.13 (1H, ddd, J=1.9, 6.5, 7.9 Hz), 7.23 (1H, s), 7.34 (1H, ddd, J=1.9, 7.0, 7.9 Hz), 8.34 (1H, s), 9.16 (1H, s), 13.94 (1H, s)

MS (ESI): M+ 448

Example 16

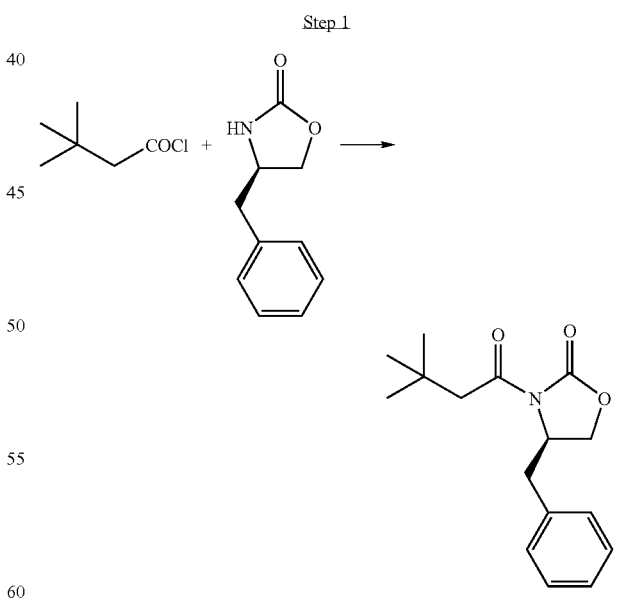

(R)-(+)-4-Benzyl-2-oxazolidinone (50.00 g, 0.28 mol) was dissolved in tetrahydrofuran (250 ml), and triethylamine (87.00 ml, 0.62 mol) and dimethylaminopyridine (3.40 g, 0.028 mol) were added. Under ice-cooling, a solution of tert-butylacetyl chloride (43.00 ml, 0.31 mol) in tetrahydrofuran (250 ml) was added dropwise, and the mixture was stirred at room temperature for 1 hr. Water was added to the reaction mixture and the mixture was extracted with ethyl acetate. The organic layer was washed successively with 2N hydrochloric acid, water and saturated brine, and dried over sodium sulfate. After filtration, the filtrate was concentrated under reduced pressure and the residue was purified by silica gel chromatography (hexane:ethyl acetate=4:1) to give the object product as a white solid (68.7 g, yield 89%).

$^1$H NMR (CDCl$_3$ 400 MHz) (δ) ppm: 1.10 (9H, s), 2.72 (1H, dd, J=13.0, 10.0 Hz), 2.87 (1H, dd, J=14.8, 1.4 Hz), 3.00 (1H, dd, J=14.8, 1.4 Hz), 3.36 (1H, dd, J=12.9, 3.1 Hz), 4.13-4.19 (2H, m), 4.67-4.73 (1H, m), 7.23-7.36 (5H, m)

Step 2

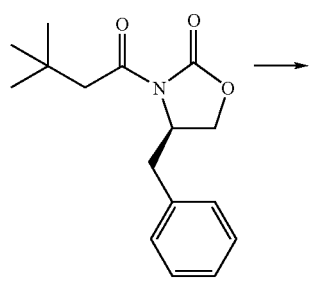

The compound (6.00 g, 21.79 mmol) obtained in Step 1 was dissolved in dichloromethane (90 ml), titanium tetrachloride (2.50 ml, 22.88 mmol) was added dropwise at 0° C., and the mixture was stirred for 20 min. Then, diisopropylethylamine (4.00 ml, 40.17 mmol) was added dropwise at 0° C. and the mixture was stirred for 5 min. Benzyl chloromethyl ether (6.10 ml, 43.58 mmol) was added dropwise and the mixture was stirred for 2 hr. A saturated aqueous ammonium chloride solution was added to the reaction mixture, and the mixture was extracted with chloroform. The organic layer was washed with water and dried over magnesium sulfate. After filtration, the organic layer was dried under reduced pressure and the residue was recrystallized from diisopropyl ether (120 ml) to give the object product as a white solid (2.78 g, yield 32%). The residue was further recrystallized from hexane:diisopropylethyl ether=1:1 to give secondary crystals (1.67 g, yield 19%).

$^1$H NMR (CDCl$_3$ 400 MHz) (δ) ppm: 0.99-1.05 (9H, m), 2.70 (1H, dd, J=13.6, 9.2 Hz), 3.22 (1H, dd, J=13.4, 3.2 Hz), 3.74 (1H, dd, J=8.7, 4.1 Hz), 4.00 (1H, dd, J=10.7, 8.6 Hz), 4.09-4.16 (2H, m), 4.46-4.61 (3H, m), 4.73-4.79 (1H, m), 7.20-7.34 (10H, m)

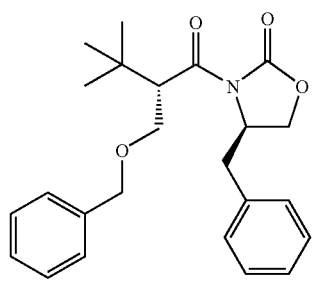

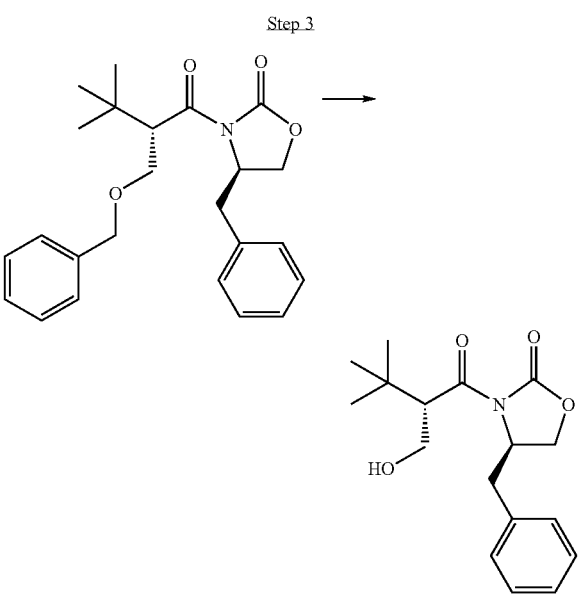

Step 3

The compound (2.78 g, 7.03 mmol) obtained in Step 2 was dissolved in tetrahydrofuran (22 ml) and methanol (22 ml), and palladium hydroxide (20 wt % palladium-carbon, containing water) (556 mg) was added. Hydrogen was added at atmospheric pressure and the mixture was stirred at room temperature for 3 hr. The reaction mixture was filtered through celite. The filtrate was concentrated under reduced pressure to give the object product as a white solid (2.15 g, yield quantitative).

$^1$H NMR (CDCl$_3$ 400 MHz) (δ) ppm: 1.05 (9H, s), 2.84 (1H, dd, J=13.6, 9.4 Hz), 3.33 (1H, dd, J=13.4, 3.2 Hz), 3.98 (1H, dd, J=10.2, 4.4 Hz), 4.08 (1H, dd, J=10.1, 10.1 Hz), 4.17 (2H, d, J=4.6 Hz), 4.22 (1H, dd, J=10.0, 4.2 Hz), 4.72-4.77 (1H, m), 7.26-7.36 (5H, m)

Step 4

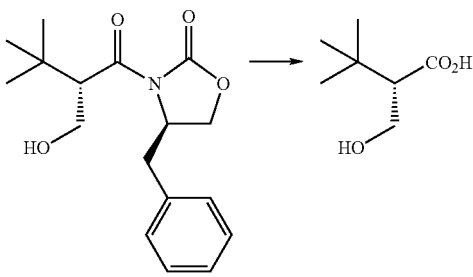

The compound (7.09 g) obtained in Step 3 was dissolved in tetrahydrofuran (27 ml) and water (9 ml), 30% aqueous hydrogen peroxide (1.30 ml, 42.12 mmol) and lithium hydroxide monohydrate (589 mg, 14.04 mmol) were added under ice-cooling, and the mixture was stirred at room temperature for 4 hr. A 8N aqueous potassium hydroxide solution (1.76 ml, 14.04 mmol) was added, and the mixture was heated under reflux for 3 hr. After allowing to cool, 10% aqueous sodium sulfite solution was added to the reaction mixture and the mixture was extracted with dichloromethane. 6N Hydrochloric acid (5 ml) was added to the aqueous layer and the mixture was extracted with chloroform. The organic layers were combined and washed with water, and dried over magnesium sulfate. After filtration, the filtrate was concentrated under reduced pressure to give the object product as a white solid (684 mg, yield 67%).

$^1$H NMR (CDCl$_3$ 400 MHz) (δ) ppm: 1.05 (9H, s), 2.53 (1H, dd, J=10.1, 4.1 Hz), 3.85 (1H, dd, J=10.8, 4.1 Hz), 3.98 (1H, dd, J=10.8, 10.1 Hz)

Step 5

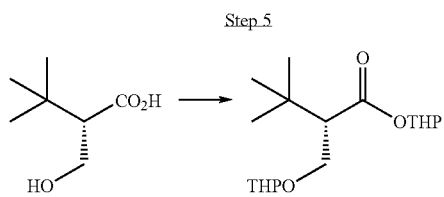

The compound (2.57 g, 17.58 mmol) obtained in Step 4 was dissolved in chloroform (100 ml), dihydropyran (4.00 ml, 43.95 mmol) and pyridinium p-toluenesulfonate (221 mg, 0.88 mmol) were added, and the mixture was stirred at room temperature for 14 hr. A saturated aqueous sodium hydrogencarbonate solution was added to the reaction mixture, and the mixture was extracted with chloroform. The organic layer was washed with saturated aqueous sodium hydrogencarbonate solution, and dried over magnesium sulfate. After filtration, the filtrate was concentrated under reduced pressure and the residue was purified by silica gel chromatography (hexane:ethyl acetate=10:1) to give the object product as a colorless oil (3.79 g, yield 69%).

Step 6

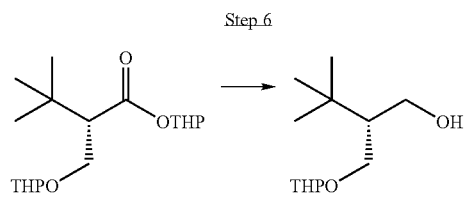

Under an argon atmosphere, to a solution of lithium aluminum hydride (915 mg, 24.12 mmol) in tetrahydrofuran (38 ml) was added dropwise a solution of the compound (3.79 g, 12.06 mmol) obtained in Step 5 in tetrahydrofuran (30 ml) solution under ice-cooling, and the mixture was stirred for 1 hr. Water (915 μl), 4N aqueous sodium hydroxide solution and water (2.75 ml) were successively added to the reaction mixture and, after stirring, the mixture was filtered through celite. The filtrate was concentrated under reduced pressure and the residue was purified by silica gel chromatography (hexane:ethyl acetate=5:1) to give the object product as a colorless oil (2.63 g, yield quantitative).

Step 7

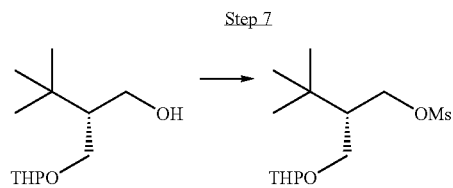

The compound (2.90 g) obtained in Step 6 was dissolved in tetrahydrofuran (26 ml), triethylamine (2.04 ml, 14.59 mmol) was added, a solution of methanesulfonyl chloride (1.04 ml, 13.38 mmol) in tetrahydrofuran (8 ml) was added dropwise under ice-cooling, and the mixture was stirred at room temperature for 1.5 hr. Water was added to the reaction mixture, and the mixture was extracted with ethyl acetate. The organic layer was washed with saturated aqueous ammonium chloride solution and saturated brine, and dried over magnesium sulfate. After filtration, the filtrate was concentrated under reduced pressure to give a crude product as a pale-yellow oil (3.70 g).

$^1$H NMR (CDCl$_3$ 400 MHz) (δ) ppm: 1.00-1.03 (9H, m), 1.53-1.82 (7H, m), 3.03 (3H, m), 3.40-3.56 (2H, m), 3.84-4.00 (2H, m), 4.37-4.49 (2H, m), 4.57-4.60 (1H, m)

Step 8

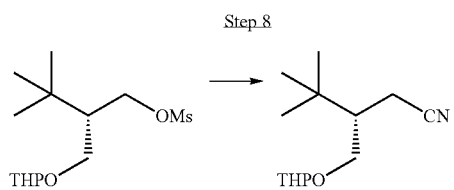

The compound (3.70 g) obtained in Step 7 was dissolved in acetonitrile (37 ml), cyanotrimethylsilane (3.30 ml, 24.32 mmol) and 1 M tetrabutylammonium fluoride tetrahydrofuran solution (24.32 ml, 24.32 mmol) was added, and the mixture was stirred with heating at 80° C. for 5 hr. After allowing to cool, water was added to the reaction mixture, and the mixture was extracted with ethyl acetate. The organic layer was washed with water and saturated brine, and dried over magnesium sulfate. After filtration, the filtrate was concentrated under reduced pressure and the obtained residue was purified by silica gel chromatography (hexane:ethyl acetate=5:1) to give the object product as a colorless oil (1.86 g, yield 68%, 2 steps).

$^1$H NMR (CDCl$_3$ 400 MHz) (δ) ppm: 1.00-1.01 (9H, m), 1.51-1.88 (7H, m), 2.51-2.55 (2H, m), 3.34-3.60 (2H, m), 3.82-4.06 (2H, m), 4.62-4.65 (1H, m)

Step 9

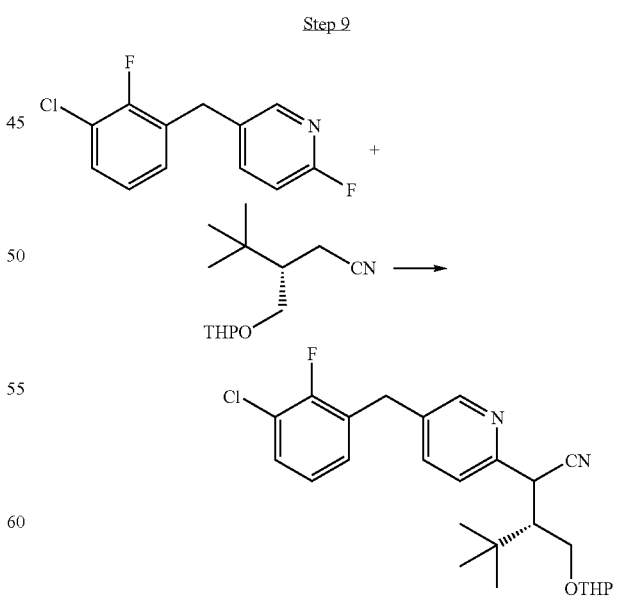

To 1.1 M sodium hexamethyldisilazide tetrahydrofuran solution (8.05 ml, 8.85 mmol) was added dropwise a solution of the compound (665 mg, 2.95 mmol) obtained in Step 8 and the compound (707 mg, 2.95 mmol) obtained in Step 1 of Example 1 in tetrahydrofuran (7 ml) at 0° C., and the mixture was stirred at room temperature for 1.5 hr. A saturated aqueous ammonium chloride solution was added to the reaction mixture, and the mixture was extracted with ethyl acetate. The organic layer was washed with water and saturated brine, and dried over sodium sulfate. After filtration, the filtrate was concentrated under reduced pressure and the residue was purified by silica gel chromatography (hexane:ethyl acetate=6:1 to 5:1) to give the object product as a yellow oil (775 mg, yield 59%).

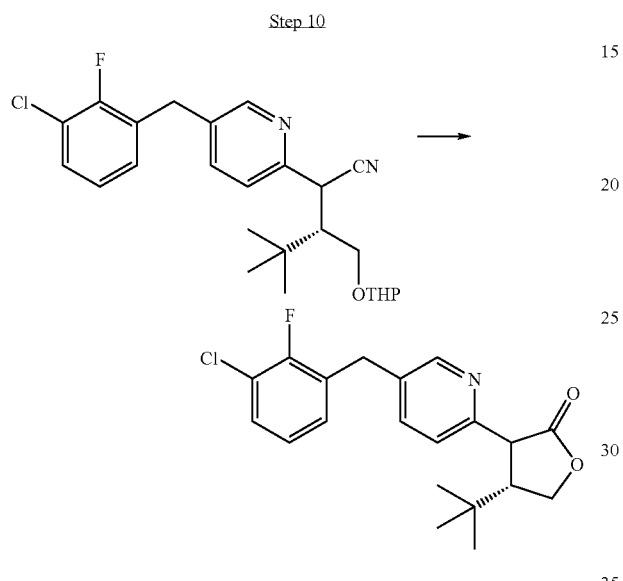

Step 10

The compound (775 mg, 1.74 mmol) obtained in Step 9 was dissolved in methanol (6 ml), concentrated hydrochloric acid (1.45 ml) was added, and the mixture was stirred at 70° C. for 30 min. After allowing to cool, the reaction mixture was poured into saturated aqueous sodium hydrogencarbonate solution, and the mixture was extracted twice with ethyl acetate. The organic layer was washed with saturated brine, and dried over sodium sulfate. After filtration, the filtrate was concentrated under reduced pressure and the residue was azeotroped twice with toluene to give the object product as a yellow oil (623 mg, yield 99%).

$^1$H NMR (CDCl$_3$ 300 MHz) (δ) ppm: 0.89 (9H, s), 3.00 (1H, m), 3.74 (1H, d, J=7.9 Hz), 3.99 (2H, s), 4.22 (1H, dd, J=9.1 Hz, 7.4 Hz), 4.54 (1H, dd, J=9.1 Hz, J=9.1 Hz), 7.01-7.05 (2H, m), 7.16-7.29 (2H, m), 7.48 (1H, dd, J=7.9 Hz, J=2.2 Hz), 8.45 (1H, d, J=2.2 Hz)

Step 11

The compound (249 mg, 0.67 mmol) obtained in Step 10 was dissolved in methanol (1.2 ml) and tetrahydrofuran (2.4 ml), and 4N aqueous sodium hydroxide solution (206 μl, 0.83 mmol) were added, and the mixture was stirred at room temperature for 13 hr. The reaction mixture was concentrated under reduced pressure and the residue was azeotroped three times with toluene, and dissolved in dimethylformamide (2.5 ml). Imidazole (141 mg, 2.06 mmol) and tert-butyldimethylsilyl chloride (311 mg, 2.06 mmol) were added under ice-cooling, and the mixture was stirred at room temperature for 20 min. Water was added to the reaction mixture, and the mixture was extracted with ethyl acetate. The organic layer was washed twice with water and then with saturated brine, and dried over sodium sulfate. After filtration, the filtrate was concentrated under reduced pressure and the residue was dissolved in tetrahydrofuran (2.5 ml) and water (0.3 ml). Lithium hydroxide monohydrate (29 mg, 0.69 mmol) was added, and the mixture was stirred at room temperature for 30 min. The reaction mixture was concentrated under reduced pressure and the residue was azeotroped four times with toluene and dissolved in dimethylformamide (2.5 ml). Under ice-cooling, potassium carbonate (95 mg, 0.69 mmol) and iodoethane (55 μl, 0.69 mmol) were added, and the mixture was stirred at room temperature for 22 hr. Water was added to the reaction mixture, and the mixture was extracted with ethyl acetate. The organic layer was washed successively with saturated aqueous ammonium chloride solution, water and saturated brine, and dried over sodium sulfate. After filtration, the filtrate was concentrated under reduced pressure and the residue was purified by silica gel chromatography (hexane:ethyl acetate=8:1) to give the object product as a yellow oil (162 mg, yield 45%).

$^1$H NMR (CDCl$_3$ 300 MHz) (δ) ppm: −0.12 (3H, s), −0.06 (3H, s), 0.84 (9H, s), 0.92 (9H, s), 1.22 (3H, t, J=7.2 Hz), 2.13 (1H, br), 3.89-4.00 (1H, m), 4.00 (2H, s), 4.14 (2H, q, J=7.2 Hz), 4.20 (1H, d, J=6.2 Hz), 7.02-7.04 (2H, m), 7.29-7.30 (1H, m), 7.35 (1H, d, J=8.1 Hz), 7.46 (1H, d, J=8.1 Hz), 8.46 (1H, s)

Step 12

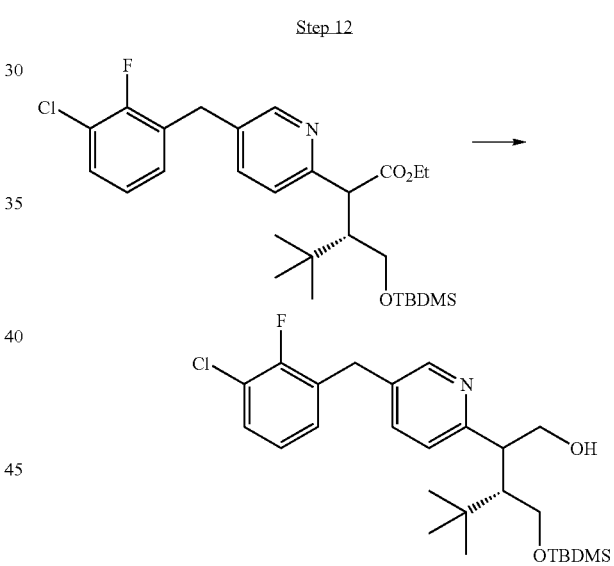

The compound (404 mg, 0.77 mmol) obtained in Step 11 was dissolved in tetrahydrofuran (4 ml) and, under an argon atmosphere, 1.0 M diisobutylaluminum hydride toluene solution (2.32 ml, 2.32 mmol) was added dropwise at −78° C. The mixture was allowed to warm to 0° C. and stirred for 1 hr. An aqueous Rochelle salt solution and ethyl acetate were added to the reaction mixture, and the mixture was stirred at room temperature for 30 min and partitioned into layers. The aqueous layer was extracted with ethyl acetate, and the organic layer was washed twice with water and then with saturated brine, and dried over sodium sulfate. After filtration, the filtrate was concentrated under reduced pressure. The residues obtained in the same manner were combined and purified by silica gel chromatography (hexane:ethyl acetate=3:1) to give the object product as a colorless oil (359 mg).

$^1$H NMR (CDCl$_3$ 300 MHz) (δ) ppm: 0.05 (3H, s), 0.06 (3H, s), 0.88 (9H, s), 0.94 (9H, s), 2.00 (1H, m), 3.26 (1H, m), 3.89-3.96 (4H, m), 4.00 (2H, s), 4.17 (1H, m), 7.01-7.07 (2H, m), 7.25-7.33 (2H, m), 7.46 (1H, dd, J=8.1 Hz, J=2.2 Hz), 8.40 (1H, s)

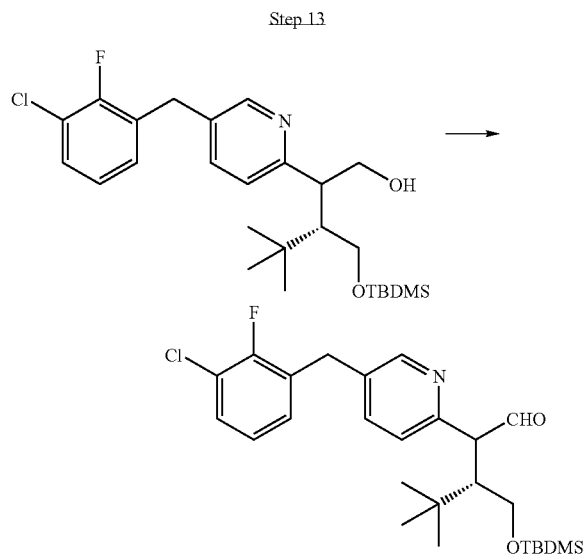

To a solution of dimethyl sulfoxide (158 µl, 2.22 mmol) in dichloromethane (1 ml) was added dropwise a solution of oxalyl chloride (97 µl, 1.11 mmol) in dichloromethane (1 ml) under an argon atmosphere at −70° C. or below, and the mixture was stirred for 10 min. Then, a solution of the compound (284 mg, 0.87 mmol) obtained in Step 12 in dichloromethane (1 ml) was added dropwise at −70° C. or below, and the mixture was stirred for 15 min. Triethylamine (517 µl, 3.71 mmol) was further added dropwise, and the mixture was stirred for 5 min, allowed to warm to −10° C. and stirred for 20 min. Water was added to the reaction mixture, and the mixture was extracted with ethyl acetate. The organic layer was washed twice with water and then with saturated brine, and dried over sodium sulfate. After filtration, the filtrate was concentrated under reduced pressure to give a crude product as a yellow oil (372 mg).

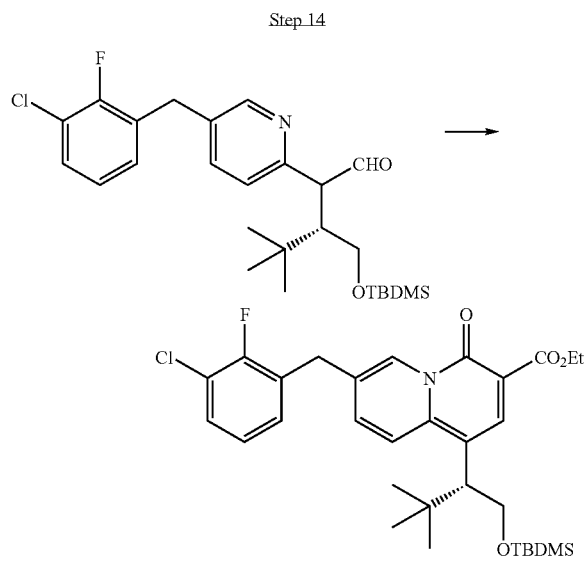

The compound (372 mg) obtained in Step 13 was dissolved in ethanol (9 ml), piperidine (0.22 ml) and diethyl malonate (591 µl, 3.89 mmol) were added, and the mixture was heated under reflux for 2 days. Piperidine (0.22 ml) and diethyl malonate (591 µl, 3.89 mmol) were added, and the mixture was further heated under reflux for 21 hr. The reaction mixture was concentrated under reduced pressure and the residue was dissolved in ethyl acetate, and the solution was washed twice with water and then with saturated brine, and dried over sodium sulfate. After filtration, the filtrate was concentrated under reduced pressure and the residue was purified by silica gel chromatography (hexane:ethyl acetate=4:1 to 2:1) to give the object product as a yellow oil (247 mg, yield 55%).

$^1$H NMR (CDCl$_3$ 300 MHz) (δ) ppm: −0.15 (3H, s), −0.03 (3H, s), 0.67 (9H, s), 0.98 (9H, s), 1.45 (3H, t, J=7.1 Hz), 3.18 (1H, m), 4.11 (2H, s), 4.11-4.20 (2H, m), 4.46 (2H, q, J=7.1 Hz), 7.06-7.12 (2H, m), 7.28-7.34 (1H, m), 7.46 (1H, d, J=9.4 Hz), 7.93 (1H, d, J=9.4 Hz), 8.43 (1H, s), 9.40 (1H, s)

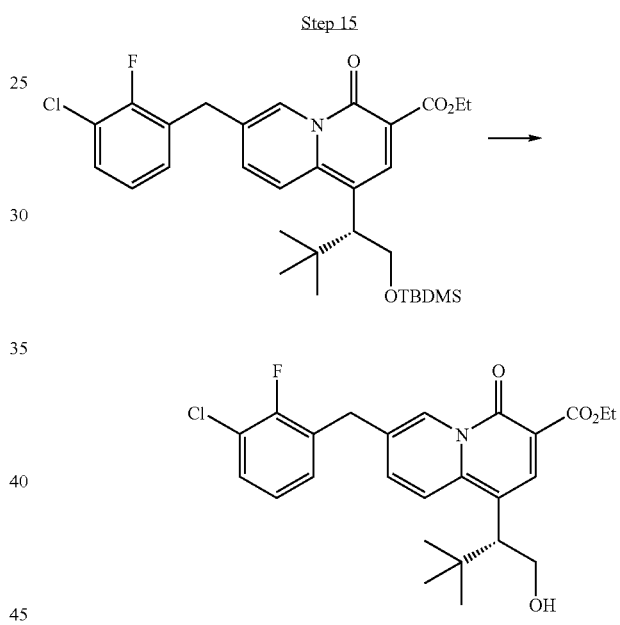

The compound (247 mg, 0.43 mmol) obtained in Step 14 was dissolved in tetrahydrofuran (2 ml), 1 M tetrabutylammonium fluoride tetrahydrofuran solution (0.65 ml, 0.65 mmol) was added, and the mixture was stirred for 40 min. 1 M tetrabutylammonium fluoride tetrahydrofuran solution (0.21 ml, 0.21 mmol) was added, and the mixture was further stirred for 1.5 hr. Water was added to the reaction mixture, and the mixture was extracted with ethyl acetate. The organic layer was washed with water and saturated brine, and dried over sodium sulfate. After filtration, the filtrate was concentrated under reduced pressure and the residue was purified by silica gel chromatography (hexane:ethyl acetate=1:1 to chloroform:methanol=9:1) to give the object product as a yellow amorphous form (169 mg, yield 85%).

$^1$H NMR (CDCl$_3$ 300 MHz) (δ) ppm: 0.94 (9H, s), 1.43 (3H, t, J=7.1 Hz), 3.24 (1H, dd, J=10.7 Hz, 5.4 Hz), 4.07-4.20 (2H, m), 4.09 (2H, s), 4.43 (2H, q, J=7.1 Hz), 7.05-7.10 (2H, m), 7.30-7.35 (1H, m), 7.50 (1H, d, J=9.4 Hz), 7.95 (1H, d, J=9.4 Hz), 8.39 (1H, s), 9.39 (1H, s)

Step 16

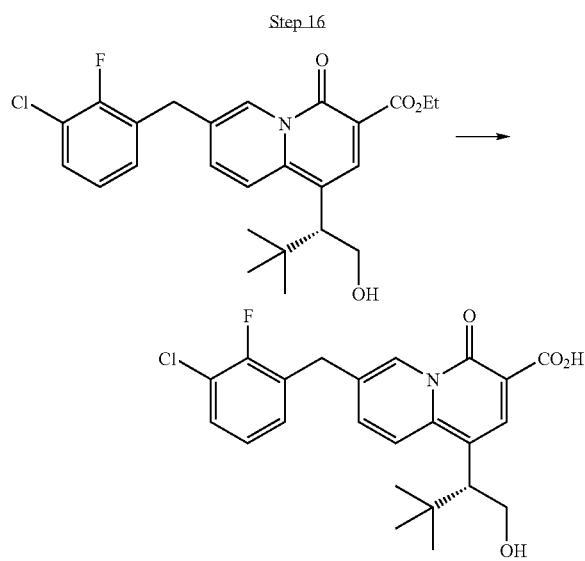

The compound (169 mg, 0.37 mmol) obtained in Step 15 was dissolved in tetrahydrofuran (5.6 ml), methanol (2.8 ml) and water (1.4 ml), lithium hydroxide monohydrate (31 mg, 0.74 mmol) was added, and the mixture was stirred at room temperature for 2 hr. A 10% aqueous citric acid solution was added to the reaction mixture, and the mixture was extracted with ethyl acetate. The organic layer was washed twice with water and then with saturated brine, and dried over sodium sulfate. After filtration, the filtrate was concentrated under reduced pressure and dried under reduced pressure to give the object product as a yellow solid (150 mg, yield 95%).

$^1$H NMR (DMSO-$d_6$ 300 MHz) (δ) ppm: 0.89 (9H, s), 3.31 (1H, m), 3.75-4.00 (2H, m), 4.30 (2H, s), 4.37 (1H, m), 7.20-7.30 (1H, m), 7.40-7.60 (2H, m), 7.90 (1H, d, J=9.4 Hz), 8.35 (1H, s), 8.47 (1H, d, J=9.4 Hz), 9.25 (1H, s), 14.30 (1H, br)

MS (ESI): M+ 432

Example 18

Step 1

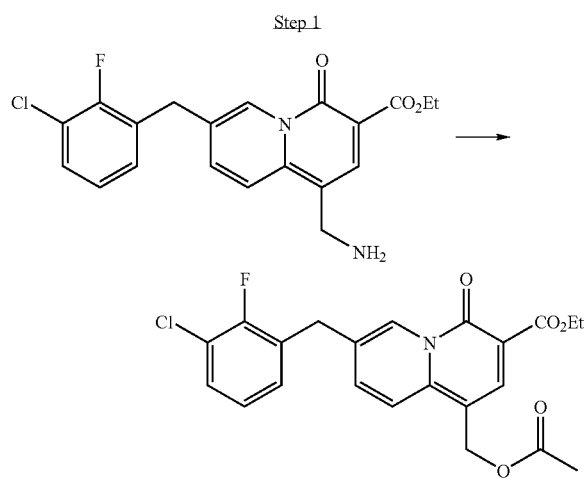

The compound (147 mg, 0.38 mmol) obtained in Step 8 of Example 37 was suspended in toluene (3 ml), acetic acid (26

μl, 0.45 mmol) and tert-butyl nitrite (54 μl, 0.45 mmol) were added, and the mixture was heated at 80° C. for 1 hr. A saturated aqueous sodium hydrogencarbonate solution was added to the reaction mixture, and the mixture was extracted three times with ethyl acetate. The organic layer was washed with water and saturated brine, and dried over sodium sulfate. After filtration, the filtrate was concentrated under reduced pressure and the residue was purified by PTLC (developing solvent: triple developments with chloroform:ethyl acetate=4:1) to give the object product as a yellow solid (77 mg, yield 47%).

$^1$H NMR (CDCl$_3$ 300 MHz) (δ) ppm: 1.42 (3H, t, J=7.1 Hz), 2.06 (3H, s), 4.13 (2H, s), 4.42 (2H, q), 5.27 (2H, s), 7.00-7.15 (2H, m), 7.30-7.40 (1H, m), 7.60 (1H, d, J=9.2 Hz), 7.80 (1H, d, J=9.2 Hz), 8.44 (1H, s), 9.39 (1H, s)

Step 2

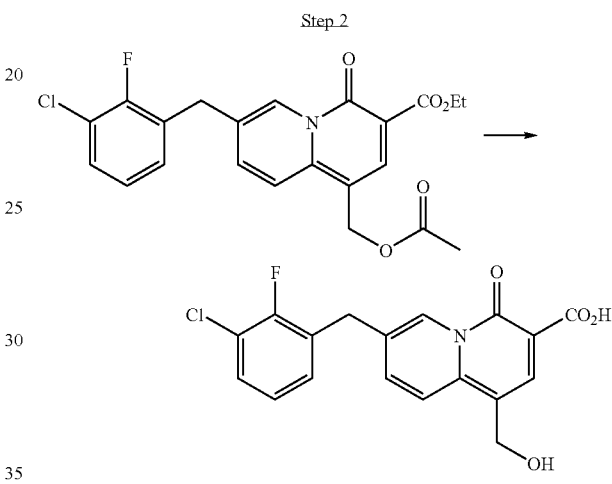

The compound (77 mg, 0.18 mmol) obtained in Step 1 was dissolved in tetrahydrofuran (4.3 ml) and water (1.1 ml), lithium hydroxide monohydrate (22 mg, 0.54 mmol) was added, and the mixture was stirred at room temperature for 12 hr. A 10% aqueous citric acid solution was added to the reaction mixture, and the mixture was extracted twice with ethyl acetate. The organic layer was washed with water and dried over sodium sulfate. After filtration, the filtrate was concentrated under reduced pressure to give a crude product (65 mg).

$^1$H NMR (DMSO-$d_6$ 300 MHz) (δ) ppm: 4.33 (2H, s), 4.77 (2H, d, J=5.4 Hz), 5.42 (1H, t, J=5.4 Hz), 7.20-7.25 (1H, m), 7.40-7.55 (2H, m), 8.00 (1H, d, J=9.2 Hz), 8.20 (1H, d, J=9.2 Hz), 8.40 (1H, s), 9.30 (1H, s)

MS (ESI): M+ 362

Example 19

Step 1

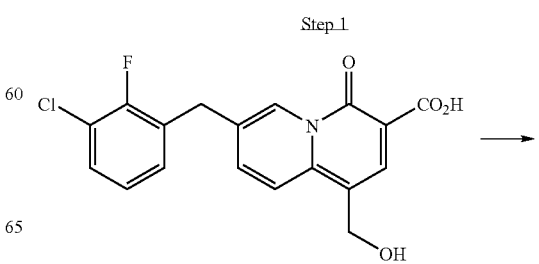

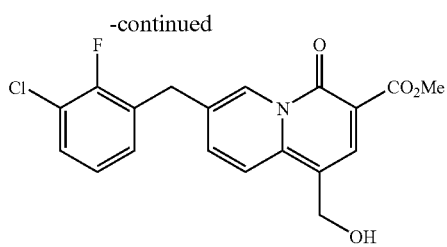

The compound (65 mg) obtained in Example 18 was dissolved in dimethylformamide, potassium carbonate (115 mg, 1.08 mmol) and iodomethane (50 μl, 0.81 mmol) were added, and the mixture was stirred at room temperature for 4.5 hr. Water was added to the reaction mixture, and the mixture was extracted twice with ethyl acetate. The organic layer was washed twice with water and then with saturated brine, and dried over sodium sulfate. After filtration, the filtrate was concentrated under reduced pressure. Ethyl acetate (0.5 ml) and hexane (3 ml) was added to the residue, and the residue was slurry-stirred. After filtration, the solid was dried under reduced pressure to give the object product as a yellow solid (31 mg, yield 46%, 2 steps).

$^1$H NMR (DMSO-$d_6$ 300 MHz) (δ) ppm: 3.77 (3H, s), 4.26 (2H, s), 4.65 (2H, d, J=5.4 Hz), 5.24 (1H, t, J=5.4 Hz), 7.20-7.25 (1H, m), 7.40-7.52 (2H, m), 7.88 (1H, d, J=9.1 Hz), 8.04 (1H, d, J=9.1 Hz), 8.25 (1H, s), 9.20 (1H, s)

Step 2

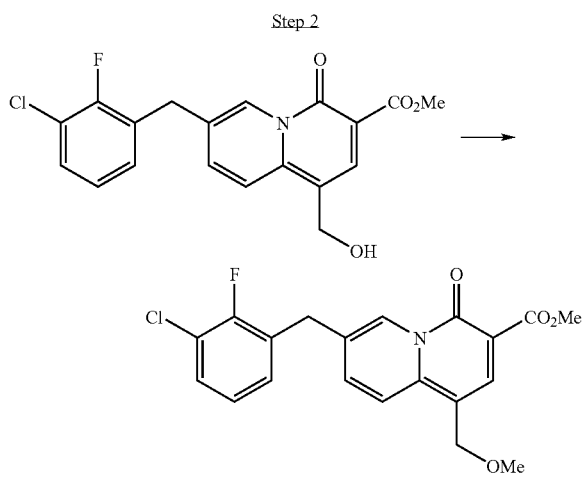

The compound (31 mg, 0.082 mmol) obtained in Step 1 was dissolved in chloroform (0.5 ml), iodomethane (30 μl, 0.49 mmol), 2,6-di-tert-butyl-4-methylpyridine (51 mg, 0.25 mmol), molecular sieves 4A (powder) and silver trifluoroacetate (63 mg, 0.25 mmol) were successively added under ice cooling, and the mixture was stirred at room temperature for 14 hr. Iodomethane (15 μl, 0.25 mmol) was added, and the mixture was further stirred for 6.5 hr. The reaction mixture was diluted with chloroform and filtered through celite. The filtrate was concentrated under reduced pressure. Ethyl acetate was added to the residue, and insoluble matter was filtered through celite. 2N Hydrochloric acid was added to the filtrate, and the mixture was extracted twice with ethyl acetate. The organic layer was washed twice with water and then with saturated brine, and dried over sodium sulfate. After filtration, the filtrate was concentrated under reduced pressure, the crude products obtained in the same manner were combined and purified by PTLC (developing solvent: double developments with chloroform:ethyl acetate=2:1) to give the object product as a yellow solid (23 mg).

$^1$H NMR (CDCl$_3$ 300 MHz) (δ) ppm: 3.37 (3H, s), 3.96 (3H, s), 4.14 (2H, s), 4.59 (2H, s), 7.00-7.15 (2H, m), 7.26-7.30 (1H, m), 7.60 (1H, d, J=9.1 Hz), 7.90 (1H, d, J=9.1 Hz), 8.36 (1H, s), 9.40 (1H, s)

Step 3

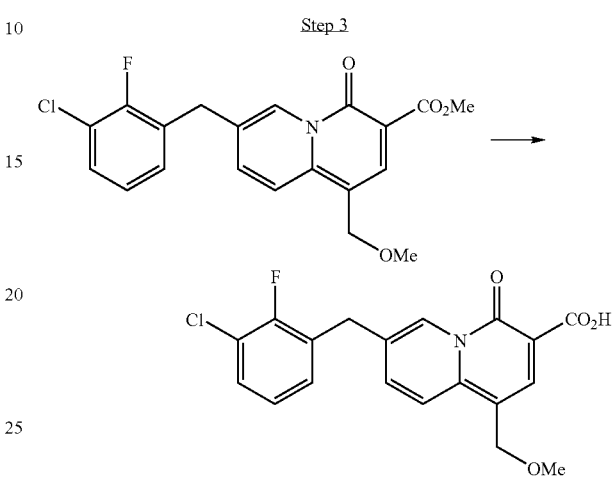

The compound (23 mg, 0.059 mmol) obtained in Step 2 was dissolved in tetrahydrofuran (1 ml), methanol (0.5 ml) and water (0.4 ml), and lithium hydroxide monohydrate (5.0 mg, 0.12 mmol) was added, and the mixture was stirred at room temperature for 3 hr. A 10% aqueous citric acid solution was added to the reaction mixture, and the mixture was extracted with ethyl acetate. The organic layer was washed twice with water and then with saturated brine, and dried over sodium sulfate. After filtration, the filtrate was concentrated under reduced pressure. Ethyl acetate (0.5 ml) and hexane (2 ml) were added to the residue, and the residue was slurry-stirred. After filtration, the solid was dried under reduced pressure to give the object product as a yellow solid (7 mg, yield 32%).

$^1$H NMR (DMSO-$d_6$ 300 MHz) (δ) ppm: 3.29 (3H, s), 4.33 (2H, s), 4.70 (2H, s), 7.20-7.25 (1H, m), 7.42-7.52 (2H, m), 8.03 (1H, d, J=9.1 Hz), 8.18 (1H, d, J=9.1 Hz), 8.39 (1H, s), 9.29 (1H, s), 14.00 (1H, br)

MS (ESI): M+ 376

Example 34

Step 1

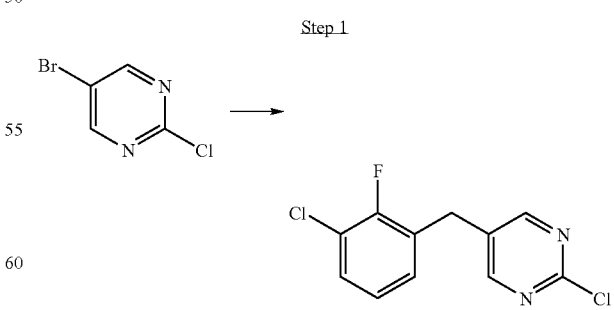

5-Bromo-2-chloropyrimidine (965 mg, 4.98 mmol) was dissolved in tetrahydrofuran (10 ml) and, under an argon atmosphere, dichlorobistriphenylphosphine palladium (II) (175 mg, 0.25 mmol) and 1M 3-chloro-2-fluorobenzylzinc bromide tetrahydrofuran solution (5.97 ml, 5.97 mmol) were added dropwise, and the mixture was heated under reflux for 1 hr. A saturated aqueous ammonium chloride solution was added to the reaction mixture, and the mixture was extracted with ethyl acetate. The organic layer was washed twice with water and then with saturated brine, and dried over sodium sulfate. After filtration, the filtrate was concentrated under reduced pressure and the residue was purified by silica gel chromatography (hexane:ethyl acetate=5:2) to give the object product as a white solid (903 mg, yield 71%).

$^1$H NMR (CDCl$_3$ 300 MHz) (δ) ppm: 3.99 (2H, s), 7.04-7.09 (2H, m), 7.32-7.37 (1H, m), 8.49 (2H, s)

Step 2

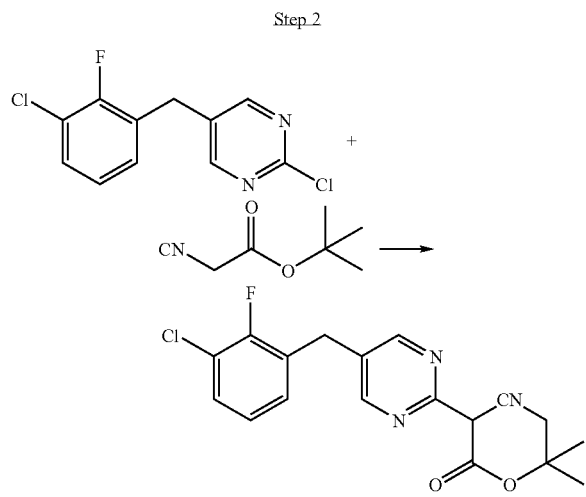

The compound (903 mg, 3.51 mmol) obtained in Step 1 was dissolved in dimethylformamide (10 ml), potassium carbonate (1.93 g, 14.05 mmol) and tert-butyl cyanoacetate (992 mg, 7.02 mmol) were added, and the mixture was stirred with heating at 120° C. for 1 hr. After allowing to cool, the reaction mixture was neutralized with aqueous citric acid solution, and extracted with ethyl acetate. The organic layer was washed twice with water and then with saturated brine, and dried over sodium sulfate. After filtration, the filtrate was concentrated under reduced pressure, and the residues obtained in the same manner were combined. Ethyl acetate and hexane were added and the residue was sonicated. After filtration, the solid was dried under reduced pressure to give the object product as a bright yellow solid (919 mg). The filtrate was concentrated under reduced pressure and the residue was purified by silica gel chromatography (hexane:ethyl acetate=1:1) to give the object product (321 mg).

$^1$H NMR (CDCl$_3$ 300 MHz) (δ) ppm: 1.52 (9H, s), 3.84 (2H, s), 7.05-7.11 (2H, m), 7.33-7.38 (1H, m), 7.54-7.57 (1H, m), 8.58 (1H, d, J=2.6 Hz), 13.88 (1H, brs)

Step 3

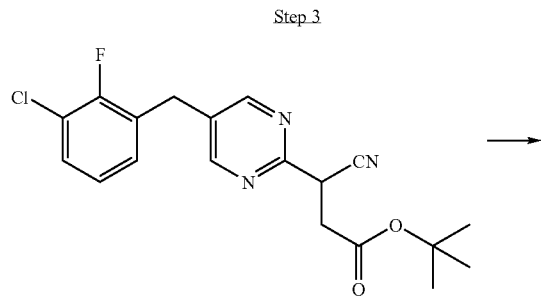

-continued

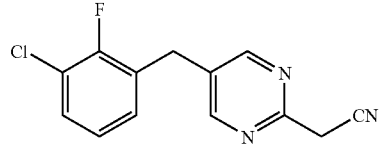

The compound (1.24 g, 3.43 mmol) obtained in Step 2 was dissolved in chloroform (12 ml), trifluoroacetic acid (2.4 ml) was added, and the mixture was stirred with heating at 60° C. for 13 hr. After allowing to cool, the reaction mixture was poured into saturated aqueous sodium hydrogencarbonate solution, and the mixture was extracted with chloroform. The organic layer was washed twice with water and then with saturated brine, and dried over sodium sulfate. After filtration, the filtrate was concentrated under reduced pressure and the residue was purified by silica gel chromatography (hexane:ethyl acetate=1:1) to give the object product as a yellow solid (733 mg, yield 82%).

$^1$H NMR (CDCl$_3$ 300 MHz) (δ) ppm: 4.01 (2H, s), 4.07 (2H, s), 7.03-7.10 (2H, m), 7.30-7.37 (1H, m), 8.60 (2H, s)

Step 4

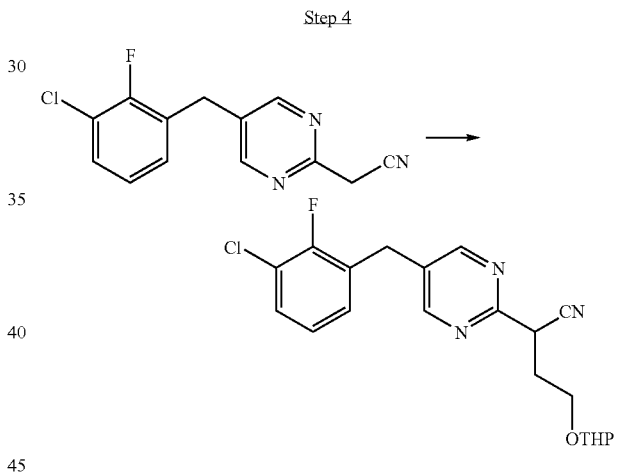

The compound (600 mg, 2.29 mmol) obtained in Step 3 was dissolved in dimethylformamide (12 ml), sodium hydride (92 mg, 2.29 mmol) was added, and the mixture was stirred at room temperature for 10 min. Under ice-cooling, 2-(2-bromoethoxy)tetrahydro-2H-pyran (346 μl, 2.29 mmol) was added, and the mixture was allowed to warm to room temperature and stirred for 3 hr. Water was added to the reaction mixture, and the mixture was extracted with ethyl acetate. The organic layer was washed three times with water and then with saturated brine, and dried over sodium sulfate. After filtration, the filtrate was concentrated under reduced pressure and the residue was purified by silica gel chromatography (hexane:ethyl acetate=1:1) to give the object product as an orange oil (382 mg, yield 43%).

$^1$H NMR (CDCl$_3$ 300 MHz) (δ) ppm: 1.42-1.81 (6H, m), 2.25-2.70 (2H, m), 3.34-3.67 (2H, m), 3.74-3.99 (2H, m), 4.00 (2H, s), 4.37-4.46 (1H, m), 4.57-4.62 (1H, m), 7.05-7.07 (2H, m), 7.30-7.37 (1H, m), 8.61 (2H, s)

Step 5

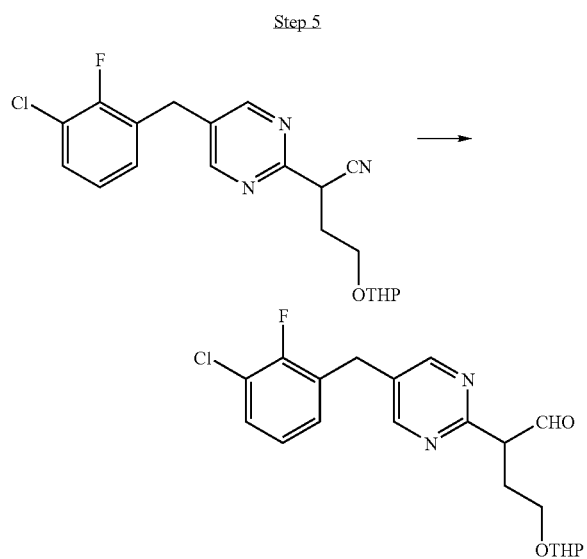

The compound (382 mg, 0.98 mmol) obtained in Step 4 was dissolved in pyridine (4 ml), acetic acid (2 ml) and water (2 ml), sodium phosphinate monohydrate (519 mg, 4.90 mmol) and Raney nickel (1 ml) were added, and the mixture was stirred with heating at 60° C. for 1.5 hr. After allowing to cool, the supernatant was filtered through celite, and ethyl acetate was added to the filtrate. The mixture was successively washed twice with water, then with saturated aqueous sodium hydrogencarbonate solution and saturated brine, and dried over sodium sulfate. After filtration, the filtrate was concentrated under reduced pressure to give a crude product as an orange oil (349 mg).

Step 6

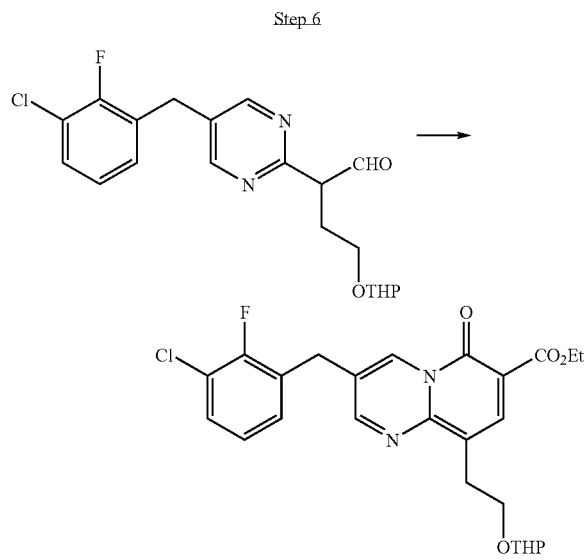

The compound (349 mg) obtained in Step 5 was dissolved in ethanol (10 ml), piperidine (245 μl) and diethyl malonate (674 μl, 4.44 mmol) were added, and the mixture was heated under reflux for 14 hr. The reaction mixture was concentrated under reduced pressure and the residue was dissolved in ethyl acetate, and the solution was washed twice with water and then with saturated brine, and dried over sodium sulfate. After filtration, the filtrate was concentrated under reduced pressure and the residue was roughly purified by silica gel chromatography (hexane:ethyl acetate=1:2) and then purified by PTLC (developing solvent: hexane:ethyl acetate=1:2) to give the object product (38 mg) as a yellow oil containing by-products.

$^1$H NMR (CDCl$_3$ 300 MHz) (δ) ppm: 1.41 (3H, t, J=7.2 Hz), 1.45-1.83 (6H, m), 3.23 (2H, t, J=6.6 Hz), 3.59-3.76 (2H, m), 3.90-3.99 (2H, m), 4.11 (2H, s), 4.41 (2H, q, J=7.2 Hz), 4.58-4.61 (1H, m), 7.05-7.17 (2H, m), 7.33-7.38 (1H, m), 8.58 (1H, s), 8.70 (1H, d, J=2.2 Hz), 9.34 (1H, d, J=2.2 Hz).

Step 7

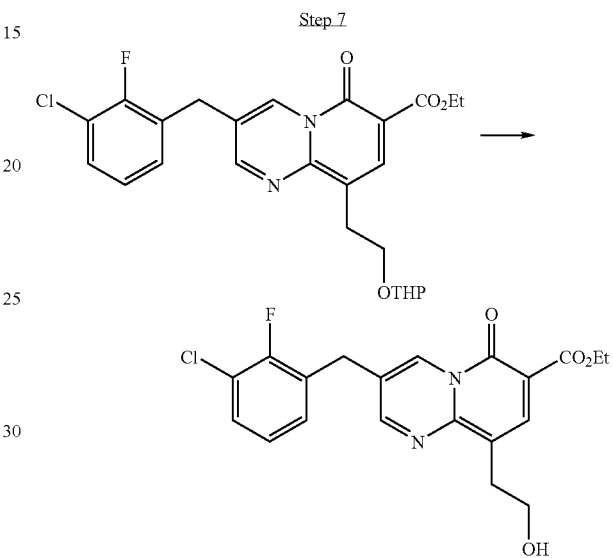

The compound (38 mg) obtained in Step 6 was dissolved in methanol (0.7 ml), p-toluenesulfonic acid monohydrate (7.0 mg, 0.039 mmol) was added, and the mixture was stirred at room temperature for 1 hr. A saturated aqueous sodium hydrogencarbonate solution was added to the reaction mixture, and the mixture was extracted with ethyl acetate. The organic layer was washed twice with water and then with saturated brine, and dried over sodium sulfate. After filtration, the filtrate was concentrated under reduced pressure and the residue was purified by PTLC (developing solvent: chloroform:methanol=20:1) to give the object product as a yellow solid (24 mg, yield 6%, 3 steps).

$^1$H NMR (CDCl$_3$ 300 MHz) (δ) ppm: 1.41 (3H, t, J=7.2 Hz), 2.02 (1H, brs), 3.19 (2H, t, J=6.2 Hz), 3.91 (2H, t, J=6.2 Hz), 4.12 (2H, s), 4.41 (2H, q, J=7.2 Hz), 7.06-7.18 (2H, m), 7.34-7.39 (1H, m), 8.51 (1H, s), 8.71 (1H, d, J=2.2 Hz), 9.36 (1H, d, J=2.2 Hz)

Step 8

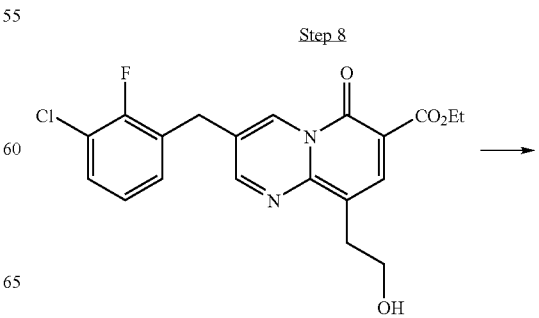

-continued

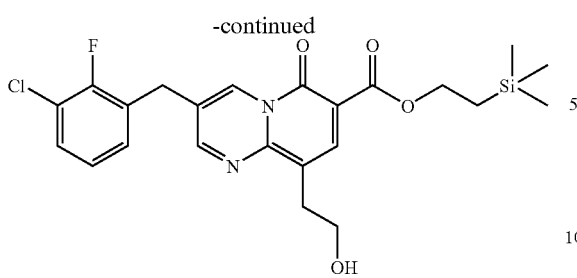

The compound (17 mg, 0.042 mmol) obtained in Step 7 was dissolved in 2-trimethylsilylethanol (0.6 ml), titanium (IV) ethoxide (9.0 μl, 0.042 mmol) was added, and the mixture was stirred with heating at 100° C. for 5 hr. 1N Hydrochloric acid was added to the reaction mixture, and the mixture was extracted with ethyl acetate. The organic layer was washed twice with water and then with saturated brine, and dried over sodium sulfate. After filtration, the filtrate was concentrated under reduced pressure and the residue was purified by PTLC (developing solvent: chloroform:methanol=20:1) to give the object product as a yellow solid (17 mg, yield 85%).

$^1$H NMR (CDCl$_3$ 300 MHz) (δ) ppm: 0.07 (9H, s), 1.19 (2H, t, J=8.6 Hz), 2.01 (1H, brs), 3.19 (2H, t, J=6.2 Hz), 3.91 (2H, t, J=6.2 Hz), 4.11 (2H, s), 4.44 (2H, t, J=8.6 Hz), 7.06-7.18 (2H, m), 7.33-7.39 (1H, m), 8.51 (1H, s), 8.70 (1H, d, J=2.2 Hz), 9.36 (1H, d, J=2.2 Hz)

Step 9

The compound (17 mg, 0.036 mmol) obtained in Step 8 was dissolved in tetrahydrofuran (0.4 ml), 1 M tetrabutylammonium fluoride tetrahydrofuran solution (71 μl, 0.071 mmol) was added, and the mixture was stirred at room temperature for 16 hr. Water was added to the reaction mixture, and the mixture was extracted with ethyl acetate. The organic layer was washed three times with water and then with saturated brine, and dried over sodium sulfate. After filtration, the filtrate was concentrated under reduced pressure and the obtained residue was purified by PTLC (developing solvent: chloroform:methanol=10:1) to give the object product as a bright yellow solid (8 mg, yield 60%).

$^1$H NMR (CDCl$_3$ 300 MHz) (δ) ppm: 1.85 (1H, br s), 3.27 (2H, t, J=6.1 Hz), 3.94 (2H, t, J=6.1 Hz), 4.19 (2H, s), 7.10-7.23 (2H, m), 7.37-7.43 (1H, m), 8.75 (1H, s), 8.84 (1H, d, J=2.2 Hz), 9.31 (1H, d, J=2.2 Hz), 13.57 (1H, br s)

MS (ESI): M+ 377

Example 37

Step 1

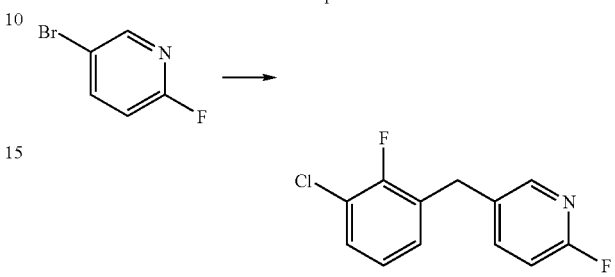

5-Bromo-2-fluoropyridine (16.10 g, 0.092 mol) was dissolved in tetrahydrofuran (160 ml) and, under an argon atmosphere, dichlorobistriphenylphosphine palladium (II) (1.93 g, 2.75 mmol) and 1M 3-chloro-2-fluorobenzylzinc bromide tetrahydrofuran solution (110.00 ml, 0.11 mol) were added dropwise, and the mixture was heated under reflux for 1 hr. A saturated aqueous ammonium chloride solution was added to the reaction mixture, and the mixture was extracted with ethyl acetate. The organic layer was washed twice with saturated aqueous ammonium chloride solution and successively with saturated brine, and dried over sodium sulfate. After filtration, the filtrate was concentrated under reduced pressure and the residue was purified by silica gel chromatography (hexane:ethyl acetate=4:1) to give the object product as a brown oil (16.30 g, yield 74%).

$^1$H NMR (CDCl$_3$ 300 MHz) (δ) ppm: 4.00 (2H, s), 6.87 (1H, dd, J=8.3 Hz, J=3.0 Hz), 7.02-7.05 (2H, m), 7.26-7.33 (1H, m), 7.60 (1H, ddd, J=8.0 Hz, 8.0 Hz, 2.6 Hz), 8.10 (1H, s)

Step 2

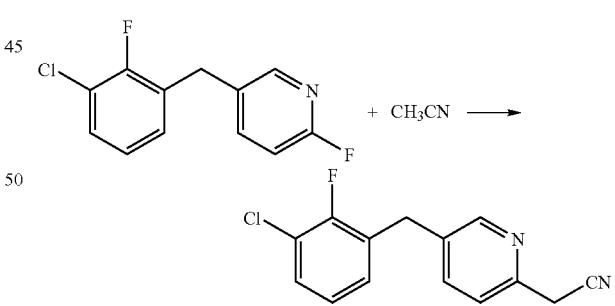

To a solution of acetonitrile (12.56 ml, 0.24 mol) in tetrahydrofuran (60 ml), 2.71 M lithium diisopropylamide hexane solution (75.00 ml, 0.20 mol) was added dropwise under an argon atmosphere, and the mixture was stirred for 20 min. Then a solution of the compound (16.30 g, 0.068 mol) obtained in Step 1 in tetrahydrofuran (60 ml) was added dropwise at −78° C., and the mixture was allowed to warm to room temperature and stirred for 30 min. Water was added to the reaction mixture, and the mixture was extracted with diisopropyl ether. The organic layer was washed with water and saturated brine, and dried over sodium sulfate. After filtration, the filtrate was concentrated under reduced pressure and the residue was purified by silica gel chromatography (hexane:ethyl acetate=1:1) to give the object product as a brown oil (3.64 g, yield 21%).

$^1$H NMR (CDCl$_3$ 400 MHz) (δ) ppm: 3.91 (2H, s), 4.02 (2H, s), 7.00-7.08 (2H, m), 7.28-7.37 (2H, m), 7.55 (1H, d, J=8.0 Hz, J=2.2 Hz), 8.47 (1H, s)

Step 3

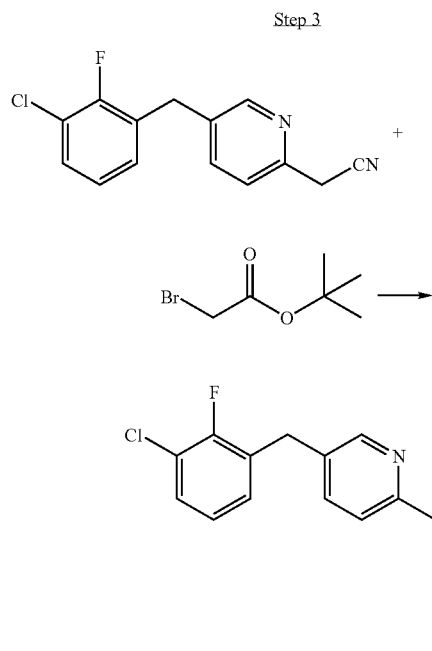

The compound (3.64 g, 13.96 mmol) obtained in Step 2 was dissolved in dimethylformamide, potassium carbonate (3.87 g, 28.00 mmol) and tert-butyl bromoacetate (2.73 g, 14.00 mmol) were added, and the mixture was stirred with heating at 60° C. for 2.5 hr. After cooling, water was added to the reaction mixture, and the mixture was extracted with ethyl acetate. The organic layer was washed twice with water and then with saturated brine, and dried over sodium sulfate. After filtration, the filtrate was concentrated under reduced pressure and the residue was purified by silica gel chromatography (hexane:ethyl acetate=3:1 to 1:2) to give the object product as a red oil (1.89 g, yield 36%).

$^1$H NMR (CDCl$_3$ 300 MHz) (δ) ppm: 1.42 (9H, s), 2.92-3.11 (2H, m) 4.01 (2H, s), 4.36 (1H, t, J=7.5 Hz), 7.03-7.04 (2H, m), 7.26-7.30 (1H, m), 7.41 (1H, d, J=8.0 Hz), 7.54 (1H, d, J=8.0 Hz), 8.47 (1H, s)

Step 4

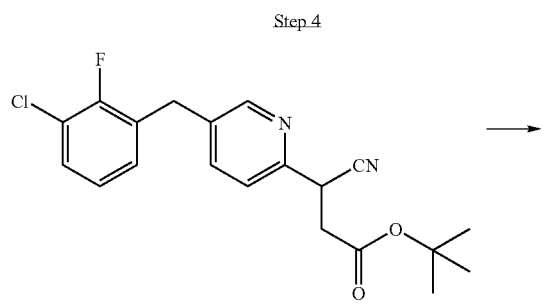

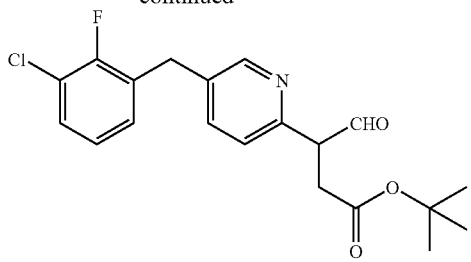

The compound (2.33 g, 6.22 mmol) obtained in Step 3 was dissolved in pyridine (23 ml), acetic acid (11 ml) and water (11 ml), sodium phosphinate monohydrate (3.29 g, 31.08 mmol) and Raney nickel (3.11 ml) were added, and the mixture was stirred with heating at 60° C. for 30 min. After cooling, the supernatant was filtered through celite. The filtrate was concentrated under reduced pressure. The residue was dissolved in ethyl acetate, and the solution was washed successively with water, saturated aqueous ammonium chloride solution (twice), saturated aqueous sodium hydrogencarbonate solution and saturated brine, and dried over sodium sulfate. After filtration, the filtrate was concentrated under reduced pressure to give a crude product (2.44 g).

Step 5

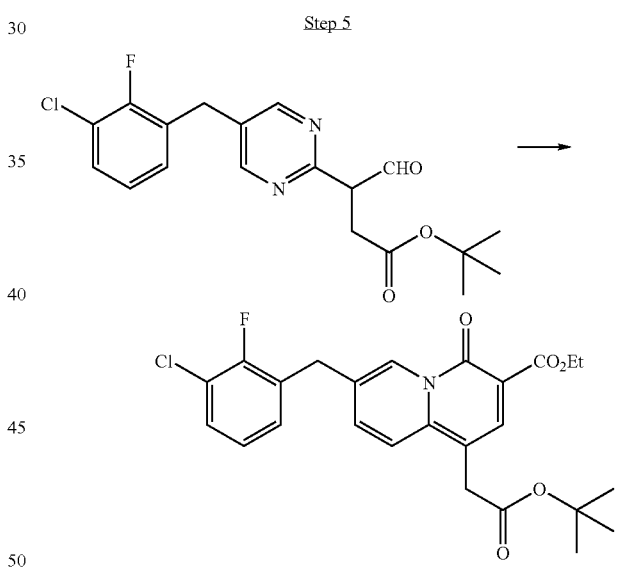

The compound (2.44 g) obtained in Step 4 was dissolved in ethanol (5.5 ml), piperidine (1.1 ml), acetic acid (1.7 ml) and diethyl malonate (4.72 ml, 31.09 mmol) were added, and the mixture was heated under reflux for 16 hr. The reaction mixture was concentrated under reduced pressure and the residue was dissolved in ethyl acetate, and the solution was washed successively with water, saturated aqueous ammonium chloride solution, saturated aqueous sodium hydrogencarbonate solution and saturated brine, and dried over sodium sulfate. After filtration, the filtrate was concentrated under reduced pressure and the residue was purified by silica gel chromatography (hexane:ethyl acetate=1:1 to 1:2) to give the object product as a yellow solid (1.30 g, yield 44%, 2 steps).

$^1$H NMR (CDCl$_3$ 300 MHz) (δ) ppm: 1.42 (9H, s), 1.42 (3H, t, J=7.1 Hz), 3.68 (2H, s), 4.11 (2H, s), 4.41 (2H, q, J=7.1

Hz), 7.05-7.10 (2H, m), 7.26-7.32 (1H, m), 7.57 (1H, d, J=9.1 Hz), 7.68 (1H, d, J=9.1 Hz), 8.29 (1H, s), 9.37 (1H, s)

Step 6

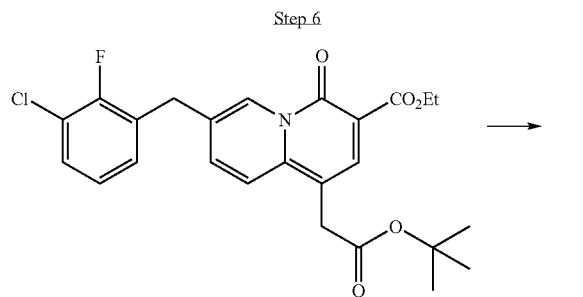

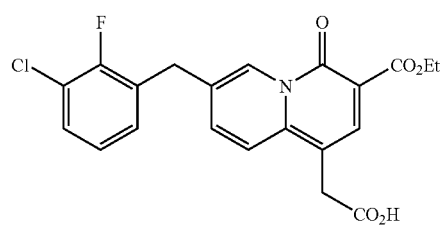

Trifluoroacetic acid (13 ml) was added to the compound (1.30 g, 2.74 mmol) obtained in Step 5, and the mixture was stirred at room temperature for 1.5 hr. The reaction mixture was concentrated under reduced pressure and azeotroped twice with toluene. Ethyl acetate (20 ml) and hexane (20 ml) were added to the residue, and the residue was slurry-stirred at room temperature for 1 hr. After filtration, the solid was dried under reduced pressure to give the object product as a yellow solid (1.01 g, yield 88%).

$^1$H NMR (CDCl$_3$ 300 MHz) (δ) ppm: 1.41 (3H, t, J=7.1 Hz), 3.80 (2H, s), 4.11 (2H, s), 4.40 (2H, q, J=7.1 Hz), 7.04-7.11 (2H, m), 7.32 (1H, m), 7.59 (1H, d, J=9.1 Hz), 7.67 (1H, d, J=9.1 Hz), 8.30 (1H, s), 9.39 (1H, s)

Step 7

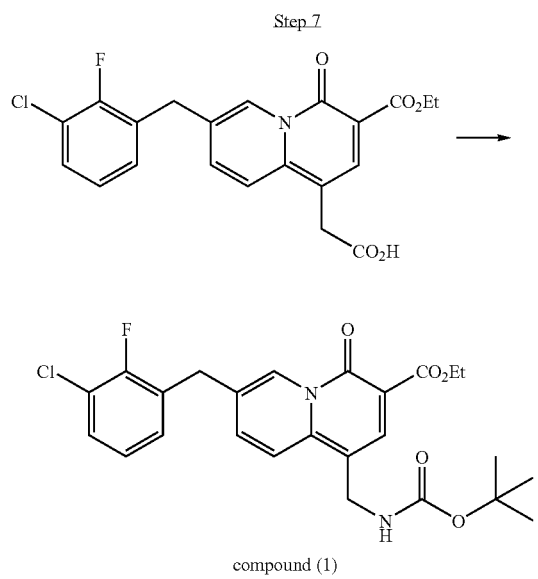

compound (1)

-continued

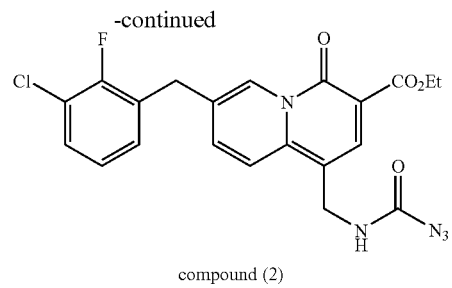

compound (2)

The compound (1.52 g, 3.64 mmol) obtained in Step 6 was dissolved in 1,4-dioxane (30 ml), triethylamine (609 μl, 4.37 mmol) and diphenylphosphoryl azide (824 μl, 3.82 mmol) were added, and the mixture was stirred at room temperature for 30 min. tert-Butanol (15 ml) was added to the reaction mixture and the mixture was heated under reflux for 22 hr. After allowing to cool, water was added to the reaction mixture, and the mixture was extracted with chloroform, and the organic layer was dried over magnesium sulfate. After filtration, the filtrate was concentrated under reduced pressure and the residue was purified by silica gel chromatography (chloroform:ethyl acetate=4:1 to 2:1) to give compound (1) as a yellow solid (759 mg, yield 48%) and compound (2) as a yellow solid (86 mg, yield 5%).

Compound (1)
$^1$H NMR (CDCl$_3$ 400 MHz) (δ) ppm: 1.43 (3H, t, J=6.8 Hz), 1.46 (9H, s), 4.13 (2H, s), 4.43 (2H, q, J=7.0 Hz), 4.51 (2H, d, J=6.0 Hz), 4.71-4.78 (1H, m), 7.05-7.14 (2H, m), 7.32-7.36 (1H, m), 7.62 (1H, dd, J=9.2, 1.7 Hz), 7.95-8.00 (1H, m), 8.32 (1H, s), 9.39 (1H, d, J=0.9 Hz)

Compound (2)
$^1$H NMR (CDCl$_3$ 400 MHz) (δ) ppm: 1.44 (3H, t, J=7.1 Hz), 4.15 (2H, s), 4.43 (2H, q, J=14.1 Hz), 4.63 (2H, d, J=6.2 Hz), 5.40-5.44 (1H, m), 7.07-7.17 (2H, m), 7.34-7.38 (1H, m), 7.67-7.69 (1H, m), 7.93-7.95 (1H, m), 8.31 (1H, s), 9.40 (1H, s)

Step 8

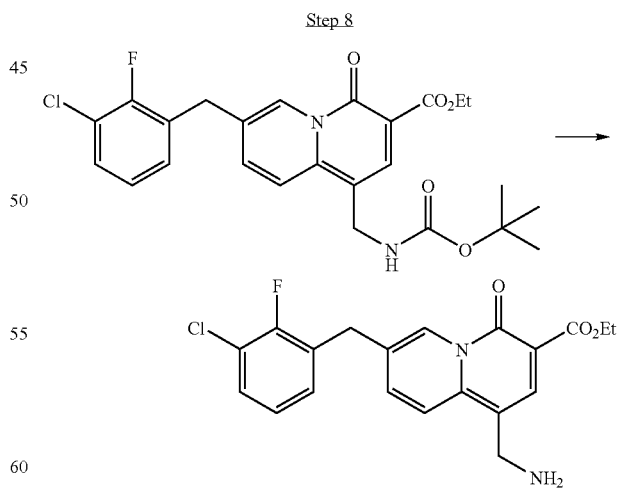

Trifluoroacetic acid (1.8 ml) was added to the compound (1) (178 mg, 0.36 mmol) obtained in Step 7, and the mixture was stirred at room temperature for 2 hr. The reaction mixture was concentrated under reduced pressure, saturated aqueous sodium hydrogencarbonate solution was added to the residue, and the mixture was extracted three times with ethyl acetate. The organic layer was washed with water, and dried over magnesium sulfate. After filtration, the filtrate was concentrated under reduced pressure to give the object product as a yellow amorphous form (134 mg, yield 95%).

¹H NMR (CDCl₃ 300 MHz) (δ) ppm: 1.40 (3H, t, J=7.1 Hz), 4.11 (2H, s), 4.11 (2H, s), 4.40 (2H, q, J=7.1 Hz), 7.01-7.13 (2H, m), 7.29-7.34 (1H, m), 7.59 (1H, d, J=9.1 Hz), 8.03 (1H, d, J=9.1 Hz), 8.34 (1H, s), 9.36 (1H, s)

Step 9

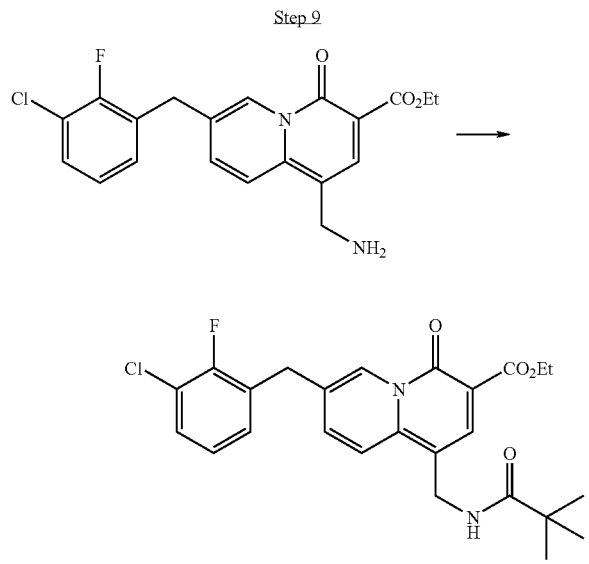

The compound (32 mg, 0.082 mmol) obtained in Step 8 was dissolved in chloroform (0.5 ml), triethylamine (23 μl, 0.16 mmol) and pivaloyl chloride (15 μl, 0.12 mmol) were added under ice-cooling, and the mixture was stirred at room temperature for 1 hr. Water was added to the reaction mixture, and the mixture was extracted twice with ethyl acetate. The organic layer was washed successively with water and saturated brine, and dried over sodium sulfate. After filtration, the filtrate was concentrated under reduced pressure and the residue was purified by PTLC (developing solvent: chloroform:methanol=20:1) to give the object product as a yellow amorphous form (34 mg, yield 88%).

¹H NMR (CDCl₃ 300 MHz) (δ) ppm: 1.19 (9H, s), 1.42 (3H, t, J=7.1 Hz), 4.11 (2H, s), 4.42 (2H, q, J=7.1 Hz), 4.63 (2H, d, J=5.7 Hz), 5.80-5.90 (1H, br), 7.05-7.12 (2H, m), 7.30-7.35 (1H, m), 7.59 (1H, d, J=9.1 Hz), 7.93 (1H, d, J=9.1 Hz), 8.31 (1H, s), 9.36 (1H, s)

Step 10

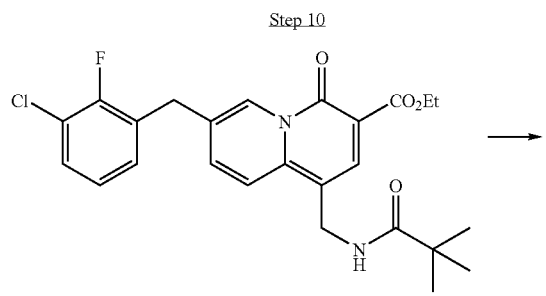

-continued

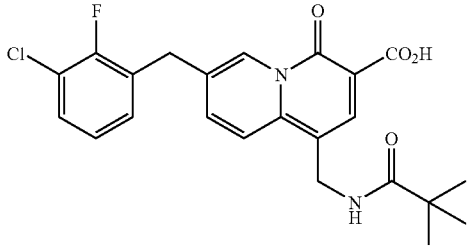

The compound (34 mg, 0.072 mmol) obtained in Step 9 was dissolved in tetrahydrofuran (1.7 ml), methanol (0.8 ml) and water (0.4 ml), lithium hydroxide monohydrate (6.0 mg, 0.14 mmol) were added, and the mixture was stirred at room temperature for 2 hr. Lithium hydroxide monohydrate (3.0 mg, 0.071 mmol) was added, and the mixture was further stirred for 3 hr. A 10% aqueous citric acid solution was added to the reaction mixture, and the mixture was extracted with ethyl acetate. The organic layer was washed twice with water and then with saturated brine, and dried over sodium sulfate. After filtration, the filtrate was concentrated under reduced pressure to give the object product as a yellow solid (20 mg, yield 63%).

¹H NMR (DMSO-d₆ 300 MHz) (δ) ppm: 1.18 (9H, s), 4.32 (2H, s), 4.52 (2H, d, J=5.6 Hz), 7.22 (1H, dd, J=7.9 Hz, 7.9 Hz), 7.42-7.52 (2H, m), 8.01 (1H, d, J=9.2 Hz), 8.10 (1H, br), 8.26 (1H, d, J=9.2 Hz), 8.35 (1H, s), 9.25 (1H, s), 14.11 (1H, s)

MS (ESI): M+ 445

Example 58

Step 1

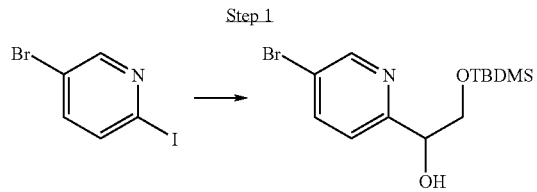

5-Bromo-2-iodopyridine (1.05 g, 3.69 mmol) was dissolved in tetrahydrofuran (8 ml) and, under an argon atmosphere, 1 M isopropyl magnesium chloride tetrahydrofuran solution (4.00 ml, 4.00 mmol) was added dropwise at 0° C. or below, and the mixture was stirred at the same temperature for 1 hr. A solution of tert-butyldimethylsilyloxyacetaldehyde (1.00 g, 5.16 mmol) in tetrahydrofuran (2 ml) was added dropwise at −5° C. or below and, after dropwise addition, the mixture was allowed to warm to room temperature and stirred for 14 hr. 1N Hydrochloric acid (4 ml) was added to the reaction mixture, and the mixture was extracted with ethyl acetate. The organic layer was washed with water and saturated brine, and dried over magnesium sulfate. After filtration, the filtrate was concentrated under reduced pressure and the residue was purified by silica gel chromatography (hexane:ethyl acetate=4:1) to give the object product as a yellow oil (830 mg, yield 68%).

¹H NMR (CDCl₃ 400 MHz) (δ) ppm: 0.08 (3H, s), 0.09 (3H, s), 0.87 (9H, s), 3.64-3.80 (2H, m), 4.72-4.80 (1H, m), 7.38-7.41 (1H, m), 7.81-7.83 (1H, m), 8.60-8.61 (1H, m)

Step 2

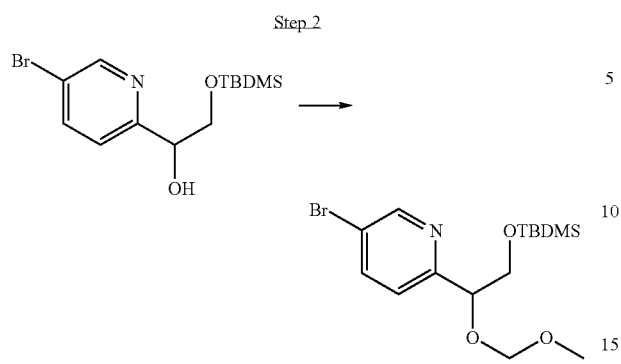

The compound (476 mg, 1.43 mmol) obtained in Step 1 was dissolved in chloroform (5 ml), diisopropylethylamine (1.50 ml, 8.60 mmol) and chloromethyl methyl ether (0.49 ml, 6.44 mmol) were added, and the mixture was stirred at room temperature for 19 hr. A saturated aqueous sodium hydrogencarbonate solution was added to the reaction mixture, and the mixture was extracted with chloroform. The organic layer was washed with water and saturated brine, and dried over sodium sulfate. After filtration, the filtrate was concentrated under reduced pressure. The residues obtained in the same manner were combined and purified by silica gel chromatography (hexane:ethyl acetate=6:1) to give the object product as a colorless oil (454 mg).

$^1$H NMR (CDCl$_3$ 300 MHz) ($\delta$) ppm: −0.04−−0.02 (6H, m), 0.83 (9H, s), 3.35 (3H, s), 3.83-3.96 (2H, m), 4.65 (1H, d, J=6.7 Hz), 4.73-4.80 (1H, m), 4.79 (1H, d, J=6.7 Hz), 7.35 (1H, d, J=8.3 Hz), 7.80 (1H, dd, J=8.3 Hz, J=2.3 Hz), 8.64 (1H, s)

Step 3

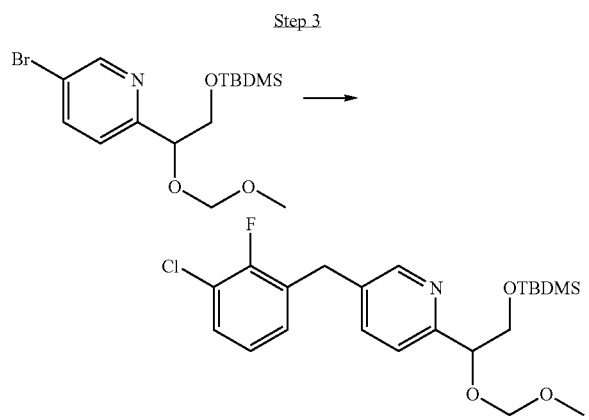

The compound (259 mg, 0.69 mmol) obtained in Step 2 was dissolved in tetrahydrofuran (2.5 ml) and, under an argon atmosphere, dichlorobistriphenylphosphine palladium (II) (15 mg, 0.21 mmol) and 1M 3-chloro-2-fluorobenzylzinc bromide tetrahydrofuran solution (0.83 ml, 0.83 mmol) were added dropwise, and the mixture was heated under reflux for 30 min. A saturated aqueous ammonium chloride solution was added to the reaction mixture, and the mixture was extracted with ethyl acetate. The organic layer was washed twice with saturated aqueous ammonium chloride solution and then with saturated brine, and dried over sodium sulfate. After filtration, the filtrate was concentrated under reduced pressure and the residue was roughly purified by silica gel chromatography (hexane:ethyl acetate=3:1) to give the object product as a colorless oil (506 mg).

Step 4

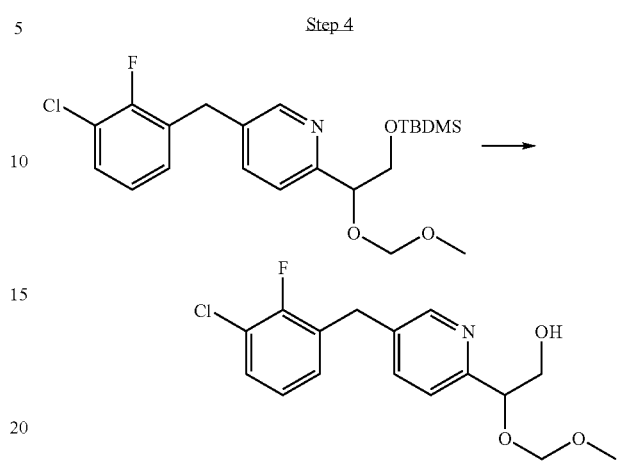

The compound (501 mg) obtained in Step 3 was dissolved in tetrahydrofuran (4 ml), 1 M tetrabutylammonium fluoride tetrahydrofuran solution (2.28 ml, 2.28 mmol) was added, and the mixture was stirred at room temperature for 1 hr. Water was added to the reaction mixture, and the mixture was extracted with ethyl acetate. The organic layer was washed with water and saturated brine, and dried over sodium sulfate. After filtration, the filtrate was concentrated under reduced pressure and the obtained residue was purified by silica gel chromatography (after elution with ethyl acetate, eluted with chloroform:methanol=20:1) to give the object product as a colorless oil (284 mg, yield 72%, 2 steps).

$^1$H NMR (CDCl$_3$ 300 MHz) ($\delta$) ppm: 3.42 (3H, s), 3.86-3.96 (2H, m), 4.01 (2H, s), 4.71-4.81 (3H, m), 7.00-7.08 (2H, m), 7.29 (1H, ddd, J=11.4 Hz, 7.3 Hz, 2.1 Hz), 7.38 (1H, d, J=8.0 Hz), 7.54 (1H, dd, J=8.0 Hz, 2.1 Hz), 8.46 (1H, d, J=1.9 Hz)

Step 5

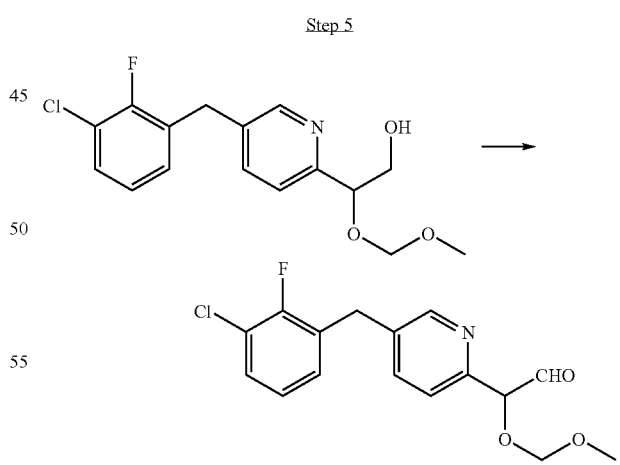

To a solution of dimethyl sulfoxide (190 µl, 2.62 mmol) in dichloromethane (1 ml) was added dropwise a solution of oxalyl chloride (114 µl, 1.31 mmol) in dichloromethane (1 ml) under an argon atmosphere at −70° C. or below, and the mixture was stirred for 15 min. Then, a solution of the compound (284 mg, 0.87 mmol) obtained in Step 4 in dichloromethane (1 ml) was added dropwise at −70° C. or below, and the mixture was stirred for 15 min. Further, triethylamine (607 µl, 4.36 mmol) was added dropwise and the mixture was stirred for 10 min, after which the mixture was allowed to warm to −10° C. and stirred for 15 min. Water was added to the reaction mixture, and the mixture was extracted with ethyl acetate. The organic layer was washed twice with water and then with saturated brine, and dried over sodium sulfate. After filtration, the filtrate was concentrated under reduced pressure to give a crude product as a brown oil (251 mg).

Step 6

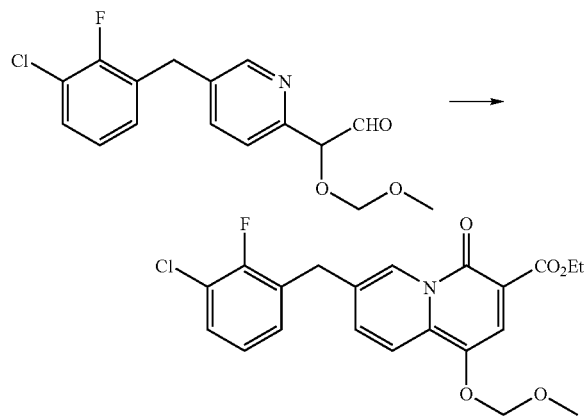

The compound (251 mg) obtained in Step 5 was dissolved in ethanol (7 ml), piperidine (248 µl) and diethyl malonate (662 µl, 4.36 mmol) were added, and the mixture was heated under reflux for 4 days. Water was added to the reaction mixture, and the mixture was extracted with ethyl acetate. The organic layer was washed three times with water and then with saturated brine, and dried over sodium sulfate. After filtration, the filtrate was concentrated under reduced pressure and the residue was roughly purified by silica gel chromatography (hexane:ethyl acetate=1:1 to ethyl acetate alone) and further by PTLC (developing solvent: triple developments with chloroform:ethyl acetate=4:1) to give the object product as an orange paste (26 mg, yield 7%, 2 steps).

$^1$H NMR (CDCl$_3$ 300 MHz) (δ) ppm: 1.43 (3H, t, J=7.1 Hz), 3.55 (3H, s), 4.12 (2H, s), 4.43 (2H, q, J=7.1 Hz), 5.18 (2H, s), 7.05-7.11 (2H, m), 7.30-7.35 (1H, m), 7.53 (1H, d, J=9.0 Hz), 8.00 (1H, d, J=9.0 Hz), 8.28 (1H, s), 9.32 (1H, s)

Step 7

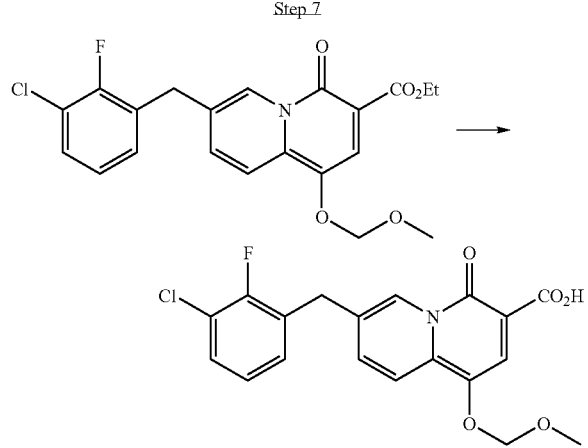

The compound (26 mg, 0.026 mmol) obtained in Step 6 was dissolved in tetrahydrofuran (1.5 ml) and water (0.4 ml), and lithium hydroxide monohydrate (5.2 mg, 0.12 mmol) was added, and the mixture was stirred at room temperature for 17 hr. A 10% aqueous citric acid solution was added to the reaction mixture, and the mixture was extracted with ethyl acetate. The organic layer was washed twice with water and then with saturated brine, and dried over sodium sulfate. After filtration, the filtrate was concentrated under reduced pressure. Ethyl acetate (0.5 ml) and hexane (2 ml) were added to the residue, and the residue was slurry-stirred. After filtration, the solid was dried under reduced pressure to give the object product as an orange solid (13 mg, yield 54%).

$^1$H NMR (DMSO-d$_6$ 300 MHz) (δ) ppm: 3.47 (3H, s), 4.34 (2H, s), 5.32 (2H, s), 7.23 (1H, dd, J=7.4 Hz, J=7.4 Hz), 7.42-7.52 (2H, m), 7.99 (1H, d, J=9.1 Hz), 8.17 (1H, s), 8.28 (1H, d, J=9.1 Hz), 9.26 (1H, s), 14.53 (1H, s)

MS (ESI): M+ 392

Example 60

Step 1

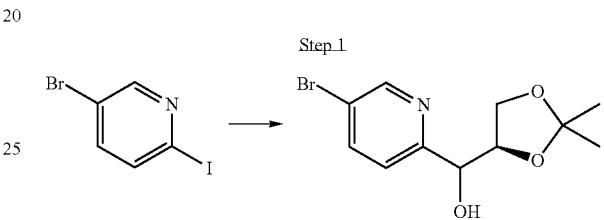

5-Bromo-2-iodopyridine (3.64 g, 12.81 mmol) was dissolved in tetrahydrofuran (14 ml) and, under an argon atmosphere, 1M isopropyl magnesium chloride tetrahydrofuran solution (14.00 ml, 14.00 mmol) was added dropwise at 0° C. or below, and the mixture was stirred at the same temperature for 1 hr. A solution of (R)-(+)-2,2-dimethyl-1,3-dioxolane-4-carboxyaldehyde (2.00 g, 15.37 mmol) in tetrahydrofuran (7 ml) was added dropwise at −5° C. or below and, after dropwise addition, the mixture was allowed to warm to room temperature and stirred for 13 hr. A saturated aqueous ammonium chloride solution was added to the reaction mixture, and the mixture was extracted with ethyl acetate. The organic layer was washed with saturated brine, and dried over magnesium sulfate. After filtration, the filtrate was concentrated under reduced pressure to give a crude product as a brown oil (1.21 g).

$^1$H NMR (CDCl$_3$ 400 MHz) (δ) ppm: 1.36-1.52 (6H, m), 3.59-4.75 (4H, m), 7.38-7.41 (1H, m), 7.83-7.86 (1H, m), 8.62-8.63 (1H, m)

Step 2

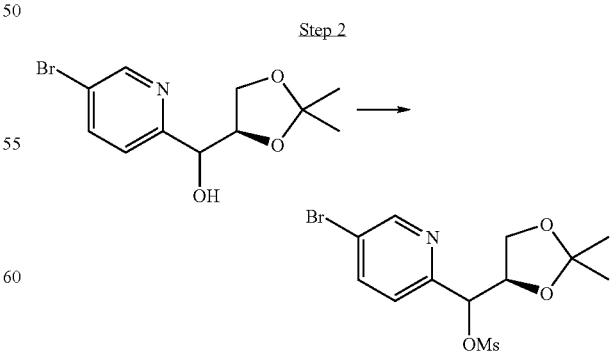

The compound (1.21 g) obtained in Step 1 was dissolved in chloroform (17 ml), dimethylaminopyridine (1.42 g, 11.62 mmol) and methanesulfonyl chloride (628 µl, 8.11 mmol)

were added under ice-cooling, and the mixture was allowed to warm to room temperature and stirred for 15 hr. Water was added to the reaction mixture, and the mixture was extracted with chloroform. The organic layer was washed with water, and dried over magnesium sulfate. After filtration, the filtrate was concentrated under reduced pressure and the residue was purified by silica gel chromatography (hexane:ethyl acetate=2:1) to give the object product as a white solid (1.87 g, yield 40%, 2 steps).

$^1$H NMR (CDCl$_3$ 400 MHz) (δ) ppm: 1.36-1.50 (6H, m), 3.02-3.14 (3H, m), 3.89-4.11 (2H, m), 4.61-4.71 (1H, m), 5.54-5.66 (1H, m), 7.42-7.47 (1H, m), 7.89-7.91 (1H, m), 8.64-8.68 (1H, m)

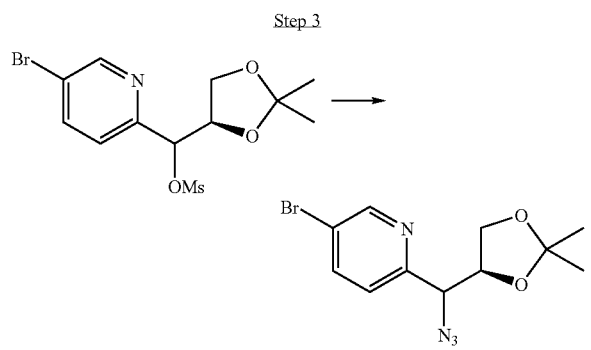

Step 3

The compound (259 mg, 0.69 mmol) obtained in Step 2 was dissolved in dimethyl sulfoxide (1.9 ml) and, under an argon atmosphere, lithium azide (498 mg, 10.18 mmol) was added, and the mixture was stirred at room temperature for 3 days. Lithium azide (498 mg, 10.18 mmol) was added, and the mixture was further stirred at room temperature for 24 hr. Water was added to the reaction mixture, and the mixture was extracted with ethyl acetate. The organic layer was washed twice with water and then with saturated brine, and dried over magnesium sulfate. After filtration, the filtrate was concentrated under reduced pressure and the residue was purified by silica gel chromatography (hexane:ethyl acetate=10:1) to give the object product as a colorless oil (1.79 g, yield 82%).

$^1$H NMR (CDCl$_3$ 300 MHz) (δ) ppm: 1.35-1.54 (6H, m), 3.85-3.99 (3H, m), 4.45-4.73 (1H, m), 7.26-7.33 (1H, m), 7.83-7.88 (1H, m), 8.63-8.66 (1H, m)

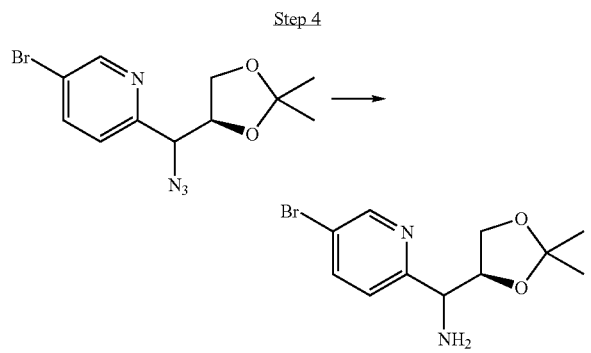

Step 4

The compound (1.31 g, 4.18 mmol) obtained in Step 3 was dissolved in tetrahydrofuran (13 ml) and water (1.3 ml), and triphenylphosphine resin (2.80 g, 8.36 mmol) was added, and the mixture was stirred at room temperature for 14 hr. The reaction mixture was filtered through celite. The filtrate was concentrated under reduced pressure and the residue was azeotroped 3 times with toluene to give the object product as a yellow oil (652 mg, yield 54%).

$^1$H NMR (CDCl$_3$ 400 MHz) (δ) ppm: 1.37 (3H, s), 1.45 (3H, s), 3.79-3.98 (3H, m), 4.29-4.34 (1H, m), 7.33-7.36 (1H, m), 7.79-7.82 (1H, m), 8.61-8.62 (1H, m)

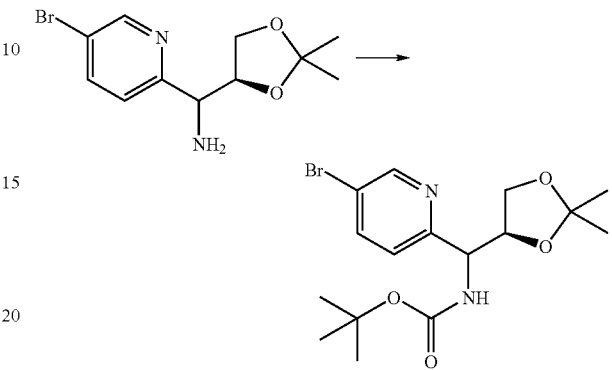

Step 5

The compound (652 mg, 2.27 mmol) obtained in Step 4 was dissolved in tetrahydrofuran (6.5 ml), di-tert-butyl dicarbonate (595 mg, 2.72 mmol) was added, and the mixture was stirred at room temperature for 2 hr. The reaction mixture was concentrated under reduced pressure and the residue was purified by silica gel chromatography (hexane:ethyl acetate=10:1) to give the object product as a yellow gum (744 mg, yield 85%).

$^1$H NMR (CDCl$_3$ 400 MHz) (δ) ppm: 1.31 (3H, s), 1.38 (3H, s), 1.46 (9H, s), 3.82-3.85 (1H, m), 4.04-4.08 (1H, m), 4.60-4.67 (1H, m), 4.83-4.89 (1H, m), 5.60-5.67 (1H, m), 7.25-7.28 (1H, m), 7.79-7.82 (1H, m), 8.62-8.63 (1H, m)

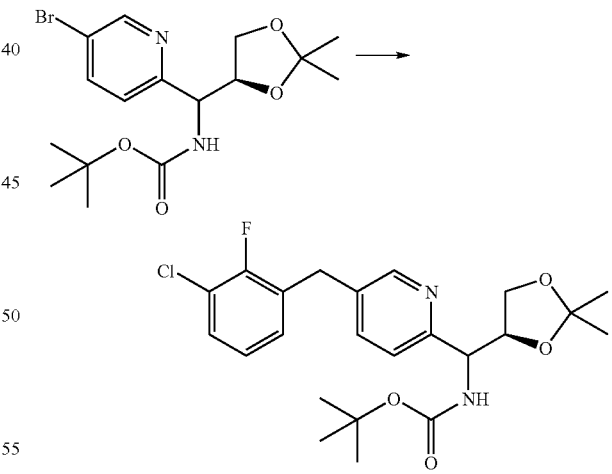

Step 6

The compound (744 mg, 1.92 mmol) obtained in Step 5 was dissolved in tetrahydrofuran (4.5 ml) and, under an argon atmosphere, dichlorobistriphenylphosphine palladium (II) (67 mg, 0.096 mmol) and 1 M 3-chloro-2-fluorobenzylzinc bromide tetrahydrofuran solution (2.88 ml, 2.88 mmol) were added dropwise, and the mixture was heated under reflux for 30 min. A saturated aqueous ammonium chloride solution was added to the reaction mixture, and the mixture was extracted with ethyl acetate. The organic layer was washed successively with water, saturated aqueous sodium hydrogencarbonate solution and saturated brine, and dried over magnesium sulfate. After filtration, the filtrate was concentrated under reduced pressure and the residue was purified by silica gel chromatography (hexane:ethyl acetate=3:1 to 2:1) to give the object product as a pale-brown oil (655 mg, yield 76%).

$^1$H NMR (CDCl$_3$ 300 MHz) (δ) ppm: 1.31 (3H, s), 1.37 (3H, s), 1.45 (9H, s), 3.82-3.86 (1H, m), 4.00 (2H, s), 4.04-4.07 (1H, m), 4.61-4.69 (1H, m), 4.83-4.90 (1H, m), 5.64-5.73 (1H, m), 7.01-7.08 (2H, m), 7.25-7.32 (2H, m), 7.48-7.53 (1H, m), 8.46-8.47 (1H, m)

Step 7

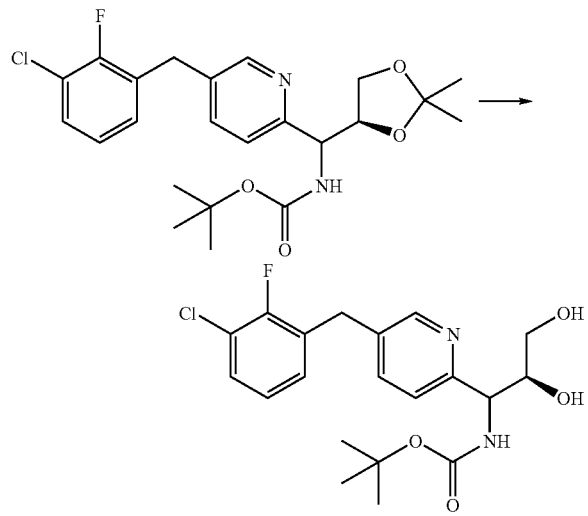

The compound (635 mg, 1.41 mmol) obtained in Step 6 was dissolved in methanol (10 ml) and water (3 ml), and trifluoroacetic acid (271 μl, 3.52 mmol) was added, and the mixture was stirred with heating at 50° C. for 5 hr. The reaction mixture was poured into saturated aqueous sodium hydrogencarbonate solution, and the mixture was extracted with ethyl acetate. The organic layer was washed with water and saturated brine, and dried over magnesium sulfate. After filtration, the filtrate was concentrated under reduced pressure and the residue was purified by silica gel chromatography (chloroform:ethyl acetate=4:1 to chloroform:methanol=9:1) to give the object product as a white solid (496 mg, yield 86%).

$^1$H NMR (CDCl$_3$ 400 MHz) (δ) ppm: 1.46 (9H, s), 3.52-3.56 (1H, m), 3.68-3.73 (1H, m), 4.02 (2H, s), 4.09-4.13 (1H, m), 4.95-4.97 (1H, m), 5.71-5.73 (1H, m), 7.01-7.10 (2H, m), 7.29-7.34 (2H, m), 7.52-7.58 (1H, m), 8.42-8.43 (1H, m)

Step 8

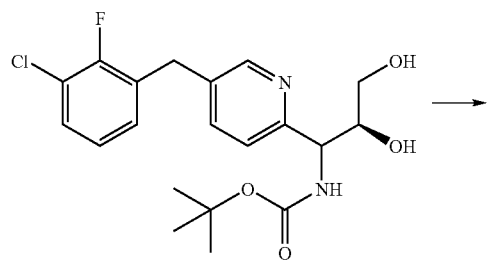

-continued

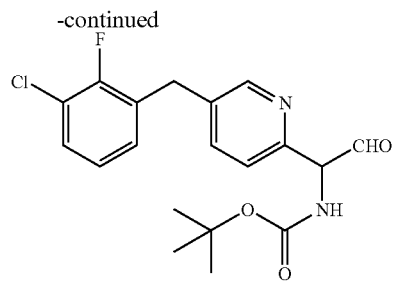

The compound (378 mg, 0.92 mmol) obtained in Step 7 was dissolved in tetrahydrofuran (3.8 ml) and water (1.9 ml), sodium periodate (216 mg, 1.01 mmol) was added under ice-cooling, and the mixture was stirred for 30 min. Sodium periodate (39 mg, 0.18 mmol) was added and the mixture was further stirred for 30 min. Water was added to the reaction mixture, and the mixture was extracted with ethyl acetate. The organic layer was washed with water (twice) and saturated brine, and dried over magnesium sulfate. After filtration, the filtrate was concentrated under reduced pressure to give a crude product as a yellow amorphous form (367 mg).

Step 9

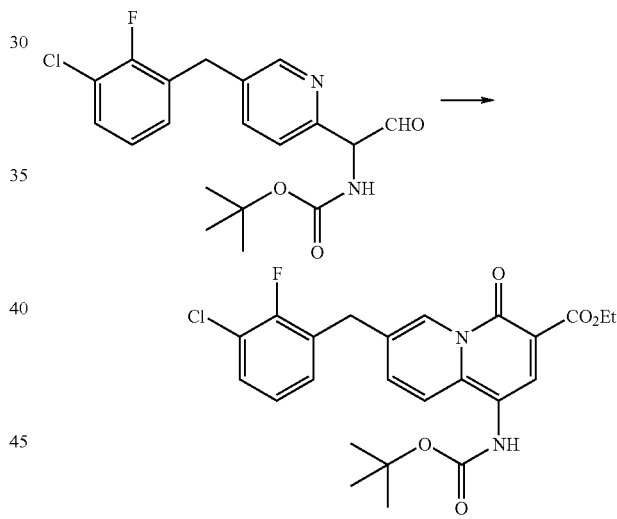

The compound (367 mg) obtained in Step 8 was dissolved in ethanol (3.7 ml), piperidine (91 μl, 0.92 mmol) and diethyl malonate (700 μl, 4.61 mmol) were added, and the mixture was heated under reflux for 48 hr. Water was added to the reaction mixture, and the mixture was extracted with ethyl acetate. The organic layer was washed with water and saturated brine, and dried over magnesium sulfate. After filtration, the filtrate was concentrated under reduced pressure. Ethyl acetate and hexane (1:1) were added to the residue and the residue was sonicated. After filtration, the solid was dried under reduced pressure to give the object product as a yellow solid (89 mg, yield 20%, 2 steps).

$^1$H NMR (CDCl$_3$ 400 MHz) (δ) ppm: 1.43 (3H, t, J=7.4 Hz), 1.51 (9H, s), 4.12 (2H, s), 4.43 (2H, q, J=7.4 Hz), 6.08 (1H, br s), 7.01-7.13 (2H, m), 7.32-7.36 (2H, m), 7.57-7.60 (1H, m), 8.33 (1H, s), 9.32 (1H, s)

MS (ESI): M+ 474

Example 59

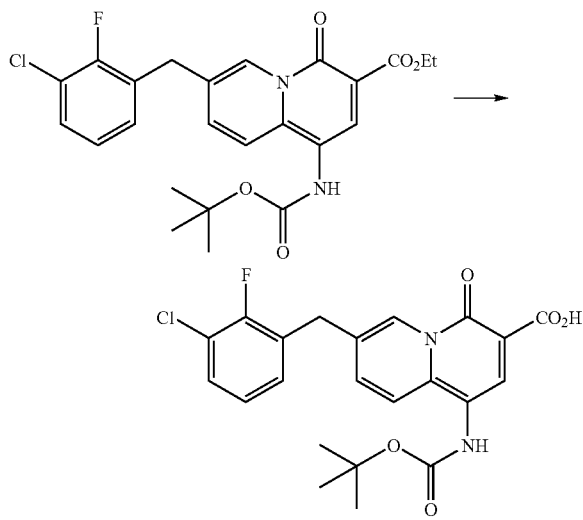

The compound (20 mg, 0.042 mmol) obtained in Example 60 was dissolved in tetrahydrofuran (0.6 ml) and water (0.2 ml), lithium hydroxide monohydrate (5 mg, 0.13 mmol) was added, and the mixture was stirred at room temperature for 14 hr. A 10% aqueous potassium hydrogensulfate solution was added to the reaction mixture, and the mixture was extracted with ethyl acetate. The organic layer was washed with water, and dried over magnesium sulfate. After filtration, the filtrate was concentrated under reduced pressure. Diethyl ether and hexane were added to the residue, and the residue was sonicated. After filtration, the solid was dried under reduced pressure to give the object product as a yellow solid (15 mg, yield 80%).

$^1$H NMR (DMSO-$d_6$ 400 MHz) (δ) ppm: 1.48 (9H, s), 4.33 (2H, s), 7.22-7.26 (1H, m), 7.40-7.44 (1H, m), 7.51-7.56 (1H, m), 7.96-8.02 (2H, m), 8.27 (1H, s), 9.22 (1H, brs), 9.26 (1H, s), 14.14 (1H, s)

MS (ESI): M+ 446

Example 65

Step 1

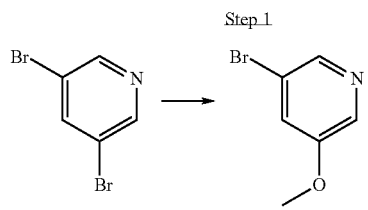

3,5-Dibromopyridine (29.41 g, 0.12 mol) was dissolved in dimethylformamide (300 ml), 28% sodium methoxide (40.00 ml, 0.19 mol) was added, and the mixture was stirred with heating at 40° C. for 1 hr, and the mixture was stirred at room temperature for 17 hr. Water (500 ml) was added to the reaction mixture, and the mixture was extracted three times with diethyl ether. The organic layer was washed with saturated brine, and dried over magnesium sulfate. After filtration, the filtrate was concentrated under reduced pressure and the residue was purified by silica gel chromatography (hexane:ethyl acetate=10:1 to 4:1) to give the object product as a white solid (20.28 g, yield 87%).

$^1$H NMR (CDCl$_3$ 400 MHz) (δ) ppm: 3.87 (3H, s), 7.38 (1H, dd, J=2.6, 1.9 Hz), 8.26 (1H, d, J=2.6 Hz), 8.30 (1H, d, J=1.9 Hz)

Step 2

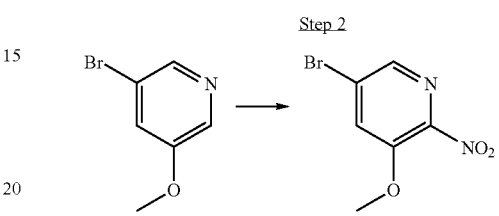

The compound (20.91 g, 0.11 mol) obtained in Step 1 was dissolved in concentrated sulfuric acid (63 ml), nitric acid (5.2 ml, 0.12 mol) was added under ice-cooling, and the mixture was stirred for 20 hr. The reaction mixture was gently poured into ice water and the mixture was stirred. The precipitated solid was filtered and washed with water. The obtained solid was dissolved in ethyl acetate, and the solution was washed with saturated aqueous sodium hydrogencarbonate solution and saturated brine, and dried over magnesium sulfate. After filtration, the filtrate was concentrated under reduced pressure to give the object product as a pale-yellow solid (21.97 g, yield 85%).

$^1$H NMR (CDCl$_3$ 400 MHz) (δ) ppm: 4.01 (3H, s), 7.68 (1H, d, J=1.6 Hz), 8.16 (1H, d, J=1.9 Hz)

Step 3

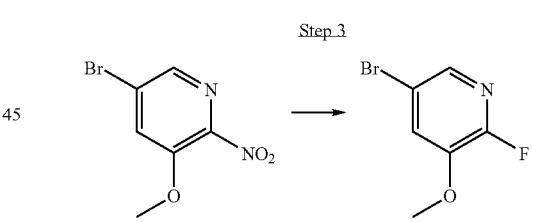

The compound (21.97 g, 94.28 mmol) obtained in Step 2 was dissolved in dimethylformamide (190 ml), 1 M tetrabutylammonium fluoride tetrahydrofuran solution (190 ml, 0.19 mol) was added, and the mixture was stirred with heating at 70° C. for 15 hr. The reaction mixture was added to water, and the mixture was extracted twice with ethyl acetate. The organic layer was washed with water and saturated brine, and dried over magnesium sulfate. After filtration, the filtrate was concentrated under reduced pressure and the residue was purified by silica gel chromatography (hexane:ethyl acetate=10:1) to give the object product as a white solid (12.21 g, yield 63%).

$^1$H NMR (CDCl$_3$ 400 MHz) (δ) ppm: 3.92 (3H, s), 7.40 (1H, dd, J=8.6, 2.1 Hz), 7.81 (1H, dd, J=2.0, 1.0 Hz)

Step 4

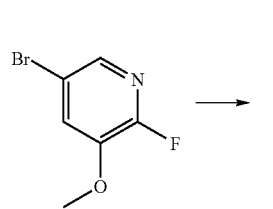

Under an argon atmosphere, 1M 3-chloro-2-fluorobenzylzinc bromide tetrahydrofuran solution (70.00 ml, 70.00 mmol) was added dropwise to dichlorobistriphenylphosphine palladium (II) (2.00 g, 2.95 mmol), and the mixture was stirred at room temperature for 5 min. Then, a solution of the compound (12.21 g, 59.27 mmol) obtained in Step 3 in tetrahydrofuran (120 ml) was added dropwise, and the mixture was stirred with heating at 60° C. for 1 hr. A saturated aqueous ammonium chloride solution was added to the reaction mixture, and the mixture was extracted with ethyl acetate. The organic layer was washed successively with water, saturated aqueous sodium hydrogencarbonate solution (twice) and saturated brine, and dried over magnesium sulfate. After filtration, the filtrate was concentrated under reduced pressure and the residue was purified by silica gel chromatography (hexane:ethyl acetate=5:1 to 4:1) to give the object product as a white solid (12.57 g, yield 79%).

$^1$H NMR (CDCl$_3$ 400 MHz) (δ) ppm: 3.87 (3H, s), 3.99 (2H, s), 7.02-7.07 (2H, m), 7.10 (1H, dd, J=9.7, 1.9 Hz), 7.28-7.33 (1H, m), 7.62-7.63 (1H, m)

Step 5

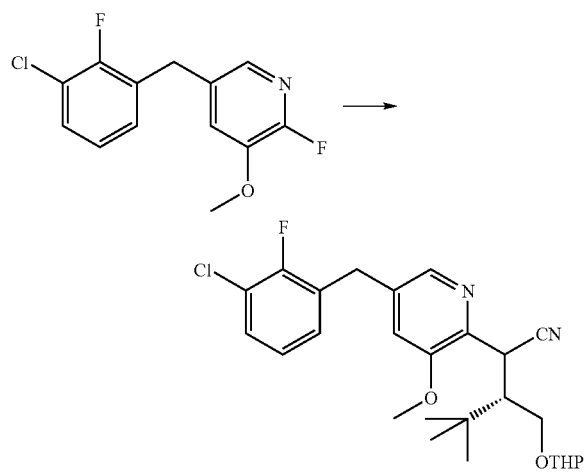

To 1.1 M sodium bistrimethylsilylamide tetrahydrofuran solution (17.00 ml, 18.55 mmol) was added dropwise a solution of the compound (2.00 g, 7.42 mmol) obtained in Step 4 and the compound (1.67 g, 7.42 mmol) obtained in Step 8 of Example 16 in tetrahydrofuran (17 ml) at −15° C., and the mixture was stirred at room temperature for 2 hr. A saturated aqueous ammonium chloride solution was added to the reaction mixture, and the mixture was extracted with ethyl acetate. The organic layer was washed with water and saturated brine, and dried over magnesium sulfate. After filtration, the filtrate was concentrated under reduced pressure and the residue was purified by silica gel chromatography (hexane:ethyl acetate=4:1 to 3:1) to give the object product as a yellow gum (2.81 g, yield 80%).

Step 6

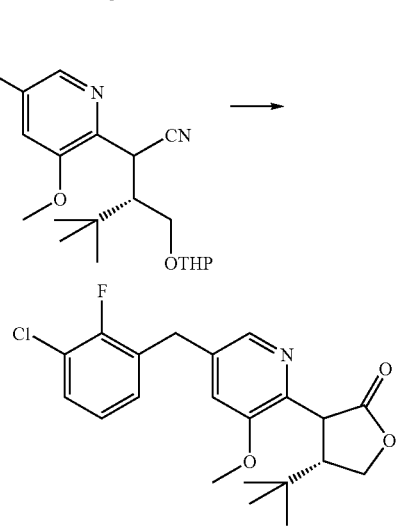

The compound (2.81 g, 5.92 mmol) obtained in Step 5 was dissolved in methanol (28 ml), concentrated hydrochloric acid (4.90 ml, 58.80 mmol) was added, and the mixture was stirred with heating at 70° C. for 1 hr. After allowing to cool, the reaction mixture was added to water, and the mixture was extracted with ethyl acetate. The organic layer was washed successively with water, saturated aqueous sodium hydrogencarbonate solution and saturated brine, and dried over magnesium sulfate. After filtration, the filtrate was concentrated under reduced pressure and the residue was purified by silica gel chromatography (hexane:ethyl acetate=4:1 to 2:1) to give the object product as a pale-yellow gum (2.08 g, yield 90%).

$^1$H NMR (CDCl$_3$ 400 MHz) (δ) ppm: 0.88 (9H, s), 2.87 (1H, dd, J=8.4, 8.4 Hz), 3.84 (3H, s), 4.00 (2H, s), 4.20 (1H, dd, J=9.2, 8.0 Hz), 4.22 (1H, d, J=8.6 Hz), 4.51 (1H, dd, J=8.8, 8.8 Hz), 7.00-7.06 (3H, m), 7.31 (1H, dt, J=10.0, 3.6 Hz), 8.06 (1H, d, J=1.6 Hz)

Step 7

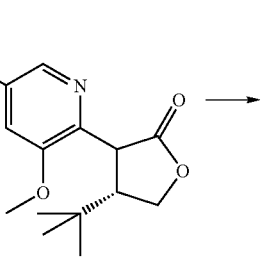

-continued

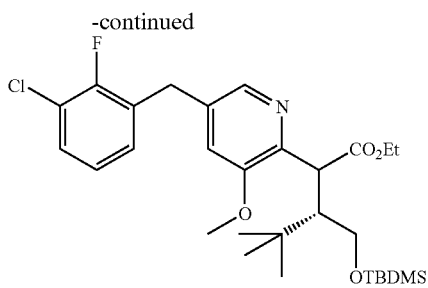

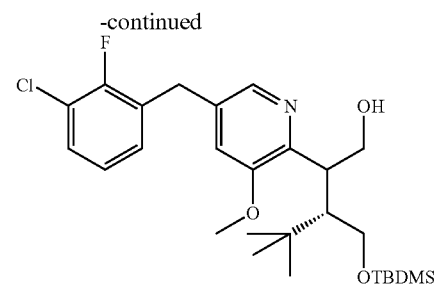

The compound (1.01 g, 2.58 mmol) obtained in Step 6 was dissolved in methanol (5 ml) and tetrahydrofuran (10 ml), and 4N aqueous sodium hydroxide solution (0.72 ml, 2.88 mmol) was added, and the mixture was stirred at room temperature for 24 hr. The reaction mixture was concentrated under reduced pressure and the residue was azeotroped three times with toluene, and dissolved in dimethylformamide (10 ml). Under ice-cooling, imidazole (490 mg, 7.20 mmol) and tert-butyldimethylsilyl chloride (1.09 g, 7.20 mmol) were added, and the mixture was stirred at room temperature for 13 hr. Water was added to the reaction mixture, and the mixture was extracted with ethyl acetate. The organic layer was washed with water (three times) and saturated brine, and dried over magnesium sulfate. After filtration, the filtrate was concentrated under reduced pressure and the residue was dissolved in tetrahydrofuran (10 ml) and water (2 ml). Lithium hydroxide monohydrate (101 mg, 2.40 mmol) was added and the mixture was stirred at room temperature for 1.5 hr. The reaction mixture was concentrated under reduced pressure and the residue was azeotroped four times with toluene, and dissolved in dimethylformamide (10 ml). Under ice-cooling, potassium carbonate (331 mg, 2.40 mmol) and iodoethane (192 µl, 2.40 mmol) were added, and the mixture was stirred at room temperature for 18 hr. A saturated aqueous ammonium chloride solution was added to the reaction mixture, and the mixture was extracted with ethyl acetate. The organic layer was washed with water and saturated brine, and dried over magnesium sulfate. After filtration, the filtrate was concentrated under reduced pressure and the residue was purified by silica gel chromatography (hexane:ethyl acetate=10:1) to give the object product as a pale-yellow oil (757 mg, yield 57%).

$^1$H NMR (CDCl$_3$ 400 MHz) (δ) ppm: −0.31 (3H, s), −0.16 (3H, s), 0.74 (9H, s), 0.95 (9H, s), 1.17 (3H, t, J=7.2 Hz), 1.92-1.95 (1H, m), 3.81 (3H, s), 3.97 (2H, s), 4.00-4.16 (4H, m), 4.46 (1H, d, J=3.9 Hz), 6.94 (1H, d, J=1.6 Hz), 6.98-7.06 (2H, m), 7.27-7.29 (1H, m), 8.05 (1H, d, J=1.6 Hz)

Step 8

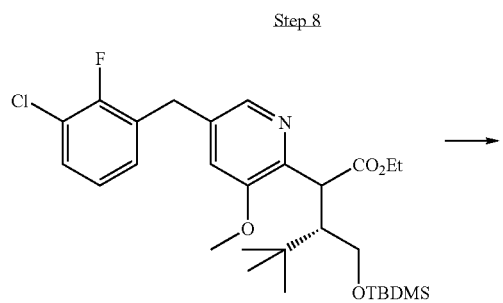

The compound (757 mg, 1.37 mmol) obtained in Step 7 was dissolved in tetrahydrofuran (8 ml) and, under an argon atmosphere, 1.5 M diisobutylaluminum hydride toluene solution (2.74 ml, 4.11 mmol) was added dropwise at −70° C., and the mixture was allowed to warm to 0° C. and stirred for 1 hr. An aqueous Rochelle salt solution was added to the reaction mixture, and the mixture was stirred at room temperature and extracted with ethyl acetate. The organic layer was washed with water (twice) and saturated brine, and dried over magnesium sulfate. After filtration, the filtrate was concentrated under reduced pressure and the residue was purified by silica gel chromatography (hexane:ethyl acetate=4:1) to give the object product as a colorless oil (535 mg, yield 77%).

$^1$H NMR (CDCl$_3$ 400 MHz) (δ) ppm: 0.01 (3H, s), 0.06 (3H, s), 0.90 (9H, s), 0.97 (9H, s), 2.01-2.05 (1H, m), 3.69-4.12 (6H, m), 3.85 (3H, s), 4.02 (2H, s), 6.98-7.35 (4H, m), 8.04 (1H, s)

Step 9

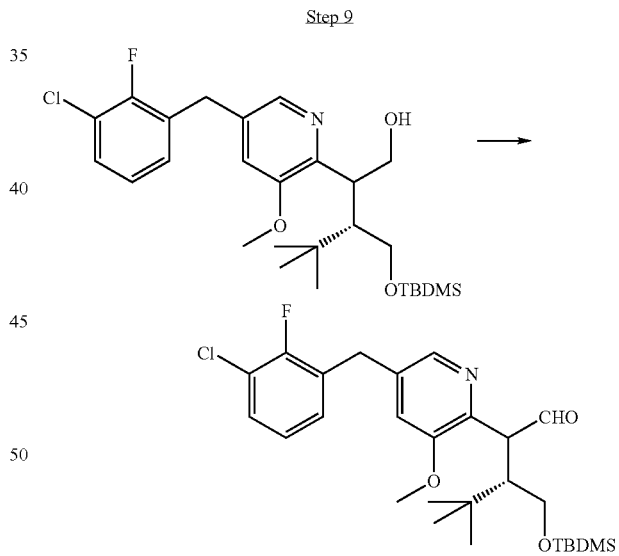

To a solution of dimethyl sulfoxide (224 µl, 3.15 mmol) in dichloromethane (1.5 ml) was added dropwise a solution of oxalyl chloride (137 µl, 1.58 mmol) in dichloromethane (1.5 ml) under an argon atmosphere at −70° C. or below, and the mixture was stirred for 15 min. Then, a solution of the compound (535 mg, 1.05 mmol) obtained in Step 8 in dichloromethane (2 ml) was added dropwise at −70° C. or below, and the mixture was stirred for 15 min. Triethylamine (732 µl, 5.25 mmol) was further added dropwise, and the mixture was stirred for 5 min, allowed to warm to −10° C. and stirred for 20 min. Water was added to the reaction mixture, and the mixture was extracted with ethyl acetate. The organic layer was washed with water and saturated brine, and dried over magnesium sulfate. After filtration, the filtrate was concentrated under reduced pressure to give a crude product as a pale-yellow oil (527 mg).

¹H NMR (CDCl₃ 400 MHz) (δ) ppm: 0.01 (3H, s), 0.04 (3H, s), 0.88 (9H, s), 0.92 (9H, s), 2.48-2.52 (1H, m), 3.80 (3H, s), 3.90 (1H, dd, J=10.7, 5.8 Hz), 4.00 (2H, s), 4.04 (1H, dd, J=10.7, 3.7 Hz), 4.26 (1H, dd, J=5.4, 3.8 Hz), 6.94 (1H, d, =1.4 Hz), 7.01-7.06 (2H, m), 7.30-7.33 (1H, m), 8.09 (1H, d, J=1.6 Hz), 9.84 (1H, d, J=3.7 Hz)

Step 10

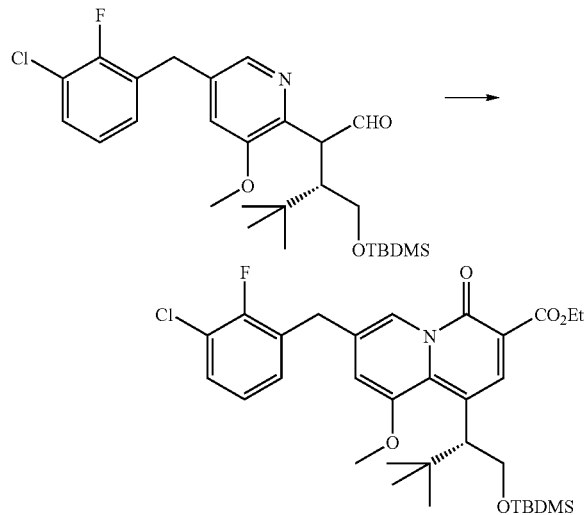

The compound (527 mg) obtained in Step 9 was dissolved in ethanol (13 ml), piperidine (622 μl, 6.30 mmol) and diethyl malonate (1.59 ml, 10.47 mmol) were added, and the mixture was heated under reflux for 7 days. Water was added to the reaction mixture, and the mixture was extracted with ethyl acetate. The organic layer was washed with water (three times) and saturated brine, and dried over magnesium sulfate. After filtration, the filtrate was concentrated under reduced pressure and the residue was purified by silica gel chromatography (hexane:ethyl acetate=10:1 to 5:1, thereafter 2:1) to give the object product as a yellow gum (270 mg, yield 43%, 2 steps).

¹H NMR (CDCl₃ 400 MHz) (δ) ppm: −0.13 (3H, s), −0.05 (3H, s), 0.67 (9H, s), 0.91 (9H, s), 1.41 (3H, t, J=7.1 Hz), 3.90-3.95 (1H, m), 3.91 (3H, s), 4.01-4.05 (1H, m), 4.03 (2H, s), 4.39-4.46 (3H, m), 6.73 (1H, d, J=1.4 Hz), 7.00-7.11 (2H, m), 7.29-7.33 (1H, m), 8.40 (1H, s), 9.12 (1H, d, J=1.4 Hz)

Step 11

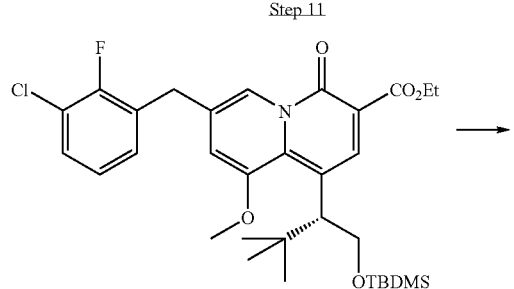

-continued

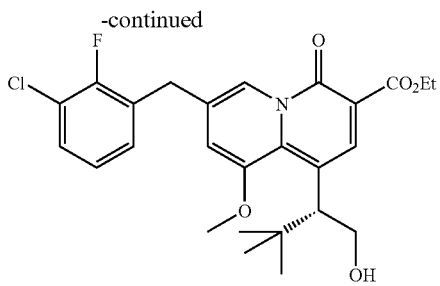

The compound (270 mg, 0.45 mmol) obtained in Step 10 was dissolved in tetrahydrofuran (2.7 ml), 1 M tetrabutylammonium fluoride tetrahydrofuran solution (900 μl, 0.90 mmol) was added, and the mixture was stirred at room temperature for 3 hr. Water was added to the reaction mixture, and the mixture was extracted with ethyl acetate. The organic layer was washed with water (twice) and saturated brine, and dried over magnesium sulfate. After filtration, the filtrate was concentrated under reduced pressure and the obtained residue was purified by silica gel chromatography (hexane:ethyl acetate=10:1 to 5:1, thereafter chloroform:methanol=20:1) to give the object product as a yellow oil (132 mg, yield 60%).

Step 12

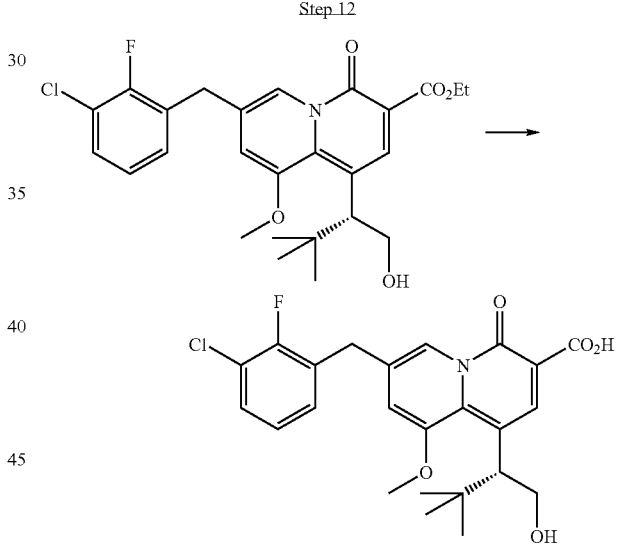

The compound (132 mg, 0.27 mmol) obtained in Step 11 was dissolved in tetrahydrofuran (2 ml) and water (1 ml), and lithium hydroxide monohydrate (23 mg, 0.54 mmol) was added, and the mixture was stirred at room temperature for 14 hr. A 5% aqueous potassium hydrogensulfate solution was added to the reaction mixture, and the mixture was extracted with ethyl acetate. The organic layer was washed with water, and dried over magnesium sulfate. After filtration, the filtrate was concentrated under reduced pressure and the residue was purified by PTLC (developing solvent: chloroform:methanol=9:1) to give the object product as a yellow amorphous form (91 mg, yield 73%).

¹H NMR (DMSO-d₆ 400 MHz) (δ) ppm: 0.86 (9H, s), 3.76-3.81 (1H, m), 3.86-3.90 (1H, m), 4.01 (3H, s), 4.24 (2H, s), 4.53 (1H, dd, J=10.0, 4.7 Hz), 7.21-7.25 (1H, m), 7.40-7.46 (2H, m), 7.51-7.55 (1H, m), 8.36 (1H, s), 8.91 (1H, s), 14.28 (1H, s)

MS (ESI): M+ 461

The compounds obtained in the above-mentioned Examples and the compounds synthesized in the same manner are shown in Tables 1-3 and Tables 5-7. The compounds of Table 4 can also be synthesized in the same manner as in the above-mentioned Examples.

TABLE 1

| Ex. No. | Structural Formula |
|---|---|
| 1 | (3-chloro-2-fluorobenzyl quinolizinone with CO₂Et) |
| 2 | (3-chloro-2-fluorobenzyl quinolizinone with CO₂H) |
| 3 | (3-chloro-2-fluorobenzyl quinolizinone with CO₂Et and ethyl) |
| 4 | (3-chloro-2-fluorobenzyl quinolizinone with CO₂H and ethyl) |
| 5 | (3-chloro-2-fluorobenzyl quinolizinone with CO₂Et and ethyl-O-THP) |
| 6 | (3-chloro-2-fluorobenzyl quinolizinone with CO₂Et and ethyl-OH) |

TABLE 1-continued

| Ex. No. | Structural Formula |
|---|---|
| 7 | (3-chloro-2-fluorobenzyl quinolizinone with CO₂H and ethyl-OH) |
| 8 | (3-chloro-2-fluorobenzyl quinolizinone with CO₂Et, OMe, and isobutyl-OMOM) |
| 9 | (3-chloro-2-fluorobenzyl quinolizinone with CO₂Et, OMe, and isobutyl-OH) |
| 10 | (3-chloro-2-fluorobenzyl quinolizinone with CO₂H, OMe, and isobutyl-OH) |

TABLE 2

| Ex. No. | Structural Formula |
|---|---|
| 11 | (benzyl quinolizinone with CO₂H) |

TABLE 2-continued

| Ex. No. | Structural Formula |
| --- | --- |
| 12 | (structure) |
| 13 | (structure) |
| 14 | (structure) |
| 15 | (structure) racemic form |

TABLE 3

| Ex. No. | Structural Formula |
| --- | --- |
| 16 | (structure) |

TABLE 3-continued

| Ex. No. | Structural Formula |
| --- | --- |
| 17 | (structure) |
| 18 | (structure) |
| 19 | (structure) |
| 20 | (structure) |
| 21 | (structure) |
| 22 | (structure) |

TABLE 3-continued

| Ex. No. | Structural Formula |
|---|---|
| 23 | 3-chloro-2-fluorobenzyl quinolizinone with CH2-NH-SO2-CH3 substituent |
| 24 | 3-chloro-2-fluorobenzyl quinolizinone with CH2-NH-C(=O)-O-CH3 substituent |
| 26 | 3-chloro-2-fluorobenzyl quinolizinone with CH2-C(=O)-NH2 substituent |
| 27 | 3-chloro-2-fluorobenzyl quinolizinone with NH-CH2CH2-OH substituent |
| 29 | 3-chloro-2-fluorobenzyl quinolizinone with NH-SO2-CH3 substituent |

TABLE 4

| Ex. No. | Structural Formula |
|---|---|
| 25 | 3-chloro-2-fluorobenzyl quinolizinone with CH2-SO2NH2 substituent |
| 28 | 3-chloro-2-fluorobenzyl quinolizinone with NH-CH2-SO2NH2 substituent |
| 30 | 3-chloro-2-fluorobenzyl quinolizinone with N(CH3)-CH2CH2-OH substituent |
| 31 | 3-chloro-2-fluorobenzyl quinolizinone with N(CH3)-CH2-SO2NH2 substituent |
| 32 | 3-chloro-2-fluorobenzyl quinolizinone with N(CH3)-SO2-CH3 substituent |

TABLE 5

| Ex. No. | Structural Formula |
|---|---|
| 33 | 3-chloro-2-fluorobenzyl quinolizinone with CN substituent |

TABLE 5-continued

| Ex. No. | Structural Formula |
|---|---|
| 34 | |
| 35 | |
| 36 | |
| 37 | |
| 38 | |
| 39 | |
| 40 | |
| 41 | |
| 42 | |
| 43 | |
| 44 | |

TABLE 6
| Ex. No. | Structural Formula |
|---|---|
| 45 | 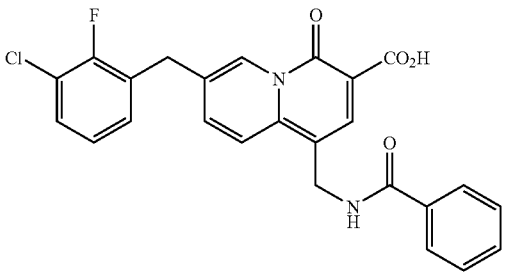 |
| 46 | 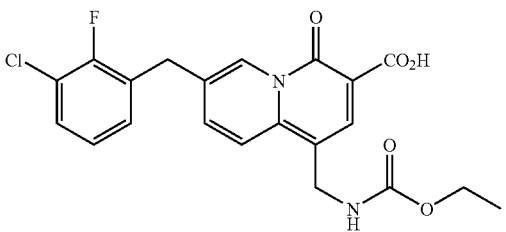 |
| 47 | 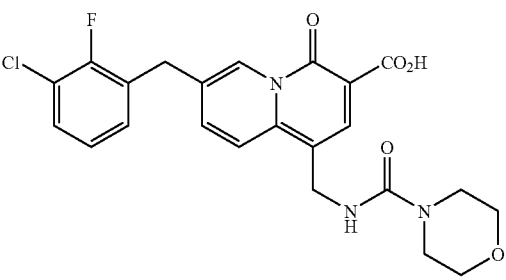 |
| 48 | 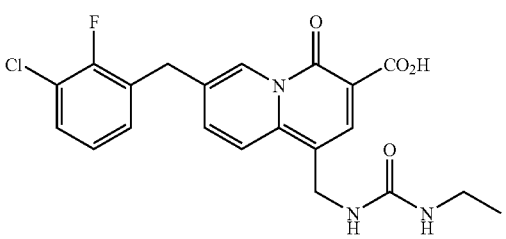 |
| 49 | 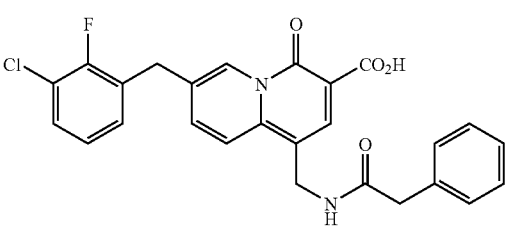 |
| 50 | 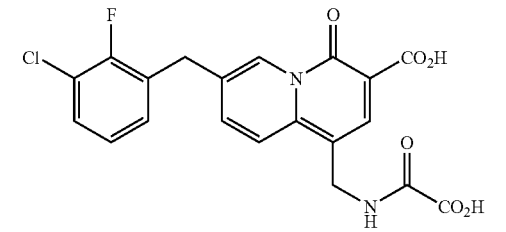 |
TABLE 6-continued
| Ex. No. | Structural Formula |
|---|---|
| 51 | 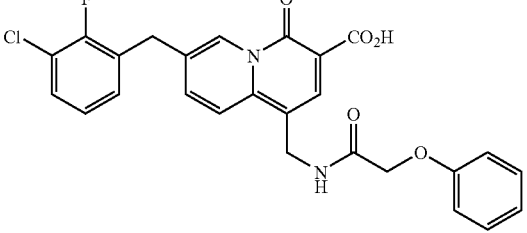 |
| 52 | 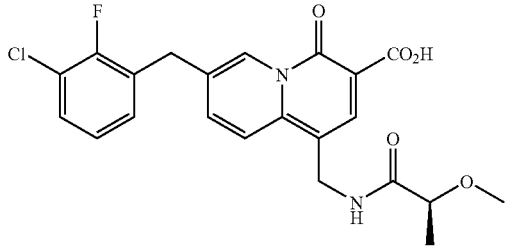 |
| 53 | 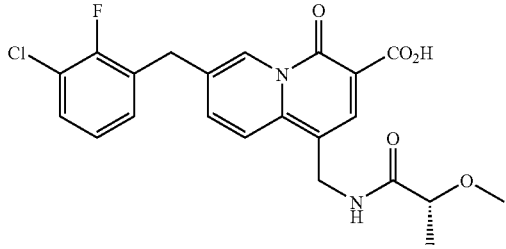 |
| 54 | 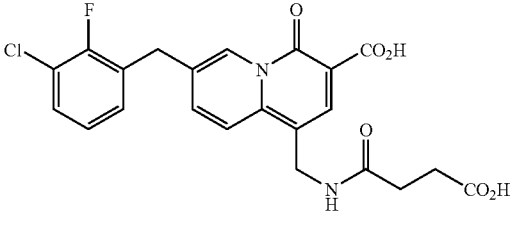 |
| 55 | 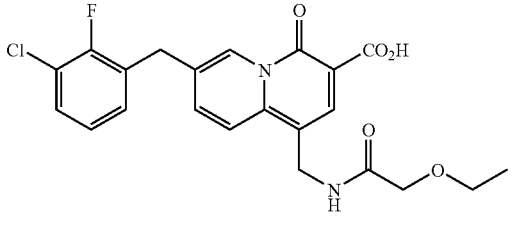 |
| 56 | 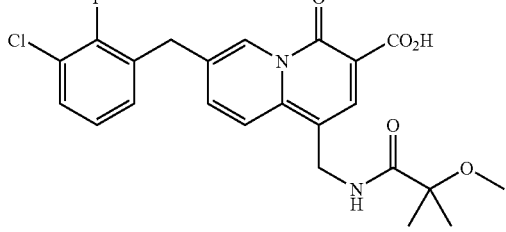 |

TABLE 7

| Ex. No. | Structural Formula |
|---|---|
| 57 | 3-chloro-2-fluorobenzyl quinolizinone with CH2-NH-C(O)-CH2-NH-C(O)-CH3 substituent, CO2H |
| 58 | 3-chloro-2-fluorobenzyl quinolizinone with O-CH2-O-CH3 substituent, CO2H |
| 59 | 3-chloro-2-fluorobenzyl quinolizinone with NH-Boc substituent, CO2H |
| 60 | 3-chloro-2-fluorobenzyl quinolizinone with NH-Boc substituent, CO2Et |
| 61 | 3-chloro-2-fluorobenzyl quinolizinone with NH-C(O)CH3 substituent, CO2H |
| 62 | 3-chloro-2-fluorobenzyl quinolizinone with CO2-tBu substituent, CO2H |

TABLE 7-continued

| Ex. No. | Structural Formula |
|---|---|
| 63 | 2,3-dichlorobenzyl quinolizinone with CH(iPr)-CH2OH substituent, CO2H |
| 64 | 2,3-dichlorobenzyl quinolizinone with CH(tBu)-CH2OH substituent, CO2H |
| 65 | 3-chloro-2-fluorobenzyl quinolizinone with OMe and CH(tBu)-CH2OH substituents, CO2H |

The NM and MS data of Example compounds in the above Tables are shown in the following.

Example 11

$^1$H NMR (DMSO-$d_6$ 400 MHz) (δ) ppm: 4.21 (2H, s), 7.23-7.35 (6H, m), 7.92 (1H, dd, J=8.8, 1.9 Hz), 8.09 (1H, d, J=8.8 Hz), 8.37 (1H, d, J=8.6 Hz), 9.19 (1H, s), 14.20 (1H, brs)

MS (ESI): M+279

Example 12

$^1$H NMR (DMSO-$d_6$ 300 MHz) (δ) ppm: 0.93 (3H, t, J=7.3 Hz), 1.60 (2H, m), 2.88 (2H, t, J=7.7 Hz), 4.31 (2H, s), 7.20-7.25 (1H, m), 7.42-7.52 (2H, m), 7.95 (1H, d, J=9.2 Hz), 8.22 (1H, d, J=9.2 Hz), 8.26 (1H, s), 9.26 (1H, s), 14.30 (1H, s)

MS (ESI): M+374

Example 13

$^1$H NMR (DMSO-$d_6$ 300 MHz) (δ) ppm: 1.29 (6H, d, J=6.8 Hz), 3.45-3.55 (1H, m), 4.32 (2H, s), 7.23-7.25 (1H, m), 7.43-7.52 (2H, m), 7.96 (1H, d, J=9.2 Hz), 8.30 (1H, s), 8.34 (1H, d, J=9.2 Hz), 9.30 (1H, s), 14.32 (1H, s)

MS (ESI): M+374

Example 14

$^1$H NMR (DMSO-$d_6$ 300 MHz) (δ) ppm: 1.27 (3H, d, J=6.6 Hz), 3.41-3.52 (1H, m), 3.52-3.59 (2H, m), 4.31 (2H, s), 4.67

(1H, t, J=5.1 Hz), 7.19-7.26 (1H, m), 7.39-7.46 (1H, m), 7.48-7.55 (1H, m), 7.92 (1H, d, J=9.5 Hz), 8.30 (1H, s), 8.34 (1H, d, J=9.5 Hz) 9.27 (1H, s), 14.30 (1H, brs)
MS (ESI): M+ 390

Example 15

$^1$H NMR (DMSO-d$_6$ 300 MHz) (δ) ppm: 0.72 (3H, d, J=6.6 Hz), 1.02 (3H, d, J=6.6 Hz), 1.98-2.11 (1H, m), 3.09-3.16 (1H, m), 3.66-3.78 (2H, m), 4.30 (2H, s), 4.47 (1H, t, J=5.1 Hz), 7.20-7.26 (1H, m), 7.41-7.46 (1H, m), 7.49-7.55 (1H, m), 7.87 (1H, d, J=9.5 Hz), 8.33 (1H, s), 8.37 (1H, d, J=9.5 Hz), 9.25 (1H, s), 14.35 (1H, brs)
MS (ESI): M+ 418

Example 17

$^1$H NMR (CDCl$_3$ 400 MHz) (δ) ppm: 0.97 (9H, s), 3.20 (1H, dd, J=10.0, 4.4 Hz), 4.07 (3H, s), 4.11 (2H, s), 4.15-4.21 (2H, m), 7.04-7.08 (1H, m), 7.09-7.14 (1H, m), 7.28 (1H, s), 7.32-7.37 (1H, m), 8.41 (1H, s), 9.17 (1H, s), 13.93 (1H, brs)
MS (ESI): M+ 462

Example 20

$^1$H NMR (DMSO-d$_6$ 400 MHz) (δ) ppm: 4.34 (2H, s), 4.40 (2H, s), 7.20-7.25 (1H, m), 7.42-7.47 (1H, m), 7.50-7.54 (1H, m), 8.07 (1H, d, J=9.3 Hz), 8.26 (3H, br s), 8.39 (1H, d, J=9.3 Hz), 8.57 (1H, s), 9.31 (1H, s), 13.83 (1H, brs)
MS (ESI): M+ 361

Example 21

$^1$H NMR (DMSO-d$_6$ 300 MHz) (δ) ppm: 2.32 (3H, s), 3.96 (2H, s), 4.32 (2H, s), 7.20-7.25 (1H, m), 7.42-7.52 (2H, m), 7.98 (1H, d, J=9.2 Hz), 8.32 (1H, d, J=9.2 Hz), 8.37 (1H, s), 9.27 (1H, s)
MS (ESI): M+375

Example 22

$^1$H NMR (DMSO-d$_6$ 400 MHz) (δ) ppm: 1.82 (3H, s), 4.31 (2H, s), 4.52 (2H, d, J=6.0 Hz), 7.19-7.24 (1H, m), 7.39-7.44 (1H, m), 7.49-7.54 (1H, m), 8.01 (1H, d, J=9.2 Hz), 8.23 (1H, d, J=9.2 Hz), 8.34 (1H, s), 8.40 (1H, t, J=6.0 Hz), 9.27 (1H, s), 14.09 (1H, brs)
MS (ESI): M+ 403

Example 23

$^1$H NMR (DMSO-d$_6$ 400 MHz) (δ) ppm: 2.98 (3H, s), 4.32 (2H, s), 4.45 (2H, d, J=5.8 Hz), 7.20-7.24 (1H, m), 7.39-7.43 (1H, m), 7.49-7.57 (2H, m), 8.07 (1H, d, J=9.2 Hz), 8.20 (1H, d, J=9.2 Hz), 8.41 (1H, s), 9.29 (1H, s), 14.03 (1H, brs)
MS (ESI): M+ 439

Example 24

$^1$H NMR (DMSO-d$_6$ 400 MHz) (δ) ppm: 3.53 (3H, s), 4.31 (2H, s), 4.46 (2H, d, J=5.3 Hz), 7.19-7.24 (1H, m), 7.39-7.43 (1H, m), 7.49-7.53 (1H, m), 7.76 (1H, br s), 8.01 (1H, d, J=9.0 Hz), 8.24 (1H, d, J=9.0 Hz), 8.34 (1H, s), 9.27 (1H, s), 14.09 (1H, brs)
MS (ESI): M+ 419

Example 26

$^1$H NMR (DMSO-d$_6$ 300 MHz) (δ) ppm: 3.77 (2H, s), 4.32 (2H, s), 7.04 (1H, br s), 7.19-7.26 (1H, m), 7.38-7.55 (3H, m), 7.98 (1H, d, J=9.2 Hz), 8.13 (1H, d, J=9.2 Hz), 8.35 (1H, s), 9.26 (1H, s), 14.17 (1H, brs)
MS (ESI): M+ 389

Example 27

$^1$H NMR (DMSO-d$_6$ 400 MHz) (δ) ppm: 3.23 (2H, q, J=6.0 Hz), 3.64 (2H, q, J=5.7 Hz), 4.31 (2H, s), 4.79 (1H, t, J=5.6 Hz), 5.58-5.60 (1H, m), 7.21-7.26 (1H, m), 7.40-7.44 (1H, m), 7.51-7.56 (1H, m), 7.79 (1H, s), 7.90 (1H, dd, J=9.4, 1.7 Hz), 8.35 (1H, d, J=9.3 Hz), 9.22 (1H, s), 15.09 (1H, s)
MS (ESI): M+390

Example 29

$^1$H NMR (DMSO-d$_6$ 400 MHz) (δ) ppm: 3.03 (3H, s), 4.34 (2H, s), 7.22-7.27 (1H, m), 7.42-7.46 (1H, m), 7.52-7.56 (1H, m), 8.04 (1H, dd, J=9.0, 1.6 Hz), 8.31-8.33 (2H, m), 9.28 (1H, s), 9.65 (1H, s), 13.96 (1H, s)
MS (ESI): M+424

Example 33

$^1$H NMR (CDCl$_3$ 400 MHz) (δ) ppm: 4.25 (2H, s), 7.12-7.21 (2H, m), 7.41 (1H, td, J=7.5, 1.7 Hz), 7.97 (1H, dd, J=9.0, 1.6 Hz), 8.20 (1H, d, J=9.0 Hz), 8.90 (1H, s), 9.34 (1H, s), 12.89 (1H, s)
MS (ESI): M+356

Example 35

$^1$H NMR (DMSO-d$_6$ 400 MHz) (δ) ppm: 1.39 (9H, s), 4.33 (2H, s), 4.41 (2H, s), 7.21-7.26 (1H, m), 7.41-7.45 (1H, m), 7.48-7.56 (2H, m), 8.03 (1H, d, J=9.2 Hz), 8.25 (1H, d, J=9.2 Hz), 8.34 (1H, s), 9.28 (1H, s), 14.00 (1H, brs)
MS (ESI): M+ 461

Example 36

$^1$H NMR (DMSO-d$_6$ 400 MHz) (δ) ppm: 3.99 (2H, s), 4.31 (2H, s), 7.20-7.24 (1H, m), 7.39-7.44 (1H, m), 7.49-7.54 (1H, m), 7.97 (1H, d, J=9.0 Hz), 8.08 (1H, d, J=9.0 Hz), 8.35 (1H, s), 9.27 (1H, s), 12.63 (1H, br s), 14.12 (1H, brs)
MS (ESI): M+ 390

Example 38

$^1$H NMR (DMSO-d$_6$ 300 MHz) (δ) ppm: 2.16 (6H, s), 3.62 (2H, s), 4.31 (2H, s), 7.20-7.25 (1H, m), 7.40-7.55 (2H, m), 7.95 (1H, d, J=9.2 Hz), 8.23 (1H, s), 8.30 (1H, d, J=9.2 Hz), 9.25 (1H, s)
MS (ESI): M+389

Example 39

$^1$H NMR (DMSO-d$_6$ 300 MHz) (δ) ppm: 3.82 (2H, d, J=5.7 Hz), 4.31 (2H, s), 4.57 (2H, d, J=6.1 Hz), 5.50-5.55 (1H, m), 7.20-7.25 (1H, m), 7.40-7.55 (2H, m), 8.00 (1H, d, J=9.2 Hz), 8.38-8.50 (3H, m), 9.26 (1H, s), 14.10 (1H, s)
MS (ESI): M+419

Example 40

$^1$H NMR (DMSO-d$_6$ 300 MHz) (δ) ppm: 3.28 (3H, s), 4.31 (2H, s), 4.57 (2H, d, J=6.0 Hz), 7.20-7.25 (1H, m), 7.42-7.52 (2H, m), 8.01 (1H, d, J=7.5 Hz), 8.35 (1H, d, J=9.2 Hz), 8.41 (1H, s), 8.48 (1H, br), 9.26 (1H, s), 14.10 (1H, s)
MS (ESI): M+433

Example 41

¹H NMR (DMSO-d₆ 300 MHz) (δ) ppm: 1.44 (9H, s), 2.71 (3H, s), 4.32 (2H, s), 4.70 (2H, s), 7.20-7.25 (1H, m), 7.40-7.55 (2H, m), 8.05 (1H, d, J=9.2 Hz), 8.20 (1H, d, J=9.2 Hz), 8.32 (1H, s), 9.27 (1H, s)
MS (ESI): M+475

Example 42

¹H NMR (DMSO-d₆ 300 MHz) (δ) ppm: 0.99 (3H, t, J=7.5 Hz), 2.10 (2H, q, J=7.5 Hz), 4.32 (2H, s), 4.54 (2H, d, J=6.1 Hz), 7.20-7.30 (1H, m), 7.40-7.55 (2H, m), 8.00 (1H, d, J=9.2 Hz), 8.25 (1H, d, J=9.2 Hz), 8.30-8.40 (1H, br), 8.35 (1H, s), 9.27 (1H, s), 13.90-14.10 (1H, br)
MS (ESI): M+417

Example 43

¹H NMR (DMSO-d₆ 300 MHz) (δ) ppm: 0.82 (3H, t, J=7.3 Hz), 1.45-1.55 (2H, m), 2.07 (2H, t, J=7.3 Hz), 4.32 (2H, s), 4.55 (2H, d, J=6.1 Hz), 7.20-7.25 (1H, m), 7.40-7.55 (2H, m), 8.00 (1H, d, J=9.2 Hz), 8.22 (1H, d, J=9.2 Hz), 8.30-8.40 (1H, br), 8.35 (1H, s), 9.27 (1H, s), 14.10 (1H, s)
MS (ESI): M+431

Example 44

¹H NMR (DMSO-d₆ 300 MHz) (δ) ppm: 1.00 (6H, d, J=6.8 Hz), 2.33-2.42 (1H, m), 4.32 (2H, s), 4.53 (2H, d, J=5.7 Hz), 7.20-7.25 (1H, m), 7.40-7.55 (2H, m), 8.01 (1H, d, J=9.2 Hz), 8.22 (1H, d, J=9.2 Hz), 8.31-8.34 (1H, br), 8.34 (1H, s), 9.27 (1H, s), 14.10 (1H, s)
MS (ESI): M+431

Example 45

¹H NMR (DMSO-d₆ 300 MHz) (δ) ppm: 4.32 (2H, s), 4.76 (2H, d, J=5.3 Hz), 7.19-7.24 (1H, m), 7.39-7.53 (5H, m), 7.85 (1H, d, J=7.1 Hz), 8.04 (1H, d, J=9.0 Hz), 8.38 (1H, d, J=9.0 Hz), 8.45 (1H, s), 9.00-9.07 (1H, m), 9.28 (1H, s), 14.11 (1H, s)
MS (ESI): M+465

Example 46

¹H NMR (DMSO-d₆ 400 MHz) (δ) ppm: 1.15 (3H, t, J=7.1 Hz), 4.00 (2H, q, J=7.1 Hz), 4.33 (2H, s), 4.47 (2H, d, J=5.8 Hz), 7.24 (1H, td, J=7.9, 1.0 Hz), 7.41-7.45 (1H, m), 7.51-7.55 (1H, m), 7.75 (1H, d, J=20.4 Hz), 8.04 (1H, dd, J=9.2, 1.7 Hz), 8.26 (1H, d, J=9.3 Hz), 8.35 (1H, s), 9.29 (1H, s), 14.13 (1H, s)
MS (ESI): M+432

Example 47

¹H NMR (DMSO-d₆ 400 MHz) (δ) ppm: 3.25-3.28 (4H, m), 3.52-3.54 (4H, m), 4.33 (2H, s), 4.52 (2H, d, J=5.3 Hz), 7.15-7.18 (1H, m), 7.22-7.26 (1H, m), 7.42-7.46 (1H, m), 7.51-7.56 (1H, m), 8.02 (1H, dd, J=9.3, 1.9 Hz), 8.37 (2H, d, J=10.2 Hz), 9.28 (1H, s), 14.17 (1H, s)
MS (ESI): M+473

Example 48

1H-NMR (DMSO-d₆ 300 MHz) (δ) ppm: 0.96 (3H, t, J=5.4 Hz), 2.98-3.01 (2H, m), 4.32 (2H, s), 4.47 (2H, d, J=5.3 Hz), 6.00 (1H, t, J=4.5 Hz), 6.46 (1H, t, J=4.5 Hz), 7.20-7.24 (1H, m), 7.42-7.52 (2H, m), 8.02 (1H, d, J=9.0 Hz), 8.31 (1H, d, J=9.0 Hz), 8.35 (1H, s), 9.27 (1H, s)
MS (ESI): M+432

Example 49

1H-NMR (DMSO-d₆ 300 MHz) (δ) ppm: 3.42 (2H, s), 4.32 (2H, s), 4.56 (2H, d, J=5.8 Hz), 7.16-7.26 (6H, m), 7.41-7.56 (2H, m), 7.94 (1H, d, J=9.0 Hz), 8.16 (1H, d, J=9.0 Hz), 8.39 (1H, s), 8.60-8.70 (1H, m), 9.28 (1H, s), 14.00-14.01 (1H, br)
MS (ESI): M+479

Example 50

1H-NMR (DMSO-d₆ 300 MHz) (δ) ppm: 4.32 (2H, s), 4.59 (2H, d, J=6.1 Hz), 7.20-7.25 (1H, m), 7.41-7.54 (2H, m), 8.03 (1H, d, J=7.8 Hz), 8.33 (1H, d, J=9.0 Hz), 8.42 (1H, s), 9.27 (1H, s), 9.40-9.50 (1H, m), 14.08 (1H, s)
MS (ESI): M+433

Example 51

¹H NMR (DMSO-d₆ 400 MHz) (δ) ppm: 4.33 (2H, s), 4.51 (2H, s), 4.63 (2H, d, J=5.8 Hz), 6.86-6.91 (3H, m), 7.17-7.21 (2H, m), 7.23-7.27 (1H, m), 7.43-7.47 (1H, m), 7.52-7.57 (1H, m), 7.97 (1H, dd, J=9.2, 1.7 Hz), 8.28 (1H, d, J=9.0 Hz), 8.44 (1H, s), 8.71-8.74 (1H, m), 9.29 (1H, s), 14.11 (1H, s)
MS (ESI): M+494

Example 52

¹H NMR (DMSO-d₆ 400 MHz) (δ) ppm: 1.21 (3H, d, J=6.7 Hz), 3.22 (3H, s), 3.71 (1H, q, J=6.7 Hz), 4.33 (2H, s), 4.57 (2H, d, J=6.0 Hz), 7.21-7.26 (1H, m), 7.41-7.45 (1H, m), 7.51-7.56 (1H, m), 8.04 (1H, dd, J=9.3, 1.9 Hz), 8.32 (1H, d, J=9.0 Hz), 8.40 (1H, s), 8.53-8.56 (1H, m), 9.27 (1H, s), 14.11 (1H, s)
MS (ESI): M+446

Example 53

¹H NMR (DMSO-d₆ 400 MHz) (δ) ppm: 1.21 (3H, d, J=6.7 Hz), 3.22 (3H, s), 3.71 (1H, q, J=6.7 Hz), 4.33 (2H, s), 4.57 (2H, d, J=6.0 Hz), 7.21-7.26 (1H, m), 7.41-7.45 (1H, m), 7.51-7.56 (1H, m), 8.03 (1H, dd, J=9.2, 1.7 Hz), 8.32 (1H, d, J=9.0 Hz), 8.40 (1H, s), 8.53-8.56 (1H, m), 9.27 (1H, s), 14.11 (1H, s)
MS (ESI): M+446

Example 54

1H-NMR (DMSO-d₆ 300 MHz) (δ) ppm: 2.32 (2H, t, J=6.3 Hz), 2.43 (2H, t, J=6.3 Hz), 4.32 (2H, s), 4.54 (2H, d, J=5.6 Hz), 7.20-7.25 (1H, m), 7.40-7.55 (2H, m), 8.02 (1H, d, J=9.1 Hz), 8.22 (1H, d, J=9.1 Hz), 8.36 (1H, s), 8.40-8.45 (1H, m), 9.27 (1H, s), 11.90-12.10 (1H, br), 14.00-14.20 (1H, br)
MS (ESI): M+461

Example 55

¹H NMR (DMSO-d₆ 400 MHz) (δ) ppm: 1.13 (3H, t, J=7.0 Hz), 3.46 (2H, q, J=7.0 Hz), 3.86 (2H, s), 4.33 (2H, s), 4.59 (2H, d, J=6.0 Hz), 7.21-7.26 (1H, m), 7.41-7.45 (1H, m), 7.51-7.55 (1H, m), 8.03 (1H, dd, J=9.2, 1.7 Hz), 8.36-8.46 (3H, m), 9.28 (1H, s), 14.13 (1H, s)
MS (ESI): M+446

Example 56

¹H NMR (DMSO-d₆ 400 MHz) (δ) ppm: 1.25 (6H, s), 3.11 (3H, s), 4.33 (2H, s), 4.54 (2H, d, J=6.0 Hz), 7.21-7.26 (1H, m), 7.41-7.45 (1H, m), 7.51-7.55 (1H, m), 8.03 (1H, dd, J=9.2, 1.7 Hz), 8.33 (1H, d, J=9.3 Hz), 8.40 (1H, s), 8.48-8.51 (1H, m), 9.26 (1H, s), 14.12 (1H, s)

MS (ESI): M+460

Example 57

¹H NMR (DMSO-d₆ 400 MHz) (δ) ppm: 1.91 (3H, s), 3.66 (2H, d, J=5.6 Hz), 4.32 (2H, s), 4.57 (2H, d, J=5.6 Hz), 7.20-7.28 (1H, m), 7.40-7.48 (1H, m), 7.50-7.57 (1H, m), 8.02 (1H, d, J=9.6 Hz), 8.08-8.15 (1H, m), 8.28 (1H, d, J=9.2 Hz), 8.42 (1H, s), 8.38-8.47 (1H, m), 9.28 (1H, s), 14.11 (1H, brs)

MS (ESI): M+ 460

Example 61

¹H NMR (DMSO-d₆ 400 MHz) (δ) ppm: 2.14 (3H, s), 4.34 (2H, s), 7.22-7.26 (1H, m), 7.40-7.44 (1H, m), 7.51-7.56 (1H, m), 7.96-8.05 (2H, m), 8.28 (1H, s), 9.24 (1H, s), 9.91 (1H, s), 14.11 (1H, s)

MS (ESI): M+388

Example 62

¹H NMR (DMSO-d₆ 300 MHz) (δ) ppm: 1.59 (9H, s), 4.33 (2H, s), 7.20-7.25 (1H, m), 7.35-7.40 (1H, m), 7.50-7.55 (1H, m), 8.15 (1H, d, J=7.7 Hz), 8.89 (1H, s), 9.18 (1H, d, J=9.2 Hz), 9.34 (1H, s), 13.20-13.30 (1H, br)

MS (ESI): M+432

Example 63

¹H NMR (DMSO-d₆ 300 MHz) (δ) ppm: 0.72 (3H, d, J=6.6 Hz), 1.03 (3H, d, J=6.6 Hz), 2.00-2.10 (1H, m), 3.10-3.20 (1H, m), 3.70-3.80 (2H, m), 4.40 (2H, s), 4.49 (1H, m), 7.37-7.42 (1H, m), 7.49 (1H, d, J=6.4 Hz), 7.61 (1H, d, J=8.0 Hz), 7.88 (1H, d, J=7.7 Hz), 8.33 (1H, s), 8.38 (1H, d, J=9.4 Hz), 9.18 (1H, s), 14.34 (1H, s)

MS (ESI): M+434

Example 64

¹H NMR (DMSO-d₆ 400 MHz) (δ) ppm: 0.90 (9H, s), 3.37-3.44 (1H, m) 3.80-3.87 (1H, m), 3.93-4.00 (1H, m), 4.39-4.42 (3H, m), 7.39-7.43 (1H, m), 7.49-7.51 (1H, m), 7.62-7.64 (1H, m), 7.89 (1H, dd, J=9.3, 1.9 Hz), 8.36 (1H, s), 8.51 (1H, d, J=9.5 Hz), 9.19 (1H, s), 14.33 (1H, s)

MS (ESI): M+447

Experimental Example 1

The following explains evaluation methods of the HIV integrase inhibitory activity of the compound of the present invention.

(i) Construction of Recombinant Integrase Gene Expression System

HIV integrase full length gene (J. Virol., 67, 425-437 (1993)) in which phenylalanine at codon 185 was substituted by histidine, was inserted between the restriction enzyme NdeI and XhoI sites of plasmid pET21a(+) (Novagen), whereby an integrase expression vector pET21a-INH was constructed.

(ii) Production and Purification of Integrase Protein

*Escherichia coli* recombinant BL21 (DE3) transformed with plasmid pET21a-INH obtained in (i) was shake cultured at 37° C. in a liquid medium containing ampicillin. When the culture reached the logarithmic growth phase, isopropyl-β-D-thiogalactopyranoside was added to promote expression of integrase gene. The culture was continued for 3 hr to promote accumulation of the integrase protein. The recombinant *E. coli* was collected in pellets by centrifugal separation and preserved at −80° C.

The *E. coli* was suspended in Lysis buffer (20 mM HEPES (pH 7.5), 5 mM DTT, 10 mM CHAPS, 10% glycerol) containing 1 M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (Pharmacia Corporation) and stirred at 4° C. for 60 min to allow adsorption of integrase protein to the resin. The resin was washed with Lysis buffer containing 100 mM sodium chloride and the integrase protein was eluted with Lysis buffer containing 1 M sodium chloride.

The eluted integrase protein solution was subjected to a Superdex 75 (Pharmacia Corporation) column for gel filtration. The protein was eluted with Lysis buffer containing 1 M sodium chloride.

The obtained fractions of the integrase protein were collected and preserved at −80° C.

(iii) Preparation of DNA Solution

The following DNA synthesized by Greiner was dissolved in TE buffer (10 mM Tris-hydrochloric acid (pH 8.0), 1 mM EDTA) and mixed with donor DNA, target DNA, and each complementary strand (+ and − strands) to 1 μM. The mixture was heated at 95° C. for 5 min, 80° C. for 10 min, 70° C. for 10 min, 60° C. for 10 min, 50° C. for 10 min and 40° C. for 10 min and kept at 25° C. to give a double stranded DNA, which was used for the test.

Donor DNA (− Strand Having Biotin Attached to the 5' Terminal)

```
                                          (SEQ ID NO:1)
Donor + strand:
5'-Biotin-ACC CTT TTA GTC AGT GTG AAA ATT CTC
TAG CA-3'

(SEQ ID NO:2)
Donor - strand:
5'-ACT GCT AGA GAT TTT CCA CAC TGA CTA AAA G-3'

Target DNA (+, - strands both having digoxigenin
added at 3'terminal)

(SEQ ID NO: 3)
Target + strand:
5'-TGA CCA AGG GCT AAT TCA CT-Dig-3'

(SEQ ID NO: 4)
Target - strand:
5'-AGT GAA TTA GCC CTT GGT CA-Dig-3'
```

(iv) Determination of Enzyme (HIV Integrase) Inhibitory Activity

The donor DNA was diluted with TE buffer to 10 nM, of which 50 μl was added to each well of streptavidin-coated microtiter plate (Roche) and allowed to adsorb at 37° C. for 60 min. The plate was washed with phosphate buffer (Dulbecco's PBS, Sanko Junyaku Co., Ltd.) containing 0.1% Tween 20 and phosphate buffer. Then, a reaction mixture (70 µl) having the following composition, a test substance (10 µl) diluted with the reaction mixture and 100 µg/ml integrase protein (10 µl) were added to each well and reacted at 37° C. for 60 min. Composition of the reaction mixture: 30 mM MOPS (3-morpholinopropanesulfonic acid), 5 mM magnesium chloride, 3 mM DTT (dithiothreitol), 0.1 mg/ml BSA (bovine serum albumin), 5% glycerol, 10% DMSO (dimethyl sulfoxide), 0.01% Tween 20.

Then, 50 nM target DNA (10 µl) was added, and the mixture was reacted at 37° C. for 10 min and washed with phosphate buffer containing 0.1% Tween 20 to stop the reaction.

Then, 100 mU/ml peroxidase labeled anti-digoxigenin antibody solution (Roche, 100 µl) was added, and the mixture was reacted at 37° C. for 60 min, followed by washing with phosphate buffer containing 0.1% Tween 20.

A peroxidase color solution (Bio Rad, 100 µl) was added and allowed to react at room temperature for 4 min. The color reaction was stopped by adding 1N sulfuric acid (100 µl). The absorbance at 450 nm was measured.

The HIV integrase inhibitory activity ($IC_{50}$) of the compound of the present invention was calculated from the inhibition rate according to the following formula.

$$\text{inhibition rate (\%)} = [1-(\text{Object}-\text{Blank})/(\text{Control}-\text{Blank})] \times 100$$

Object; absorbance of well in the presence of test compound

Control; absorbance of well in the absence of test compound

Blank; absorbance of well in the absence of test compound, in the absence of integrase protein Evaluation of Antiviral Activity The results are shown in Table 8-Table 12. $IC_{50}$ shows the following ranges.
+: not less than 1 µM and less than 10 µM
++: not less than 0.1 µM and less than 1 µM
+++: not less than 0.01 µM and less than 0.1 µM
++++: less than 0.01 µM

TABLE 8

| Example No. | Anti-integrase activity ($IC_{50}$ value) |
| --- | --- |
| 2 | ++ |
| 4 | +++ |
| 7 | +++ |
| 10 | ++++ |
| 11 | + |
| 12 | +++ |
| 13 | +++ |
| 14 | +++ |
| 15 | +++ |

TABLE 9

| Example No. | Anti-integrase activity ($IC_{50}$ value) |
| --- | --- |
| 16 | ++++ |
| 17 | ++++ |
| 18 | +++ |
| 19 | ++ |
| 20 | ++ |
| 21 | ++ |
| 22 | +++ |
| 23 | + |
| 24 | +++ |
| 26 | +++ |
| 27 | ++ |
| 29 | ++ |

TABLE 10

| Example No. | Anti-integrase activity ($IC_{50}$ value) |
| --- | --- |
| 33 | +++ |
| 34 | ++ |
| 35 | +++ |
| 36 | +++ |
| 37 | +++ |
| 38 | ++ |
| 39 | +++ |
| 40 | +++ |
| 41 | +++ |
| 42 | +++ |
| 43 | +++ |
| 44 | +++ |

TABLE 11

| Example No. | Anti-integrase activity ($IC_{50}$ value) |
| --- | --- |
| 45 | +++ |
| 46 | +++ |
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | ++ |

TABLE 12

| Example No. | Anti-integrase activity ($IC_{50}$ value) |
| --- | --- |
| 57 | ++ |
| 58 | ++ |
| 60 | ++ |
| 61 | ++ |
| 62 | ++ |
| 63 | ++++ |
| 64 | ++++ |

Experimental Example 2

Evaluation of Antiviral Activity

The effect of combined use of the compound of the present invention and existent anti-HIV agents can be determined in the following manner.

For example, the effect of combined use of two agents from existent nucleoside reverse transcriptase inhibitors (zidovudine, lamivudine, tenofovir), non-nucleoside reverse transcriptase inhibitors (efavirenz) or protease inhibitors (indinavir, nelfinavir) and test substance A and the like are evaluated using CEM-SS cells infected with HIV-1 IIIB by XTT method.

In addition, the effect of combined use of three agents of test substance A, zidovudine and lamivudine, or test substance A, tenofovir and lamivudine, and the like is evaluated.

Prior to the combined use test, $IC_{50}$ and $CC_{50}$ of each pharmaceutical agent alone are measured. 5 concentrations of pharmaceutical agent A and 9 concentrations of pharmaceutical agent B, determined based on these results, are combined to evaluate the effect of combined use of two agents. For combined use of three agents, a high concentration pharmaceutical agent B and a pharmaceutical agent C are mixed and pharmaceutical agent A and the concentration are combined for evaluation.

The test results of the test substance and combination drug alone or in combination thereof are analyzed based on the programs of Prichard and Shipman MacSynergy II version 2.01 and Deltagraph version 1.5d. A three-dimensional plot is drawn from % inhibition at the concentrations of each combined pharmaceutical agent, obtained from 3 times of tests, with 95% (or 68%, 99%) confidence limits, and the effect of the combined use is evaluated based on the numerical values of $\mu M^2\%$ calculated therefrom. The criteria of evaluation are shown in the following.

| Definition of interaction | $\mu M^2\%$ |
|---|---|
| Strong synergistic action | >100 |
| Slight synergistic action | +51-+100 |
| Additive action | +50--50 |
| Slight antagonistic action | -51--100 |
| Strong antagonistic action | <-100 |

As is clear from the above results, the compounds of the present invention have high HIV integrase inhibitory activity.

Therefore, the compounds can be useful pharmaceutical agents for the prophylaxis or therapy of AIDS, as anti-HIV agents having HIV integrase inhibitory activity. Moreover, by a combined use with other anti-HIV agents such as protease inhibitors, reverse transcriptase inhibitors and the like, the compounds can become more effective anti-HIV agents. Since the compounds have high inhibitory activity specific for integrases, they can provide safe pharmaceutical agents for human with a fewer side effects.

Formulation examples are shown below, which are not to be construed as limitative.

Formulation Example

| (a) compound of Example 2 | 10 g |
|---|---|
| (b) lactose | 50 g |
| (c) cornstarch | 15 g |
| (d) carboxymethylcellulose sodium | 44 g |
| (e) magnesium stearate | 1 g |

The entire amounts of (a), (b) and (c) and 30 g of (d) are kneaded with water, dried in vacuo and granulated. The granules are mixed with 14 g of (d) and 1 g of (e) and tableted with a tableting machine to give 1000 tablets containing 10 mg of (a) per tablet.

INDUSTRIAL APPLICABILITY

As is clear from the above results, the compound of the present invention has high HIV integrase inhibitory activity.

Therefore, the compounds can be effective pharmaceutical agents for the prophylaxis or therapy of AIDS, as anti-HIV agents having HIV integrase inhibitory activity. Moreover, by a combined use with other anti-HIV agents such as protease inhibitors, reverse transcriptase inhibitors and the like, the compounds can become more effective anti-HIV agents. Since the compounds have high inhibitory activity specific for integrases, they can provide safe pharmaceutical agents for human with a fewer side effects.

This application is based on patent application Nos. 2004-272820 and 2005-234884 filed in Japan, the contents of which are all hereby incorporated by reference.

Sequence Listing Free Text

SEQ ID NO:1: Donor+chain for HIV integrase activity determination

SEQ ID NO:2: Donor−chain for HIV integrase activity determination

SEQ ID NO:3: Target+chain for HIV integrase activity determination

SEQ ID NO:4: Target−chain for HIV integrase activity determination

The invention claimed is:

1. A pharmaceutical composition comprising a quinolizinone compound represented by the following formula [I], or a pharmaceutically acceptable salt thereof, as an active ingredient:

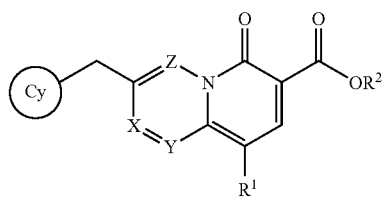

wherein ring Cy is a phenyl or naphthyl group optionally substituted by 1 to 5 substituents selected from group A below, wherein the group A is a group consisting of a cyano group, a nitro group, a halogen atom, a $C_{1-4}$ alkyl group, a halo $C_{1-4}$ alkyl group, a halo $C_{1-4}$ alkyloxy group, —$OR^{a1}$, —$SR^{a1}$, $NR^{a1}R^{a2}$, —$CONR^{a1}R^{a2}$, —$SO_2NR^{a1}R^{a2}$, —$COR^{a3}$, —$NR^{a1}COR^{a3}$, $SO_2R^{a3}$, —$NR^{a1}SO_2R^{a3}$, —$COOR^{a1}$, and —$NR^{a2}COOR^{a3}$, wherein $R^{a1}$ and $R^{a2}$ are the same or different and each is a hydrogen atom, or a $C_{1-4}$ alkyl group, and $R^{a3}$ is a $C_{1-4}$ alkyl group;

$R^1$ is a hydrogen atom, a group selected from group B below, or a $C_{1-10}$ alkyl group optionally substituted by 1 to 3 substituents selected from a halogen atom and group B below, wherein the group B is a group consisting of a $C_{3-10}$ carbon ring group optionally substituted by 1 to 5 substituents selected from group A above, a heterocyclic group (the heterocyclic group is as defined above) optionally substituted by 1 to 5 substituents selected from group A above, a cyano group, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$, —$NR^{a5}COOR^{a6}$, —$NR^{a4}CO$—$NR^{a5}R^{a12}$, —$NR^{a4}CO$—$COOR^{a5}$, —O—W—$OR^{a5}$, —$NR^{a4}$—W—$OR^{a5}$, —$NR^{a4}$—W—$SO_2NR^{a5}R^{a12}$, —$NR^{a4}CO$—W—$R^{a5}$, —$NR^{a4}CO$—W—$OR^{a5}$, —$NR^{a4}CO$—W—$COOR^{a5}$, and —$NR^{a4}CO$—W—$NR^{a5}COR^{a6}$, wherein $R^{a4}$, $R^{a5}$ and $R^{a12}$ are the same or different and each is a hydrogen atom, a $C_{1-4}$ alkyl group, a $C_{3-10}$ carbon ring group optionally substituted by 1 to 5 substituents selected from group A above, or a heterocyclic group (the heterocyclic group is as defined above) optionally substituted by 1 to 5 substituents selected from group A above, $R^{a6}$ is a $C_{1-4}$ alkyl group, a $C_{3-10}$ carbon ring group optionally substituted by 1 to 5 substituents selected from group A above, or a heterocyclic group (the heterocyclic group is as defined above) optionally substituted by 1 to 5 substituents selected from group A above, and W is a $C_{1-10}$ alkylene group;

$R^2$ is a hydrogen atom or a $C_{1-4}$ alkyl group;

Z is C—$R^{31}$ or a nitrogen atom,
  wherein $R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group, or a halo $C_{1-4}$ alkyloxy group;
X is C—$R^{32}$ or a nitrogen atom; and
Y is C—$R^{33}$ or a nitrogen atom,
  wherein $R^{32}$ and $R^{33}$ are the same or different and each is a hydrogen atom, a cyano group, a nitro group, a halogen atom,
  a $C_{3-10}$ carbon ring group optionally substituted by 1 to 5 substituents selected from group A above,
  a heterocyclic group (the heterocyclic group is as defined above) optionally substituted by 1 to 5 substituents selected from group A above, a $C_{1-10}$ alkyl group optionally substituted by 1 to 3 substituents selected from a halogen atom and group B above, —$OR^{a7}$, —$SR^{a7}$, —$NR^{a7}R^{a8}$, —$NR^{a7}COR^{a9}$, —$COOR^{a10}$, or —N=CH—$NR^{a10}R^{a11}$,
    wherein $R^{a7}$ and $R^{a8}$ are the same or different and each is a hydrogen atom, a group selected from group B above, or a $C_{1-10}$ alkyl group optionally substituted by 1 to 3 substituents selected from a halogen atom and group B above, $R^{a9}$ is a $C_{1-4}$ alkyl group, and $R^{a10}$ and $R^{a11}$ are the same or different and each is a hydrogen atom or a $C_{1-4}$ alkyl group and a pharmaceutically acceptable carrier.

2. The pharmaceutical composition of claim 1, wherein X is C—$R^{32}$ and Z is C—$R^{31}$.

3. The pharmaceutical composition of claim 1, wherein ring Cy is a group represented by the formula:

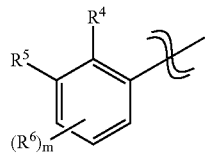

wherein
  $R^6$ is a group selected from the group A (the group A is as defined in claim 1);
  $R^4$ and $R^5$ are the same or different and each is a group selected from a hydrogen atom and the group A (the group A is as defined in claim 1), or
  $R^4$ and $R^5$ may form a fused ring together with a benzene ring they substitute; and
  m is 0 or an integer of 1 to 3, and when m is 2 or 3, then $R^6$ of each may be the same or different.

4. A quinolizinone compound represented by the following formula [II] or a pharmaceutically acceptable salt thereof:

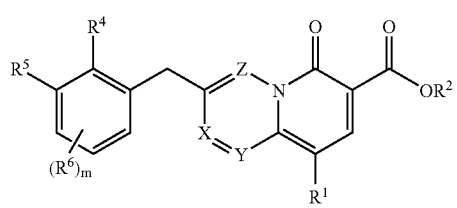

[II]

wherein
  $R^6$ is a group selected from group A below,
    wherein the group A is a group consisting of a cyano group, a nitro group, a halogen atom, a $C_{1-4}$ alkyl group, a halo $C_{1-4}$ alkyl group, a halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a2}COR^{a3}$, —$SO_2R^{a3}$, —$NR^{a1}SO_2R^{a3}$, —$COOR^{a1}$, and —$NR^{a2}COOR^{a3}$,
      wherein $R^{a1}$ and $R^{a2}$ are the same or different and each is a hydrogen atom, or a $C_{1-4}$ alkyl group, and $R^{a3}$ is a $C_{1-4}$ alkyl group;
  $R^4$ and $R^5$ are the same or different and each is a group selected from a hydrogen atom and group A above, or
  $R^4$ and $R^5$ may form a fused ring together with a benzene ring they substitute;
  m is 0 or an integer of 1 to 3, and when m is 2 or 3, then $R^6$ of each may be the same or different;
  $R^1$ is a hydrogen atom, a group selected from group B below or a $C_{1-10}$ alkyl group optionally substituted by 1 to 3 substituents selected from a halogen atom and group B below,
    wherein the group B is a group consisting of a $C_{3-10}$ carbon ring group optionally substituted by 1 to 5 substituents selected from group A above,
    a heterocyclic group optionally substituted by 1 to 5 substituents selected from group A above,
      wherein the heterocyclic group is a saturated or unsaturated ring group containing, besides carbon atom(s), at least one hetero atom selected from a nitrogen atom, an oxygen atom, and a sulfur atom,
    a cyano group, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$, —$NR^{a5}COOR^{a6}$, —$NR^{a4}CO$—$NR^{a5}R^{a12}$, —$NR^{a4}CO$—$COOR^{a5}$, —O—W—$OR^{a5}$, —$NR^{a4}$—W—$OR^{a5}$, —$NR^{a4}$—W—$SO_2NR^{a5}R^{a12}$, —$NR^{a4}CO$—W—$R^{a5}$, —$NR^{a4}CO$—W—$NR^{a5}$, —$NR^{a4}CO$—W—$COOR^{a5}$, and —$NR^{a4}CO$—W—$NR^{a5}COR^{a6}$,
      wherein $R^{a4}$, $R^{a5}$ and $R^{a12}$ are the same or different and each is a hydrogen atom, a $C_{1-4}$ alkyl group, a $C_{3-10}$ carbon ring group optionally substituted by 1 to 5 substituents selected from group A above, or a heterocyclic group (the heterocyclic group is as defined above) optionally substituted by 1 to 5 substituents selected from group A above, $R^{a6}$ is a $C_{1-4}$ alkyl group, a $C_{3-10}$ carbon ring group optionally substituted by 1 to 5 substituents selected from group A above or a heterocyclic group (the heterocyclic group is as defined above) optionally substituted by 1 to 5 substituents selected from group A above, and W is a $C_{1-10}$ alkylene group;
  $R^2$ is a hydrogen atom or a $C_{1-4}$ alkyl group;
  Z is C—$R^{31}$ or a nitrogen atom,
    wherein $R^{31}$ is a hydrogen atom, a cyano group, a hydroxy group, an amino group, a nitro group, a halogen atom, a $C_{1-4}$ alkyl group, a $C_{1-4}$ alkoxy group, a $C^{1-4}$ alkylsulfanyl group, a halo $C_{1-4}$ alkyl group, or a halo $C_{1-4}$ alkyloxy group;
  X is C—$R^{32}$ or a nitrogen atom; and
  Y is C—$R^{33}$ or a nitrogen atom,
    wherein $R^{32}$ and $R^{33}$ are the same or different and each is a hydrogen atom, a cyano group, a nitro group, a halogen atom, a $C_{3-10}$ carbon ring group optionally substituted by 1 to 5 substituents selected from group A above, a heterocyclic group (the heterocyclic group is as defined above) optionally substituted by 1 to 5 substituents selected from group A above, a $C_{1-10}$ alkyl group optionally substituted by 1 to 3 substituents selected from a halogen atom and group B above, —$OR^{a7}$, —$SR^{a7}$, —$NR^{a7}R^{a8}$, —$NR^{a7}COR^{a9}$, —$COOR^{a10}$ or —N=CH—$NR^{a10}R^{a11}$, wherein $R^{a7}$ and $R^{a8}$ are the same or different and each is a hydrogen atom, a group selected from group B above, or a $C_{1-10}$ alkyl group optionally substituted by 1 to 3 substituents selected from a halogen atom and group B above, $R^{a9}$ is a $C_{1-4}$ alkyl group, and $R^{a10}$ and $R^{a11}$ are the same or different and each is a hydrogen atom or a $C_{1-4}$ alkyl group.

5. The quinolizinone compound of claim 4, wherein X is C—$R^{32}$ and Z is C—$R^{31}$, or a pharmaceutically acceptable salt thereof.

6. The quinolizinone compound of claim 4, wherein $R^{31}$ is a hydrogen atom, a cyano group, a hydroxy group or a $C_{1-4}$ alkoxy group, or a pharmaceutically acceptable salt thereof.

7. The quinolizinone compound of claim 4, wherein $R^{31}$ is a hydrogen atom, or a pharmaceutically acceptable salt thereof.

8. The quinolizinone compound of claim 4, wherein $R^{32}$ is a hydrogen atom, a cyano group, a halogen atom, a heterocyclic group (the heterocyclic group is as defined in claim 4) optionally substituted by 1 to 5 substituents selected from the group A (the group A is as defined in claim 4), a $C_{1-10}$ alkyl group optionally substituted by 1 to 3 substituents selected from a halogen atom and the group B (the group B is as defined in claim 4), —$OR^{a7}$, —$SR^{a7}$, —$NR^{a7}R^{a5}$, —$NR^{a7}COR^{a9}$, —$COOR^{a10}$, or —N=CH—$NR^{a10}R^{a11}$ wherein $R^{a7}$, $R^{a8}$, $R^{a9}$, $R^{a10}$ and $R^{a11}$ are as defined in claim 4, or a pharmaceutically acceptable salt thereof.

9. The quinolizinone compound of claim 4, wherein $R^{32}$ is a hydrogen atom, a cyano group, a halogen atom, a $C_{1-10}$ alkyl group optionally substituted by 1 to 3 substituents selected from a halogen atom and the group B (the group B is as defined in claim 4), —$OR^{a7}$, —$SR^{a7}$, —$NR^{a7}R^{a8}$, —$NR^{a7}COR^{a9}$ or —$COO^{a10}$, wherein $R^{a7}$, $R^{a8}$, $R^{a9}$ and $R^{a10}$ are as defined in claim 4, or a pharmaceutically acceptable salt thereof.

10. The quinolizinone compound of claim 4, wherein $R^{32}$ is a hydrogen atom, —$OR^{a7}$, —$SR^{a7}$ or —$NR^{a7}R^{a8}$, wherein $R^{a7}$ and $R^{a8}$ are as defined in claim 4, or a pharmaceutically acceptable salt thereof.

11. The quinolizinone compound of claim 4, wherein Y is C—$R^{33}$, or a pharmaceutically acceptable salt thereof.

12. The quinolizinone compound of claim 4, wherein $R^{33}$ is a hydrogen atom, a cyano group, a halogen atom, a heterocyclic group (the heterocyclic group is as defined in claim 4) optionally substituted by 1 to 5 substituents selected from the group A (the group A is as defined in claim 4), a $C_{1-10}$ alkyl group optionally substituted by 1 to 3 substituents selected from a halogen atom and the group B (the group B is as defined in claim 4), —$OR^{a7}$, —$SR^{a7}$, —$NR^{a7}R^{a8}$, —$NR^{a7}COR^{a9}$, —$COOR^{a10}$, or —N=CH—$NR^{a10}R^{a11}$, wherein $R^{a7}$, $R^{a8}$, $R^{a9}$, $R^{a10}$ and $R^{a11}$ are as defined in claim 4, or a pharmaceutically acceptable salt thereof.

13. The quinolizinone compound of claim 4, wherein $R^{33}$ is a hydrogen atom, a $C_{1-10}$ alkyl group optionally substituted by 1 to 3 substituents selected from a halogen atom and the group B (the group B is as defined in claim 4), —$OR^{a7}$ or —$NR^{a7}R^{a8}$, wherein $R^{a7}$ and $R^{a8}$ are as defined in claim 4, or a pharmaceutically acceptable salt thereof.

14. The quinolizinone compound of claim 4, wherein $R^{33}$ is a hydrogen atom, —$OR^{a7}$ or —$NR^{a7}R^{a8}$, wherein $R^{a7}$ and $R^{a8}$ are as defined in claim 4, or a pharmaceutically acceptable salt thereof.

15. The quinolizinone compound of claim 8, wherein $R^{a7}$ and $R^{a8}$ are the same or different and each is a $C_{1-10}$ alkyl group optionally substituted by 1 to 3 substituents selected from a halogen atom and the group B (the group B is as defined in claim 4), or a pharmaceutically acceptable salt thereof.

16. The quinolizinone compound of claim 4, wherein $R^4$ and $R^5$ are the same or different and each is a hydrogen atom, a cyano group, a nitro group, a halogen atom, a $C_{1-4}$ alkyl group, a halo $C_{1-4}$ alkyl group, a halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$NR^{a1}COR^{a3}$, —$SO_2R^{a3}$, —$NR^{a1}SO_2R^{a3}$, —$COOR^{a1}$ or —$NR^{a2}COOR^{a3}$, wherein $R^{a1}$, $R^{a2}$ and $R^{a3}$ are as defined in claim 4, or a pharmaceutically acceptable salt thereof.

17. The quinolizinone compound of claim 4, wherein $R^4$ is a hydrogen atom, a halogen atom, a $C_{1-4}$ alkyl group, a halo $C_{1-4}$ alkyloxy group, —$OR^{a1}$, —$NR^{a1}R^{a2}$, —$CONR^{a1}R^{a2}$, —$SO_2NR^{a1}R^{a2}$, —$NR^{a1}COR^{a3}$, —$SO_2R^{a3}$, —$NR^{a1}SO_2R^{a3}$ or —$COOR^{a1}$, wherein $R^{a1}$, $R^{a2}$ and $R^{a3}$ are as defined in claim 4, or a pharmaceutically acceptable salt thereof.

18. The quinolizinone compound of claim 4, wherein $R^4$ is a hydrogen atom or a halogen atom, or a pharmaceutically acceptable salt thereof.

19. The quinolizinone compound of claim 4, wherein $R^5$ is a hydrogen atom, a cyano group, a nitro group, a halogen atom, a $C_{1-4}$ alkyl group, a halo $C_{1-4}$ alkyl, —$OR^{a1}$, —$SR^{a1}$, —$NR^{a1}R^{a2}$, —$CONR^{a1}R^{a2}$, —$SO_2NR^{a1}R^{a2}$ or —$NR^{a1}COR^{a3}$, wherein $R^{a1}$, $R^{a2}$ and $R^{a3}$ are as defined in claim 4, or a pharmaceutically acceptable salt thereof.

20. The quinolizinone compound of claim 4, wherein $R^6$ is a halogen atom, or a pharmaceutically acceptable salt thereof.

21. The quinolizinone compound of claim 4, wherein m is 0 or 1, or a pharmaceutically acceptable salt thereof.

22. The quinolizinone compound of claim 4, wherein $R^1$ is a hydrogen atom, a $C_{3-10}$ carbon ring group optionally substituted by 1 to 5 substituents selected from the group A (the group A is as defined in claim 4), a cyano group, —$NR^{a4}R^{a5}$, —$NR^{a4}COR^{a6}$, —$NR^{a4}SO_2R^{a6}$, —$COOR^{a4}$, —$NR^{a5}COO$ $R^{a6}$, —O—W—$OR^{a5}$, —$NR^{a4}$—W—$OR^{a5}$, —$NR^{a4}$—W—$SO_2NR^{a5}R^{a12}$, wherein $R^{a4}$, $R^{a5}$, $R^{a6}$ and $R^{a12}$ are as defined in claim 4, or a $C_{1-10}$ alkyl group optionally substituted by 1 to 3 substituents selected from a halogen atom and the group B (the group B is as defined in claim 4), or a pharmaceutically acceptable salt thereof.

23. The quinolizinone compound of claim 4, wherein R$^1$ is a hydrogen atom, a cyano group, —NR$^{a4}$COR$^{a6}$, —NR$^{a4}$SO$_2$R$^{a6}$, —COOR$^{a4}$, —NR$^{a5}$COOR$^{a6}$, —O—W—OR$^{a5}$, —NR$^{a4}$—W—OR$^{a5}$, —NR$^{a4}$—W—SO$_2$NR$^{a5}$R$^{a12}$,
wherein R$^{a4}$, R$^{a5}$, R$^{a6}$ and R$^{a12}$ are as defined in claim 4, or a C$_{1-10}$ alkyl group optionally substituted by 1 to 3 substituents selected from a halogen atom and the group B (the group B is as defined in claim 4), or a pharmaceutically acceptable salt thereof.

24. The quinolizinone compound of claim 4, wherein R$^2$ is a hydrogen atom, or a pharmaceutically acceptable salt thereof.

25. The quinolizinone compound of claim 4, which is represented by the following formula [II-1] or [II-2],

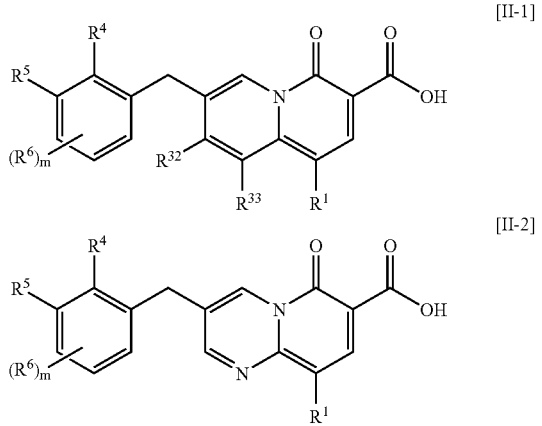

wherein R$^{32}$ and R$^{33}$ are the same or different and each is a hydrogen atom or —OR$^{a7}$ (R$^{a7}$ is as defined in claim 4), and the other symbols are as defined in claim 4, or a pharmaceutically acceptable salt thereof.

26. The quinolizinone compound of claim 4, which is selected from the group consisting of
 7-(3-chloro-2-fluorobenzyl)-4-oxo-4H-quinolizine-3-carboxylic acid,
 7-(3-chloro-2-fluorobenzyl)-1-ethyl-4-oxo-4H-quinolizine-3-carboxylic acid,
 7-(3-chloro-2-fluorobenzyl)-1-(2-hydroxyethyl)-4-oxo-4H-quinolizine-3-carboxylic acid,
 7-(3-chloro-2-fluorobenzyl)-1-((R)-1-hydroxymethyl-2-methylpropyl)-8-methoxy-4-oxo-4H-quinolizine-3-carboxylic acid,
 7-benzyl-4-oxo-4H-quinolizine-3-carboxylic acid,
 7-(3-chloro-2-fluorobenzyl)-4-oxo-1-propyl-4H-quinolizine-3-carboxylic acid,
 7-(3-chloro-2-fluorobenzyl)-1-isopropyl-4-oxo-4H-quinolizine-3-carboxylic acid,
 7-(3-chloro-2-fluorobenzyl)-1-((R)-2-hydroxy-1-methylethyl)-4-oxo-4H-quinolizine-3-carboxylic acid,
 7-(3-chloro-2-fluorobenzyl)-1-(1-hydroxymethyl-2-methylpropyl)-4-oxo-4H-quinolizine-3-carboxylic acid,
 7-(3-chloro-2-fluorobenzyl)-1-((R)-1-hydroxymethyl-2,2-dimethylpropyl)-4-oxo-4H-quinolizine-3-carboxylic acid,
 7-(3-chloro-2-fluorobenzyl)-1-((R)-1-hydroxymethyl-2,2-dimethylpropyl)-8-methoxy-4-oxo-4H-quinolizine-3-carboxylic acid,
 7-(3-chloro-2-fluorobenzyl)-1-hydroxymethyl-4-oxo-4H-quinolizine-3-carboxylic acid,
 7-(3-chloro-2-fluorobenzyl)-1-methoxymethyl-4-oxo-4H-quinolizine-3-carboxylic acid,
 1-aminomethyl-7-(3-chloro-2-fluorobenzyl)-4-oxo-4H-quinolizine-3-carboxylic acid hydrochloric acid,
 7-(3-chloro-2-fluorobenzyl)-l-methylaminomethyl-4-oxo-4}4H-quinolizine-3-carboxylic acid,
 1-(acetylaminomethyl)-7-(3-chloro-2-fluorobenzyl)-4-oxo-4H-quinolizine-3-carboxylic acid,
 7-(3-chloro-2-fluorobenzyl)-1-(methylsulfonylaminomethyl)-4-oxo-4H-quinolizine-3-carboxylic acid,
 7-(3-chloro-2-fluorobenzyl)-1-(methoxycarbonylaminomethyl)-4-oxo-4H-quinolizine-3-carboxylic acid,
 1-(aminocarbonyl)methyl-7-(3-chloro-2-fluorobenzyl)-4-oxo-4H-quinolizine-3-carboxylic acid,
 7-(3-chloro-2-fluorobenzyl)-1-(2-hydroxyethylamino)-4-oxo-4H-quinolizine-3-carboxylic acid,
 7-(3-chloro-2-fluorobenzyl)-1-methylsulfonylamino-4-oxo-4H-quinolizine-3-carboxylic acid,
 7-(3-chloro-2-fluorobenzyl)-1-cyano-4-oxo-4H-quinolizine-3-carboxylic acid,
 3-(3-chloro-2-fluorobenzyl)-9-(2-hydroxyethyl)-6-oxo-6H-pyrido[1,2-a]pyrimidine-7-carboxylic acid,
 1-(tert-butoxycarbonylaminomethyl)-7-(3-chloro-2-fluorobenzyl)-4-oxo-4H-quinolizine-3-carboxylic acid,
 l-carboxymethyl-7-(3-chloro-2-fluorobenzyl)-4-oxo-4H-quinolizine-3-carboxylic acid,
 7-(3-chloro-2-fluorobenzyl)-1-[(2,2-dimethylpropionylamino)methyl]-4-oxo-4H-quinolizine-3-carboxylic acid,
 7-(3-chloro-2-fluorobenzyl)-1-dimethylaminomethyl-4-oxo-4H-quinolizine-3-carboxylic acid,
 7-(3-chloro-2-fluorobenzyl)-1-[(2-hydroxyacetylamino)methyl]-4-oxo-4H-quinolizine-3-carboxylic acid,
 7-(3-chloro-2-fluorobenzyl)-1-[(2-methoxyacetylamino)methyl]-4-oxo-4H-quinolizine-3-carboxylic acid,
 1-1(N-(tert-butoxycarbonyl)-N-methylamino)methyl]-7-(3-chloro-2-fluorobenzyl)-4-oxo-4H-quinolizine-3-carboxylic acid,
 7-(3-chloro-2-fluorobenzyl)-4-oxo-1-(propionylaminomethyl)-4H-quinolizine-3-carboxylic acid,
 1-(butyrylaminomethyl)-7-(3-chloro-2-fluorobenzyl)-4-oxo-4H quinolizine-3-carboxylic acid,
 7-(3-chloro-2-fluorobenzyl)-1-(isobutyrylaminomethyl)-4-oxo-4H-quinolizine-3-carboxylic acid,
 1-(benzoylaminomethyl)-7-(3-chloro-2-fluorobenzyl)-4-oxo-4H-quinolizine-3-carboxylic acid,
 7-(3-chloro-2-fluorobenzyl)-1-(ethoxycarbonylaminomethyl)-4-oxo-4H-quinolizine-3-carboxylic acid,
 7-(3-chloro-2-fluorobenzyl)-1-[(morpholinocarbonyl)amino]methyl}-4H-oxo-4H-quinolizine-3-carboxylic acid,
 7-(3-chloro-2-fluorobenzyl)-1-[(3-ethylureido)methyl]-4-oxo-4H-quinolizine-3-carboxylic acid,
 7-(3-chloro-2-fluorobenzyl)-4-oxo-1-(phenylacetylaminomethyl)-4H-quinolizine-3-carboxylic acid,
 7-(3-chloro-2-fluorobenzyl)-1-[(oxalylamino)methyl]-4-oxo-4H-quinolizine-3-carboxylic acid,
 7-(3-chloro-2-fluorobenzyl)-4-oxo-1-[(2-phenoxyacetylamino)methyl]-4H-quinolizine-3-carboxylic acid,
 7-(3-chloro-2-fluorobenzyl)-1-[((S)-2-methoxypropionylamino)methyl]-4-oxo-4H-quinolizine-3-carboxylic acid,
 7-(3-chloro-2-fluorobenzyl)-1-[C(R)-2-methoxypropionylainino)methyl]-4-oxo-4H-quinolizine-3-carboxylic acid,
 1-[(3-carboxyproplonylamino)methyl]7-(3-chloro-2-fluorobenzyl)-4-oxo-4H quinolizine-3-carboxylic acid, 7-(3-chloro-2-fluorobenzyl)-1-[(2-ethoxyacetylamino)methyl]-4-oxo-4H-quinolizine-3-carboxylic acid,
7-(3-chloro-2-fluorobenzyl)-1-[(2-methoxy-2-methylpropionylamino)methyl]-4-oxo-4H-quinolizine-3-carboxylic acid,
1-1(2-acetylaminoacetylamino)methyl]-7-(3-chloro-2 fluorobenzyl)-4-oxo-4H-quinolizine-3-carboxylic acid,
7-(3-chloro-2-fluorobenzyl)-1-methoxymethoxy-4-oxo-4H-quinolizine-3-carboxylic acid,
1-(tert-butozycarbonylamino)-7-(3-chloro-2-fluorobenzyl)-4-oxo-4H-quinolizine-3-carboxylic acid,
1-acetylamino-7-(3-chloro-2-fluorobenzyl)-4-oxo-4H-quinolizine-3-carboxylic acid,
7-(3-fluorobenzyl)-4-oxo-4H-quinolizine-1,3-dicarboxylic acid 1-tert-butylester,
7-(2,3-dichlorobenzyl)-1-((R)-1-hydroxymethyl-2-methylpropyl)-4H-oxo-4H-quinolizine-3-carboxylic acid,
7-(2,3-dichlorobenzyl)-1-((R)-1-hydroxymethyl-2,2-dimethylpropyl)-4-oxo-4H-quinolizine-3-carboxylic acid, and
7-(3-chloro-2-fluorobenzyl)-1-((R)-1-hydroxymethyl-2,2-dimethylpropyl)-9-methoxy-4-oxo-4H-quinolizine-3-carboxylic acid,
or a pharmaceutically acceptable salt thereof.

27. A pharmaceutical composition comprising a quinolizinone compound of claim 4, or a pharmaceutically acceptable salt thereof, and a pharmaceutically acceptable carrier.

28. A method for the treatment of an HIV infectious disease in a mammal, which comprises administering an effective amount of a quinolizinone compound of claim 4, or a pharmaceutically acceptable salt thereof to said mammal.

29. The method for the treatment of an HIV infectious disease according to claim 28, which further comprises administering an effective amount of one or more other kinds of anti-HIV active substances to said mammal.

30. A method for inhibiting HIV integrase in a mammal, which comprises administering an effective amount of the pharmaceutical composition agent of claim 1 or a pharmaceutically acceptable salt thereof to said mammal.

31. A method for the treatment of an HIV infectious disease in a mammal, which comprises administering an effective amount of the pharmaceutical composition of claim 1, or a pharmaceutically acceptable salt thereof to said mammal.

32. A commercial package comprising the composition of claim 27 and a written matter associated therewith, the written matter stating that the composition can or should be used for the treatment of an HIV infectious disease.

33. A commercial package comprising the composition of claim 27 and a written matter associated therewith, the written matter stating that the composition can or should be used for inhibiting integrase.

* * * * *

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination of
      HIV integrase.

<400> SEQUENCE: 1 accctttag tcagtgtgga aaatctctag ca                                        32

<210> SEQ ID NO 2
```

```
-continued

<211> LENGTH: 31
<212> TYPE: DNA
<213> ORGANISM: Artificial Sequence
<220> FEATURE:
<223> OTHER INFORMATION: Donor minus strand for activity determination
      of HIV integrase.

<400> SEQUENCE: 2
actgctagag attttccaca ctgactaaaa g                            31

<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination
      of HIV integrase.

<400> SEQUENCE: 3
tgaccaaggg ctaattcact                                         20

<210> SEQ ID NO 4
<211> LENGTH: 20
<212> TYPE: DNA
<213> ORGANISM: Artificial Sequence
<220> FEATURE:
<223> OTHER INFORMATION: Target minus strand for activity determination
      of HIV integrase.

<400> SEQUENCE: 4
agtgaattag cccttggtca                                         20
```